US012319676B2

(12) United States Patent
Wacker et al.

(10) Patent No.: US 12,319,676 B2
(45) Date of Patent: Jun. 3, 2025

(54) SUBSTITUTED AMIDE COMPOUNDS USEFUL AS FARNESOID X RECEPTOR MODULATORS

(71) Applicant: BRISTOL-MYERS SQUIBB COMPANY, Princeton, NJ (US)

(72) Inventors: Dean A. Wacker, Yardley, PA (US); Susheel Jethanand Nara, Mumbai (IN); Srinivas Cheruku, Bangalore (IN); Kandhasamy Sarkunam, Hosur (IN); Firoz Ali Jaipuri, Bengaluru (IN); Soodamani Thangavel, Krishnagiri (IN); Rishikesh Narayan, Mumbai (IN); Srinivas Jogi, Bangalore (IN); Pavan Kalyan Kathi, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 962 days.

(21) Appl. No.: 17/430,903

(22) PCT Filed: Feb. 14, 2020

(86) PCT No.: PCT/US2020/018211
§ 371 (c)(1),
(2) Date: Aug. 13, 2021

(87) PCT Pub. No.: WO2020/168149
PCT Pub. Date: Aug. 20, 2020

(65) Prior Publication Data
US 2022/0081430 A1    Mar. 17, 2022

Related U.S. Application Data

(60) Provisional application No. 62/806,060, filed on Feb. 15, 2019.

(51) Int. Cl.
| C07D 413/12 | (2006.01) |
| C07C 237/24 | (2006.01) |
| C07D 213/26 | (2006.01) |
| C07D 271/06 | (2006.01) |
| C07D 401/12 | (2006.01) |
| C07D 417/12 | (2006.01) |

(52) U.S. Cl.
CPC .......... *C07D 413/12* (2013.01); *C07C 237/24* (2013.01); *C07D 213/26* (2013.01); *C07D 271/06* (2013.01); *C07D 401/12* (2013.01); *C07D 417/12* (2013.01)

(58) Field of Classification Search
None
See application file for complete search history.

(56) References Cited

U.S. PATENT DOCUMENTS

| 8,158,665 | B2 | 4/2012 | Caldwell et al. |
| 8,907,095 | B2 | 12/2014 | Xia et al. |
| 9,539,244 | B2 | 1/2017 | Kinzel et al. |
| 9,751,874 | B2 | 9/2017 | Gege et al. |
| 2010/0152166 | A1 | 6/2010 | Genin et al. |
| 2011/0034507 | A1 | 2/2011 | Akwabi-Ameyaw et al. |
| 2015/0366856 | A1 | 12/2015 | Tully et al. |
| 2016/0176861 | A1 | 6/2016 | Gege et al. |
| 2017/0298068 | A1 | 10/2017 | Gege et al. |
| 2017/0304270 | A1 | 10/2017 | Or et al. |
| 2017/0304271 | A1 | 10/2017 | Or et al. |
| 2017/0304272 | A1 | 10/2017 | Or et al. |
| 2017/0333399 | A1 | 11/2017 | Or et al. |
| 2017/0355693 | A1 | 12/2017 | Blomgren et al. |
| 2017/0355694 | A1 | 12/2017 | Gege |
| 2017/0368038 | A1 | 12/2017 | Badman et al. |
| 2019/0002452 | A1 | 1/2019 | Zhang et al. |
| 2019/0127358 | A1 | 5/2019 | Yoon et al. |

FOREIGN PATENT DOCUMENTS

| CN | 106146483 A | 11/2016 |
| CN | 106632294 A | 5/2017 |

(Continued)

OTHER PUBLICATIONS

The Organic Chemistry of Drug Design and Drug Action, Richard B. Silverman, Chemical Industry Press, Jan. 2008, 1st Edition, pp. 19-22.

(Continued)

*Primary Examiner* — Bong-Sook Baek
(74) *Attorney, Agent, or Firm* — Gary Greenblatt

(57) ABSTRACT

Disclosed are compounds of Formula (I): or a stereoisomer, a tautomer, or a pharmaceutically acceptable salt or solvate thereof, when Q is: (i) halo, cyano, hydroxyl, $NR^aR^x$, $C(O)OH$, $C(O)NH_2$, $C_{1-6}$ alkyl substituted with zero to 6 $R^{1a}$, or $P(O)R^{1c}R^{1c}$, or (ii) L $R^1$; and A, $X^1$, $X^2$, $X^3$, $X^4$, $Z^1$, $Z^2$, $R^1$, $R^{1a}$, $R^{1c}$, $R^2$, $R^{3a}$, $R^{3b}$, $R^x$, L, a, b, and d are defined herein. Also disclosed are methods of using these compounds to modulate the activity of farnesoid X receptor (FXR); pharmaceutical compositions comprising these compounds; and methods of treating a disease, disorder, or condition associated with FXR dysregulation, such as pathological fibrosis, transplant rejection, cancer, osteoporosis, and inflammatory disorders, by using the compounds and pharmaceutical compositions.

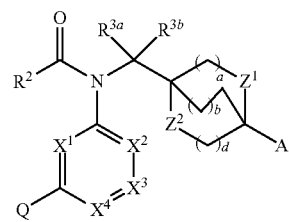

(I)

13 Claims, No Drawings

(56) References Cited

FOREIGN PATENT DOCUMENTS

| | | |
|---|---|---|
| CN | 107021958 A | 8/2017 |
| EP | 3034499 A1 | 6/2016 |
| EP | 3034501 A1 | 6/2016 |
| EP | 3401315 A1 | 11/2018 |
| WO | 9313101 A1 | 7/1993 |
| WO | 9817276 A1 | 4/1998 |
| WO | 03099821 A1 | 12/2003 |
| WO | 2004046162 A2 | 6/2004 |
| WO | 2006006490 A1 | 1/2006 |
| WO | 2007076260 A2 | 7/2007 |
| WO | 2008051942 A2 | 5/2008 |
| WO | 2008094556 A2 | 8/2008 |
| WO | 2008109177 A2 | 9/2008 |
| WO | 2008109179 A1 | 9/2008 |
| WO | 2008109180 A2 | 9/2008 |
| WO | 2009009059 A1 | 1/2009 |
| WO | 2009149795 A2 | 12/2009 |
| WO | 2010058318 A1 | 5/2010 |
| WO | 2011006935 A2 | 1/2011 |
| WO | 2011045292 A1 | 4/2011 |
| WO | 2012087520 A1 | 6/2012 |
| WO | 2013007387 A1 | 1/2013 |
| WO | 2013186159 A1 | 12/2013 |
| WO | 2014054053 A1 | 4/2014 |
| WO | 2015138969 A1 | 9/2015 |
| WO | 2015172747 A1 | 11/2015 |
| WO | 2016096115 A1 | 6/2016 |
| WO | 2017049173 A1 | 3/2017 |
| WO | 2017049176 A1 | 3/2017 |
| WO | 2017133521 A1 | 8/2017 |
| WO | 2017145040 A1 | 8/2017 |
| WO | 2017145041 A1 | 8/2017 |
| WO | 2017161002 A1 | 9/2017 |
| WO | 2018059314 A1 | 4/2018 |
| WO | 2018170165 A1 | 9/2018 |
| WO | 2018170166 A1 | 9/2018 |
| WO | 2018170167 A1 | 9/2018 |
| WO | 2018170173 A1 | 9/2018 |
| WO | 2018170182 A1 | 9/2018 |
| WO | 2020061114 A1 | 3/2020 |

OTHER PUBLICATIONS

Claudel, Thierry et al., "The Farnesoid X Receptor: A Novel Drug Target?", Expert Opin. Investig. Drugs, vol. 13(9), pp. 1135-1148, (2004).

Crawley, Matthew Lantz, "Farnesoid X receptor modulators: a patent review," Expert Opinion on Therapeutic Patents, (2010) 20:8, pp. 1047-1057.

International Preliminary Report on Patentability Application No. PCT/US2020/018211, Issued Aug. 10, 2021.

International Search Report Application No. PCT/US2020/018211, mailed Jun. 12, 2020.

Sepe, Valentina et al., "Farnesoid X Receptor Modulators 2014-present: A Patent Review", Expert Opinion on Therapeutic Patents, vol. 28, No. 5, pp. 351-364 (2018).

Tully, David C. et al., "Discovery of Tropifexor (LJN452), a Highly Potent Non-bile Acid FXR Agonist for the Treatment of Cholestatic Liver Diseases and Nonalcoholic Steatohepatitis (NASH)", Journal of Medicinal Chemistry, vol. 60, pp. 9960-9973 (2017).

SUBSTITUTED AMIDE COMPOUNDS USEFUL AS FARNESOID X RECEPTOR MODULATORS

CROSS REFERENCE

This application is a 371 application of International Application No. PCT/US2020/018211, filed on Feb. 14, 2020, which claims the benefit of U.S. Provisional Application Ser. 62/806,060, filed Feb. 15, 2019, the content of each is hereby fully incorporated by reference in its entirety for all purposes.

DESCRIPTION

The present invention relates generally to substituted amide compounds useful as farnesoid X receptor (FXR) modulators, pharmaceutical compositions comprising such compounds and to their use in therapy, especially in the treatment or prophylaxis of diseases, disorders, and conditions for which an FXR modulator is indicated.

BACKGROUND OF THE INVENTION

FXR or NR1H4 (nuclear receptor subfamily 1, group H, member 4) is a nuclear receptor that can activate the expression of specific target genes in a ligand-dependent manner. FXR is expressed in the liver, throughout the gastrointestinal tract, colon, ovary, adrenal gland, kidney, and in the gall bladder and biliary tree in humans. FXR forms a heterodimer with Retinoid X Receptor (RXR) and binds to specific response elements in target genes to regulate gene transcription (B. M. Forman et al., Cell 1995; 81: 687; W. Seol et al., Mol. Endocrinol. 1995; 9: 72). The FXR/RXR heterodimer typically binds to an inverted repeat of a consensus hexanucleotide sequence (AGGTCA) separated by a single nucleotide, i.e. an IR-1 sequence. The relevant physiological ligands of FXR are bile acids including chenodeoxycholic acid and its taurine-conjugate (D. J. Parks et al., Science 1999; 284: 1365; M. Makishima et al., Science 1999; 284: 1362). FXR activation regulates the expression of multiple genes that encode enzymes and transporters involved in bile acid synthesis, influx, and efflux from the liver and intestine resulting in a net decrease in total endogenous bile acids in a negative feedback loop. FXR is involved in paracrine and endocrine signaling by upregulating the expression of the cytokine Fibroblast Growth Factor 15 (rodents) or 19 (primates), which can also contribute to the regulation of bile acid concentrations (Holt et al., Genes Dev. 2003; 17: 1581; Inagaki et al., Cell Metab 2005; 2: 217). Therefore, FXR is considered to be a master regulator of bile acid homeostasis.

One use of FXR agonists is for the treatment of diseases in which bile acids are dysregulated, including cholestatic diseases (e.g. primary biliary cirrhosis and primary sclerosing cholangitis) that can lead to fibrosis, cirrhosis, cholangiocarcinoma, hepatocellular carcinoma, liver failure, and death. While elevated bile acid concentrations in the liver have deleterious effects, bile acids also affect the microflora and integrity of the small intestine. Obstruction of bile flow in humans or rodents causes proliferation of intestinal bacteria and mucosal injury, which can lead to bacterial translocation across the mucosal barrier and systemic infection (Berg, Trends Microbiol. 1995; 3: 149-154). Mice lacking FXR have increased ileal levels of bacteria and a compromised epithelial barrier, while activation of intestinal FXR plays an important role in preventing bacterial overgrowth and maintaining the integrity of the intestinal epithelium (Inagaki et al., Proc Natl Acad Sci 2006; 103: 3920-3925). Over time, FXR null mice spontaneously develop hepatocellular carcinoma, and this can be abrogated by selective re-activation of FXR in the intestine (Degirolamo et al., Hepatology 61: 161-170). Pharmacological activation of FXR with a small molecule agonist or transgenic expression of FXR in the intestine can normalize bile acid concentrations, decrease cellular proliferation in hepatic bile ducts, and reduce inflammatory cell infiltration, necrotic area, and liver fibrosis in rodent models of cholestasis (Liu et al., J. Clin. Invest. 2003; 112:1678-1687; Modica et al., Gastroenterology. 2012; 142: 355-365). Some of these beneficial effects observed in preclinical models of cholestasis have translated to human patients, and the FXR agonist, obeticholic acid (OCA or OCALIVA™), has been approved for the treatment of primary biliary cirrhosis (https://www.fda.gov/newsevents/newsroom/pressannouncements/ucm503964.htm).

In addition to controlling bile acid homeostasis, FXR agonists regulate the hepatic expression of hundreds of genes encoding proteins involved in cholesterol and lipid metabolism and transport, glucose homeostasis, inflammation, chemotaxis, and apoptosis among other pathways (Zhan et al., PLoS One 2014; 9: e105930; Ijssennagger et al., J Hepatol 2016; 64: 1158-1166). Consistent with these broad effects on gene expression, FXR agonists have also been investigated in preclinical models of fibrosis, cancer, inflammatory diseases, and metabolic disorders, including dyslipidemia, obesity, type 2 diabetes, nonalcoholic fatty liver disease (NAFLD) and metabolic syndrome (Crawley, Expert Opin. Ther. Patents 2010; 20:1047-1057).

FXR agonists are also being investigated in human clinical trials for the treatment of NAFLD, a more advanced form of fatty liver disease, nonalcoholic steatohepatitis (NASH), and associated complications. NAFLD is one of the most common causes of chronic liver disease in the world today (Vernon et al., Aliment Pharmacol Ther 2011; 34:274-285). The risk factors for developing NAFLD include obesity, type 2 diabetes mellitus (T2DM), insulin resistance, hypertension, and dyslipidemia. In a 6-week clinical trial in T2DM patients with NAFLD, the FXR agonist OCA statistically significantly improved insulin sensitivity and reduced body weight, showing beneficial effects on some of these risk factors (Mudaliar et al., Gastroenterology 2013; 145: 574-582). NASH is the most severe and progressive form of NAFLD and includes the histological findings of hepatic steatosis, inflammation, and ballooning degeneration with varying amounts of pericellular fibrosis (Sanyal et al., Hepatology 2015; 61:1392-1405). In a 72-week clinical trial in patients with NASH, OCA statistically significantly improved hepatic steatosis, lobular inflammation, hepatocyte ballooning, and fibrosis as assessed by histological analyses of liver biopsies (Neuschwander-Tetri et al., Lancet 2015; 385: 956-965). These data also suggest the potential for FXR agonists to show benefit on clinical outcomes given that NASH is the second leading cause of hepatocellular carcinoma (HCC) and liver transplantation in the United States (Wong et al., Hepatology 2014; 59: 2188-2195).

Applicants have found compounds useful for treating a disease, disorder, or condition associated with farnesoid X receptor (FXR) activity in a patient in need thereof. These compounds are provided to be useful as pharmaceuticals with desirable stability, bioavailability, therapeutic index, and toxicity values that are important to their druggability.

SUMMARY OF THE INVENTION

The present invention provides compounds of Formula (I) as well as the subgenera and species thereof, including stereoisomers, tautomers, pharmaceutically acceptable salts, and solvates thereof, which are useful as FXR modulators.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of Formula (I) and compositions comprising the compounds of Formula (I) may be used in therapy, either alone or in combination with one or more additional therapeutic agents.

The present invention also provides processes and intermediates for making the compounds of Formula (I) and/or salts thereof.

The compounds of the invention may be used in the treatment of a disease, disorder, or condition associated with activity of farnesoid X receptor (FXR) in a patient in need of such treatment by administering a therapeutically effective amount of the compound, or a stereoisomer, a tautomer, or a pharmaceutically acceptable salt or solvate thereof, to the patient. The disease, disorder, or condition may be related to pathological fibrosis. The compounds of the invention can be used alone, in combination with one or more compounds of the present invention, or in combination with one or more, e.g., one to two, other therapeutic agents.

The compounds of the invention may be used, either as a single agent or in combination with other agents, in the treatment of a disease, disorder, or condition selected from nonalcoholic steatohepatitis (NASH), non-alcoholic fatty liver disease (NAFLD), chronic kidney disease, diabetic kidney disease, primary sclerosing cholangitis (PSC), and primary biliary cirrhosis (PBC). The compounds of the invention may be used, either as a single agent or in combination with other agents, in the treatment of idiopathic pulmonary fibrosis (IPF).

The compounds of the invention may be used for the manufacture of a medicament for the treatment of a disease, disorder, or condition in a patient in need of such treatment.

Other features and advantages of the invention will be apparent from the following detailed description and claims.

DETAILED DESCRIPTION

The present application provides compounds, including all stereoisomers, solvates, prodrugs and pharmaceutically acceptable salt and solvate forms thereof, according to Formula (I). The present application also provides pharmaceutical compositions containing at least one compound according to Formula (I), or a stereoisomer, a tautomer, or a pharmaceutically acceptable salt or a solvate thereof, and optionally at least one additional therapeutic agent. Additionally, the present application provides methods for treating a patient suffering from a FXR-modulated disease or disorder such as for example, biliary fibrosis, liver fibrosis, renal fibrosis, Non-Alcoholic Fatty Liver Disease (NAFLD), Non-Alcoholic Steato-Hepatitis (NASH), primary sclerosing cholangitis (PSC), primary biliary cirrhosis (PBC), and pancreatic fibrosis, by administering to a patient in need of such treatment a therapeutically effective amount of a compound of the present invention, or a stereoisomer, a tautomer, or a pharmaceutically acceptable salt or a solvate thereof, and optionally in combination with at least one additional therapeutic agent.

The first aspect of the present invention provides at least one compound of Formula (I):

(I)

or a stereoisomer, a tautomer, or a salt or solvate thereof, wherein:

$X^1$ is $CR^{5a}$ or N;
$X^2$ is $CR^{5b}$ or N;
$X^3$ is $CR^{5c}$ or N;
$X^4$ is $CR^{5d}$ or N; provided that zero, 1, or 2 of $X^1$, $X^2$, $X^3$, and $X^4$ are N;
$Z^1$ and $Z^2$ are independently $CH_2$ or O; provided that at least one of $Z^1$ and $Z^2$ is $CH_2$;
a is zero or 1;
b is zero, 1, or 2;
d is zero, 1, or 2; provided that $Z^1$ and $Z^2$ are each $CH_2$ when a, b, and d are each zero;

Q is:
  (i) halo, cyano, hydroxyl, —$NR^xR^x$, —C(O)OH, C(O)$NH_2$, $C_{1-6}$ alkyl substituted with zero to 6 $R^{1a}$, or —$P(O)R^{1c}R^{1c}$; or
  (ii) -L-$R^1$;

L is —O—, —$OCR^{1d}R^{1d}C(O)$—, —C(O)—, —C(O)O—, —$C(O)NR^{1e}$—, —$C(O)NR^{1e}C(O)$—, —$NR^{1e}$—, —$NR^{1e}C(O)$—, —$NR^{1e}C(O)O$—, —$NR^{1e}C(O)NR^{1e}$—, —$NR^{1e}S(O)_2$—, —$S(O)_2$—, or —$S(O)_2NR^{1e}$—;

$R^1$ is $C_{1-6}$ alkyl substituted with zero to 6 $R^{1a}$, or a cyclic group selected from 3- to 8-membered carbocyclyl, 6- to 10-membered aryl, 4- to 10-membered heterocyclyl, and 5- to 10-membered heteroaryl, wherein said cyclic group is substituted with zero to 3 $R^{1b}$; provided that when $R^1$ is said cyclic group, $Z^1$ and $Z^2$ are each $CH_2$;

each $R^{1a}$ is independently halo, hydroxyl, —$NR^wR^w$, oxo, cyano, $C_{1-3}$ alkoxy, $C_{1-3}$ haloalkoxy, —$C(O)OR^x$, —$C(O)NR^wR^w$, or —$NR^xC(O)R^y$;

each $R^{1b}$ is independently halo, oxo, cyano, hydroxyl, —$NH_2$, $C_{1-6}$ alkyl, $C_{1-6}$ alkoxy, —$NH(C_{1-6}$ alkyl), —$N(C_{1-6}$ alkyl$)_2$, —$NR^xC(O)(C_{1-6}$ alkyl), or $C_{3-6}$ cycloalkyl, wherein each of said alkyl, alkoxy, and cycloalkyl is substituted with zero to 6 $R^{1a}$;

each $R^{1c}$ is independently $C_{1-6}$ alkyl;
each $R^{1d}$ is independently hydrogen, halo, $C_{1-3}$ alkyl, or $C_{3-6}$ cycloalkyl;
each $R^{1e}$ is independently hydrogen, $C_{1-3}$ alkyl, or $C_{3-6}$ cycloalkyl;

$R^2$ is:
  (i) $C_{1-6}$ alkyl, $C_{2-6}$ alkenyl, $C_{2-6}$ alkynyl, $C_{1-6}$ alkoxy, or —$NR^vR^v$, wherein each of said alkyl, alkenyl, alkynyl, and alkoxy is substituted with zero to 6 $R^{2a}$;
  (ii) $C_{3-8}$ carbocyclyl, $C_{6-8}$ spirobicyclyl, 4- to 7-membered heterocyclyl, phenyl, or 5- to 6-membered heteroaryl, wherein each of said carbocyclyl, spirobicyclyl, heterocyclyl, phenyl, and heteroaryl is substituted with zero to 3 $R^{2b}$; or (iii) —CH$_2$(C$_{3-6}$ cycloalkyl), —CH$_2$(4- to 6-membered heterocyclyl), —NR$^x$(CH$_2$)$_{0-2}$(C$_{3-6}$ cycloalkyl), —NR$^x$(CH$_2$)$_{0-2}$(C$_{5-8}$ bicycloalkyl), —NR$^x$(CH$_2$)$_{0-2}$(C$_{5-8}$ spirobicycloalkyl), —NR$^x$(CH$_2$)$_{0-2}$(4- to 6-membered heterocyclyl), —NR$^x$(CH$_2$)$_{0-2}$(5- to 6-membered heteroaryl), —NR$^x$(CH$_2$)$_{0-2}$(phenyl), —O(CH$_2$)$_{0-2}$(C$_{3-6}$ cycloalkyl), —O(CH$_2$)$_{0-2}$(C$_{5-8}$ bicycloalkyl), —O(CH$_2$)$_{0-2}$(C$_{5-8}$ spirobicycloalkyl), —O(CH$_2$)$_{0-2}$(4- to 6-membered heterocyclyl), —O(CH$_2$)$_{0-2}$(5- to 6-membered heteroaryl), or —O(CH$_2$)$_{0-2}$(phenyl), wherein each of said cycloalkyl, heterocyclyl, bicycloalkyl, spirobicycloalkyl, aryl, and heteroaryl is substituted with zero to 3 R$^{2b}$;

each R$^{2a}$ is independently halo, alkyl, cyano, hydroxyl, oxo, C$_{1-3}$ haloalkyl, C$_{1-3}$ alkoxy, C$_{1-3}$ haloalkoxy, —NR$^x$R$^x$, —C(O)(C$_{1-6}$ alkyl), —C(O)(C$_{3-6}$ cycloalkyl), —NR$^x$C(O)R$^y$, —C(O)(C$_{1-6}$ alkyl), —C(O)OR$^x$, —C(O)NR$^w$R$^w$, —S(O)$_2$R$^y$, —S(O)$_2$(C$_{1-3}$ fluoroalkyl), —NR$^x$S(O)$_2$(C$_{1-3}$ alkyl), —NR$^x$S(O)$_2$(C$_{3-6}$ cycloalkyl), —S(O)$_2$NR$^z$R$^z$, or —P(O)R$^y$R$^y$;

each R$^{2b}$ is independently halo, cyano, hydroxyl, oxo, C$_{1-6}$ alkyl, C$_{1-6}$ alkoxy, —NR$^x$R$^x$, —NR$^x$C(O)O(C$_{1-3}$ alkyl), —C(O)(C$_{1-3}$ alkyl), or —S(O)$_2$(C$_{1-3}$ alkyl), wherein each of said alkyl and alkoxy is substituted with zero to 6 R$^{2a}$;

R$^{3a}$ and R$^{3b}$ are independently hydrogen, C$_{1-3}$ alkyl, C$_{1-3}$ haloalkyl, or C$_{3-6}$ cycloalkyl, or R$^{3a}$ and R$^{3b}$, taken together with the carbon atom to which they are attached, form a C$_{3-6}$ cycloalkyl;

A is:
(i) cyano;
(ii) phenyl or a 5- to 10-membered heteroaryl containing 1 to 4 heteroatoms independently selected from N, O, and S, wherein each of said phenyl and heteroaryl is substituted with zero to 3 R$^{4a}$; or (iii)

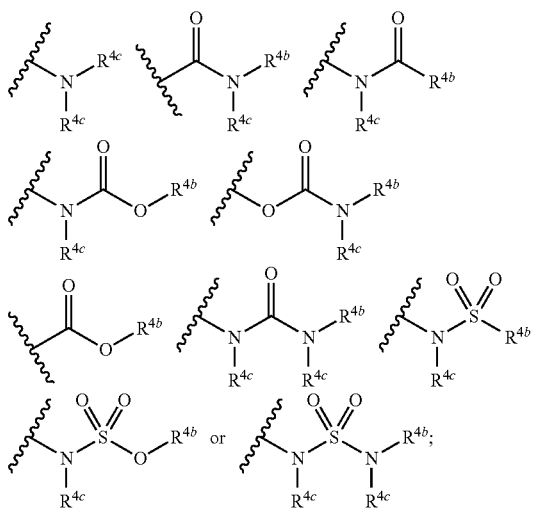

each R$^{4a}$ is independently halo, cyano, hydroxyl, —NH$_2$, C$_{1-6}$ alkyl, C$_{2-6}$ alkenyl, C$_{2-6}$ alkynyl, C$_{1-6}$ alkoxy, —(CH$_2$)$_{0-3}$NH(C$_{1-6}$ alkyl), —(CH$_2$)$_{0-2}$N(C$_{1-6}$ alkyl)$_2$, —(CH$_2$)$_{0-3}$(C$_{3-6}$ carbocyclyl), or —(CH$_2$)$_{0-3}$(4- to 6-membered heterocyclyl), wherein each of said alkyl, alkoxy, alkenyl, and alkynyl is substituted with zero to 6 R$^{4d}$ and each of said carbocyclyl and heterocyclyl is substituted with zero to 3 R$^{4e}$;

R$^{4b}$ is C$_{1-6}$ alkyl, —(CH$_2$)$_{0-3}$(C$_{3-6}$ cycloalkyl), or —(CH$_2$)$_{0-3}$(4- to 6-membered heterocyclyl), wherein each of said alkyl is substituted with zero to 6 R$^{4d}$ and each of said cycloalkyl and heterocyclyl is substituted with zero to 3 R$^{4e}$;

each R$^{4d}$ is independently hydrogen, C$_{1-6}$ alkyl, C$_{3-6}$ cycloalkyl, 4- to 6-membered heterocyclyl, phenyl, or 5- to 6-membered heteroaryl;

each R$^{4d}$ is independently halo, hydroxyl, —NR$^x$R$^x$, oxo, cyano, C$_{1-3}$ alkoxy, or C$_{1-3}$ haloalkoxy;

each R$^{4e}$ is independently halo, oxo, cyano, hydroxyl, —NH$_2$, C$_{1-6}$ alkyl, C$_{1-6}$ alkoxy, —NH(C$_{1-6}$ alkyl), or —N(C$_{1-6}$ alkyl)$_2$, wherein each of said alkyl and alkoxy is substituted with zero to 6 R$^{4d}$;

each of R$^{5a}$, R$^{5b}$, R$^{5c}$, and R$^{5d}$ is independently hydrogen, halo, hydroxy, cyano, C$_{1-6}$ alkyl substituted with zero to 6 R$^{5e}$, C$_{1-6}$ alkoxy substituted with zero to 6 R$^{5e}$, —C(O)OR$^x$, —C(O)NR$^w$R$^w$, —S(O)$_2$R$^y$, —S(O)$_2$NR$^z$R$^z$, or phenyl substituted with zero to 3 R$^{5f}$;

each of R$^{5e}$ is independently halo, hydroxyl, NR$^x$R$^x$, oxo, cyano, C$_{1-3}$ alkoxy, or C$_{1-3}$ haloalkoxy;

each R$^{5f}$ is independently halo, oxo, cyano, hydroxyl, —NH$_2$, C$_{1-6}$ alkyl, C$_{1-6}$ alkoxy, —NH(C$_{1-6}$ alkyl), or —N(C$_{1-6}$ alkyl)$_2$, wherein each of said alkyl and alkoxy is substituted with zero to 6 R$^{5e}$;

each R$^v$ is independently hydrogen, C$_{1-6}$ alkyl, or alternatively, two R$^v$, taken together with the nitrogen atom to which they are attached, form a 4- to 7-membered bicyclic or spirocyclic ring moiety containing zero to 2 additional heteroatoms independently selected from N, O, and S, wherein each ring can be substituted with zero to 6 R$^{2a}$;

each R$^w$ is independently hydrogen, C$_{1-6}$ alkyl, or C$_{3-6}$ cycloalkyl; or alternatively, two R$^w$, taken together with the nitrogen atom to which they are attached, form a 4- to 7-membered ring moiety containing zero to 2 additional heteroatoms independently selected from N, O, and S;

each R$^x$ is independently hydrogen, C$_{1-6}$ alkyl, or C$_{3-6}$ cycloalkyl;

R$^y$ is C$_{1-6}$ alkyl or C$_{3-6}$ cycloalkyl; and each R$^z$ is independently hydrogen, C$_{1-6}$ alkyl, or C$_{3-6}$ cycloalkyl; or alternatively, two R$^z$, taken together with the nitrogen atom to which they are attached, form a 4- to 7-membered ring moiety containing zero to 2 additional heteroatoms independently selected from N, O, and S.

In one embodiment, a compound of Formula (I) or a stereoisomer, a tautomer, or a salt or solvate thereof is provided, wherein:

Q is:
(i) F, Cl, Br, cyano, hydroxyl, —NR$^x$R$^x$, —C(O)OH, —C(O)NH$_2$, C$_{1-4}$ alkyl substituted with zero to 6 R$^{1d}$, or —P(O)R$^{1c}$R$^{1c}$; or
(ii) -L-R$^1$;

L is —O—, —OCR$^{1a}$R$^{1a}$C(O)—, —C(O)—, —C(O)—C(O)O—, —C(O)NR$^{1b}$—, —NR$^{1b}$C(O)—, —NR$^{1b}$C(O)NR$^{1b}$—, —NR$^{1b}$S(O)$_2$—, —S(O)$_2$—, or —S(O)$_2$NR$^{1b}$—;

R$^1$ is C$_{1-6}$ alkyl substituted with zero to 6 R$^{1a}$, or a cyclic group selected C$_{3-6}$ cycloalkyl, phenyl, 4- to 10-membered heterocyclyl, and 5- to 10-membered heteroaryl, wherein said cyclic group is substituted with zero to 3 R$^{1b}$;

each R$^{1a}$ is independently F, Cl, hydroxyl, —NR$^w$R$^w$, oxo, cyano, C$_{1-3}$ alkoxy, C$_{1-3}$ haloalkoxy, —C(O)OH, or —C(O)O(C$_{1-2}$ alkyl);

each $R^{1b}$ is independently F, Cl, cyano, hydroxyl, oxo, —$NH_2$, $C_{1-4}$ alkyl, $C_{1-4}$ alkoxy, —$NH(C_{1-4}$ alkyl), —$N(C_{1-4}$ alkyl$)_2$, —$NR^xC(O)(C_{1-6}$ alkyl), or $C_{3-4}$ cycloalkyl, wherein each of said alkyl, alkoxy, and cycloalkyl is substituted with zero to 6 $R^{1a}$;

each $R^{1c}$ is independently $C_{1-4}$ alkyl;

$R^2$ is:
(i) $C_{1-4}$ alkyl, $C_{1-4}$ alkoxy, or —$NR^vR^v$, wherein each of said alkyl and alkoxy is substituted with zero to 4 $R^{2a}$;
(ii) $C_{3-8}$ carbocyclyl, $C_{6-8}$ spirobicyclyl, phenyl, or 4- to 7-membered heterocyclyl, wherein each of said carbocyclyl, spirobicyclyl, and heterocyclyl is substituted with zero to 3 $R^{2b}$; or
(iii) —$CH_2(C_{3-5}$ cycloalkyl), —$CH_2$(4- to 6-membered heterocyclyl), —$NR^x(CH_2)_{0-2}(C_{3-5}$ cycloalkyl), —$NR^x(CH_2)_{0-2}$(4- to 6-membered heterocyclyl), —$NR^x(CH_2)_{0-2}$(phenyl), or —O(phenyl), wherein each of said cycloalkyl, heterocyclyl, phenyl, and pyridinyl is substituted with zero to 3 $R^{2b}$;

each $R^{2a}$ is independently F, Cl, hydroxyl, —$NR^xR^x$, oxo, cyano, $C_{1-3}$ alkoxy, $C_{1-3}$ haloalkoxy, or —C(O)OH;

each $R^{2b}$ is independently F, Cl, cyano, hydroxyl, $C_{1-4}$ alkyl, $C_{1-3}$ alkoxy, —$NR^xR^x$, —$NR^xC(O)O(C_{1-3}$ alkyl), —$C(O)(C_{1-2}$ alkyl), or —$S(O)_2(C_{1-2}$ alkyl), wherein each of said alkyl and alkoxy is substituted with zero to 4 $R^{2a}$;

A is:
(i) cyano;
(ii) phenyl or a 5- to 6-membered heteroaryl containing 1 to 4 heteroatoms independently selected from N, O, and S, wherein each of said phenyl and heteroaryl is substituted with zero to 3 $R^{4a}$; or (iii)

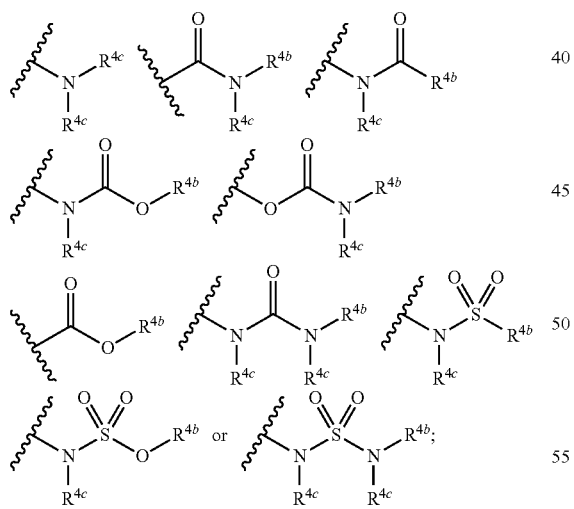

each $R^{4a}$ is independently F, Cl, cyano, hydroxyl, —$NH_2$, $C_{1-4}$ alkyl, $C_{1-4}$ alkoxy, —$(CH_2)_{0-3}NH(C_{1-6}$ alkyl), —$(CH_2)_{0-3}N(C_{1-6}$ alkyl$)_2$, —$(CH_2)_{0-3}(C_{3-6}$ carbocyclyl), or —$(CH_2)_{0-3}$(4- to 6-membered heterocyclyl), wherein each of said alkyl and alkoxy is substituted with zero to 4 $R^{4d}$; and each of said carbocyclyl and heterocyclyl is substituted with zero to 3 $R^{4e}$;

$R^{4b}$ is $C_{1-4}$ alkyl, —$(CH_2)_{0-3}(C_{3-6}$ cycloalkyl), or —$(CH_2)_{0-3}$(4- to 6-membered heterocyclyl), wherein each of said alkyl is substituted with zero to 4 $R^{4d}$ and each of said cycloalkyl and heterocyclyl is substituted with zero to 3 $R^{4e}$;

each $R^{4c}$ is independently hydrogen, $C_{1-3}$ alkyl, or $C_{3-6}$ cycloalkyl;

each $R^{4d}$ is independently F, Cl, hydroxyl, $NR^xR^x$, oxo, cyano, $C_{1-3}$ alkoxy, or $C_{1-3}$ fluoroalkoxy;

each $R^{4e}$ is independently F, Cl, oxo, cyano, hydroxyl, —$NH_2$, $C_{1-4}$ alkyl, $C_{1-4}$ alkoxy, —$NH(C_{1-6}$ alkyl), or —$N(C_{1-6}$ alkyl$)_2$, wherein each of said alkyl and alkoxy is substituted with zero to 4 $R^{4d}$;

each of $R^{5a}$, $R^{5b}$, $R^{5c}$, and $R^{5d}$ is independently hydrogen, F, Cl, hydroxy, cyano, $C_{1-3}$ alkyl substituted with zero to 4 $R^{5e}$, $C_{1-3}$ alkoxy substituted with zero to 4 $R^{5e}$, —$C(O)OR^x$, —$C(O)NR^wR^w$, —$S(O)_2R^y$, —$S(O)_2NR^zR^z$, or phenyl substituted with zero to 3 $R^{5f}$;

each of $R^{5a}$, $R^{5b}$, $R^{5c}$, and $R^{5d}$ is independently hydrogen, F, Cl, hydroxy, cyano, $C_{1-3}$ alkyl substituted with zero to 4 $R^{5e}$, $C_{1-3}$ alkoxy substituted with zero to 4 $R^{5e}$, —$C(O)OR^x$, —$C(O)NR^wR^w$, —$S(O)_2R^y$, —$S(O)_2NR^zR^z$, or phenyl substituted with zero to 3 $R^{5f}$;

each $R^w$ is independently hydrogen, $C_{1-4}$ alkyl, or $C_{3-6}$ cycloalkyl; or alternatively, two $R^w$, taken together with the nitrogen atom to which they are attached, form a 4- to 7-membered ring moiety containing zero to 2 additional heteroatoms independently selected from N, O, and S;

each $R^x$ is independently H, $C_{1-4}$ alkyl, or $C_{3-6}$ cycloalkyl; $R^y$ is $C_{1-4}$ alkyl or $C_{3-6}$ cycloalkyl; and each $R^z$ is independently hydrogen, $C_{1-4}$ alkyl, or $C_{3-6}$ cycloalkyl; or alternatively, two $R^z$, taken together with the nitrogen atom to which they are attached, form a 4- to 7-membered ring moiety containing zero to 2 additional heteroatoms independently selected from N, O, and S.

In one embodiment, a compound of Formula (I) or a stereoisomer, a tautomer, or a salt or solvate thereof is provided, wherein $X^1$ is $CR^{5a}$; $X^2$ is $CR^{5b}$; $X^3$ is $CR^{5c}$; $X^4$ is $CR^{5d}$. Compounds of this embodiment have the structure of Formula (Ia):

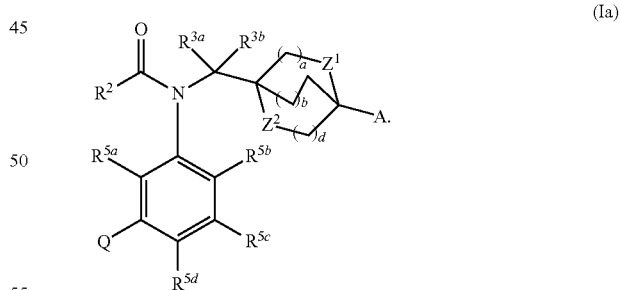

(Ia)

Included in this embodiment are compounds in which each of $R^{5a}$, $R^{5b}$, $R^{5c}$, and $R^{5d}$ is independently hydrogen, F, Cl, cyano, —$CH_3$, or —$CF_3$. Also included in this embodiment are compounds in which one of $R^{5a}$, $R^{5b}$, $R^{5c}$, and $R^{5d}$ is F, Cl, cyano, —$CH_3$, or —$CF_3$; and three of $R^{5a}$, $R^{5b}$, $R^{5c}$, and $R^{5d}$ are hydrogen.

In one embodiment, a compound of Formula (I) or a stereoisomer, a tautomer, or a salt or solvate thereof is provided, wherein $X^1$ is $CR^{5a}$ or N; $X^2$ is $CR^{5b}$ or N; $X^3$ is $CR^{5c}$ or N; $X^4$ is $CR^{5d}$ or N; and one of $X^1$, $X^2$, $X^3$, and $X^4$ is N. Compounds of this embodiment have one of the following structures: the structure of Formula (Ib), the structure of Formula (Ic), the structure of Formula (Id), and the structure of Formula (Ie):

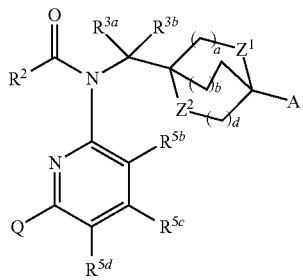
(Ib)

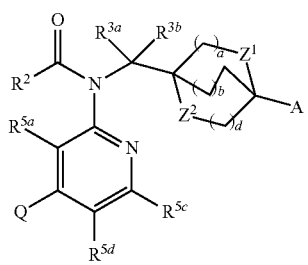
(Ic)

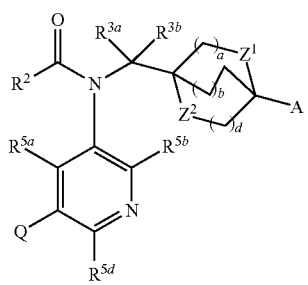
(Id)

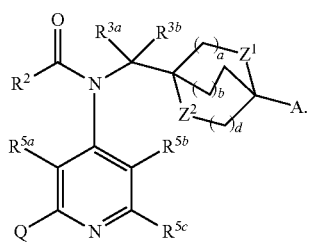
(Ie)

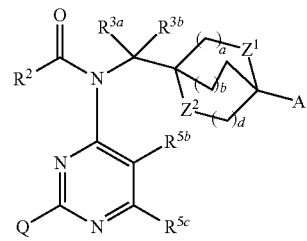
(If)

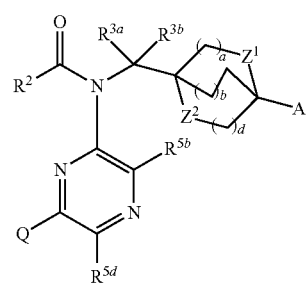
(Ig)

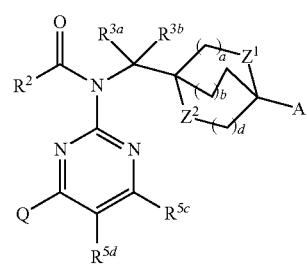
(Ih)

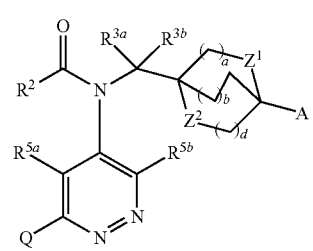
(Ii)

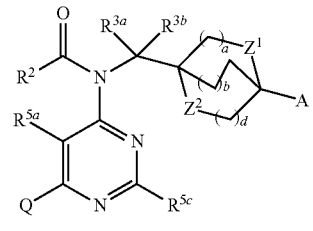
(Ij)

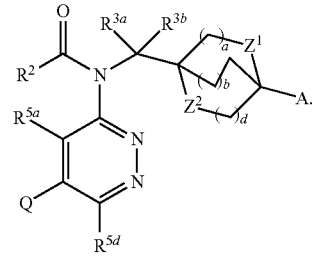
(Ik)

Included in this embodiment are compounds in which each of $R^{5a}$, $R^{5b}$, $R^{5c}$, and $R^{5d}$ is independently hydrogen, F, Cl, cyano, —CH$_3$, or —CF$_3$.

In one embodiment, a compound of Formula (I) or a stereoisomer, a tautomer, or a salt or solvate thereof is provided, wherein $X^1$ is $CR^{5a}$ or N; $X^2$ is $CR^{5b}$ or N; $X^3$ is $CR^{5c}$ or N; $X^4$ is $CR^{5d}$ or N; and two of $X^1$, $X^2$, $X^3$, and $X^4$ are N. Compounds of this embodiment have one of the following structures: the structure of Formula (If), the structure of Formula (Ig), the structure of Formula (Ih), the structure of Formula (Ii), the structure of Formula (Ij), and the structure of Formula (Ik):

Included in this embodiment are compounds in which each of $R^{5a}$, $R^{5b}$, $R^{5c}$, and $R^{5d}$ is independently hydrogen, F, Cl, cyano, —CH$_3$, or —CF$_3$.

In one embodiment, a compound of Formula (I) or a stereoisomer, a tautomer, or a salt or solvate thereof is provided, wherein $Z^1$ and $Z^2$ are each $CH_2$. Compounds of this embodiment have the structure of Formula (II):

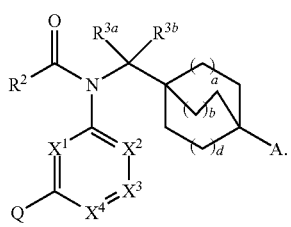

(II)

Included in this embodiment are compounds in which each of a, b, and d is 1. Also included in this embodiment are compounds in which each of a, b, and d is zero or 1. Additionally, included in this embodiment are compounds in which each of a, b, and d is 1 or 2.

In one embodiment, a compound of Formula (I) or a stereoisomer, a tautomer, or a salt or solvate thereof is provided, wherein one of $Z^1$ and $Z^2$ is $CH_2$, and the other of $Z^1$ and $Z^2$ is O. Compounds of this embodiment have either the structure of Formula (Im) and the structure of Formula (In):

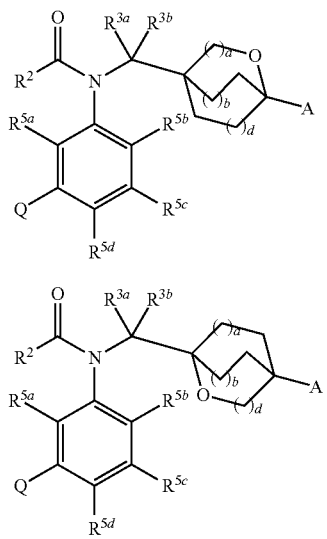

Included in this embodiment are compounds in which each of a, b, and d is 1. Also included in this embodiment are compounds in which each of a, b, and d is zero or 1. Additionally, included in this embodiment are compounds in which each of a, b, and d is 1 or 2.

In one embodiment, a compound of Formula (I) or a stereoisomer, a tautomer, or a salt or solvate thereof is provided, wherein Q is: (i) F, Cl, Br, cyano, hydroxyl, $-NR^xR^x$, $-C(O)OH$, $-C(O)NH_2$, $C_{1-4}$ alkyl substituted with zero to 6 $R^{1d}$, or $-P(O)R^{1c}R^{1c}$; or (ii) -L-$R^1$. Included in this embodiment are compounds in which Q is: (i) F, Cl, Br, cyano, hydroxyl, $-CF_3$, $-C(CH_3)_2OH$, $-CH_2CH_2C(O)OCH_3$, $-C(O)OH$, $-C(O)NH_2$, or $-P(O)(CH_3)_2$; or (ii) -L-$R^1$; L is $-O-$, $-OCR^{1a}R^{1a}C(O)O-$, $-C(O)O-$, $-C(O)NR^{1b}-$, $-NR^{1b}-$, $-NR^{1b}C(O)O-$, $-NR^{1b}$ $S(O)_2$, $-S(O)_2-$, or $-S(O)_2NR^{1b}-$; $R^1$ is $C_{1-4}$ alkyl substituted with zero to 4$R^{1a}$, $C_{3-4}$ cycloalkyl, or a cyclic group selected phenyl, thiazolyl, pyridinyl, and pyrimidinyl, wherein said cyclic group is substituted with zero to 1 $R^{1b}$. Also included in this embodiment are compounds in which $R^1$ is $-CH_3$, $-CH_2CH_3$, $-C(CH_3)_3$, $-CHF_2$, cyclopropyl, thiazolyl, or phenyl substituted with $-CHF_2$, $-CF_3$, $-CH_2CH_3$, or $-OCH_2CH_3$. Additionally, included in this embodiment are compounds in which Q is: (i) F, Cl, Br, cyano, $-CF_3$, $-CH_2CH_2C(O)OCH_3$, $-C(O)NH_2$, or $-P(O)(CH_3)_2$; or (ii) $-C(O)OCH_3$, $-C(O)NH(CH_2CH_3)$, $-OCH_3$, $-OCH_2CH_3$, $-OCHF_2$, $-OCH_2C(O)OCH_3$, $-NHC(O)OC(CH_3)_3$, $-NHS(O)_2CH_3$, $-S(O)_2CH_3$, $-S(O)_2NH(cyclopropyl)$, $-S(O)_2NH(CH_3)$, $-P(O)(CH_3)_2$, $-C(O)NH(thiazolyl)$, $-NH(trifluoromethylphenyl)$, $-NH(ethylphenyl)$, $-NH(ethoxyphenyl)$, or $-NH(difluoromethylphenyl)$.

In one embodiment, a compound of Formula (I) or a stereoisomer, a tautomer, or a salt or solvate thereof is provided, wherein A is cyano. Included in this embodiment are compounds in which each of $X^1$, $X^2$, $X^3$, and $X^4$ is CH. Also included in this embodiment are compounds in which each of $Z^1$ and $Z^2$ is $CH_2$.

In one embodiment, a compound of Formula (I) or a stereoisomer, a tautomer, or a salt or solvate thereof is provided, wherein A is: (i) phenyl or a 5- to 6-membered heteroaryl containing 1 to 4 heteroatoms independently selected from N, O, and S, wherein each of said phenyl and heteroaryl is substituted with zero to 3 $R^{4a}$; or

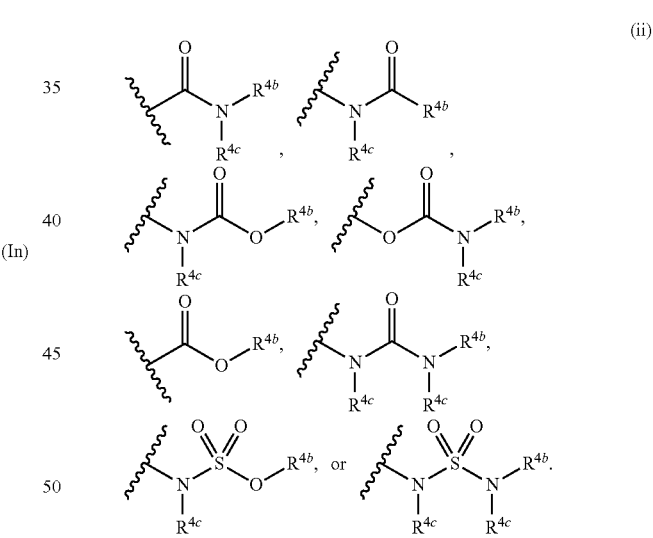

(ii)

Included in this embodiment are compounds in which each $R^{4a}$ is independently F, Cl, cyano, hydroxyl, $-NH_2$, $C_{1-4}$ alkyl, $C_{1-4}$ alkoxy, $-(CH_2)_{0-3}NH(C_{1-6}$ alkyl), $-(CH_2)_{0-3}N(C_{1-6}$ alkyl)$_2$, $-(CH_2)_{0-3}(C_{3-6}$ carbocyclyl), or $-(CH_2)_{0-3}$ (4- to 6-membered heterocyclyl), wherein each of said alkyl and alkoxy is substituted with zero to 4 $R^{4d}$; and each of said carbocyclyl and heterocyclyl is substituted with zero to 3 $R^{4e}$; $R^{4b}$ is $C_{1-4}$ alkyl, $-(CH_2)_{0-3}(C_{3-6}$ cycloalkyl), or $-(CH_2)_{0-3}$(4- to 6-membered heterocyclyl), wherein each of said alkyl is substituted with zero to 4 $R^{4d}$ and each of said cycloalkyl and heterocyclyl is substituted with zero to 3 $R^{4e}$; each $R^{4c}$ is independently hydrogen, $C_{1-3}$ alkyl, or $C_{3-6}$ cycloalkyl; each $R^{4d}$ is independently F, Cl, hydroxyl, $-NR^xR^x$, oxo, cyano, $C_{1-3}$ alkoxy, or $C_{1-3}$ fluoroalkoxy; and each $R^{4e}$ is independently F, Cl, oxo, cyano, hydroxyl, —$NH_2$, $C_{1-4}$ alkyl, $C_{1-4}$ alkoxy, —$NH(C_{1-6}$ alkyl), or —$N(C_{1-6}$ alkyl)$_2$, wherein each of said alkyl and alkoxy is substituted with zero to 4 $R^{4d}$.

In one embodiment, a compound of Formula (I) or a stereoisomer, a tautomer, or a salt or solvate thereof is provided, wherein A is phenyl or a 5- to 6-membered heteroaryl containing 1 to 4 heteroatoms independently selected from N, O, and S, wherein each of said phenyl and heteroaryl is substituted with zero to 3 $R^{4a}$. Included in this embodiment are compounds in which A is phenyl, furanyl, thiophenyl, pyrrolyl, oxazolyl, thiazolyl, imidazolyl, pyrazolyl, isoxazolyl, isothiazolyl, oxadiazolyl, thiadiazolyl, triazolyl, tetrazolyl, oxatriazolyl, pyridinyl, pyrazinyl, pyrimidinyl, or pyridazinyl, each substituted with zero to 3 $R^{4a}$. Also included in this embodiment are compounds in which A is oxadiazolyl, oxazolyl, phenyl, pyrazolyl, pyridinyl, pyrimidinyl, or thiazolyl, each substituted with zero to 2 substituents independently selected from azetidinyl, fluorobicyclo[1.1.1]pentyl, $C_{1-4}$ alkyl, $C_{1-2}$ fluoroalkyl, —$C(CH_3)_2$ CN, —$C(CH_3)_2OH$, —$OCH_3$, —$N(CH_3)_2$, —$CH_2$(cyclopropyl), cyclopropyl, trifluoromethylcyclopropyl, cyanocyclopropyl, difluorocyclopropyl, methylcyclopropyl, morpholinyl, methyl oxetanyl, and tetrahydropyranyl.

In one embodiment, a compound of Formula (I) or a stereoisomer, a tautomer, or a salt or solvate thereof is provided, wherein A is a 5-membered heteroaryl containing 1 to 4 heteroatoms independently selected from N, O, and S, substituted with zero to 3 $R^{4a}$. Included in this embodiment are compounds in which A is furanyl, thiophenyl, pyrrolyl, oxazolyl, thiazolyl, imidazolyl, pyrazolyl, isoxazolyl, isothiazolyl, oxadiazolyl, thiadiazolyl, triazolyl, tetrazolyl, or oxatriazolyl, each substituted with zero to 3 $R^{4a}$. Also included in this embodiment are compounds in which A is pyrazolyl, oxadiazolyl, oxazolyl, or thiazolyl, each substituted with zero to 2 substituents independently selected from Cl, —$CH_3$, —$C(CH_3)_3$, —$CF_3$, —$CF_2CH_3$, —$N(CH_3)_2$, cyclopropyl, and fluorocyclopropyl.

In one embodiment, a compound of Formula (I) or a stereoisomer, a tautomer, or a salt or solvate thereof is provided, wherein A is:

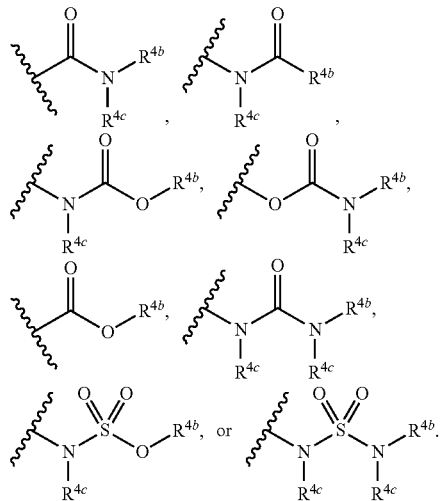

Included in this embodiment are compounds in which A is:

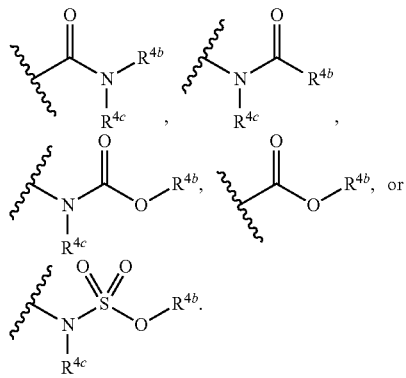

Also included in this embodiment are compounds in which $R^{4b}$ is $C_{1-4}$ alkyl, —$(CH_2)_{0-3}(C_{3-6}$ cycloalkyl), or —$(CH_2)_{0-3}$(4- to 6-membered heterocyclyl), wherein each of said alkyl is substituted with zero to 4 $R^{4d}$ and each of said cycloalkyl and heterocyclyl is substituted with zero to 3 $R^{4e}$; each $R^{4c}$ is independently hydrogen, $C_{1-3}$ alkyl, or $C_{3-6}$ cycloalkyl; each $R^{4d}$ is independently F, Cl, hydroxyl, —$NR^xR^x$, oxo, cyano, $C_{1-3}$ alkoxy, or $C_{1-3}$ fluoroalkoxy; and each $R^{4e}$ is independently F, Cl, oxo, cyano, hydroxyl, —$NH_2$, $C_{1-4}$ alkyl, $C_{1-4}$ alkoxy, —$NH(C_{1-6}$ alkyl), or —$N(C_{1-6}$ alkyl)$_2$, wherein each of said alkyl and alkoxy is substituted with zero to 4 $R^{4d}$.

In one embodiment, a compound of Formula (I) or a stereoisomer, a tautomer, or a salt or solvate thereof is provided, wherein $R^2$ is (i) $C_{1-4}$ alkyl, $C_{1-4}$ alkoxy, or —$NR^vR^v$, wherein each of said alkyl and alkoxy is substituted with zero to 4 $R^{2a}$; (ii) $C_{3-8}$ carbocyclyl, $C_{6-8}$ spirobicyclyl, phenyl, or 4- to 7-membered heterocyclyl, wherein each of said carbocyclyl, spirobicyclyl, and heterocyclyl is substituted with zero to 3 $R^{2b}$; or (iii) —$CH_2(C_{3-5}$ cycloalkyl), —$CH_2$(4- to 6-membered heterocyclyl), —$NR^x(CH_2)_{0-2}(C_{3-5}$ cycloalkyl), —$NR^x(CH_2)_{0-2}$(4- to 6-membered heterocyclyl), —$NR^x(CH_2)_{0-2}$(phenyl), —O(phenyl), or —$S(O)_2(C_{3-6}$ cycloalkyl), wherein each of said cycloalkyl, heterocyclyl, and phenyl is substituted with zero to 3 $R^{2b}$. Included in this embodiment are compounds in which $R^2$ is $C_{1-3}$ alkyl, $C_{1-3}$ alkoxy, or —$NR^vR^v$, wherein each of said alkyl and alkoxy is substituted with zero to 4 $R^{2a}$; (ii) $C_{3-8}$ carbocyclyl, $C_{6-8}$ spirobicyclyl, phenyl, or 4- to 7-membered heterocyclyl, wherein each of said carbocyclyl, spirobicyclyl, and heterocyclyl is substituted with zero to 3 $R^{2b}$; or (iii) —$CH_2(C_{3-5}$ cycloalkyl), —$CH_2$(4- to 6-membered heterocyclyl), —$NR^x(CH_2)_{0-2}(C_{3-5}$ cycloalkyl), —$NR^x(CH_2)_{0-2}$(4- to 6-membered heterocyclyl), —$NR^x(CH_2)_{0-2}$(phenyl), —O(phenyl), or —$S(O)_2(C_{3-6}$ cycloalkyl), wherein each of said cycloalkyl, heterocyclyl, and phenyl is substituted with zero to 3 $R^{2b}$.

In one embodiment, a compound of Formula (I) or a stereoisomer, a tautomer, or a salt or solvate thereof is provided, wherein $R^2$ is (i) $C_{1-4}$ alkyl, $C_{1-4}$ alkoxy, or —$NR^vR^v$, wherein each of said alkyl and alkoxy is substituted with zero to 4 $R^{2a}$; or (ii) $C_{3-8}$ carbocyclyl, $C_{6-8}$ spirobicyclyl, phenyl, or 4- to 5-membered heterocyclyl, wherein each of said carbocyclyl, spirobicyclyl, and heterocyclyl is substituted with zero to 3 $R^{2b}$.

In one embodiment, a compound of Formula (I) or a stereoisomer, a tautomer, or a salt or solvate thereof is provided, wherein $R^2$ is $C_{3-5}$ carbocyclic, $C_{6-8}$ spirobicyclyl, —$NR^x(CH_2)_{0-2}(C_{3-6}$ cycloalkyl), or 4- to 5-membered heterocyclyl having 1 or 2 heteroatoms independently selected from N, O, and S, wherein each of said cycloalkyl, carbocyclic, and heterocyclyl is independently substituted with zero to 3 $R^{2b}$. Additionally included in this embodiment are compounds in which $R^2$ is —NH(methyl-hydroxycyclopropyl) or a cyclic group selected from cyclopropyl, cyclobutyl, cyclohexyl, tetrahydropyranyl, bicyclo[1.1.1]pentyl, and dioxotetrahydrothiopyranyl, each cyclic group substituted with zero to 2 substituents independently selected from F, —OH, —CH$_3$, and —CF$_3$.

In one embodiment, a compound of Formula (I) or a stereoisomer, a tautomer, or a salt or solvate thereof is provided, wherein $R^2$ is:

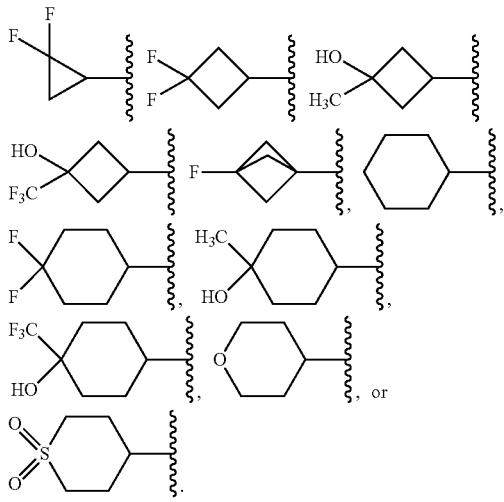

In one embodiment, a compound of Formula (I) or a stereoisomer, a tautomer, or a salt or solvate thereof is provided, wherein $R^2$ is:

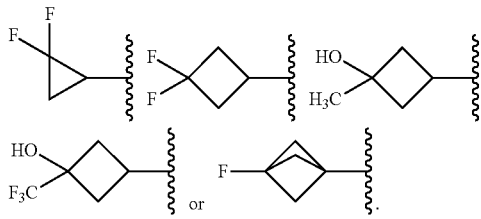

In one embodiment, a compound of Formula (I) or a stereoisomer, a tautomer, or a salt or solvate thereof is provided, wherein $R^2$ is:

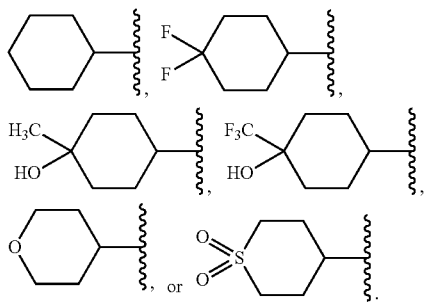

In one embodiment, a compound of Formula (I) or a stereoisomer, a tautomer, or a salt or solvate thereof is provided, wherein:
Q is:
(i) F, Cl, Br, cyano, hydroxyl, —NR$^x$R$^x$, —C(O)OH, —C(O)NH$_2$, C$_{1-4}$ alkyl substituted with zero to 6 R$^{1d}$, or —P(O)R$^{1c}$R$^{1c}$, or
(ii) -L-R$^1$;
L is —O—, —OCR$^{1a}$R$^{1a}$C(O)—, —C(O)—, —C(O)O—, —C(O)NR$^{1b}$—, —NR$^{1b}$—, —NR$^{1b}$—C(O)—, —NR$^{1b}$C(O)NR$^{1b}$—, —NR$^{1b}$S(O)$_2$—, —S(O)$_2$—, or —S(O)$_2$NR$^{1b}$—;
R$^1$ is C$_{1-6}$ alkyl substituted with zero to 6 R$^{1a}$, or a cyclic group selected C$_{3-6}$ cycloalkyl, phenyl, 4- to 10-membered heterocyclyl, and 5- to 10-membered heteroaryl, wherein said cyclic group is substituted with zero to 3 R$^{1b}$;
R$^2$ is (i) C$_{1-4}$ alkyl, C$_{1-4}$ alkoxy, or —NR$^v$R$^v$, wherein each of said alkyl and alkoxy is substituted with zero to 4 R$^{2a}$; (ii) C$_{3-5}$ carbocyclyl or 4- to 5-membered heterocyclyl having 1 or 2 heteroatoms independently selected from N, O, and S, wherein each of said cycloalkyl, carbocyclic, and heterocyclyl is independently substituted with zero to 3 R$^{2b}$; or (iii) —NR$^x$(CH$_2$)$_{0-2}$(C$_{3-5}$ cycloalkyl), or —NR$^x$(CH$_2$)$_{0-2}$(phenyl); and
A is a 5-membered heteroaryl containing 1 to 3 heteroatoms independently selected from N, O, and S, substituted with zero to 3 R$^{4a}$.

In one embodiment, a compound of Formula (I) or a stereoisomer, a tautomer, or a salt or solvate thereof is provided, wherein:
Q is:
(i) F, Cl, Br, cyano, —CF$_3$, —CH$_2$CH$_2$C(O)OCH$_3$, —C(O)NH$_2$, or —P(O)(CH$_3$)$_2$; or
(ii) -L-R$^1$;
L is —O—, —OCR$^{1a}$R$^{1a}$C(O)O—, —C(O)O—, —C(O)NR$^{1b}$—, —NR$^{1b}$—, —NR$^{1b}$C(O)O—, —NR$^{1b}$S(O)$_2$—, —S(O)$_2$—, or —S(O)$_2$NR$^{1b}$—;
R$^1$ is —CH$_3$, —CH$_2$CH$_3$, —C(CH$_3$)$_3$, —CHF$_2$, cyclopropyl, thiazolyl, or phenyl substituted with —CHF$_2$, —CF$_3$, —CH$_2$CH$_3$, or —OCH$_2$CH$_3$;
R$^2$ is —NH(methyl-hydroxycyclopropyl) or a cyclic group selected from cyclopropyl, cyclobutyl, and bicyclo[1.1.1]pentyl, each cyclic group substituted with zero to 2 substituents independently selected from F, —OH, —CH$_3$, and —CF$_3$;
A is a 5-membered heteroaryl containing 1 to 3 heteroatoms independently selected from N, O, and S, substituted with zero to 3 R$^{4a}$.

Included in this embodiment are compounds in which A is pyrazolyl or oxadiazolyl, each substituted with zero to 3 R$^{4a}$. Also included in this embodiment are compounds in which Q is: (i) —CF$_3$, —CH$_2$CH$_2$C(O)OCH$_3$, —C(O)NH$_2$, or —P(O)(CH$_3$)$_2$; or (ii) —C(O)OCH$_3$, —C(O)NH(CH$_2$CH$_3$), —OCH$_3$, —OCH$_2$CH$_3$, —OCHF$_2$, —OCH$_2$C(O)OCH$_3$, —NHC(O)OC(CH$_3$)$_3$, —NHS(O)$_2$CH$_3$, —S(O)$_2$CH$_3$, —S(O)$_2$NH(cyclopropyl), —S(O)$_2$NH(CH$_3$), —P(O)(CH$_3$)$_2$, —C(O)NH(thiazolyl), —NH(trifluoromethylphenyl), —NH(ethylphenyl), —NH(ethoxyphenyl), or —NH(difluoromethylphenyl).

In one embodiment, a compound of Formula (I) or a stereoisomer, a tautomer, or a salt or solvate thereof is provided, wherein A is pyrazolyl, oxadiazolyl, phenyl, pyridinyl, or indazolyl, each substituted with zero to 3 R$^{4a}$; and Q is: (i) —CF$_3$, —CH$_2$CH$_2$C(O)OCH$_3$, —C(O)NH$_2$, or —P(O)(CH$_3$)$_2$; or (ii) —C(O)OCH$_3$, —C(O)NH(CH$_2$CH$_3$), —OCH$_3$, —OCH$_2$CH$_3$, —OCHF$_2$, —OCH$_2$C(O)OCH$_3$, —NHC(O)OC(CH$_3$)$_3$, —NHS(O)$_2$CH$_3$, —S(O)$_2$CH$_3$, —S(O)$_2$NH(cyclopropyl), —S(O)$_2$NH(CH$_3$), —P(O)(CH$_3$)$_2$, —C(O)NH(thiazolyl), —NH(trifluoromethylphenyl), —NH(ethylphenyl), —NH(ethoxyphenyl), or —NH(difluoromethylphenyl). Included in this embodiment are compounds in which A is pyrazolyl or oxadiazolyl, each substituted with zero to 3 $R^{4a}$;

In one embodiment, a compound of Formula (I) or a stereoisomer, a tautomer, or a salt or solvate thereof is provided wherein each of $Z^1$ and $Z^2$ is CH$_2$; a is 1; b is 1; d is 1; and A is pyrazolyl, oxadiazolyl, phenyl, pyridinyl, or indazolyl, each substituted with zero to 3 $R^{4a}$.

In one embodiment, a compound of Formula (I) or a stereoisomer, a tautomer, or a salt or solvate thereof is provided, wherein $R^{3a}$ and $R^{3b}$ are independently hydrogen, $C_{1-3}$ alkyl, $C_{1-3}$ fluoroalkyl, or $C_{3-6}$ cycloalkyl; or $R^{3a}$ and $R^{3b}$, taken together with the carbon atom to which they are attached, form a $C_{3-6}$ cycloalkyl. Included in this embodiment are compounds in which $R^{3a}$ and $R^{3b}$ are independently hydrogen, $C_{1-2}$ alkyl, —CH$_2$F, —CHF$_2$, —CF$_3$, or $C_{3-4}$ cycloalkyl; or $R^{3a}$ and $R^{3b}$, taken together with the carbon atom to which they are attached, form a $C_{3-4}$ cycloalkyl. Also included in this embodiment are compounds in which $R^{3a}$ and $R^{3b}$ are independently hydrogen, —CH$_3$, or cyclopropyl; or $R^{3a}$ and $R^{3b}$, taken together with the carbon atom to which they are attached, form a cyclopropyl. Additionally, included in this embodiment are compounds in which one of $R^{3a}$ and $R^{3b}$ is hydrogen or —CH$_3$, and the other of $R^{3a}$ and $R^{3b}$ is hydrogen.

In one embodiment, a compound of Formula (I) or a stereoisomer, a tautomer, or a salt or solvate thereof is provided, wherein:
$X^1$ is CH; $X^2$ is CH; $X^3$ is CH; $X^4$ is CR$^{5d}$ or N;
a is 1;
b is 1;
d is 1;
Q is:
  (i) F, Cl, Br, cyano, hydroxyl, —CF$_3$, —C(CH$_3$)$_2$OH, —CH$_2$CH$_2$C(O)OCH$_3$, —C(O)OH, —C(O)NH$_2$, or —P(O)(CH$_3$)$_2$; or
  (ii) -L-R$^1$;
L is —O—, —OCR$^{1a}$R$^{1a}$C(O)O—, —C(O)O—, —C(O)NR$^{1b}$—, —NR$^{1b}$—, —NR$^{1b}$C(O)O—, —NR$^{1b}$S(O)$_2$—, —S(O)$_2$—, or —S(O)$_2$NR$^{1b}$—;
R$^1$ is —CH$_3$, —CH$_2$CH$_3$, —C(CH$_3$)$_3$, —CHF$_2$, cyclopropyl, thiazolyl, or phenyl substituted with —CHF$_2$, —CF$_3$, —CH$_2$CH$_3$, or —OCH$_2$CH$_3$;
A is pyrazolyl, oxadiazolyl, phenyl, pyridinyl, or indazolyl, each substituted with zero to 3 $R^{4a}$.
each $R^{4a}$ is independently Cl, —CH$_3$, —C(CH$_3$)$_3$, —CF$_3$, —CF$_2$CH$_3$, —N(CH$_3$)$_2$, cyclopropyl, or fluorocyclopropyl;
$R^{5d}$ is hydrogen, F, or Cl.

Included in this embodiment are compounds in which A is pyrazolyl or oxadiazolyl, each substituted with zero to 3 $R^{4a}$.

In one embodiment, a compound of Formula (I) or a stereoisomer, a tautomer, or a salt or solvate thereof is provided, wherein A is:

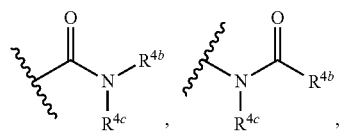

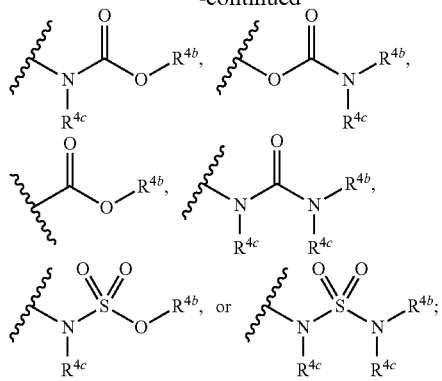

each $R^{4a}$ is independently F, Cl, cyano, hydroxyl, —NH$_2$, $C_{1-4}$ alkyl, $C_{1-4}$ alkoxy, —(CH$_2$)$_{0-3}$NH(C$_{1-6}$ alkyl), —(CH$_2$)$_{0-3}$N(C$_{1-6}$ alkyl)$_2$, —(CH$_2$)$_{0-3}$(C$_{3-6}$ carbocyclyl), or —(CH$_2$)$_{0-3}$(4- to 6-membered heterocyclyl), wherein each of said alkyl and alkoxy is substituted with zero to 4 $R^{4d}$; and each of said carbocyclyl and heterocyclyl is substituted with zero to 3 $R^{4e}$; $R^{4b}$ is $C_{1-4}$ alkyl, —(CH$_2$)$_{0-3}$(C$_{3-6}$ cycloalkyl), or —(CH$_2$)$_{0-3}$(4- to 6-membered heterocyclyl), wherein each of said alkyl is substituted with zero to 4 $R^{4d}$ and each of said cycloalkyl and heterocyclyl is substituted with zero to 3 $R^{4e}$; each $R^{4c}$ is independently hydrogen, $C_{1-3}$ alkyl, or $C_{3-6}$ cycloalkyl; each $R^{4d}$ is independently F, Cl, hydroxyl, —NR$^x$R$^x$, oxo, cyano, $C_{1-3}$ alkoxy, or $C_{1-3}$ fluoroalkoxy; and each $R^{4e}$ is independently F, Cl, oxo, cyano, hydroxyl, —NH$_2$, $C_{1-4}$ alkyl, $C_{1-4}$ alkoxy, —NH(C$_{1-6}$ alkyl), or —N(C$_{1-6}$ alkyl)$_2$, wherein each of said alkyl and alkoxy is substituted with zero to 4 $R^{4d}$.

In one embodiment, a compound of Formula (I) or a stereoisomer, a tautomer, or a salt or solvate thereof is provided, wherein each $R^w$ is independently hydrogen, $C_{1-4}$ alkyl, or $C_{3-6}$ cycloalkyl; or alternatively, two $R^w$, taken together with the nitrogen atom to which they are attached, form a 4- to 7-membered ring moiety containing zero to 2 additional heteroatoms independently selected from N, O, and S. Included in this embodiment are compounds in which each $R^w$ is independently hydrogen, $C_{1-4}$ alkyl, or $C_{3-6}$ cycloalkyl. Also included in this embodiment are compounds in which two $R^w$, taken together with the nitrogen atom to which they are attached, form a 4- to 7-membered ring moiety selected from pyrrolidinyl, piperidinyl, piperazinyl, and morpholinyl.

In one embodiment, a compound of Formula (I) or a stereoisomer, a tautomer, or a salt or solvate thereof is provided, wherein each $R^z$ is independently hydrogen, $C_{1-4}$ alkyl, or $C_{3-6}$ cycloalkyl; or alternatively, two $R^z$, taken together with the nitrogen atom to which they are attached, form a 4- to 7-membered ring moiety containing zero to 2 additional heteroatoms independently selected from N, O, and S. Included in this embodiment are compounds in which each $R^z$ is independently hydrogen, $C_{1-4}$ alkyl, or $C_{3-6}$ cycloalkyl. Also included in this embodiment are compounds in which two $R^w$, taken together with the nitrogen atom to which they are attached, form a 4- to 7-membered ring moiety selected from pyrrolidinyl, piperidinyl, piperazinyl, and morpholinyl.

In one embodiment, a compound of Formula (I) or a stereoisomer, a tautomer, or a salt or solvate thereof is provided, wherein said compound is N-(3-chlorophenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1- carboxamide (1); N-(3-chlorophenyl)-N-((4-(5-(1,1-difluoroethyl)-1,2,4-oxadiazol-3-yl)bicyclo[2.2.2]octan-1-yl)methyl)-3-hydroxy-3-(trifluoromethyl)cyclobutane-1-carboxamide (2); N-(3-chlorophenyl)-N-((4-(5-(1,1-difluoroethyl)-1,2,4-oxadiazol-3-yl)bicyclo[2.2.2]octan-1-yl)methyl)-4,4-difluorocyclohexane-1-carboxamide (3); N-(3-cyanophenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide (4); N-(3-cyanophenyl)-N-((4-(5-(1,1-difluoroethyl)-1,2,4-oxadiazol-3-yl)bicyclo[2.2.2]octan-1-yl)methyl)-3-hydroxy-3-(trifluoromethyl)cyclobutane-1-carboxamide (5); N-(3-cyanophenyl)-N-((4-(5-(1,1-difluoroethyl)-1,2,4-oxadiazol-3-yl)bicyclo[2.2.2]octan-1-yl)methyl)-4,4-difluorocyclohexane-1-carboxamide (6); N-((4-(5-(1,1-difluoroethyl)-1,2,4-oxadiazol-3-yl)bicyclo[2.2.2]octan-1-yl)methyl)-3-fluoro-N-(3-fluorophenyl)bicyclo[1.1.1]pentane-1-carboxamide (7); N-((4-(5-(1,1-difluoroethyl)-1,2,4-oxadiazol-3-yl)bicyclo[2.2.2]octan-1-yl)methyl)-N-(3-fluorophenyl)-3-hydroxy-3-(trifluoromethyl)cyclobutane-1-carboxamide (8); N-((4-(5-(1,1-difluoroethyl)-1,2,4-oxadiazol-3-yl)bicyclo[2.2.2]octan-1-yl)methyl)-4,4-difluoro-N-(3-fluorophenyl)cyclohexane-1-carboxamide (9); N-((4-(5-(1,1-difluoroethyl)-1,2,4-oxadiazol-3-yl)bicyclo[2.2.2]octan-1-yl)methyl)-N-(3,4-difluorophenyl)-3-fluorobicyclo[1.1.1]pentane-1-carboxamide (10); N-((4-(5-(1,1-difluoroethyl)-1,2,4-oxadiazol-3-yl)bicyclo[2.2.2]octan-1-yl)methyl)-N-(3,4-difluorophenyl)-4,4-difluorocyclohexane-1-carboxamide (11); N-((4-(5-(1,1-difluoroethyl)-1,2,4-oxadiazol-3-yl)bicyclo[2.2.2]octan-1-yl)methyl)-N-(3-(difluoromethoxy)phenyl)-3-fluorobicyclo[1.1.1]pentane-1-carboxamide (12); N-((4-(5-(1,1-difluoroethyl)-1,2,4-oxadiazol-3-yl)bicyclo[2.2.2]octan-1-yl)methyl)-N-(3-(difluoromethoxy)phenyl)-3-hydroxy-3-(trifluoromethyl)cyclobutane-1-carboxamide (13); N-((4-(5-(1,1-difluoroethyl)-1,2,4-oxadiazol-3-yl)bicyclo[2.2.2]octan-1-yl)methyl)-3-fluoro-N-(3-(trifluoromethyl)phenyl)bicyclo[1.1.1]pentane-1-carboxamide (14); N-((4-(5-(1,1-difluoroethyl)-1,2,4-oxadiazol-3-yl)bicyclo[2.2.2]octan-1-yl)methyl)-3-hydroxy-3-(trifluoromethyl)-N-(3-(trifluoromethyl)phenyl)cyclobutane-1-carboxamide (15); N-((4-(5-(1,1-difluoroethyl)-1,2,4-oxadiazol-3-yl)bicyclo[2.2.2]octan-1-yl)methyl)-4,4-difluoro-N-(3-(trifluoromethyl)phenyl)cyclohexane-1-carboxamide (16); N-((4-(5-(1,1-difluoroethyl)-1,2,4-oxadiazol-3-yl)bicyclo[2.2.2]octan-1-yl)methyl)-3-fluoro-N-(2-methoxypyridin-4-yl)bicyclo[1.1.1]pentane-1-carboxamide (17); N-(3-(N-cyclopropylsulfamoyl)phenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide (18); (1S,3S)—N-(3-(N-cyclopropylsulfamoyl)phenyl)-N-((4-(5-(1,1-difluoroethyl)-1,2,4-oxadiazol-3-yl)bicyclo[2.2.2]octan-1-yl)methyl)-3-hydroxy-3-(trifluoromethyl) cyclobutane-1-carboxamide (19); N-(3-(N-cyclopropylsulfamoyl)phenyl)-N-((4-(5-(1,1-difluoroethyl)-1,2,4-oxadiazol-3-yl)bicyclo[2.2.2]octan-1-yl)methyl)-4,4-difluorocyclohexane-1-carboxamide (20); N-((4-(5-(1,1-difluoroethyl)-1,2,4-oxadiazol-3-yl)bicyclo[2.2.2]octan-1-yl)methyl)-3-fluoro-N-(3-(N-methylsulfamoyl)phenyl) bicyclo[1.1.1]pentane-1-carboxamide (21); (1S,3S)—N-((4-(5-(1,1-difluoroethyl)-1,2,4-oxadiazol-3-yl)bicyclo[2.2.2]octan-1-yl)methyl)-3-hydroxy-N-(3-(N-methylsulfamoyl) phenyl)-3-(trifluoromethyl)cyclobutane-1-carboxamide (22); N-((4-(5-(1,1-difluoroethyl)-1,2,4-oxadiazol-3-yl)bicyclo[2.2.2]octan-1-yl)methyl)-4,4-difluoro-N-(3-(N-methylsulfamoyl)phenyl)cyclohexane-1-carboxamide (23); N-((4-(5-(1,1-difluoroethyl)-1,2,4-oxadiazol-3-yl)bicyclo[2.2.2]octan-1-yl)methyl)-N-(3-(dimethylphosphoryl)phenyl)-4,4-difluorocyclohexane-1-carboxamide (24); N-((4-(5-(1,1-difluoroethyl)-1,2,4-oxadiazol-3-yl)bicyclo[2.2.2]octan-1-yl)methyl)-N-(3-(dimethylphosphoryl)phenyl)-3-fluorobicyclo[1.1.1]pentane-1-carboxamide (25); (1S,3S)—N-((4-(5-(1,1-difluoroethyl)-1,2,4-oxadiazol-3-yl)bicyclo[2.2.2]octan-1-yl)methyl)-N-(3-(dimethylphosphoryl)phenyl)-3-hydroxy-3-(trifluoromethyl)cyclobutane-1-carboxamide (26); methyl 3-(N-((4-(5-(1,1-difluoroethyl)-1,2,4-oxadiazol-3-yl)bicyclo[2.2.2]octan-1-yl)methyl)-3-fluorobicyclo[1.1.1] pentane-1-carboxamido)benzoate (27); N-((4-(5-(1,1-difluoroethyl)-1,2,4-oxadiazol-3-yl)bicyclo[2.2.2]octan-1-yl)methyl)-N-(3-(ethylcarbamoyl)phenyl)-3-fluorobicyclo[1.1.1]pentane-1-carboxamide (28); N-(3-carbamoylphenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide (29); 1-(3-bromophenyl)-1-((4-(5-(1,1-difluoroethyl)-1,2,4-oxadiazol-3-yl)bicyclo[2.2.2]octan-1-yl)methyl)-3-((1R,4R)-4-hydroxy-4-methylcyclohexyl)urea (30); N-(3-bromophenyl)-N-((4-(5-(1,1-difluoroethyl)-1,2,4-oxadiazol-3-yl)bicyclo[2.2.2]octan-1-yl)methyl)-2,2-difluorocyclopropane-1-carboxamide (31); tert-butyl (3-(N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamido)phenyl)carbamate (32); N-(3-bromophenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide (33); N-(3-bromophenyl)-3-fluoro-N-((4-(5-(1-fluorocyclopropyl)-1,2,4-oxadiazol-3-yl)bicyclo[2.2.2]octan-1-yl)methyl)bicyclo[1.1.1]pentane-1-carboxamide (34); N-(3-bromophenyl)-3-fluoro-N-((4-(5-(trifluoromethyl)-1,2,4-oxadiazol-3-yl) bicyclo[2.2.2]octan-1-yl)methyl)bicyclo[1.1.1]pentane-1-carboxamide (35); (1S,3S)—N-(3-bromophenyl)-N-((4-(3-(tert-butyl)-1,2,4-oxadiazol-5-yl)bicyclo[2.2.2]octan-1-yl) methyl)-3-hydroxy-3-(trifluoromethyl)cyclobutane-1-carboxamide (36); N-(3-bromo-4-chlorophenyl)-N-((4-(3-(tert-butyl)-1,2,4-oxadiazol-5-yl)bicyclo[2.2.2]octan-1-yl) methyl)-3-fluorobicyclo[1.1.1]pentane-1-carboxamide (37); N-((4-(3-(tert-butyl)-1,2,4-oxadiazol-5-yl)bicyclo[2.2.2]octan-1-yl)methyl)-N-(3-cyanophenyl)-3-fluorobicyclo[1.1.1]pentane-1-carboxamide (38); (1S,3S)—N-((4-(3-(tert-butyl)-1,2,4-oxadiazol-5-yl)bicyclo[2.2.2]octan-1-yl)methyl)-N-(3-cyanophenyl)-3-hydroxy-3-(trifluoromethyl)cyclobutane-1-carboxamide (39); (1S,3S)—N-((4-(3-(tert-butyl)-1,2,4-oxadiazol-5-yl)bicyclo[2.2.2]octan-1-yl)methyl)-N-(3-cyanophenyl)-3-hydroxy-3-methylcyclobutane-1-carboxamide (40); N-((4-(3-(tert-butyl)-1,2,4-oxadiazol-5-yl) bicyclo[2.2.2]octan-1-yl)methyl)-N-(3-cyanophenyl)-3,3-difluorocyclobutane-1-carboxamide (41); N-((4-(3-(tert-butyl)-1,2,4-oxadiazol-5-yl)bicyclo[2.2.2]octan-1-yl)methyl)-N-(3-cyanophenyl)-4,4-difluorocyclohexane-1-carboxamide (42); N-((4-(3-(tert-butyl)-1,2,4-oxadiazol-5-yl)bicyclo[2.2.2]octan-1-yl)methyl)-N-(3-(dimethylphosphoryl) phenyl)-3-fluorobicyclo[1.1.1]pentane-1-carboxamide (43); N-((4-(3-(tert-butyl)-1,2,4-oxadiazol-5-yl)bicyclo[2.2.2]octan-1-yl)methyl)-N-(3-(dimethylphosphoryl)phenyl)-3,3-difluorocyclobutane-1-carboxamide (44); (1S,3S)—N-((4-(3-(tert-butyl)-1,2,4-oxadiazol-5-yl)bicyclo[2.2.2]octan-1-yl)methyl)-N-(3-(dimethylphosphoryl) phenyl)-3-hydroxy-3-(trifluoromethyl)cyclobutane-1-carboxamide (45); N-((4-(3-(tert-butyl)-1,2,4-oxadiazol-5-yl)bicyclo[2.2.2]octan-1-yl)methyl)-N-(3-(dimethylphosphoryl)phenyl)tetrahydro-2H-pyran-4-carboxamide (46); N-((4-(3-(tert-butyl)-1,2,4-oxadiazol-5-yl) bicyclo[2.2.2]octan-1-yl) methyl)-N-(3-(dimethylphosphoryl)phenyl)tetrahydro-2H-thiopyran-4-carboxamide 1,1-dioxide (47); N-(3-bromophenyl)-N-((4-(5-(1,1-difluoroethyl)pyridin-2-yl)

bicyclo[2.2.2]octan-1-yl)methyl)-3-fluorobicyclo[1.1.1]pentane-1-carboxamide (48); N-(3-cyanophenyl)-N-((4-(5-(1,1-difluoroethyl)pyridin-2-yl)bicyclo[2.2.2]octan-1-yl)methyl)-3-fluorobicyclo[1.1.1]pentane-1-carboxamide (49); (1S,3S)—N-(3-cyanophenyl)-N-((4-(5-(1,1-difluoroethyl)pyridin-2-yl)bicyclo[2.2.2]octan-1-yl)methyl)-3-hydroxy-3-methylcyclobutane-1-carboxamide (50); (1S,3S)—N-(3-cyanophenyl)-N-((4-(5-(1,1-difluoroethyl)pyridin-2-yl)bicyclo[2.2.2]octan-1-yl)methyl)-3-hydroxy-3-(trifluoromethyl)cyclobutane-1-carboxamide (51); N-((4-(3-cyclopropyl-1,2,4-oxadiazol-5-yl)bicyclo[2.2.2]octan-1-yl)methyl)-N-(3-ethoxyphenyl)-3-fluorobicyclo[1.1.1]pentane-1-carboxamide (52); N-((4-(3-cyclopropyl-1,2,4-oxadiazol-5-yl)bicyclo[2.2.2]octan-1-yl)methyl)-N-(3-ethoxyphenyl)-3,3-difluorocyclobutane-1-carboxamide (53); N-((4-(3-cyclopropyl-1,2,4-oxadiazol-5-yl)bicyclo[2.2.2]octan-1-yl)methyl)-N-(3-ethoxyphenyl)-3-hydroxy-3-(trifluoromethyl)cyclobutane-1-carboxamide (54); N-((4-(3-cyclopropyl-1,2,4-oxadiazol-5-yl)bicyclo[2.2.2]octan-1-yl)methyl)-N-(3-ethoxyphenyl)tetrahydro-2H-pyran-4-carboxamide (55); N-((4-(3-cyclopropyl-1,2,4-oxadiazol-5-yl)bicyclo[2.2.2]octan-1-yl)methyl)-N-(3-ethoxyphenyl)tetrahydro-2H-thiopyran-4-carboxamide 1,1-dioxide (56); (1S,3S)—N-((4-(3-cyclopropyl-1,2,4-oxadiazol-5-yl)bicyclo[2.2.2]octan-1-yl)methyl)-3-hydroxy-N-(3-methoxyphenyl)-3-(trifluoromethyl)cyclobutane-1-carboxamide (57); N-((4-(3-cyclopropyl-1,2,4-oxadiazol-5-yl)bicyclo[2.2.2]octan-1-yl)methyl)-3-fluoro-N-(3-methoxyphenyl) bicyclo[1.1.1]pentane-1-carboxamide (58); N-((4-(3-cyclopropyl-1,2,4-oxadiazol-5-yl) bicyclo[2.2.2]octan-1-yl)methyl)-3,3-difluoro-N-(3-methoxyphenyl)cyclobutane-1-carboxamide (59); N-((4-(3-cyclopropyl-1,2,4-oxadiazol-5-yl)bicyclo[2.2.2]octan-1-yl) methyl)-N-(3-methoxyphenyl)tetrahydro-2H-pyran-4-carboxamide (60); N-((4-(3-cyclopropyl-1,2,4-oxadiazol-5-yl)bicyclo[2.2.2]octan-1-yl)methyl)-N-(3-methoxyphenyl)tetrahydro-2H-thiopyran-4-carboxamide 1,1-dioxide (61); N-(3-cyano-5-fluorophenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide (62); (1S,3S)—N-(3-cyano-5-fluorophenyl)-N-((4-(3-cyclopropyl-1,2,4-oxadiazol-5-yl)bicyclo[2.2.2]octan-1-yl) methyl)-3-hydroxy-3-(trifluoromethyl)cyclobutane-1-carboxamide (63); N-(3-cyano-5-fluorophenyl)-N-((4-(3-cyclopropyl-1,2,4-oxadiazol-5-yl)bicyclo[2.2.2]octan-1-yl) methyl)-3,3-difluorocyclobutane-1-carboxamide (64); N-((4-(3-cyclopropyl-1,2,4-oxadiazol-5-yl)bicyclo[2.2.2]octan-1-yl)methyl)-3,3-difluoro-N-(3-(methylsulfonamido) phenyl)cyclobutane-1-carboxamide (65); N-((4-(3-cyclopropyl-1,2,4-oxadiazol-5-yl) bicyclo[2.2.2]octan-1-yl)methyl)-3-fluoro-N-(3-(methylsulfonamido)phenyl) bicyclo[1.1.1]pentane-1-carboxamide (66); (1S,3S)—N-((4-(3-cyclopropyl-1,2,4-oxadiazol-5-yl)bicyclo[2.2.2]octan-1-yl)methyl)-3-hydroxy-N-(3-(methylsulfonamido)phenyl)-3-(trifluoromethyl)cyclobutane-1-carboxamide (67); N-((4-(3-cyclopropyl-1,2,4-oxadiazol-5-yl)bicyclo[2.2.2]octan-1-yl)methyl)-3-fluoro-N-(3-(methylsulfonyl)phenyl)bicyclo[1.1.1]pentane-1-carboxamide (68); N-((4-(3-cyclopropyl-1,2,4-oxadiazol-5-yl)bicyclo[2.2.2]octan-1-yl)methyl)-4,4-difluoro-N-(3-(methylsulfonyl)phenyl)cyclohexane-1-carboxamide (69); N-(3-cyanophenyl)-N-(1-(4-(3-cyclopropyl-1,2,4-oxadiazol-5-yl)bicyclo[2.2.2]octan-1-yl)ethyl)-3-fluorobicyclo[1.1.1]pentane-1-carboxamide (70); N-(3-bromophenyl)-N-((4-(3-cyclopropyl-1,2,4-oxadiazol-5-yl)bicyclo[2.2.2]octan-1-yl) methyl)cyclopropanesulfonamide (71); N-(3-cyanophenyl)-N-((4-(3-cyclopropyl-1-methyl-1H-pyrazol-5-yl)bicyclo[2.2.2]octan-1-yl)methyl)-3-fluorobicyclo[1.1.1]pentane-1-carboxamide (72); N-(3-cyanophenyl)-N-((4-(3-cyclopropyl-1-methyl-1H-pyrazol-5-yl)bicyclo[2.2.2]octan-1-yl)methyl)-4,4-difluorocyclohexane-1-carboxamide (73); (1S,3S)—N-(3-cyanophenyl)-N-((4-(3-cyclopropyl-1-methyl-1H-pyrazol-5-yl) bicyclo[2.2.2]octan-1-yl)methyl)-3-hydroxy-3-methylcyclobutane-1-carboxamide (74); (1S,3S)—N-(3-cyanophenyl)-N-((4-(3-cyclopropyl-1-methyl-1H-pyrazol-5-yl) bicyclo[2.2.2]octan-1-yl)methyl)-3-hydroxy-3-(trifluoromethyl)cyclobutane-1-carboxamide (75); (1S,3S)—N-((4-(3-cyclopropyl-1-methyl-1H-pyrazol-5-yl) bicyclo[2.2.2]octan-1-yl)methyl)-3-hydroxy-N-(3-(methylsulfonyl)phenyl)-3-(trifluoromethyl)cyclobutane-1-carboxamide (76); N-((4-(3-cyclopropyl-1-methyl-1H-pyrazol-5-yl)bicyclo[2.2.2]octan-1-yl)methyl)-4,4-difluoro-N-(3-(methylsulfonyl) phenyl)cyclohexane-1-carboxamide (77); N-((4-(3-cyclopropyl-1-methyl-1H-pyrazol-5-yl)bicyclo[2.2.2]octan-1-yl)methyl)-3-fluoro-N-(3-(methylsulfonyl)phenyl)bicyclo[1.1.1]pentane-1-carboxamide (78); methyl 2-(3-(N-((4-(3-chloro-4-(dimethylamino)phenyl)bicyclo[2.2.2]octan-1-yl)methyl)cyclohexanecarboxamido)phenoxy)acetate (79); methyl 2-(3-(N-((4-(4-(dimethylamino)phenyl)bicyclo[2.2.2]octan-1-yl)methyl) cyclohexanecarboxamido)phenoxy)acetate (80); methyl 2-(3-(N-((1-(1-methyl-1H-indazol-5-yl)-2-oxabicyclo[2.2.2]octan-4-yl)methyl) tetrahydro-2H-pyran-4-carboxamido) phenoxy)acetate (81); 3-(N-((4-(3-methyl-1,2,4-oxadiazol-5-yl)bicyclo[2.2.2]octan-1-yl) methyl)cyclohexanecarboxamido)-N-(thiazol-2-yl)benzamide (82); N-((4-(3-(tert-butyl)-1,2,4-oxadiazol-5-yl)bicyclo[2.2.2]octan-1-yl)methyl)-N-(3-((4-ethoxyphenyl)amino) phenyl)-3-fluorobicyclo[1.1.1]pentane-1-carboxamide (83); N-((4-(5-(tert-butyl)-1,2,4-oxadiazol-3-yl)bicyclo[2.2.2]octan-1-yl)methyl)-N-(3 ((4-(difluoromethoxy)phenyl) amino)phenyl)-3-fluorobicyclo[1.1.1]pentane-1-carboxamide (84); N-((4-(5-(tert-butyl)-1,2,4-oxadiazol-3-yl)bicyclo[2.2.2]octan-1-yl)methyl)-N-(3-((4-ethoxyphenyl)amino) phenyl)-3-fluorobicyclo[1.1.1]pentane-1-carboxamide (85); N-((4-(5-(tert-butyl)-1,2,4-oxadiazol-3-yl)bicyclo[2.2.2]octan-1-yl)methyl)-N-(3-((4-ethylphenyl)amino)phenyl)-3-fluorobicyclo[1.1.1]pentane-1-carboxamide (86); N-((4-(5-(tert-butyl)-1,2,4-oxadiazol-3-yl)bicyclo[2.2.2]octan-1-yl)methyl)-3-fluoro-N-(3-((4-(trifluoromethyl)phenyl)amino) phenyl)bicyclo[1.1.1]pentane-1-carboxamide (87); methyl 3-(3-(N-((4-(4-(dimethylamino)phenyl)bicyclo[2.2.2]octan-1-yl)methyl) cyclohexanecarboxamido) phenyl)propanoate (88); methyl 3-(3-(N-((4-(4-(dimethylamino)phenyl) bicyclo[2.2.2]octan-1-yl)methyl) cyclohexanecarboxamido)phenyl)propanoate (89); (1S,3S)—N-((4-(3-cyclopropyl-1,2,4-oxadiazol-5-yl)bicyclo[2.2.2]octan-1-yl)methyl)-3-hydroxy-N-(3-(methylsulfonyl)phenyl)-3-(trifluoromethyl)cyclobutane-1-carboxamide (90); (1S,3S)—N-(3-((4-(1-cyanocyclopropyl)phenyl)amino)phenyl)-N-((4-(5-(1-fluorocyclopropyl)-1,2,4-oxadiazol-3-yl)bicyclo[2.2.2]octan-1-yl) methyl)-3-hydroxy-3-(trifluoromethyl)cyclobutane-1-carboxamide (91); (1S,3S)—N-3-((4-(2-cyanopropan-2-yl) oxy)phenyl)amino)phenyl)-N-((4-(5-(1,1-difluoroethyl) pyridin-2-yl) bicyclo[2.2.2]octan-1-yl)methyl)-3-hydroxy-3-(trifluoromethyl)cyclobutane-1-carboxamide (92); (1S,3S)—N-(3((4-(1-cyanocyclopropyl)phenyl)amino)phenyl)-N-((4-(5-(1,1-difluoroethyl) pyridin-2-yl)bicyclo[2.2.2]octan-1-yl)methyl)-3-hydroxy-3-(trifluoromethyl)cyclobutane-1-carboxamide (93); N-((4-(3-(tert-butyl)-1,2,4-oxadiazol-5-yl)bicyclo[2.2.2]octan-1-yl)methyl)-N-(5-cyanopyridin-3-yl)-3-fluorobicyclo[1.1.1]pentane-1-carboxamide (94); 1-(3-(cyanophenyl)-1-((4-(5-(2-fluoropropan-2-yl)-1,2,4-oxadiazol-3-yl)bicyclo[2.2.2]octan-1-yl)methyl)-3-(((1R,4R)-4-hydroxy-4- methylcyclohexyl)urea (95); 1-(3-cyanophenyl)-1-((4-(5-(2-fluoropropan-2-yl)-1,2,4-oxadiazol-3-yl)bicyclo[2.2.2]octan-1-yl)methyl)-3-((1R,4R)-4-hydroxycyclohexyl)urea (96); 1-(3-cyanophenyl)-1-((4-(5-(2-fluoropropan-2-yl)-1,2,4-oxadiazol-3-yl)bicyclo[2.2.2]octan-1-yl)methyl)-3-(3-hydroxy-2,2-dimethylpropyl)urea (97); 1-(3-cyanophenyl)-1-((4-(5-(1,1-difluoroethyl)-1,2,4-oxadiazol-3-yl) bicyclo[2.2.2]octan-1-yl)methyl)-3-((1R,4R)-4-hydroxycyclohexyl)urea (98); 1-(3-cyanophenyl)-1-((4-(5-(1,1-difluoroethyl)-1,2,4-oxadiazol-3-yl)bicyclo[2.2.2]octan-1-yl)methyl)-3-((1R,4R)-4-hydroxy-4-methylcyclohexyl)urea (99); 1-(3-cyanophenyl)-1-((4-(5-(1,1-difluoroethyl)-1,2,4-oxadiazol-3-yl)bicyclo[2.2.2]octan-1-yl)methyl)-3-(3-hydroxy-2,2-dimethylpropyl)urea (100); 1-(3-bromo-4-fluorophenyl)-1-((4-(5-(2-fluoropropan-2-yl)-1,2,4-oxadiazol-3-yl)bicyclo[2.2.2]octan-1-yl)methyl)-3-((1R,4R)-4-hydroxycyclohexyl)urea (101); N-((4-(5-(tert-butyl)-1,2,4-oxadiazol-3-yl) bicyclo[2.2.2]octan-1-yl)methyl)-N-(3-((5-(difluoromethoxy)pyrimidin-2-yl)amino) phenyl)-3-fluorobicyclo[1.1.1]pentane-1-carboxamide (102); N-((4-(5-(tert-butyl)-1,2,4-oxadiazol-3-yl)bicyclo[2.2.2]octan-1-yl)methyl)-N-(3-((2-cyclopropylpyrimidin-5-yl) amino)phenyl)-3-fluorobicyclo[1.1.1]pentane-1-carboxamide (103); N-((4-(5-(tert-butyl)-1,2,4-oxadiazol-3-yl)bicyclo[2.2.2]octan-1-yl)methyl)-N-(3-((5-(difluoromethoxy) pyridin-2-yl)amino)phenyl)-3-fluorobicyclo[1.1.1]pentane-1-carboxamide (104); N-(3-((5-cyclopropylpyrimidin-2-yl) amino)phenyl)-3-fluoro-N-((4-(5-(trifluoromethyl) pyridin-2-yl)bicyclo[2.2.2]octan-1-yl)methyl)bicyclo[1.1.1]pentane-1-carboxamide (105); N-(3-((5-(difluoromethoxy) pyrimidin-2-yl)amino)phenyl)-3-fluoro-N-((4-(5-(trifluoromethyl)pyridin-2-yl)bicyclo[2.2.2]octan-1-yl)methyl)bicyclo[1.1.1]pentane-1-carboxamide (106); N-(3-((4-(difluoromethoxy)phenyl)amino)phenyl)-3-fluoro-N-((4-(5-(trifluoromethyl)pyridin-2-yl)bicyclo[2.2.2]octan-1-yl)methyl) bicyclo[1.1.1]pentane-1-carboxamide (107); N-(3-((5-(difluoromethoxy)pyridin-2-yl)amino)phenyl)-3-fluoro-N-((4-(5-(trifluoromethyl)pyridin-2-yl)bicyclo[2.2.2]octan-1-yl)methyl) bicyclo[1.1.1]pentane-1-carboxamide (108); N-(3-((5-cyclopropylpyridin-2-yl)amino) phenyl)-3-fluoro-N-((4-(5-(trifluoromethyl)pyridin-2-yl)bicyclo[2.2.2]octan-1-yl)methyl) bicyclo[1.1.1]pentane-1-carboxamide (109); N-((4-(5-(tert-butyl)-1,2,4-oxadiazol-3-yl) bicyclo[2.2.2]octan-1-yl)methyl)-3-fluoro-N-(3-hydroxyphenyl)bicyclo[1.1.1]pentane-1-carboxamide (110); N-((4-(5-(tert-butyl)-1,2,4-oxadiazol-3-yl)bicyclo[2.2.2]octan-1-yl) methyl)-N-(3-(cyanomethoxy)phenyl)-3-fluorobicyclo[1.1.1]pentane-1-carboxamide (111); N-((4-(5-(tert-butyl)-1,2,4-oxadiazol-3-yl)bicyclo[2.2.2]octan-1-yl)methyl)-3-fluoro-N-(3-(2-hydroxy-2-methylpropoxy)phenyl)bicyclo[1.1.1]pentane-1-carboxamide (112); 2-(3-(N-((4-(5-(tert-butyl)-1,2,4-oxadiazol-3-yl)bicyclo[2.2.2]octan-1-yl)methyl)-3-fluorobicyclo[1.1.1]pentane-1-carboxamido)phenoxy)-2-methylpropanoic acid (113); N-(3-cyanophenyl)-3-fluoro-N-((4-(5-(trifluoromethyl)-1,2,4-oxadiazol-3-yl) bicyclo[2.2.2]octan-1-yl)methyl)bicyclo[1.1.1]pentane-1-carboxamide (114); (1S,3S)—N-(3-cyanophenyl)-3-hydroxy-3-(trifluoromethyl)-N-((4-(5-(trifluoromethyl)-1,2,4-oxadiazol-3-yl)bicyclo[2.2.2]octan-1-yl)methyl)cyclobutane-1-carboxamide (115); N-(3-cyanophenyl)-N-((4-(5-(trifluoromethyl)-1,2,4-oxadiazol-3-yl)bicyclo[2.2.2]octan-1-yl) methyl)tetrahydro-2H-pyran-4-carboxamide (116); (1S,3S)—N-(3-cyanophenyl)-3-hydroxy-3-methyl-N-((4-(5-(trifluoromethyl)-1,2,4-oxadiazol-3-yl)bicyclo[2.2.2]octan-1-yl)methyl) cyclobutane-1-carboxamide (117); N-((4-(5-(tert-butyl)-1,2,4-oxadiazol-3-yl) bicyclo[2.2.2]octan-1-yl)methyl)-N-(3-((5-(difluoromethoxy)pyrimidin-2-yl)oxy) phenyl)-3-fluorobicyclo[1.1.1]pentane-1-carboxamide (118); N-((4-(5-(tert-butyl)-1,2,4-oxadiazol-3-yl)bicyclo[2.2.2]octan-1-yl)methyl)-N-(3-((5-(difluoromethoxy)pyridin-2-yl) oxy)phenyl)-3-fluorobicyclo[1.1.1]pentane-1-carboxamide (119); 3-(N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamido)benzoic acid (120); N-((4-(3-(tert-butyl)-1,2,4-oxadiazol-5-yl)bicyclo[2.2.2]octan-1-yl) methyl)-N-(3-carbamoyl-4-fluorophenyl)-3-fluorobicyclo[1.1.1]pentane-1-carboxamide (121); N-((4-(3-(tert-butyl)-1,2,4-oxadiazol-5-yl)bicyclo[2.2.2]octan-1-yl)methyl)-N-(3-(ethylcarbamoyl)-4-fluorophenyl)-3-fluorobicyclo[1.1.1]pentane-1-carboxamide (122); (1S,3S)—N-((4-(3-(tert-butyl)-1,2,4-oxadiazol-5-yl)bicyclo[2.2.2]octan-1-yl) methyl)-3-hydroxy-N-(3-isopropoxyphenyl)-3-(trifluoromethyl)cyclobutane-1-carboxamide (123); (1S,3S)—N-((4-(3-(tert-butyl)-1,2,4-oxadiazol-5-yl)bicyclo[2.2.2]octan-1-yl)methyl)-3-hydroxy-N-(3-isopropoxyphenyl)-3-(trifluoromethyl)cyclobutane-1-carboxamide (124); (1S,3S)—N-((4-(5-(1,1-difluoroethyl)-1,2,4-oxadiazol-3-yl)bicyclo[2.2.2]octan-1-yl)methyl)-3-hydroxy-N-(3-isopropoxyphenyl)-3-methylcyclobutane-1-carboxamide (125); (1S,3S)—N-((4-(5-(1,1-difluoroethyl)-1,2,4-oxadiazol-3-yl)bicyclo[2.2.2]octan-1-yl)methyl)-3-hydroxy-N-(3-isopropoxyphenyl)-3-(trifluoromethyl)cyclobutane-1-carboxamide (126); N-((4-(5-(1,1-difluoroethyl)-1,2,4-oxadiazol-3-yl)bicyclo[2.2.2]octan-1-yl)methyl)-3-fluoro-N-(3-isopropoxyphenyl)bicyclo[1.1.1]pentane-1-carboxamide (127); N-((4-(3-(tert-butyl)-1,2,4-oxadiazol-5-yl)bicyclo[2.2.2]octan-1-yl)methyl)-3-fluoro-N-(4-fluoro-3-(2-hydroxypropan-2-yl)phenyl)bicyclo[1.1.1]pentane-1-carboxamide (128); N-((4-(5-(1,1-difluoroethyl)-1,2,4-oxadiazol-3-yl)bicyclo[2.2.2]octan-1-yl)methyl)-3-fluoro-N-(3-methoxyphenyl)bicyclo[1.1.1]pentane-1-carboxamide (129); N-((4-(5-(1,1-difluoroethyl)-1,2,4-oxadiazol-3-yl)bicyclo[2.2.2]octan-1-yl)methyl)-N-(3-ethoxyphenyl)-3-fluorobicyclo[1.1.1]pentane-1-carboxamide (130); (S)-1-(3-bromophenyl)-1-((4-(5-(1,1-difluoroethyl)-1,2,4-oxadiazol-3-yl)bicyclo[2.2.2]octan-1-yl)methyl)-3-(2-fluoro-3-hydroxy-3-methylbutyl)urea (131); N-(3-bromophenyl)-N-((4-(3-(tert-butyl)-1,2,4-oxadiazol-5-yl)bicyclo[2.2.1]heptan-1-yl)methyl)-3-fluorobicyclo[1.1.1]pentane-1-carboxamide (132); (1s, 3s)-N-(3-bromophenyl)-N-((4-(3-(tert-butyl)-1,2,4-oxadiazol-5-yl)bicyclo[2.2.1]heptan-1-yl)methyl)-3-hydroxy-3-(trifluoromethyl) cyclobutane-1-carboxamide (133); N-(3-bromophenyl)-N-((4-(5-(2-fluoropropan-2-yl)-1, 2, 4-oxadiazol-3-yl)bicyclo[2.2.2]octan-1-yl)methyl)-3-(2-hydroxypropan-2-yl)bicyclo[1.1.1]pentane-1-carboxamide (134); N-(3-cyano-5-fluorophenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide (135); (1S,3S)—N-(3-cyano-5-fluorophenyl)-N-((4-(5-(1,1-difluoroethyl)-1,2,4-oxadiazol-3-yl)bicyclo[2.2.2]octan-1-yl)methyl)-3-hydroxy-3-(trifluoromethyl)cyclobutane-1-carboxamide (136); N-(3-cyano-5-fluorophenyl)-N-((4-(5-(1,1-difluoroethyl)-1,2,4-oxadiazol-3-yl)bicyclo[2.2.2]octan-1-yl)methyl)-3,3-difluorocyclobutane-1-carboxamide (137); N-(3-cyano-5-fluorophenyl)-N-((4-(5-(1,1-difluoroethyl)-1,2,4-oxadiazol-3-yl)bicyclo[2.2.2]octan-1-yl) methyl) tetrahydro-2H-thiopyran-4-carboxamide 1,1-dioxide (138); 3-(4-(((1S,3S)—N-(3-bromophenyl)-3-hydroxy-3-(trifluoromethyl)cyclobutane-1-carboxamido)methyl) bicyclo[2.2.2]octan-1-yl)-1,2,4-oxadiazole-5-carboxamide (139); or 3-(4-((N-(3-bromophenyl)-3-fluorobicyclo[1.1.1]

pentane-1-carboxamido)methyl)bicyclo[2.2.2]octan-1-yl)-1,2,4-oxadiazole-5-carboxamide (140).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds and/or salts thereof" refers to at least one compound, at least one salt of the compounds, or a combination thereof. For example, compounds of Formula (I) and/or salts thereof includes a compound of Formula (I); two compounds of Formula (I); a salt of a compound of Formula (I); a compound of Formula (I) and one or more salts of the compound of Formula (I); and two or more salts of a compound of Formula (I).

Unless otherwise indicated, any atom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "hydroxy" refers to the group —OH.

The term "amino" refers to the group —NH$_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to four carbon atoms.

The term "haloalkyl" as used herein is intended to include both branched and straight-chain saturated aliphatic hydrocarbon groups substituted with one or more halo atoms. For example, "$C_{1-4}$ haloalkyl" is intended to include $C_1$, $C_2$, $C_3$, and $C_4$ alkyl groups substituted with one or more halo atoms. Representative examples of haloalkyl groups include, but are not limited to, —CF$_3$, —CCl$_3$, —CHF$_2$, and —CF$_2$CCl$_3$.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The term "hydroxyalkyl" as used herein is intended to include both branched and straight-chain saturated aliphatic hydrocarbon groups substituted with one or more hydroxyl groups. For example, "$C_{1-4}$ hydroxyalkyl" is intended to include $C_1$, $C_2$, $C_3$, and $C_4$ alkyl groups substituted with one or more hydroxyl groups. Representative examples of fluoroalkyl groups include, but are not limited to, —CH$_2$OH, —CH$_2$CH$_2$OH, and —C(CH$_3$)$_2$OH.

The term "alkenyl" refers to a straight or branched chain hydrocarbon radical containing from 2 to 12 carbon atoms and at least one carbon-carbon double bond. Exemplary such groups include ethenyl or allyl. For example, "$C_{2-6}$ alkenyl" denotes straight and branched chain alkenyl groups with two to six carbon atoms.

The term "alkynyl" refers to a straight or branched chain hydrocarbon radical containing from 2 to 12 carbon atoms and at least one carbon to carbon triple bond. Exemplary such groups include ethynyl. For example, "$C_{2-6}$ alkynyl" denotes straight and branched chain alkynyl groups with two to six carbon atoms.

The term "alkoxy" as used herein, refers to an alkyl group attached to the parent molecular moiety through an oxygen atom, for example, methoxy group (—OCH$_3$). For example, "$C_{1-3}$ alkoxy" denotes alkoxy groups with one to three carbon atoms.

The terms "haloalkoxy" and "—O(haloalkyl)" represent a haloalkyl group as defined above attached through an oxygen linkage (—O—). For example, "$C_{1-4}$ haloalkoxy" is intended to include $C_1$, $C_2$, $C_3$, and $C_4$ haloalkoxy groups.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms. The terms "carbocyclo", "carbocyclic" or "carbocyclyl" may be used interchangeably and refer to cyclic groups having at least one saturated or partially saturated non-aromatic ring wherein all atoms of all rings are carbon, and includes groups having one or more bridged rings in which the bridged ring occurs when one or more carbon atoms link two non-adjacent carbon atoms. The term includes nonaromatic rings such as for example, cycloalkyl and cycloalkenyl, bicyclo[1.1.1]pentyl, bicyclo[2.2.2]octanyl, adamantyl, and tetrahydronaphthyl.

The term "bicycloalkyl," as used herein, refers to a carbocyclyl group having a at least one bridge. Representative examples of bicycloalkyl groups include, but are not limited to, bicyclo[1.1.1]pentyl, bicyclo[2.2.2]octanyl, and adamantyl.

The term "aryl" as used herein, refers to a group of atoms derived from a molecule containing aromatic ring(s) by removing one hydrogen that is bonded to the aromatic ring(s). Representative examples of aryl groups include, but are not limited to, phenyl and naphthyl. The aryl ring may be unsubstituted or may contain one or more substituents as valence allows.

The term "heteroatom" refers to oxygen (O), sulfur (S), and nitrogen (N).

The terms "heterocyclo", "heterocyclic", or "heterocyclyl" may be used interchangeably and refer to cyclic groups having at least saturated or partially saturated non-aromatic ring and wherein one or more of the rings have at least one heteroatom (O, S or N), said heteroatom containing ring preferably having 1 to 3 heteroatoms independently selected from O, S, and/or N. The ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The heterocyclo group may be attached at any available nitrogen or carbon atom. The heterocyclo ring may be unsubstituted or may contain one or more substituents as valence allows.

Exemplary monocyclic heterocyclyl groups include pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, dihydroisoindolyl, and tetrahydroquinolinyl.

The terms "spirobicyclyl" and spirobicyclo" may be used interchangeably and refer to bicyclic groups in which the two rings are attached at a single carbon atom that is a member of each of the two rings. The term includes both spirobicycloalkyls, in which the two rings are cycloalkyl rings attached at a single carbon atom that is a member of each of the two rings, and spirobicycloheteroalkyls, in which one ring is a heterocyclyl ring and the other ring is a cycloalkyl ring attached at a single carbon atom that is a member of each of the two rings, or in which both rings are heterocyclyl rings attached at a single carbon atom that is a member of each of the two rings. Examples of spirobicyclyl groups include spiro[3.3]heptenyl, spiro[3.4]octanyl, azaspiro[3.3]heptanyl, oxaazaspiro[3.3]heptanyl, oxaazaspiro[3.3]heptanyl, and azaspiro[3.4]octanyl.

The term "heteroaryl" refers to substituted and unsubstituted aromatic 5- or 6-membered monocyclic groups and 9- or 10-membered bicyclic groups that have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group are aromatic and may contain only carbon atoms. The nitrogen and sulfur atoms may optionally be oxidized and the nitrogen atoms may optionally be quaternized. Bicyclic heteroaryl groups must include only aromatic rings. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, and pyrrolopyridyl.

As used herein, the term "tautomer" refers to each of two or more isomers of a compound that exist together in equilibrium, and are readily interchanged by migration of an atom or group within the molecule. For example, one skilled in the art would readily understand that a 1,2,3-triazole exists in two tautomeric forms as defined above:

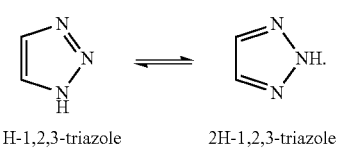

1H-1,2,3-triazole     2H-1,2,3-triazole

Thus, this disclosure is intended to cover all possible tautomers even when a structure depicts only one of them. For example, the compounds of Formula (Ia) wherein when $R^{5c}$ is hydroxy and each of $R^{5a}$, $R^{5b}$, and $R^{5d}$ are hydrogen, can exist in tautomeric forms:

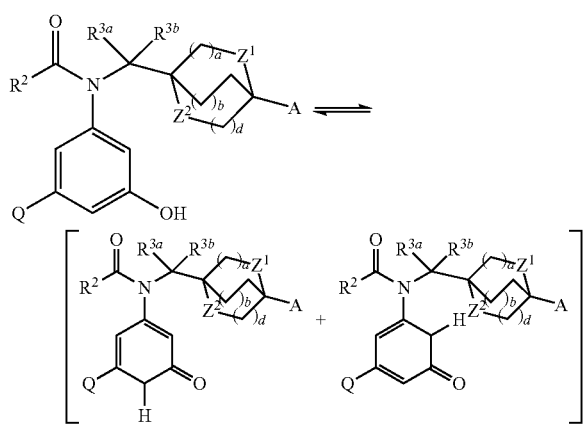

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can form salts which are also within the scope of this invention. Unless otherwise indicated, reference to an inventive compound is understood to include reference to one or more salts thereof. The term "salt(s)" denotes acidic and/or basic salts formed with inorganic and/or organic acids and bases. In addition, the term "salt(s) may include zwitterions (inner salts), e.g., when a compound of Formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the Formula (I) with an amount of acid or base, such as an equivalent amount, in a medium such as one in which the salt precipitates or in an aqueous medium followed by lyophilization. Lists of suitable salts are found in Remington's Pharmaceutical Sciences, 18th Edition, Mack Publishing Company, Easton, PA (1990), the disclosure of which is hereby incorporated by reference.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:
a) *The Practice of Medicinal Chemistry*, Camille G. Wermuth et al., Ch 31, (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch 5, pgs 113-191 (Harwood Academic Publishers, 1991); and
d) *Hydrolysis in Drug and Prodrug Metabolism*, Bernard Testa and Joachim M. Mayer, (Wiley-VCH, 2003).
e) Rautio, J. et al., *Nature Review Drug Discovery*, 17, 559-587, (2018).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an agonist of FXR, or effective to treat or prevent disorders associated with dysregulation of bile acids, such as pathological fibrosis, cancer, inflammatory disorders, metabolic, or cholestatic disorders.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

In another embodiment, the present invention provides a composition comprising at least one of the compounds of the present invention, or a stereoisomer, a tautomer, or a pharmaceutically acceptable salt or a solvate thereof.

In another embodiment, the present invention provides a pharmaceutical composition comprising a pharmaceutically acceptable carrier and at least one of the compounds of the present invention or a stereoisomer, a tautomer, or a pharmaceutically acceptable salt or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, or a pharmaceutically acceptable salt or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising one or more additional therapeutic agents.

Utility

In one embodiment, the present invention provides a method for the treatment of a disease, disorder, or condition associated with dysregulation of bile acids in a patient in need of such treatment, and the method comprises administering a therapeutically effective amount of a compound of the present invention, or a stereoisomer, a tautomer, or a pharmaceutically acceptable salt or solvate thereof, to the patient.

In another embodiment, the present invention provides a method for the treatment of a disease, disorder, or condition associated with activity of farnesoid X receptor (FXR) in a patient in need of such treatment comprising administering a therapeutically effective amount of a compound of the present invention, or a stereoisomer, a tautomer, or a pharmaceutically acceptable salt or solvate thereof, to the patient.

In another embodiment, the present invention provides a method for the treatment of the disease, disorder, or condition comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for eliciting an farnesoid X receptor (FXR) agonizing effect in a patient comprising administering a therapeutically effective amount of a compound of the present invention, or a stereoisomer, a tautomer, or a pharmaceutically acceptable salt or solvate thereof, to the patient.

In some embodiments, the disease, disorder, or condition is associated with FXR dysfunction include pathological fibrosis, cancer, inflammatory disorders, metabolic, or cholestatic disorders.

In some embodiments, the disease, disorder, or condition is associated with fibrosis, including liver, biliary, renal, cardiac, dermal, ocular, and pancreatic fibrosis.

In other embodiments, the disease, disorder, or condition is associated with cell-proliferative disorders, such as cancer. In some embodiments, the cancer includes solid tumor growth or neoplasia. In other embodiments, the cancer includes tumor metastasis. In some embodiments, the cancer is of the liver, gall bladder, small intestine, large intestine, kidney, prostate, bladder, blood, bone, brain, breast, central nervous system, cervix, colon, endometrium, esophagus, genitalia, genitourinary tract, head, larynx, lung, muscle tissue, neck, oral or nasal mucosa, ovary, pancreas, skin, spleen, stomach, testicle, or thyroid. In other embodiments, the cancer is a carcinoma, sarcoma, lymphoma, leukemia, melanoma, mesothelioma, multiple myeloma, or seminoma.

Examples of diseases, disorders, or conditions associated with the activity of FXR that can be prevented, modulated, or treated according to the present invention include, but are not limited to, transplant injection, fibrotic disorders (e. g., liver fibrosis, kidney fibrosis), inflammatory disorders (e.g., acute hepatitis, chronic hepatitis, non-alcoholic steatohepatitis (NASH), irritable bowel syndrome (IBS), inflammatory bowel disease (IBD)), as well as cell-proliferative disorders (e.g., cancer, myeloma, fibroma, hepatocellular carcinoma, colorectal cancer, prostate cancer, leukemia, Kaposi's sarcoma, solid tumors).

The fibrotic disorders, inflammatory disorders, as well as cell-proliferative disorders that are suitable to be prevented or treated by the compounds of the present invention include, but are not limited to, non-alcoholic fatty liver disease (NAFLD), alcoholic or non-alcoholic steatohepatitis (NASH), acute hepatitis, chronic hepatitis, liver cirrhosis, primary biliary cirrhosis, primary sclerosing cholangitis, drug-induced hepatitis, biliary cirrhosis, portal hypertension, regenerative failure, liver hypofunction, hepatic blood flow disorder, nephropathy, irritable bowel syndrome (IBS), inflammatory bowel disease (IBD), abnormal pancreatic secretion, benign prostatic hyperplasia, neuropathic bladder disease, diabetic nephropathy, focal segmental glomerulosclerosis, IgA nephropathy, nephropathy induced by drugs or transplantation, autoimmune nephropathy, lupus nephritis, liver fibrosis, kidney fibrosis, chronic kidney disease (CKD), diabetic kidney disease (DKD), skin fibrosis, keloids, systemic sclerosis, scleroderma, virally-induced fibrosis, idiopathic pulmonary fibrosis (IPF), interstitial lung disease, non-specific interstitial pneumonia (NSIP), usual interstitial pneumonia (UIP), radiation-induced fibrosis, familial pulmonary fibrosis, airway fibrosis, chronic obstructive pulmonary disease (COPD), spinal cord tumor, hernia of intervertebral disk, spinal canal stenosis, heart failure, cardiac fibrosis, vascular fibrosis, perivascular fibrosis, foot-and-mouth disease, cancer, myeloma, fibroma, hepatocellular carcinoma, colorectal cancer, prostate cancer, leukemia, chronic lymphocytic leukemia, Kaposi's sarcoma, solid tumors, cerebral infarction, cerebral hemorrhage, neuropathic pain, peripheral neuropathy, age-related macular degeneration (AMD), glaucoma, ocular fibrosis, corneal scarring, diabetic retinopathy, proliferative vitreoretinopathy (PVR), cicatricial pemphigoid glaucoma filtration surgery scarring, Crohn's disease or systemic lupus erythematosus; keloid formation resulting from abnormal wound healing; fibrosis occurring after organ transplantation, myelofibrosis, and fibroids. In one embodiment, the present invention provides a method for the treatment of a fibrotic disorder, an inflammatory disorder, or a cell-proliferative disorder, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of a fibrotic disorder, an inflammatory disorder, or a cell-proliferative disorder thereof.

In another embodiment, the present invention also provides the use of a compound of the present invention for the manufacture of a medicament for the treatment of a fibrotic disorder, an inflammatory disorder, or a cell-proliferative disorder thereof.

In another embodiment, the present invention provides a method for the treatment of a fibrotic disorder, an inflammatory disorder, or a cell-proliferative disorder, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of a fibrotic disorder, an inflammatory disorder, or a cell-proliferative disorder.

The compounds of the present invention may be employed in combination with additional therapeutic agent(s), such as one or more anti-fibrotic and/or anti-inflammatory therapeutic agents.

In one embodiment, additional therapeutic agent(s) used in combined pharmaceutical compositions or combined methods or combined uses, are selected from one or more, preferably one to three, of the following therapeutic agents: TGFβ receptor inhibitors (for example, galunisertib), inhibitors of TGFβ synthesis (for example, pirfenidone), inhibitors of vascular endothelial growth factor (VEGF), platelet-derived growth factor (PDGF) and fibroblast growth factor (FGF) receptor kinases (for example, nintedanib), humanized anti-$\alpha_v\beta6$ integrin monoclonal antibody (for example, 3G9), human recombinant pentraxin-2, recombinant human Serum Amyloid P, recombinant human antibody against TGFβ-1, -2, and -3, endothelin receptor antagonists (for example, macitentan), interferon gamma, c-Jun amino-terminal kinase (JNK) inhibitor (for example, 4-[[9-[(3S)-tetrahydro-3-furanyl]-8-[(2,4,6-trifluorophenyl)amino]-9H-purin-2-yl]amino]-trans-cyclohexanol, 3-pentylbenzeneacetic acid (PBI-4050), tetra-substituted porphyrin derivative containing manganese (III), monoclonal antibody targeting eotaxin-2, interleukin-13 (IL-13) antibody (for example, lebrikizumab, tralokinumab), bispecific antibody targeting interleukin 4 (IL-4) and interleukin 13 (IL-13), NK1 tachykinin receptor agonist (for example, Sar$^9$, Met $(O_2)^{11}$-Substance P), Cintredekin Besudotox, human recombinant DNA-derived, IgG1 kappa monoclonal antibody to connective growth factor, and fully human IgG1 kappa antibody, selective for CC-chemokine ligand 2 (for example, carlumab, CCX140), antioxidants (for example, N-acetylcysteine), phosphodiesterase 5 (PDE5) inhibitors (for example, sildenafil), agents for treatment of obstructive airway diseases such as muscarinic antagonists (for example, tiotropium, ipatropium bromide), adrenergic β2 agonists (for example, salbutamol, salmeterol), corticosteroids (for example, triamcinolone, dexamethasone, fluticasone), immunosuppressive agents (for example, tacrolimus, rapamycin, pimecrolimus), and therapeutic agents useful for the treatment of fibrotic conditions, such as liver, biliary, and kidney fibrosis, Non-Alcoholic Fatty Liver Disease (NALFD), Non-Alcoholic Steato-Hepatitis (NASH), cardiac fibrosis, Idiopathic Pulmonary Fibrosis (IPF), and systemic sclerosis. The therapeutic agents useful for the treatment of such fibrotic conditions include, but are not limited to, FXR agonists (for example OCA, GS-9674, and LJN452), LOXL2 inhibitors (for example simtuzumab), LPA1 antagonists (for example, BMS-986020 and SAR 100842), PPAR modulators (for example, elafibrinor, pioglitazone, and saroglitazar, IVA337), SSAO/VAP-1 inhibitors (for example, PXS-4728A and SZE5302), ASK-1 inhibitors (for example GS-4997 or selonsertib), ACC inhibitors (for example, CP-640186 and NDI-010976 or GS-0976), FGF21 mimetics (for example, LY2405319 and BMS-986036), caspase inhibitors (for example, emricasan), NOX4 inhibitors (for example, GKT137831), MGAT2 inhibitor (for example, BMS-963272), αV integrin inhibitors (for example, abituzumab) and bile acid/fatty acid conjugates (for example aramchol). The FXR agonists of various embodiments of the present invention may also be used in combination with one or more therapeutic agents such as CCR2/5 inhibitors (for example, cenicriviroc), Galectin-3 inhibitors (for example, TD-139, GR-MD-02), leukotriene receptor antagonists (for example, tipelukast, montelukast), SGLT2 inhibitors (for example, dapagliflozin, remogliflozin), GLP-1 receptor agonists (for example, liraglutide and semaglutide), FAK inhibitors (for example, GSK-2256098), CB1 inverse agonists (for example, JD-5037), CB2 agonists (for example, APD-371 and JBT-101), autotaxin inhibitors (for example, GLPG1690), prolyl t-RNA synthetase inhibitors (for example, halofugenone), FPR2 agonists (for example, ZK-994), and THR agonists (for example, MGL:3196). In another embodiment, additional therapeutic agent(s) used in combined pharmaceutical compositions or combined methods or combined uses, are selected from one or more, preferably one to three, of immunoncology agents, such as alemtuzumab, atezolizumab, ipilimumab, nivolumab, ofatumumab, pembrolizumab, and rituximab.

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally;

parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The terms "treating" or "treatment" as used herein refer to an approach for obtaining beneficial or desired results, including clinical results, by using a compound or a composition of the present invention. For purposes of this invention, beneficial or desired clinical results include, but are not limited to, one or more of the following: decreasing the severity and/or frequency one or more symptoms resulting from the disease, disorder, or condition; diminishing the extent of or causing regression of the disease, disorder, or condition; stabilizing the disease, disorder, or condition (e.g., preventing or delaying the worsening of the disease, disorder, or condition); delay or slowing the progression of the disease, disorder, or condition; ameliorating the disease, disorder, or condition state; decreasing the dose of one or more other medications required to treat the disease, disorder, or condition; and/or increasing the quality of life.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 Volumes), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.01 to about 1000 mg per day, and most preferably between about 0.01 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., ASK-1 inhibitors, CCR2/5 antagonists, autotaxin inhibitors, LPA1 receptor antagonists or other pharmaceutically active material.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The compounds of the present invention are also useful as standard or reference compounds, for example as a quality standard or control, in tests or assays involving FXR agonists. Such compounds may be provided in a commercial kit, for example, for use in pharmaceutical research involving FXR agonist activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of fibrosis and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic) on which the desired information has been formed (e.g., printed or applied).

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Examples of compounds of the present invention prepared by methods described in the general schemes are given in the Examples section set out hereinafter. Preparation of homochiral examples may be carried out by techniques known to one skilled in the art. For example, homochiral compounds may be prepared by separation of racemic products or diastereomers by chiral phase preparative HPLC. Alternatively, the example compounds may be prepared by methods known to give enantiomerically or diastereomerically enriched products.

The reactions and techniques described in this section are performed in solvents appropriate to the reagents and materials employed and are suitable for the transformations being effected. Also, in the description of the synthetic methods given below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art, with alternatives required when incompatible substituents are present. This will sometimes require a judgment to modify the order of the synthetic steps or to select one particular process scheme over another in order to obtain a compound of the invention. It will also be recognized that another major consideration in the planning of any synthetic route in this field is the judicious choice of a protecting group used for protection of reactive functional groups present in the compounds described in this invention. An authoritative account describing the many alternatives to the trained practitioner is Wuts and Greene, Greene's Protective Groups in Organic Synthesis, Fourth Edition, Wiley and Sons (2007).

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined below. Common intermediates are generally useful for the preparation of more than one Example and are identified sequentially (e.g., Intermediate 1, Intermediate 2) and are abbreviated as Int. 1 or I1, Int. 2 or I2. Compounds of the Examples are identified by the example and STEP in which they were prepared (e.g., "1-A" denotes the Example 1, STEP A), or by the example only where the compound is the title compound of the example (for example, "1" denotes the title compound of Example 1). In some instances, alternate preparations of intermediates or examples are described. Frequently chemists skilled in the art of synthesis may devise alternative preparations which may be desirable based on one or more considerations such as shorter reaction time, less expensive starting materials, ease of operation or isolation, improved yield, amenable to catalysis, avoidance of toxic reagents, accessibility of specialized instrumentation, and decreased number of linear STEPs. The intent of describing alternative preparations is to further enable the preparation of the examples of this invention. In some instances, some functional groups in the outlined examples and claims may be replaced by well-known bioisosteric replacements known in the art, for example, replacement of a carboxylic acid group with a tetrazole or a phosphate moiety. $^1$H NMR data collected in deuterated dimethyl sulfoxide used water suppression in the data processing. The reported spectra are uncorrected for the effects of water suppression. Protons adjacent to the water suppression frequency of 3.35 ppm exhibit diminished signal intensity.

ABBREVIATIONS

The following abbreviations are employed in the Schemes, Examples and elsewhere herein:
EtOAc=ethyl acetate
PE=petroleum ether
DMF=dimethylformamide
THF=tetrahydrofuran
$K_2CO_3$=potassium carbonate
$Na_2CO_3$=sodium carbonate
$MgSO_4$=magnesium sulfate
DCM=$CH_2Cl_2$=methylene chloride
MeOH=methanol
HCl=hydrochloric acid
AcOH=acetic acid
$Cs_2CO_3$=cesium carbonate
DMSO=dimethylsulfoxide
TEA=triethylamine
BOP=(benzotriazol-1-yloxy)tris(dimethylamino)phosphonium hexafluorophosphate
DMAP=4-dimethylaminopyridine
2-DMAP=2-dimethylaminopyridine
PCC=pyridinium chlorochromate
PDC=pyridinium dichromate DIBAL-H=diisobutylaluminium hydride
rotovap=rotary evaporation
min=minute(s)
h or hr=hour(s)
d=day(s)
rt=room temperature
mL=milliliter
g=gram(s)
mg=milligram(s)
mmol=millimole(s)
LRMS=low resolution mass spectrometry
NMR=nuclear magnetic resonance
HPLC=high performance liquid chromatography Synthesis The compounds of the present invention can be prepared in a number of ways well known to one skilled in the art of organic synthesis. The compounds of the present invention can be synthesized using the methods described below, together with synthetic methods known in the art of organic chemistry, or variations thereon as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

SCHEME 1

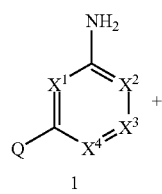

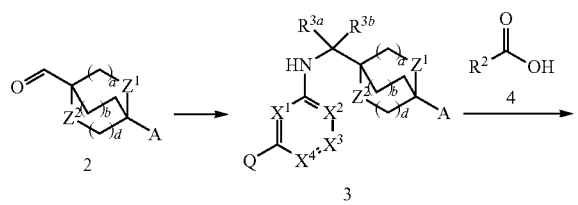

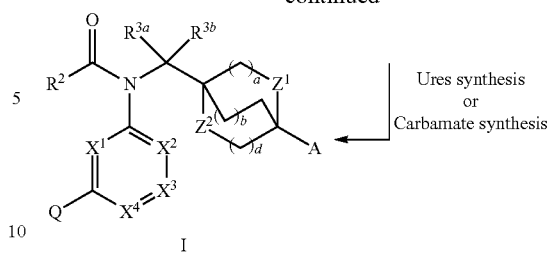

Scheme 1 describes the synthesis of compounds of Formula I. Intermediate 3 can be synthesized by coupling intermediate 1 and intermediate 2 under reductive amination conditions which are known methods recognizable by one skilled in the art. The imine synthesis can occur in presence of acid such as acetic acid in a suitable polar protic solvent (e.g. MeOH, EtOH, etc.) at room temperature or reflux temperature followed by reduction of imine with reducing agents (e.g. sodium cyanoborohydride, sodium triacetoxyborohydride, etc.) to afford intermediate 3. Intermediate 3 can be subjected to a variety of different transformations using numerous known methods recognized by one skilled in the art, including but not limited to the following methods to afford variations of Formula I:

Amides: Intermediate 4 can be obtained from commercial sources or can be synthesized by known methods readily recognizable by one skilled in the art. Intermediate 4 can be activated for acylation using any number of reagents recognizable by one skilled in the art (e.g. phosphorus oxychloride, thionyl chloride, oxalyl chloride, methyl or ethylchloroformate, etc.), in a polar aprotic solvent (e.g. DCM, THF, etc.), at temperatures ranging between −30° C. to reflux temperatures. The activated acid intermediate can then be reacted with intermediate 3 in presence of a base (e.g. pyridine, DMAP, 2-(dimethylamino)pyridine, N-methylmorpholine, etc. or a combination of at least two of these) to generate compounds of Formula I.

Ureas: Intermediate 3 can be subjected to treatment with isocyanates in presence of base (e.g. Et$_3$N, DIPEA, pyridine etc.) in polar aprotic solvent (e.g. DCM, DCE, etc.) at room temperature to afford ureas represented by formula I. Alternatively, the intermediate 3 can be activated by treatment with triphosgene in presence of base (e.g. Et$_3$N, DIPEA, etc.) in solvent (e.g. DCM, DCE, etc.) at 0° C. to room temperature. The activated intermediate 3 can then be treated with substituted alkyl or aryl or heteroaryl amine in presence of base (e.g. Et$_3$N, DIPEA, etc.) in solvent (e.g. DCM, DCE, THF, etc.) at room temperature to afford ureas represented by formula I.

Carbamates: Intermediate 3 can be treated with chloroformates (or alcohols, activated as carbonates) in presence of base (e.g. Et$_3$N, DIPEA, pyridine, t-BuOK etc.) in polar aprotic solvent (e.g. DCM, DCE, THF, etc.) at 0° C. to room temperature to afford carbamates represented by formula I.

Intermediate 1 (Scheme 1) can be obtained from commercial sources or can be synthesized by known methods readily recognizable by one skilled in the art. Intermediates 1 can be accessed in various ways as depicted in Schemes 2-10 using numerous known methods recognized by the one skilled in the art including but not limited to the following methods.

SCHEME 2

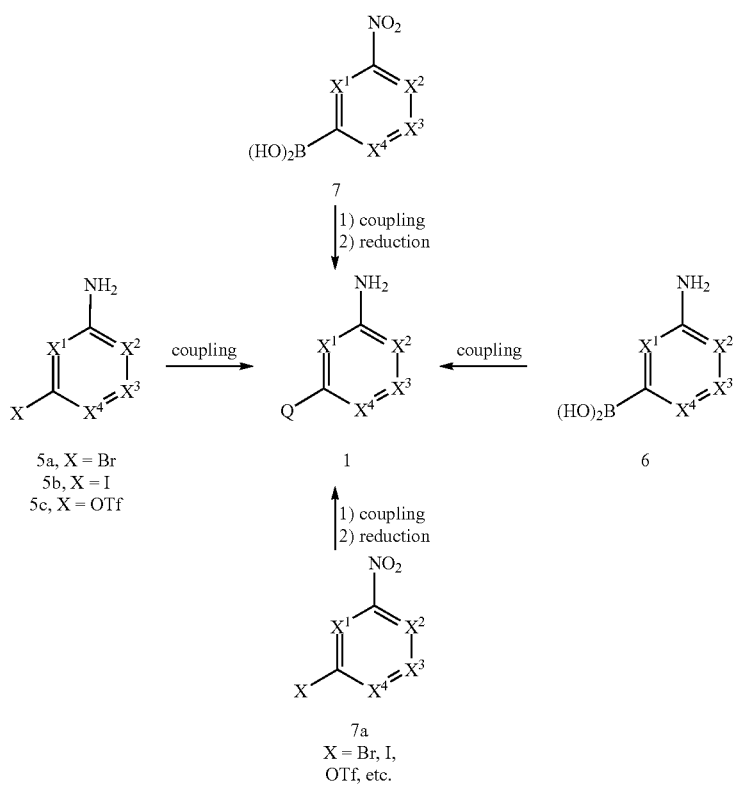

Intermediate 1 can be accessed in various ways as depicted in Scheme 2. Intermediates 5, 6 and 7 can be obtained from commercial sources or can be synthesized by known methods readily recognizable by one skilled in the art. Intermediates 5, 6 and 7 can be subjected to metal catalyzed cross coupling reactions using numerous known methods recognized by the one skilled in the art including but not limited to the ones described in Metal-Catalyzed Cross-Coupling Reactions, Armin de Meijere, François Diederich, 2 Volumes, Second, Revised and Enlarged Edition, 2004, ISBN: 3-527-30518-1, Wiley-VCH and references cited therein. Intermediate 5, 6 and 7 can be subjected to various metal catalyzed reactions (including but not limited to reactions such as Ullmann, Buchwald, Suzuki, Stille, Sonogashira coupling, etc.) These coupling reactions can be carried out in presence of metal catalyst (e.g. CuBr, $Pd(OAc)_2$, $Pd_2(dba)_3$, $Pd(PPh_3)_4$, $Pd(PPh_3)_2Cl_2$, $Pd(dppf)Cl_2$, etc.) and appropriate ligand (including but not limited to ligands such as proline, 1,10-phenanthroline, tricyclohexylphosphine, dppf, etc.) as required. The Ullmann and Buchwald coupling reactions of intermediate 5 can be carried out with various coupling partners such as alkyl or cycloalkyl or heterocyclyl or heteroaryl amines, alkyl or cycloalkyl or heterocyclyl or heteroaryl alcohols, phenols, etc. The Suzuki, Heck, Chan-Lam coupling reaction of intermediate 6 and 7 can be carried out with various coupling partners such as alkenes, alkenyl halides or triflates etc. Intermediate 5 can be subjected to Suzuki, Stille, etc. cross couplings with coupling partners such as alkyl, allyl, alkenyl boronic acids, boronic acid esters, trifluoroborate salts; alkyl, allyl, alkynyl, organotin reagents, etc. The coupling reactions can be carried out in presence of base as necessary (including but not limited to $Na_2CO_3$, $K_2CO_3$, $NaHCO_3$, $K_3PO_4$, $NaO^tBu$, etc.) and solvent (e.g. dioxane, THF, DME, toluene, methanol, DMF, water, etc. or the mixture of two or three of these solvents) under heating conditions to afford intermediate 1. Alternatively, intermediate 5 can be converted to organotin reagent using hexamethylditin in presence of a palladium catalyst and in solvent (e.g. Toluene, THF etc.) at reflux temperature, which upon coupling with suitable coupling partners such as alkyl, acyl, alkenyl, allyl halides, triflates etc. in a Stille coupling (Sherer, B., et al. PCT Int. Appl., 2016/039734, 2016) afforded compounds represented by formula I. Intermediate 5 can be converted to organoboron reagent using bis(pinacolato)diboron, bis(neopentyl glycolato)diboron, etc in presence of a palladium catalyst such as $Pd(dppf)Cl_2$ and base such as potassium acetate in solvent (e.g. dioxane, DMSO etc.) at reflux temperature, which upon coupling with suitable coupling partners such as alkenes, alkenyl halides or triflates etc. in a Suzuki coupling afforded compounds represented by formula I. Intermediate 7a can be subjected to coupling reaction with dimethyl phosphine oxide in presence of palladium catalyst such as bis(dibenzylideneacetone)palladium and ligand such as XantPhos and inorganic base such as cesium carbonate in solvent (e.g. dioxane, DMSO etc.) under heating conditions to afford corresponding phosphine oxide.

Intermediate 7 or 7a followed by the coupling reactions as described above afforded the nitro intermediate, which can be reduced using the conditions recognized by one skilled in the art including but not limited to reduction in presence of catalyst such as Pd and hydrogen gas at ambient pressure and temperature to yield intermediate 1.

SCHEME 3

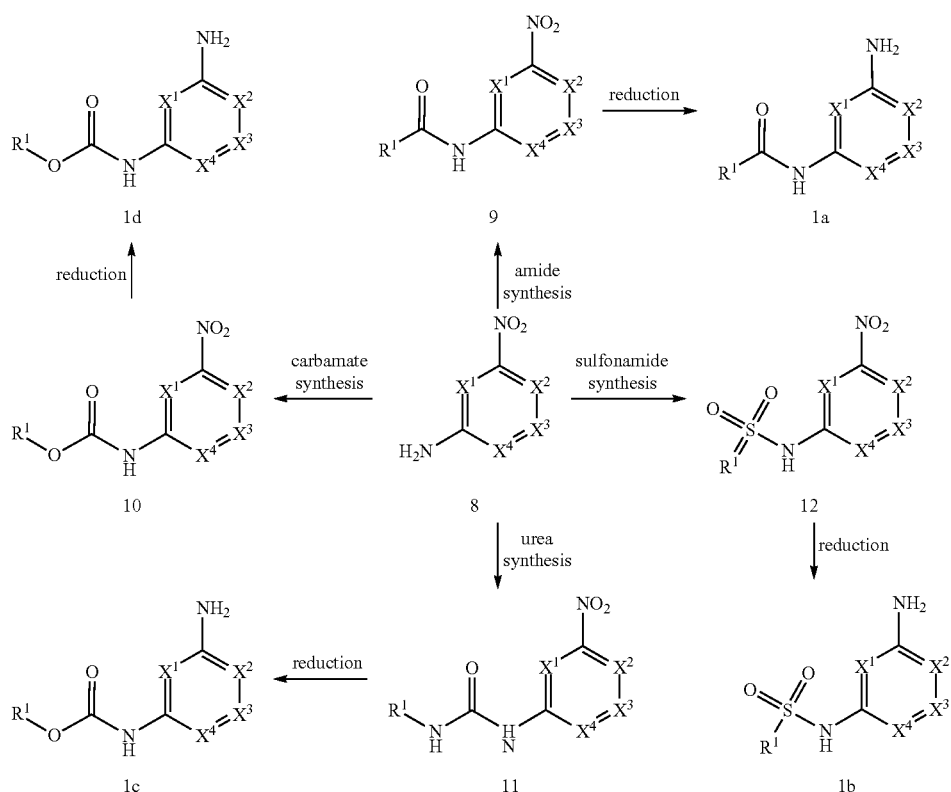

Intermediate 1a-d can be accessed in various ways as depicted in Scheme 3. Intermediate 8 can be obtained from commercial sources or can be synthesized by known methods readily recognizable by one skilled in the art. Intermediate 8 can be subjected to a variety of different transformations using numerous known methods recognized by one skilled in the art, including but not limited to the following methods to afford intermediates 9-12:

Amides: Intermediate 8 can be reacted with activated acid intermediates in presence of base (e.g. pyridine, DMAP, 2-(dimethylamino)pyridine, N-methylmorpholine, etc.) in polar aprotic solvent (e.g. DCM, THF, etc.) to generate intermediates 9.

Carbamates: Intermediate 8 can be treated with chloroformates (or alcohols, activated as carbonates) in presence of base (e.g. $Et_3N$, DIPEA, pyridine, t-BuOK etc.) in polar aprotic solvent (e.g. DCM, DCE, THF, etc.) at 0° C. to room temperature to afford intermediates 10.

Ureas: Intermediate 8 can be subjected to treatment with isocyanates in presence of base (e.g. $Et_3N$, DIPEA, pyridine etc.) in polar aprotic solvent (e.g. DCM, DCE, etc.) at room temperature to afford intermediates 11. Alternatively, intermediate 8 can be activated by treatment with triphosgene in presence of base (e.g. $Et_3N$, DIPEA, etc.) in solvent (e.g. DCM, DCE, etc.) at 0° C. to room temperature. The activated intermediate 8 can then be treated with substituted alkyl or aryl or heteroaryl amine in presence of base (e.g. $Et_3N$, DIPEA, etc.) in solvent (e.g. DCM, DCE, etc.) at room temperature to afford intermediates 11.

Sulfonamides: Intermediate 8 can be treated with sulfonyl chlorides in presence of a base (e.g. pyridine, DMAP, 2-(dimethylamino)pyridine, N-methylmorpholine, etc.) in a polar aprotic solvent (e.g. DCM, THF, etc.), at temperatures ranging between 0° C. to 90° C. to generate intermediates 12.

Intermediates 9-12 can be can be reduced using the conditions recognized by one skilled in the art including but not limited to reduction in presence of catalyst such as Pd and hydrogen gas at ambient pressure and temperature to yield intermediates 1a-d respectively (as shown in Scheme 3).

SCHEME 4

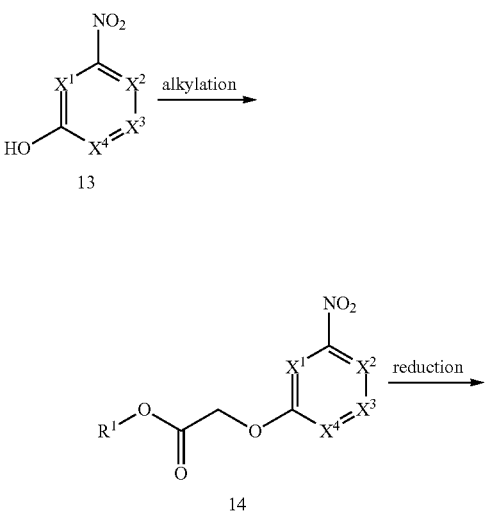

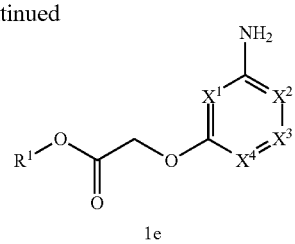

Intermediate 1e can be accessed as depicted in Scheme 3. Intermediate 13 can be obtained from commercial sources or can be synthesized by known methods readily recognizable by one skilled in the art. Intermediate 13 can be subjected to alkylation using numerous known methods recognized by one skilled in the art, including but not limited to the reaction with alkyl or aryl or heteroaryl 2-bromoacetate in presence of a base (e.g. $K_2CO_3$, $Na_2CO_3$, etc.) in polar aprotic solvent (e.g. acetone etc.) under heating conditions to afford intermediate 14. Intermediate 14 can be can be reduced using the conditions recognized by one skilled in the art including but not limited to reduction in presence of catalyst such as Pd and hydrogen gas at ambient pressure and temperature to yield intermediate 1e.

SCHEME 5

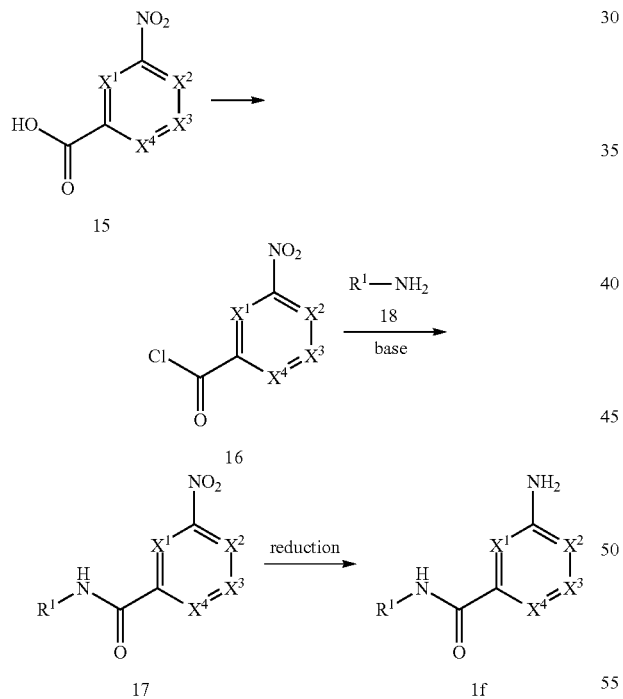

Scheme 5 describes the synthesis of intermediates 1f. Intermediates 15 can be obtained from commercial sources or can be synthesized by known methods readily recognizable by one skilled in the art. Intermediate 16 can be prepared from intermediate 15 by using any number of reagents recognizable by one skilled in the art but not limited to the ones described here (e.g. phosphorus oxychloride, thionyl chloride, oxalyl chloride, methyl or ethylchloroformate, etc.), in a polar aprotic solvent (e.g. DCM, THF, etc.), at temperatures ranging between −30° C. to reflux temperatures. The activated acid intermediate 16 can then be reacted with intermediate 18 in presence of a base (e.g. pyridine, DMAP, 2-(dimethylamino)pyridine, N-methylmorpholine, etc.) to generate intermediate 17. Intermediate 17 can be can be reduced using the conditions recognized by one skilled in the art including but not limited to reduction in presence of catalyst such as Pd and hydrogen gas at ambient pressure and temperature to yield intermediate 1f.

SCHEME 6

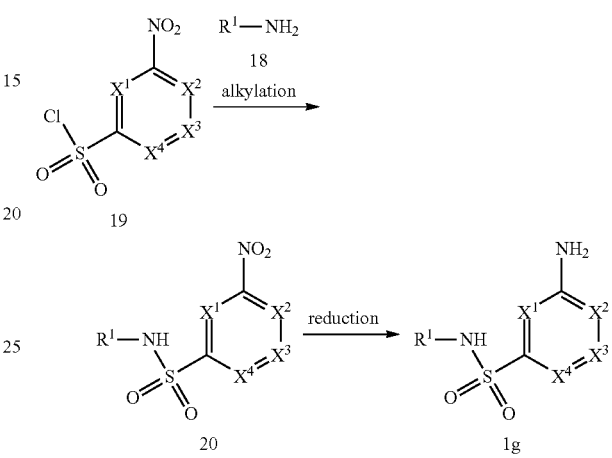

Scheme 6 describes the synthesis of intermediates 1g. Intermediates 19 can be obtained from commercial sources or can be synthesized by known methods readily recognizable by one skilled in the art. The intermediate 19 can then be reacted with intermediate 18 in presence of a base (e.g. pyridine, DMAP, 2-(dimethylamino)pyridine, N-methylmorpholine, etc.) to generate intermediate 20. Intermediate 20 can be can be reduced using the conditions recognized by one skilled in the art including but not limited to reduction in presence of catalyst such as Pd and hydrogen gas at ambient pressure and temperature to yield intermediate 1g.

SCHEME 7

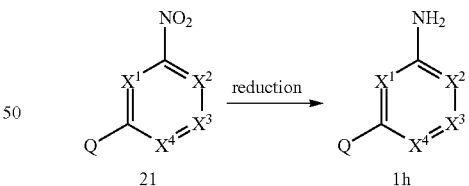

Scheme 7 describes the synthesis of intermediates 1h. Intermediates 21 can be obtained from commercial sources or can be synthesized by known methods readily recognizable by one skilled in the art. Intermediate 21 can be can be reduced using the conditions recognized by one skilled in the art including but not limited to reduction in presence of catalyst such as Pd and hydrogen gas at ambient pressure and temperature to yield intermediate 1h. Intermediates 1h can be obtained from commercial sources as well or can be synthesized by known methods readily recognizable by one skilled in the art including but not limited to the ones described here.

SCHEME 8

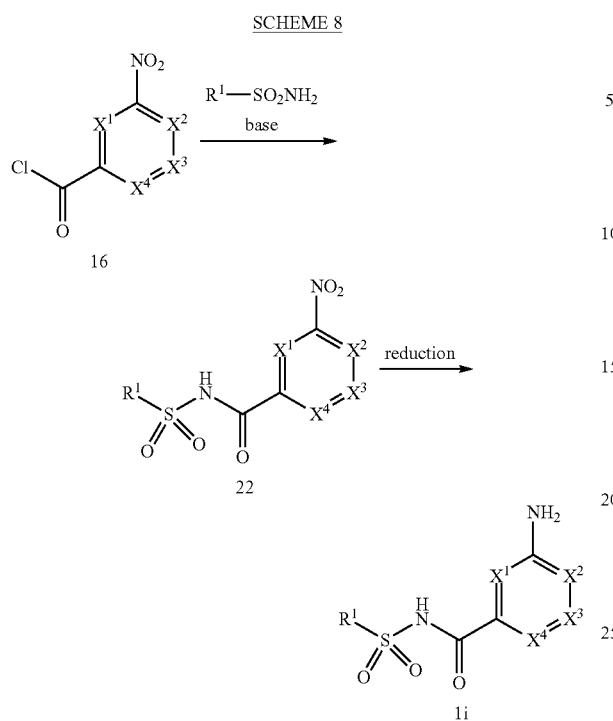

Scheme 8 describes the synthesis of intermediates 1i. Intermediate 16 (synthesized as described in Scheme 5) can be reacted with a sulfonamides in presence of a base (e.g. pyridine, DMAP, 2-(dimethylamino)pyridine, N-methylmorpholine, etc.) in a polar aprotic solvent (e.g. DCM, THF, etc.), at temperatures ranging between 0° C. to 90° C. to generate intermediate 22. Intermediate 22 can be can be reduced using the conditions recognized by one skilled in the art including but not limited to reduction in presence of catalyst such as Pd and hydrogen gas at ambient pressure and temperature to yield intermediate 1i.

SCHEME 9

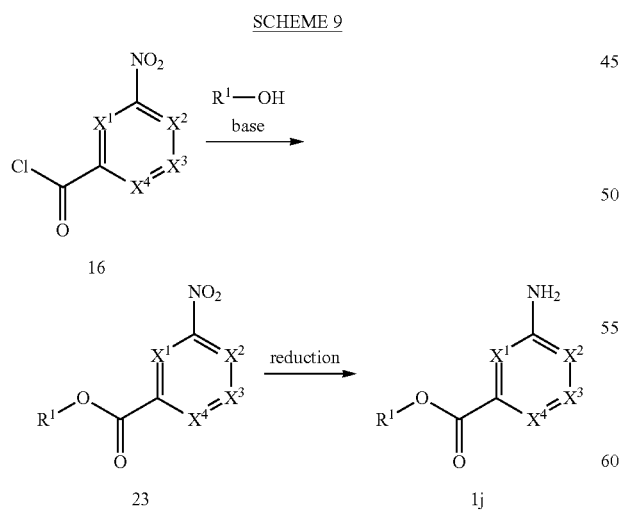

Scheme 9 describes the synthesis of intermediates 1j. Intermediate 16 (synthesized as described in Scheme 5) can be reacted with alcohols or phenols in presence of a base (e.g. pyridine, DMAP, 2-(dimethylamino)pyridine, N-methylmorpholine, etc.) in a polar aprotic solvent (e.g. DCM, THF, etc.), at temperatures ranging between 0° C. to 90° C. to generate intermediate 23. Intermediate 23 can be can be reduced using the conditions recognized by one skilled in the art including but not limited to reduction in presence of catalyst such as Pd and hydrogen gas at ambient pressure and temperature to yield intermediate 1j.

SCHEME 10

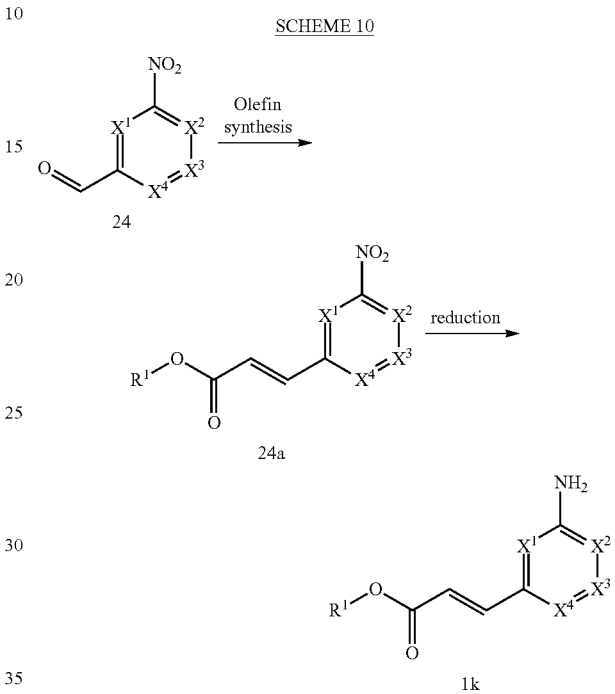

Scheme 10 describes the synthesis of intermediates 1k. Intermediate 24 can be obtained from commercial sources or can be synthesized by known methods readily recognizable by one skilled in the art. Intermediate 24 can be subjected to reaction with alkyl 2-(dimethoxyphosphoryl)acetate in presence of a base (e.g. $K_2CO_3$, $Na_2CO_3$, etc.) in polar protic solvent (e.g. water, methanol, ethanol, etc.) to afford intermediate 24a. Intermediate 24a can be subjected to reduction using the conditions recognized by one skilled in the art including but not limited to one described such as heating in presence of tin(II)chloride dihydrate in polar protic solvent such as water to afford intermediate 1k. Intermediate 1k can be converted to compounds of formula I by using steps described in Scheme 1.

Intermediates 2 (Scheme 1) can be accessed in various ways as depicted in Scheme 11 using numerous known methods recognized by the one skilled in the art including but not limited to the following methods.

SCHEME 11

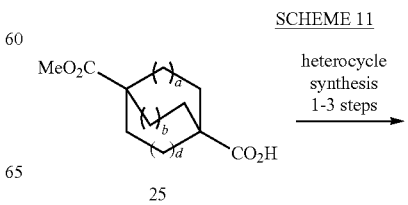

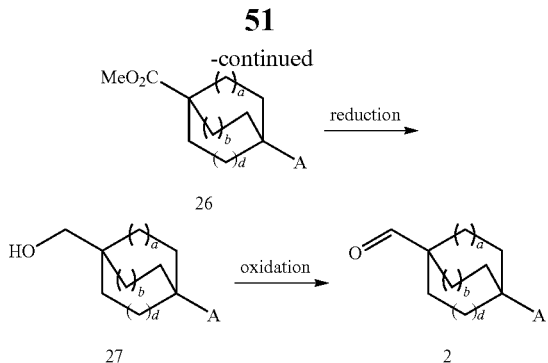

Scheme 11 describes the synthesis of intermediate 2. Commercially available 4-(methoxycarbonyl)bicyclo[2.2.2]octane-1-carboxylic acid 25 can be subjected to heterocycle ring synthesis to afford compounds of intermediate 26.

Heterocycle formation (A). The carboxylic acid moiety of compound 25 can be converted to various heterocycles (A) using numerous known methods recognized by one skilled in the art, including but not limited to the following methods:

A=1,2,4-oxadiazole. Intermediate 25 can be coupled with various amide oximes (derived from the corresponding nitriles by reaction with hydroxylamine; see Hirawat, S., et al. WO 2006/110483) using an amide bond coupling reagent (e.g. CDI, BOP, EDC, etc.) in a polar aprotic solvent (e.g. THF, 1,4-dioxane, DMF, etc.) at room temperature. The acyclic intermediate can be subsequently cyclized at elevated temperatures (60° C. to 100° C.). Alternatively, in situ cyclization can be accomplished by conducting the coupling of acid 25 with amide oximes at elevated temperatures (60° C. to 100° C.).

A=1,2,5-oxadiazole. Intermediate 25 can be converted to 1,2,5-oxadiazole as described in Broström, J. et al. *J. Med. Chem.* 2012, 55, 1817-1830 and references described therein.

A=1,3,4-oxadiazole or A=1,3,4-thiadiazole. Intermediate 25 can be coupled with acetic acid hydrazide (described in WO 2014/071247, Bradner, J. E., et al.), using an amide bond coupling reagent (e.g. CDI, BOP, EDC, etc.) in a polar aprotic solvent (e.g. THF, 1,4-dioxane DMF, MeCN, etc.). The acyclic hydrazide intermediate can then be cyclized to either 1,3,4-oxadiazole or 1,3,4-thiadiazole using respectively, 4-toluenesulfonic acid (Stabile, P. et al. *Tetrahedron Lett.* 2010, 51, 4801-4805) or Lawesson's reagent (Kitamura, S., et al. PCT Int. Appl., 2008011130, 2008).

A=3-substituted 5-alkyl-1-methyl-1H-pyrazole. Methyl ketones can be treated with base and acid chloride of intermediate 25 to afford a diketone, which upon reaction with substituted or unsubstituted hydrazine salt in polar protic solvent such as ethanol at reflux temperature afforded ester 26 where A is alkyl substituted or unsubstituted pyrazole. (As described in Cadilla, R., et al. WO 03/074495 A1).

A=Isoxazole. The diketone prepared from intermediate 25 as described above can be upon reaction with hydroxyl amine hydrochloride salt in polar protic solvent such as ethanol at reflux temperature afforded ester 26 where A is alkyl substituted isoxazole (as described in Cadilla, R., et al. WO 03/074495 A1).

A=5-(3-alkyl-1-methyl-1H-pyrazole). The diketone prepared from intermediate 25 as described above can be upon reaction with alkyl hydrazine in polar protic solvent such as ethanol at reflux temperature afforded ester 26 where A is alkyl substituted pyrazole.

A=substituted heteroaryl. Intermediate 25 can be subjected to Minisci reaction with substituted heteroaryl compounds such as pyridine, pyrimidine, pyridazine, pyrazine, quinoline, pyrazole, etc in presence of silver nitrate and potassium persulfate or ammonium persulfate in DCM (or any other conditions that can be used to generate carbon-centered radical) and water mixture as a solvent at ambient temperature to afford ester 26 (as described in Ling-Bo, Qu et al. *Org. Biomol. Chem.*, 2015, 13, 2750-2755 and Review: Duncton, M. A. *J. Med. Chem. Commun.*, 2011, 2, 1135-1161 and references described therein).

A=2-Benzothiazole. Method A: Intermediate 25 can be coupled with substituted 2-aminobenzenethiol (See generally Chedekel, M. R., et al. *Synth. Commun.* 1980, 10, 167-173; synthesis of various 2-aminobenzenethiols), using an amide bond coupling reagent (e.g. BOP, T3P, EDC, etc.) in a polar aprotic solvent (e.g. DCE, THF, etc.). The coupling reaction can be conducted at elevated temperatures (60° C. to 80° C.) thereby accomplishing the in situ formation of the cyclized 2-benzothiazole.

Method B: Alternatively, intermediate 25 can be coupled with substituted 2-chloroaniline (commercial available) using an amide bond coupling reagent (e.g. T3P, BOP, etc.), or by activating intermediate 25 for acylation using any number of reagents (e.g. oxalyl chloride, POCl$_3$, etc.). The resultant carboxamide can be treated with Lawesson's reagent at elevated temperature (120° C.), thereby accomplishing an in situ cyclization to 2-benzothiazole.

A=2-Benzoxazole. Intermediate 25 can be coupled with substituted 2-aminophenol (commercial available) using an amide bond coupling reagent (e.g. BOP, EDC, etc.), in a polar aprotic solvent (e.g. DMF, THF, etc.). Cyclization can be accomplished in refluxing toluene in the presence of tosic acid.

A=2-Benzimidazole. Intermediate 25 can be coupled with ethyl 3,4-diaminobenzoate using an amide bond coupling reagent (e.g. TBTU, T3P, PyBOP, etc.) in a polar aprotic solvent (e.g. DMF, NMP, etc.), then cyclized to the 2-benzimidazole under acidic conditions (AcOH neat) at elevated temperatures (115° C.).

A=2-Quinazoline. Intermediate 25 can be coupled with 4-amino-3-(aminomethyl)benzoate dihydrochloride (Pascal, R. et al. Eur. *J. Org. Chem.* 2000, 22, 3755-3761), using an amide bond coupling reagent (e.g. HBTU, EDC, PyBOP, etc.) in a polar aprotic solvent (e.g. MeCN, THF, etc.). Cyclization can be accomplished under acidic conditions (AcOH neat) at elevated temperatures (115° C.). The resultant dihydroquinazoline intermediate can be oxidized to the 2-quinazoline using an oxidizing agent such as DDQ.

A=1-triazole. Intermediate 25 can be converted to corresponding amine via Curtius rearrangement (as described in Shioiri, T. et al. *J. Am. Chem. Soc.* 1972, 94, 6203-6205). The amine upon treatment with reagent such as p-toluene sulfonyl azide can be converted to corresponding azide which upon reaction with suitable alkyne (as described in Boren, B. C. et al *J. Am. Chem. Soc.*, 2008, 130, 8923-8930) afforded triazole.

A=Substituted 1,2,4-triazole. Intermediate 25 can be converted to corresponding hydrazide and can be subjected to reaction with substituted carboxamide in presence of trifluoromethanesulfonic anhydride and 2-fluoropyridine under heating conditions as described by Charette, A. B. et al. *Org. Lett.*, 2015, 17, 1184-1187.

'A' can be other heterocycles such as substituted as well as unsubstituted oxazoles, thiazoles imidazoles, isoxazoles, triazoles, pyrazoles and can be synthesized as described in reference: Wlochal, J. et al *Org. Lett.* 2014, 16, 4094-4097 and references cited therein. Alternatively, acid functional group of intermediate 25 can be converted to heterocycles as described in schemes 2-9 using methods and literature references described therein.

Intermediate 26 can be subjected to reduction by a reducing agent (e.g. LAH, DIBAL-H, NaBH$_4$, etc.) in chlorinated or ethereal solvent (e.g. DCM, ether, 1,4-dioxane, THF, etc.) to afford intermediate 27. Intermediate 27 can be oxidized by methodologies recognized by one skilled in the art using oxidation conditions (e.g. Dess-Martin periodinane, Swern oxidation conditions, PDC, etc.) to afford intermediate 2.

acetic acid in a suitable polar protic solvent (e.g. MeOH, EtOH, etc.) at room temperature or reflux temperature followed by reduction with reducing agents (e.g. sodium cyanoborohydride, sodium triacetoxyborohydride, etc.) to afford intermediate 30. Intermediate 4 can be activated for acylation using any number of reagents recognizable by one skilled in the art (e.g. Thionyl chloride, phosphorus oxychloride, oxalyl chloride, methyl or ethylchloroformate, etc.), in a polar aprotic solvent (e.g. DCM, THF, etc.), at temperatures ranging between −30° C. to reflux temperatures. The activated acid intermediate can be reacted with

SCHEME 12

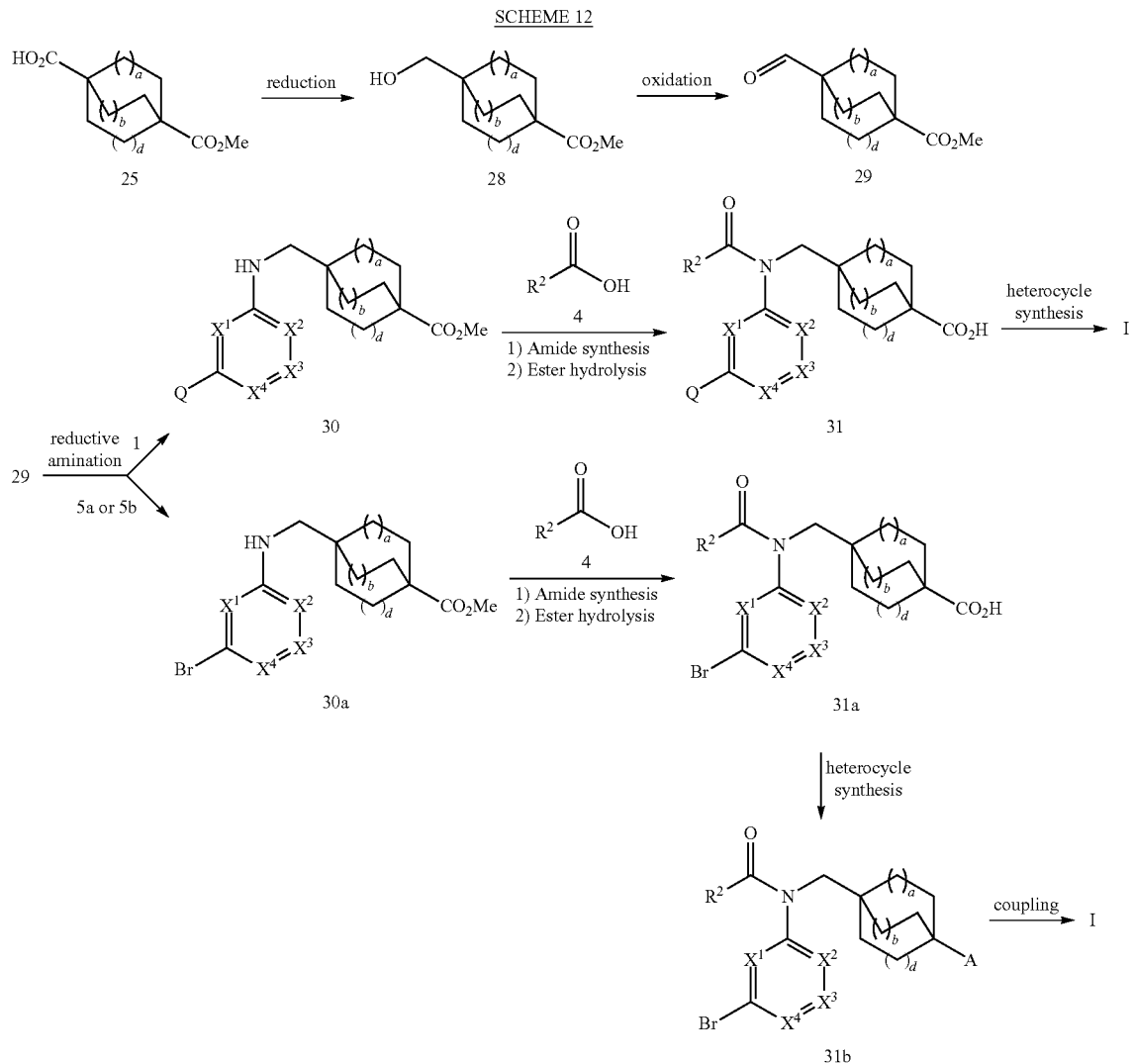

Scheme 12 describes an alternative synthesis of compounds of Formula I with the modified sequence of steps. Commercially available 4-(methoxycarbonyl)bicyclo[2.2.2]octane-1-carboxylic acid 25 can be subjected to reduction in presence of hydride based reducing agent (e.g. LAH, DIBAL-H, NaBH$_4$, etc.) to afford intermediate 28. Intermediate 28 can be oxidized to intermediate 29, by methodologies recognized by one skilled in the art using oxidation conditions (e.g. Dess-Martin periodinane, Swern oxidation conditions, PDC or PCC, etc.). The intermediate 1 and intermediate 29 can be reacted in presence of acid such as intermediate 30 in presence of a base to generate corresponding amide. Subsequent hydrolysis of the methyl ester with an alkali hydroxide base can provide intermediate 31. Intermediate 31 can be converted to various heterocycles (A) using numerous known methods recognized by one skilled in the art, including but not limited to the methods described in Scheme 11 to afford compounds of formula I.

Alternatively, intermediate 29 and intermediate 5a or 5b can be subjected to reductive amination using numerous known methods recognizable by one skilled in the art. The imine synthesis in presence of acid such as acetic acid in a suitable polar protic solvent (e.g. MeOH, EtOH, etc.) at room temperature or reflux temperature followed by reduction of imine with reducing agents (e.g. sodium cyanoborohydride, sodium triacetoxyborohydride, etc.) afforded intermediate 30a. Intermediate 4 can be activated for acylation using any number of reagents recognizable by one skilled in the art (e.g. Thionyl chloride, phosphorus oxychloride, oxalyl chloride, methyl or ethylchloroformate, etc.), in a polar aprotic solvent (e.g. DCM, THF, etc.), at temperatures ranging between −30° C. to reflux temperatures. The activated acid intermediate can be reacted with intermediate 30a in presence of a base to generate corresponding amide. Subsequent hydrolysis of the methyl ester with an alkali hydroxide base can provide intermediate 31a. Intermediate 31a can be converted to various heterocycles (A) using numerous known methods recognized by one skilled in the art, including but not limited to the methods described in Scheme 11 to afford intermediate 31b. Intermediate 31b can be subjected to metal catalyzed cross coupling reactions using numerous known methods recognized by the one skilled in the art including but not limited to the ones described in Metal-Catalyzed Cross-Coupling Reactions, Armin de Meijere, François Diederich, 2 Volumes, Second, Revised and Enlarged Edition, 2004, ISBN: 3-527-30518-1, Wiley-VCH and references cited therein. Intermediate 31b can be subjected to various metal catalyzed reactions (including but not limited to reactions such as Ullmann, Buchwald, Suzuki, Stille, Sonogashira coupling, etc.) These coupling reactions can be carried out in presence of metal catalyst (e.g. CuBr, Pd(OAc)$_2$, Pd$_2$(dba)$_3$, Pd(PPh$_3$)$_4$, Pd(PPh$_3$)$_2$Cl$_2$, Pd(dppf)Cl$_2$, etc.) and appropriate ligand (including but not limited to ligands such as proline, 1,10-phenanthroline, tricyclohexylphosphine, dppf, etc.) as and when required. The Ullmann and Buchwald coupling reactions of intermediate 31b can be carried out with various coupling partners such as alkyl or cycloalkyl or heterocyclyl or heteroaryl amines, alkyl or cycloalkyl or heterocyclyl or heteroaryl alcohols, phenols, etc. Intermediate 31b can be subjected to Suzuki, Heck, Stille, etc. cross couplings with coupling partners such as alkyl, allyl, alkenyl boronic acids, boronic acid esters, trifluoroborate salts; alkyl, allyl, alkynyl, organotin reagents, etc. The coupling reactions can be carried out in presence of base as necessary (including but not limited to Na$_2$CO$_3$, K$_2$CO$_3$, NaHCO$_3$, K$_3$PO$_4$, NaO$^t$Bu, etc.) and solvent (e.g. dioxane, THF, DME, toluene, methanol, DMF, water, etc. or the mixture of two or three of these solvents) under heating conditions to afford compounds of formula I. Alternatively, intermediate 31b can be converted to organotin reagent using hexamethylditin in presence of a palladium catalyst and in solvent (e.g. Toluene, THF etc.) at reflux temperature, which upon coupling with suitable coupling partners such as alkyl, acyl, alkenyl, allyl halides, triflates etc. in a Stille coupling (Sherer, B., et al. PCT Int. Appl., 2016/039734, 2016) afforded compounds represented by formula I. Intermediate 31b can be converted to organoboron reagent using bis(pinacolato)diboron, bis(neopentyl glycolato)diboron, etc in presence of a palladium catalyst such as Pd(dppf)Cl$_2$ and base such as potassium acetate in solvent (e.g. dioxane, DMSO etc.) at reflux temperature, which upon coupling with suitable coupling partners such as alkenes, alkenyl halides or triflates etc. in a Suzuki coupling afforded compounds represented by formula I. Intermediate 31b can be subjected to coupling reaction with dimethyl phosphine oxide in presence of palladium catalyst such as bis(dibenzylideneacetone)palladium and ligand such as XantPhos and inorganic base such as cesium carbonate in solvent (e.g. dioxane, DMSO etc.) under heating conditions to afford corresponding phosphine oxide.

SCHEME 13

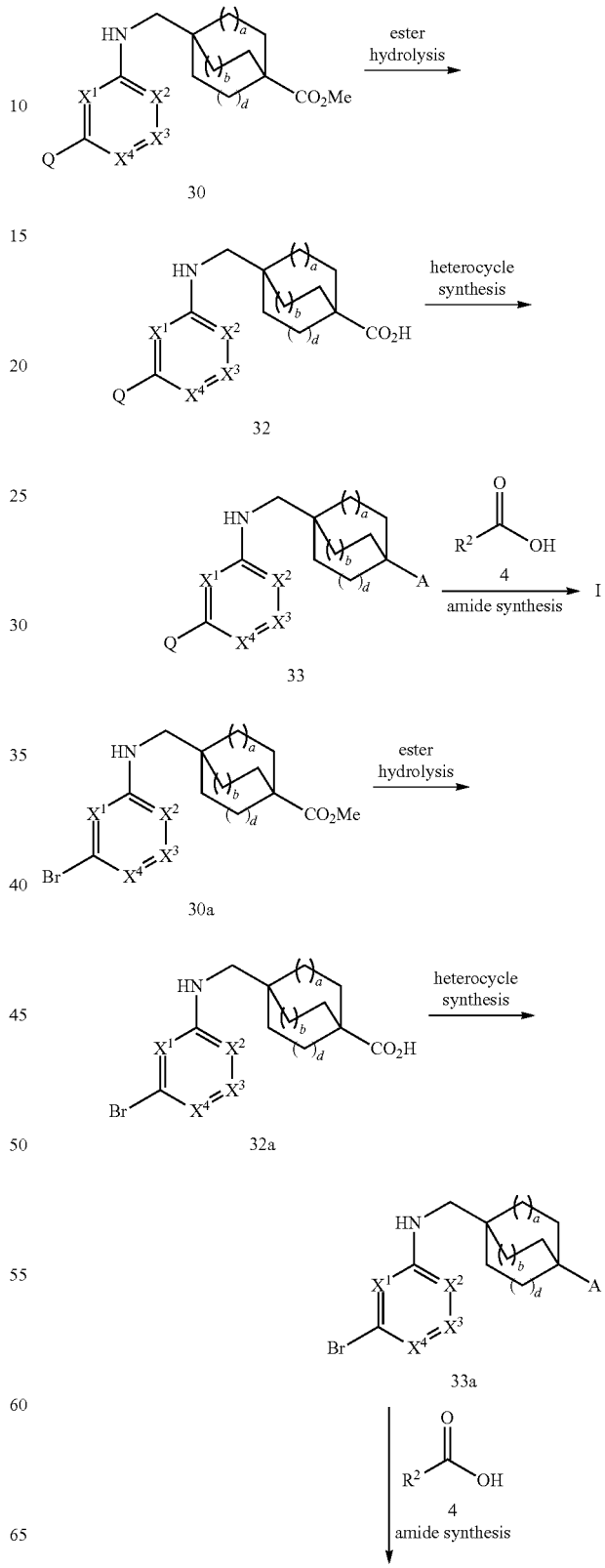

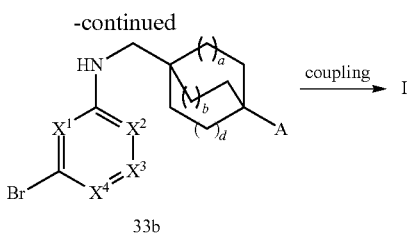

33b

Scheme 13 describes an alternative synthesis of compounds of Formula I with the modified sequence of steps.

Intermediate 30 (described in Scheme 12) can be subjected to hydrolysis of the methyl ester with an alkali hydroxide base to provide intermediate 32. Intermediate 32 can be converted to various heterocycles (A) using numerous known methods recognized by one skilled in the art, including but not limited to the methods described in Scheme 11 to afford compounds of formula 33. Intermediate 4 can be activated for acylation using any number of reagents recognizable by one skilled in the art (e.g. Thionyl chloride, phosphorus oxychloride, oxalyl chloride, methyl or ethylchloroformate, etc.), in a polar aprotic solvent (e.g. DCM, THF, etc.), at temperatures ranging between −30° C. to reflux temperatures. The activated acid intermediate can be reacted with intermediate 33 in presence of a base to generate compounds of formula I.

Alternatively, intermediate 30a (described in Scheme 12) can be subjected to hydrolysis of the methyl ester with an alkali hydroxide base to provide intermediate 32a. Intermediate 32a can be converted to various heterocycles (A) using numerous known methods recognized by one skilled in the art, including but not limited to the methods described in Scheme 11 to afford compounds of formula 33a. Intermediate 4 can be activated for acylation using any number of reagents recognizable by one skilled in the art (e.g. Thionyl chloride, phosphorus oxychloride, oxalyl chloride, methyl or ethylchloroformate, etc.), in a polar aprotic solvent (e.g. DCM, THF, etc.), at temperatures ranging between −30° C. to reflux temperatures. The activated acid intermediate can be reacted with intermediate 33a in presence of a base to generate intermediate 33b. Intermediate 33b can be subjected to metal catalyzed cross coupling reactions using numerous known methods recognized by the one skilled in the art including but not limited to the ones described in Metal-Catalyzed Cross-Coupling Reactions, Armin de Meijere, François Diederich, 2 Volumes, Second, Revised and Enlarged Edition, 2004, ISBN: 3-527-30518-1, Wiley-VCH and references cited therein. Intermediate 33b can be subjected to various metal catalyzed reactions (including but not limited to reactions such as Ullmann, Buchwald, Suzuki, Stille, Sonogashira coupling, etc.) These coupling reactions can be carried out in presence of metal catalyst (e.g. CuBr, Pd(OAc)$_2$, Pd$_2$(dba)$_3$, Pd(PPh$_3$)$_4$, Pd(PPh$_3$)$_2$Cl$_2$, Pd(dppf)Cl$_2$, etc.) and appropriate ligand (including but not limited to ligands such as proline, 1,10-phenanthroline, tricyclohexylphosphine, dppf, etc.) as and when required. The Ullmann and Buchwald coupling reactions of intermediate 33b can be carried out with various coupling partners such as alkyl or cycloalkyl or heterocyclyl or heteroaryl amines, alkyl or cycloalkyl or heterocyclyl or heteroaryl alcohols, phenols, etc. Intermediate 33b can be subjected to Suzuki, Heck, Stille, etc. cross couplings with coupling partners such as alkyl, allyl, alkenyl boronic acids, boronic acid esters, trifluoroborate salts; alkyl, allyl, alkynyl, organotin reagents, etc. The coupling reactions can be carried out in presence of base as necessary (including but not limited to Na$_2$CO$_3$, K$_2$CO$_3$, NaHCO$_3$, K$_3$PO$_4$, NaO$^t$Bu, etc.) and solvent (e.g. dioxane, THF, DME, toluene, methanol, DMF, water, etc. or the mixture of two or three of these solvents) under heating conditions to afford compounds of formula I. Alternatively, intermediate 33b can be converted to organotin reagent using hexamethylditin in presence of a palladium catalyst and in solvent (e.g. Toluene, THF etc.) at reflux temperature, which upon coupling with suitable coupling partners such as alkyl, acyl, alkenyl, allyl halides, triflates etc. in a Stille coupling (Sherer, B., et al. PCT Int. Appl., 2016/039734, 2016) afforded compounds represented by formula I. Intermediate 33b can be converted to organoboron reagent using bis(pinacolato)diboron, bis(neopentyl glycolato)diboron, etc in presence of a palladium catalyst such as Pd(dppf)Cl$_2$ and base such as potassium acetate in solvent (e.g. dioxane, DMSO etc.) at reflux temperature, which upon coupling with suitable coupling partners such as alkenes, alkenyl halides or triflates etc. in a Suzuki coupling afforded compounds represented by formula I. Intermediate 33b can be subjected to coupling reaction with dimethyl phosphine oxide in presence of palladium catalyst such as bis(dibenzylideneacetone)palladium and ligand such as XantPhos and inorganic base such as cesium carbonate in solvent (e.g. dioxane, DMSO etc.) under heating conditions to afford corresponding phosphine oxide.

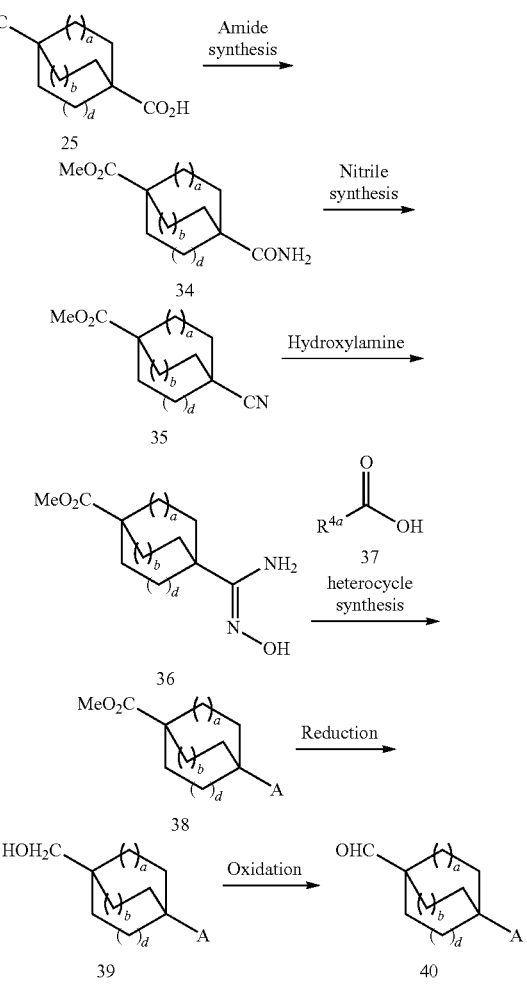

SCHEME 14

Scheme 14 describes the synthesis of intermediate 40 where A is 3-(5-substituted-1,2,4-oxadiazolyl) ring. Commercially available 4-(methoxycarbonyl)bicyclo[2.2.2]octane-1-carboxylic acid 25 can be subjected to amide synthesis by treating with activation agent such as BOP, HATU, etc. in presence of solvent such as DCM, DMF, etc. and an organic base such as Et₃N, DIPEA, etc. at ambient temperature in presence of ammonium chloride to afford intermediate 34. Intermediate 34 can be converted to intermediate 35 by treatment with trifluoroacetic anhydride in pyridine at 0° C. or by treatment with POCl₃ and a base such as imidazole. Intermediate 36 can be synthesized by reaction of intermediate 35 with hydroxylamine; see Hirawat, S., et al. WO 2006/110483. Variously substituted intermediates 37 can be coupled with intermediates 36 using an amide bond coupling reagent (e.g. CDI, BOP, EDC, etc.) in a polar aprotic solvent (e.g. THF, 1,4-dioxane, DMF, etc.) at room temperature. The acyclic intermediate can be subsequently cyclized at elevated temperatures (60° C. to 100° C.). Alternatively, in situ cyclization can be accomplished by conducting the coupling of acids 37 with amide oximes 36 at elevated temperatures (60° C. to 100° C.) to afford intermediates of formula 38. Reduction of intermediate 38 can be accomplished in presence of hydride based reducing agents (e.g. LAH, DIBAL-H, NaBH₄, etc.) in chlorinated or ethereal solvent such as DCM, ether, 1,4-dioxane, THF, etc. To afford intermediate 39. Intermediate 39 can be oxidized to intermediate 40, by methodologies recognized by one skilled in the art using oxidation conditions (e.g. Dess-Martin periodinane, Swern oxidation conditions, PDC or PCC, etc.). Intermediates 40 can be converted to compounds of formula I by steps described in Scheme 1.

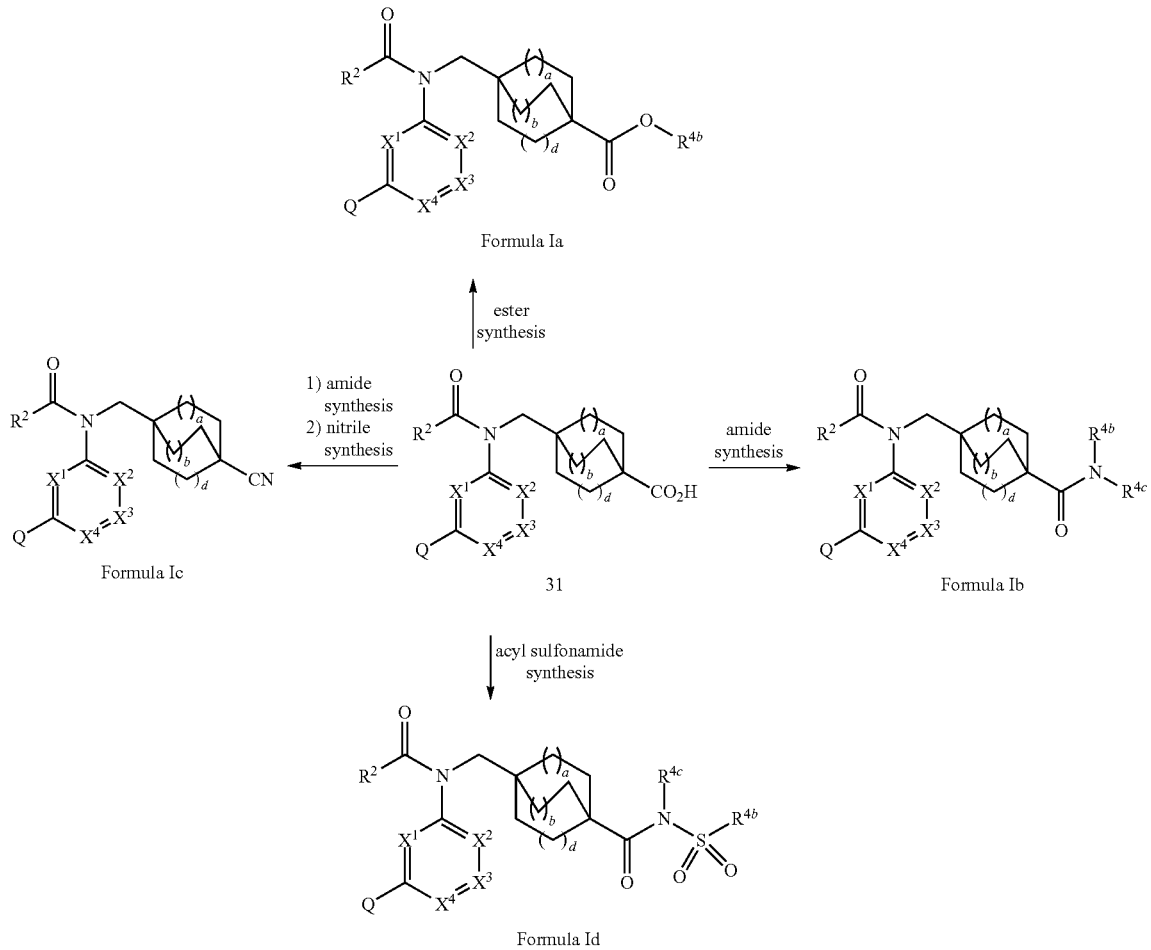

Scheme 15 describes the synthesis of compounds of formula I(a-d). The intermediates represented by formula 31 (synthesis described in Scheme 12) can be subjected to esterification. Intermediate 31 can be activated for acylation using any number of reagents recognizable by one skilled in the art (e.g. Thionyl chloride, phosphorus oxychloride, oxalyl chloride, methyl or ethylchloroformate, etc.), in a polar aprotic solvent (e.g. DCM, THF, etc.), at temperatures ranging between −30° C. to reflux temperatures. The activated acid intermediate can be reacted with alcohols in presence of a base to generate compounds of formula Ia. Intermediate 31 can be subjected to amide synthesis by activating acid with activation agent (e.g. BOP, CDI, HATU, etc.) in solvent (e.g. DCM, DMF, etc.) in presence of base (e.g. Et₃N, DIPEA, etc.) at ambient temperature or heating conditions in presence of ammonium chloride or substituted amine (e.g. alkyl, cycloalkyl, aryl, heteroaryl, etc.) to afford amides of formula Ib. Intermediate 31 can be subjected to primary amide synthesis by treating with activation agent (e.g. BOP, CDI, HATU, etc.) in solvent (e.g. DCM, DMF, etc.) in presence of base (e.g. Et$_3$N, DIPEA, etc.) and ammonium chloride at ambient temperature. The primary amide so obtained can be treated with i) trifluoroacetic anhydride in pyridine at 0° C. or ii) POCl$_3$ and imidazole to afford nitriles of formula Ic. Intermediate 31 can be activated using any number of reagents recognizable by one skilled in the art (e.g. Thionyl chloride, phosphorus oxychloride, oxalyl chloride, methyl or ethylchloroformate, etc.), in a polar aprotic solvent (e.g. DCM, THF, etc.), at temperatures ranging between −30° C. to reflux temperatures. The activated acid intermediate can be reacted with a sulfonamides in presence of a base (e.g. pyridine, DMAP, 2-(dimethylamino)pyridine, N-methylmorpholine, etc.) in a polar aprotic solvent (e.g. DCM, THF, etc.), at temperatures ranging between 0° C. to 90° C. to generate acyl sulfonamides of formula Id.

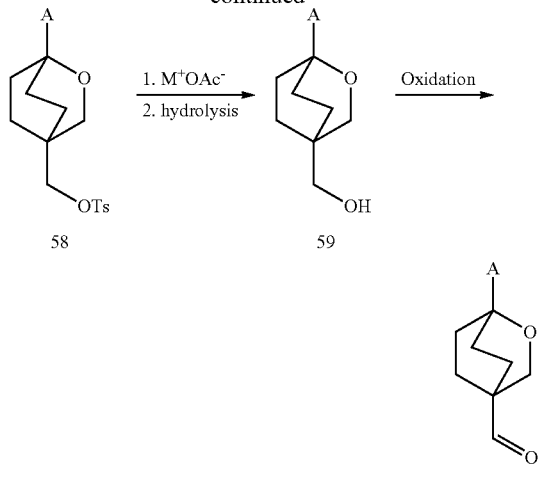

Scheme 16 describes the synthesis of intermediate 2a. Intermediate 52 can be synthesized according to methods described by Singh, S. B. et al. (*ACS Med. Chem. Lett.* 2014, 5, 609-614). Intermediate 53 can be deprotonated with n-BuLi in an ethereal solvent (e.g. THF, 1,4-dioxane, etc.) with temperature varying between −78° C. and 0° C., then reacted with intermediate 52 to yield intermediate 54. Intermediate 54 can be cyclized in the presence of an alkali hydroxide base at elevated temperature (70° C.) to form intermediate 55. Thioacetal deprotection can be accomplished using any number of reagents (e.g. NCS, Hg(ClO$_4$)$_2$, DDQ, etc.) to provide the aldehyde, which can be oxidized to the acid by use of an oxidizing agent (NaClO$_2$, PCC or PDC, KMnO$_4$, etc.) then subsequently esterified by reaction with iodomethane to provide intermediate 56. Subsequent hydrolysis of the intermediate 56 with an alkali hydroxide base can provide intermediate 57. Intermediate 57 can be converted to various heterocycles (A) using numerous known methods recognized by one skilled in the art, including but not limited to the methods described in Scheme 11 to afford compounds of intermediate 58. Intermediate 58 can be treated with an acetate salt (e.g. CsOAc, KOAc, etc.) in a polar aprotic solvent (e.g. DMF, NMP, etc.) at elevated temperatures (120° C.) to provide corresponding acetate, which upon subsequent hydrolysis under acidic conditions (HCl) afforded intermediate 59. Intermediate 59 can be oxidized by methodologies recognized by one skilled in the art using oxidation conditions (e.g. Dess-Martin periodinane, Swern oxidation conditions, PDC or PCC, etc.) to afford compounds of formula 2a. The intermediates 2a can be converted to compounds of formula I by using steps described in Scheme 1.

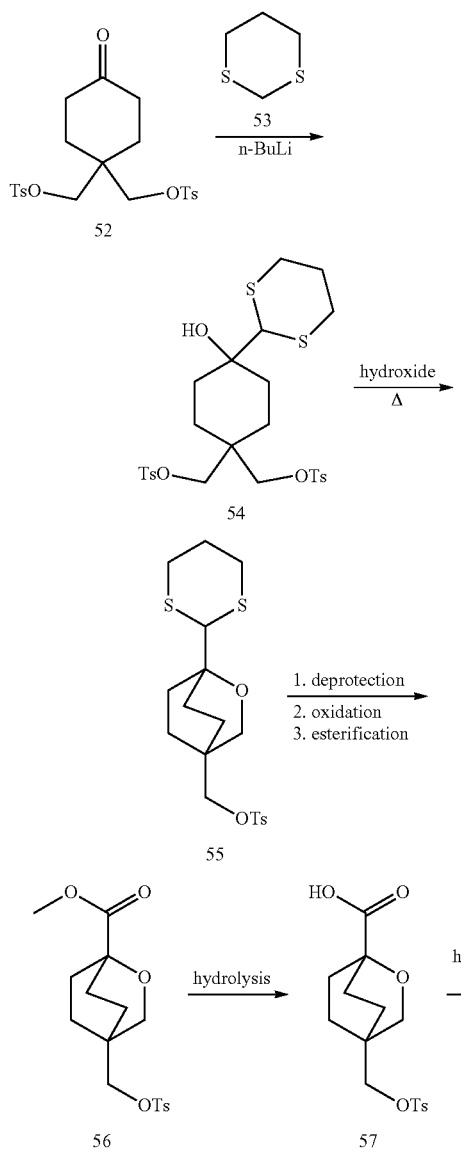

SCHEME 17

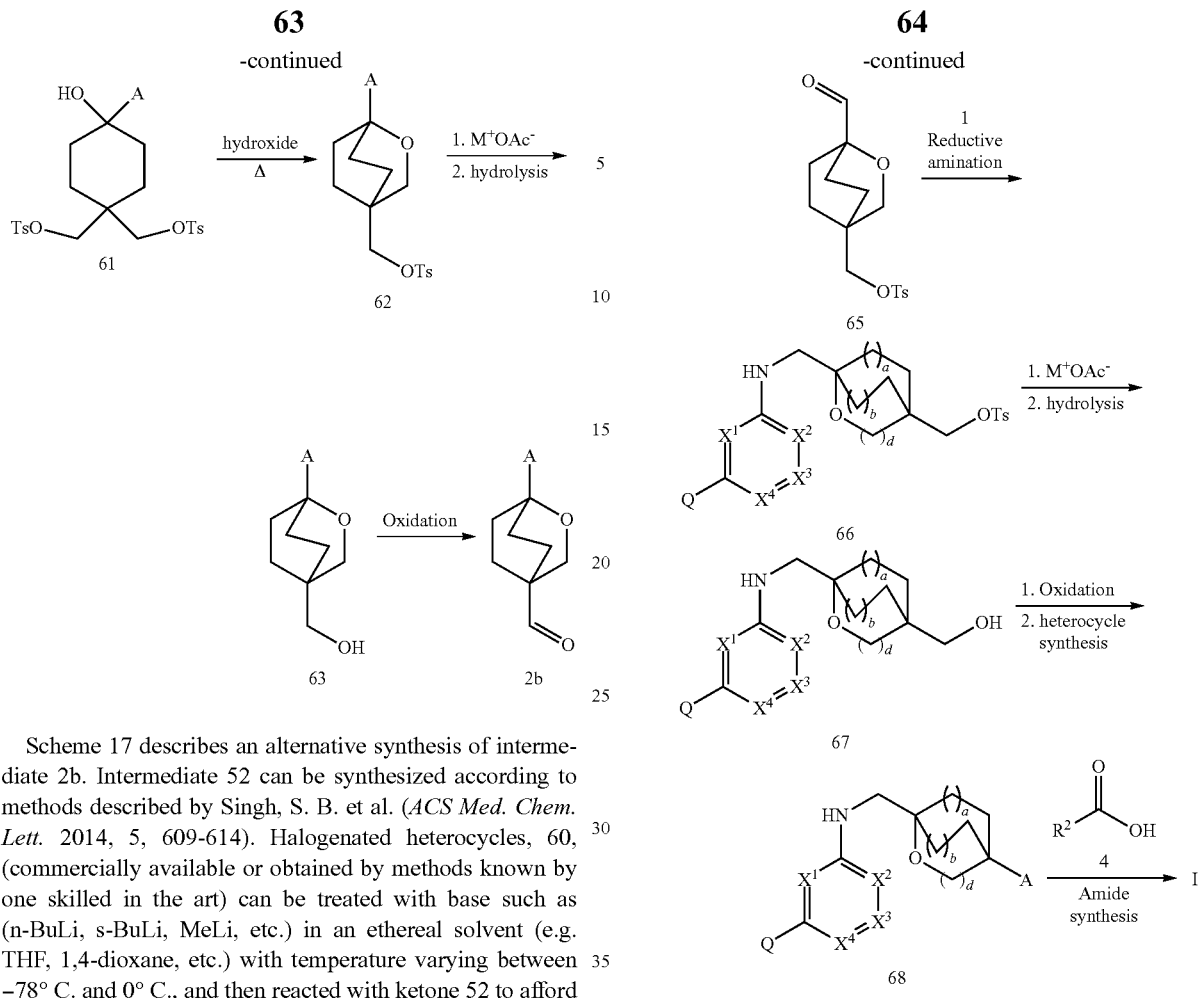

Scheme 17 describes an alternative synthesis of intermediate 2b. Intermediate 52 can be synthesized according to methods described by Singh, S. B. et al. (*ACS Med. Chem. Lett.* 2014, 5, 609-614). Halogenated heterocycles, 60, (commercially available or obtained by methods known by one skilled in the art) can be treated with base such as (n-BuLi, s-BuLi, MeLi, etc.) in an ethereal solvent (e.g. THF, 1,4-dioxane, etc.) with temperature varying between −78° C. and 0° C., and then reacted with ketone 52 to afford intermediate 61. Intermediate 61 can be cyclized in the presence of an alkali hydroxide base at elevated temperature (70° C.) to afford intermediate 62. Intermediate 62 can be treated with an acetate salt (e.g. CsOAc, KOAc, etc.) in a polar aprotic solvent (e.g. DMF, NMP, etc.) at elevated temperatures (120° C.) to provide corresponding acetate, which upon subsequent hydrolysis under acidic conditions (HCl) afforded intermediate 63. Intermediate 63 can be oxidized by methodologies recognized by one skilled in the art using oxidation conditions (e.g. Dess-Martin periodinane, Swern oxidation conditions, PDC or PCC, etc.) to afford intermediate 2b. Intermediate 2b can be converted to compounds of formula I by using steps described in Scheme 1.

SCHEME 18A

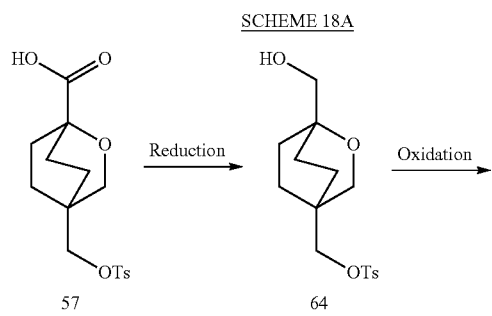

Scheme 18A describes an alternative synthesis of compounds of Formula I. Intermediate 57 (synthesis described in Scheme 16) can be subjected to reduction in presence of hydride based reducing agent (e.g. LAH, DIBAL-H, NaBH$_4$, etc.) to afford intermediate 64. The intermediate 64 can be oxidized to aldehyde 65, by methodologies recognized by one skilled in the art using oxidation conditions (e.g. Dess-Martin periodinane, Swern oxidation conditions, PDC or PCC, etc.). The intermediate 1 and intermediate 65 can be subjected to reductive amination, using numerous known methods recognizable by one skilled in the arts, in presence of acid such as acetic acid in a suitable polar protic solvent (e.g. MeOH, EtOH, etc.) at room temperature or reflux temperature followed by reduction of imine with reducing agents (e.g. sodium cyanoborohydride, sodium triacetoxyborohydride, etc.) afforded intermediate 66. Intermediate 66 can be treated with an acetate salt (e.g. CsOAc, KOAc, etc.) in a polar aprotic solvent (e.g. DMF, NMP, etc.) at elevated temperatures (120° C.) to provide corresponding acetate, which upon subsequent hydrolysis under acidic conditions (HCl) afforded intermediate 67. The intermediate 67 can be oxidized to the acid by use of an oxidizing agent (NaClO$_2$, PCC or PDC, KMnO$_4$, etc.) followed by synthesis of various heterocycles (A) using numerous known methods recognized by one skilled in the art, including but not limited to the methods described in Scheme 11 to afford intermediate 68. Intermediate 4 can be activated for acylation using any number of reagents recognizable by one skilled in the art (e.g. Thionyl chloride, phosphorus oxychloride, oxalyl chloride, methyl or ethylchloroformate, etc.), in a polar aprotic solvent (e.g. DCM, THF, etc.), at temperatures ranging between −30° C. to reflux temperatures. The activated acid intermediate can be reacted with intermediate 68 in presence of a base to generate compounds of formula I.

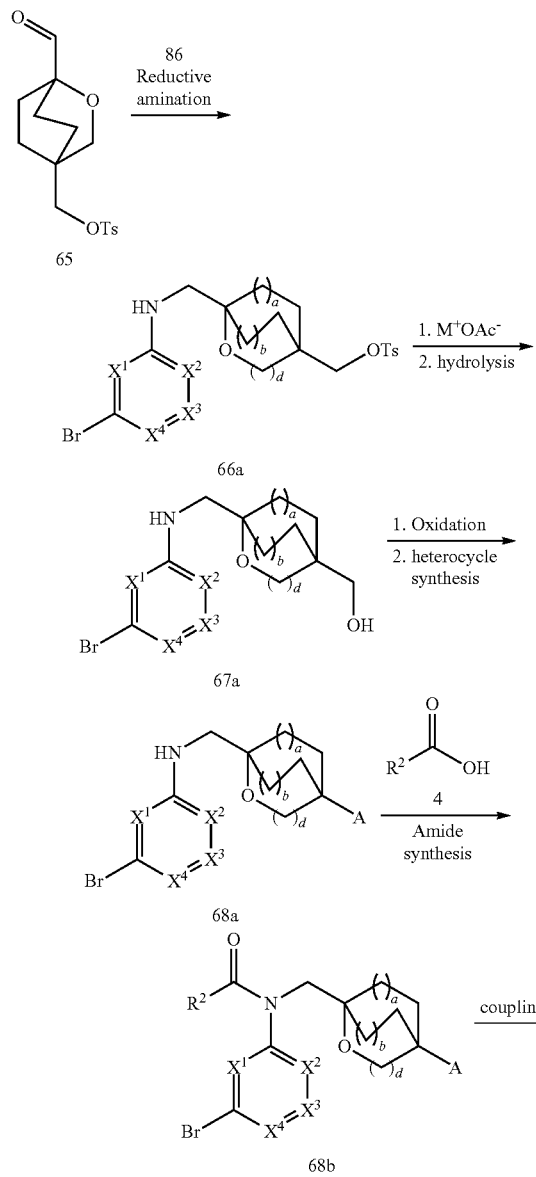

Scheme 18B describes an alternative synthesis of compounds of Formula I. The intermediate 86 and intermediate 65 (as described in Scheme 18A) can be subjected to reductive amination, using numerous known methods recognizable by one skilled in the art, in presence of acid such as acetic acid in a suitable polar protic solvent (e.g. MeOH, EtOH, etc.) at room temperature or reflux temperature followed by reduction of imine with reducing agents (e.g. sodium cyanoborohydride, sodium triacetoxyborohydride, etc.) afforded intermediate 66a. Intermediate 66a can be treated with an acetate salt (e.g. CsOAc, KOAc, etc.) in a polar aprotic solvent (e.g. DMF, NMP, etc.) at elevated temperatures (120° C.) to provide corresponding acetate, which upon subsequent hydrolysis under acidic conditions (HCl) afforded intermediate 67a. The intermediate 67a can be oxidized to the acid by use of an oxidizing agent (NaClO$_2$, PCC or PDC, KMnO$_4$, etc.) followed by synthesis of various heterocycles (A) using numerous known methods recognized by one skilled in the art, including but not limited to the methods described in Scheme 11 to afford intermediate 68a. Intermediate 68a can be converted via sequential amide synthesis and coupling to compounds of formula I by following steps described in Scheme 13.

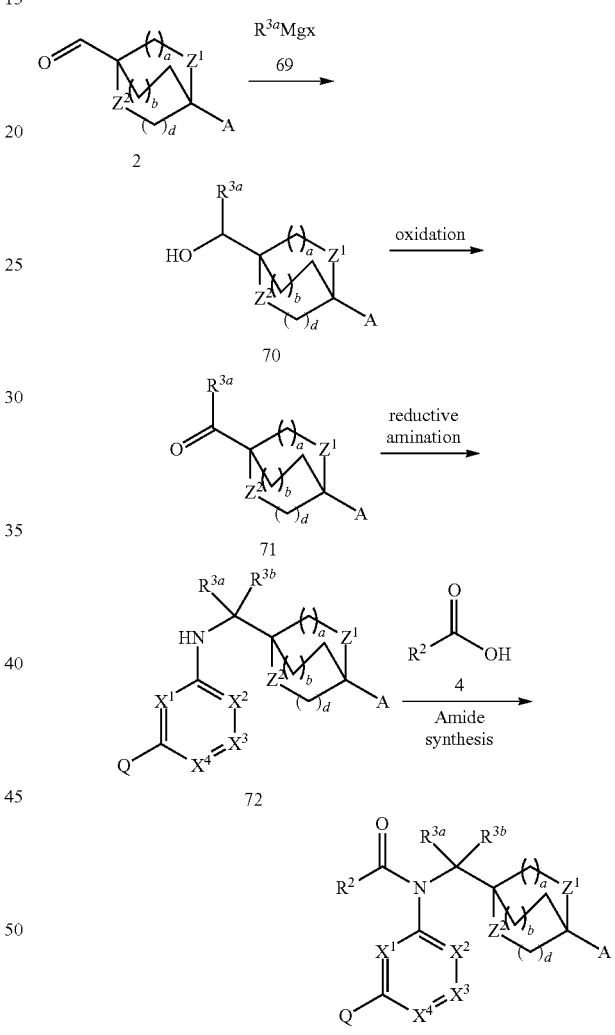

Scheme 19 describes an alternative synthesis of compounds of Formula I. Intermediate 2 can be subjected to treatment with organo magnesium reagents in ethereal solvent (such as Et$_2$O, THF, etc.) with temperature varying between −78° C. and 0° C. to afford intermediate 70. The intermediate 70 can be oxidized to intermediate 71, by methodologies recognized by one skilled in the art under oxidation conditions using oxidizing agents such as Dess-Martin periodinane, PDC or PCC, etc. Intermediate 71 and intermediate 1 in polar protic solvent such as (MeOH, EtOH, etc.) can be treated with triethyl silane and indium chloride at ambient temperature to afford intermediates of formula 72. Intermediate 4 can be activated for acylation using any number of reagents recognizable by one skilled in the art (e.g. Thionyl chloride, phosphorus oxychloride, oxalyl chloride, methyl or ethylchloroformate, etc.), in a polar aprotic solvent (e.g. DCM, THF, etc.), at temperatures ranging between −30° C. to reflux temperatures. The activated acid intermediate can be reacted with intermediate 72 in presence of a base to generate compounds of formula I.

Scheme 20 describes synthesis of compounds of formula I(e-g) (where 'A' is amide, sulfonamide, urea or carbamate). Intermediate 25 can be converted to intermediate 73 via Curtius rearrangement (as described in Shioiri, T. et al. *J. Am. Chem. Soc.* 1972, 94, 6203-6205). Intermediate 73 can be subjected to reduction in presence of hydride based reducing agent (e.g. LAH, DIBAL-H, NaBH$_4$, etc.) to afford intermediate 74. The intermediate 74 can be oxidized to aldehyde 75, by methodologies recognized by one skilled in the art using oxidation conditions (e.g. Dess-Martin perio-

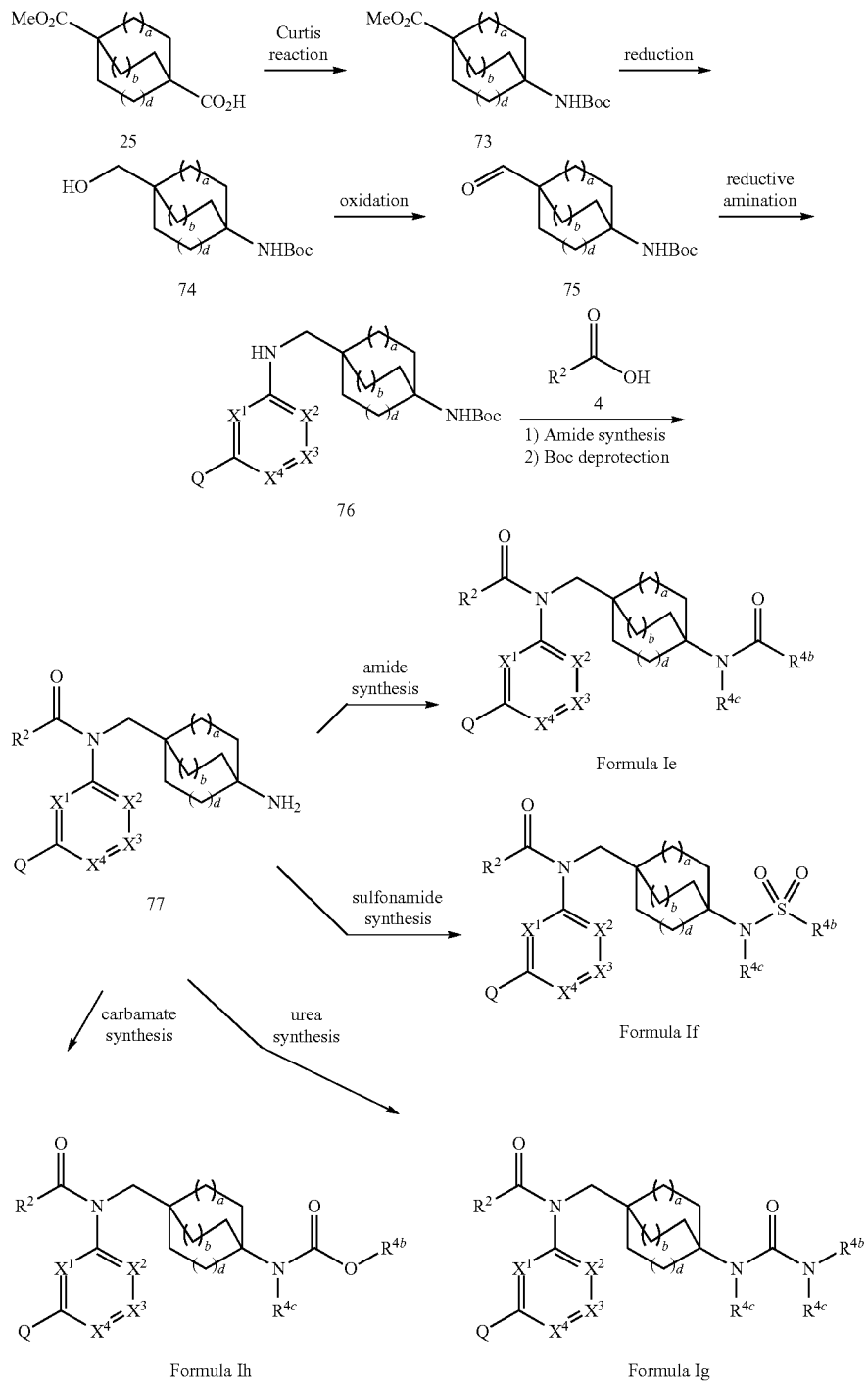

dinane, Swern oxidation conditions, PDC or PCC, etc.). The intermediate 1 and intermediate 75 can be subjected to reductive amination, using numerous known methods recognizable by one skilled in the art, in presence of acid such as acetic acid in a suitable polar protic solvent (e.g. MeOH, EtOH, etc.) at room temperature or reflux temperature followed by reduction of imine with reducing agents (e.g. sodium cyanoborohydride, sodium triacetoxyborohydride, etc.) to afford intermediate 76. Intermediate 4 can be activated for acylation using any number of reagents recognizable by one skilled in the art (e.g. Thionyl chloride, phosphorus oxychloride, oxalyl chloride, methyl or ethylchloroformate, etc.), in a polar aprotic solvent (e.g. DCM, THF, etc.), at temperatures ranging between −30° C. to reflux temperatures. The activated acid intermediate can be reacted with intermediate 76 in presence of a base to generate corresponding amide. The amide intermediate can be subjected to Boc-deprotection in polar aprotic solvent (e.g. DCM, THF, etc.) using trifluoroacetic acid at room temperature to afford intermediate 77. Intermediate 77 can be subjected to a variety of different transformations using numerous known methods recognized by one skilled in the art, including but not limited to the following methods to afford variations of Formula I:

Amides: Intermediate 77 can be reacted with activated acid intermediates in presence of base (e.g. pyridine, DMAP, 2-(dimethylamino)pyridine, N-methylmorpholine, etc.) in polar aprotic solvent (e.g. DCM, THF, etc.) to generate amides of Formula Ie.

Sulfonamides: Intermediate 77 can be treated with sulfonyl chlorides in presence of a base (e.g. pyridine, DMAP, 2-(dimethylamino)pyridine, N-methylmorpholine, etc.) in a polar aprotic solvent (e.g. DCM, THF, etc.), at temperatures ranging between 0° C. to 90° C. to generate sulfonamides of Formula If.

Ureas: Intermediate 77 can be subjected to treatment with isocyanates in presence of base (e.g. Et₃N, DIPEA, pyridine etc.) in polar aprotic solvent (e.g. DCM, DCE, etc.) at room temperature to afford ureas represented by formula Ig. Alternatively, intermediate 77 can be activated by treatment with triphosgene in presence of base (e.g. Et₃N, DIPEA, etc.) in solvent (e.g. DCM, DCE, etc.) at 0° C. to room temperature. The activated intermediate 77 can then be treated with substituted alkyl or aryl or heteroaryl amine in presence of base (e.g. Et₃N, DIPEA, etc.) in solvent (e.g. DCM, DCE, etc.) at room temperature to afford ureas represented by formula Ig.

Carbamates: Intermediate 77 can be treated with chloroformates (or alcohols, activated as carbonates) in presence of base (e.g. Et₃N, DIPEA, pyridine, t-BuOK etc.) in polar aprotic solvent (e.g. DCM, DCE, THF, etc.) at 0° C. to room temperature to afford carbamates represented by formula Ih.

SCHEME 21

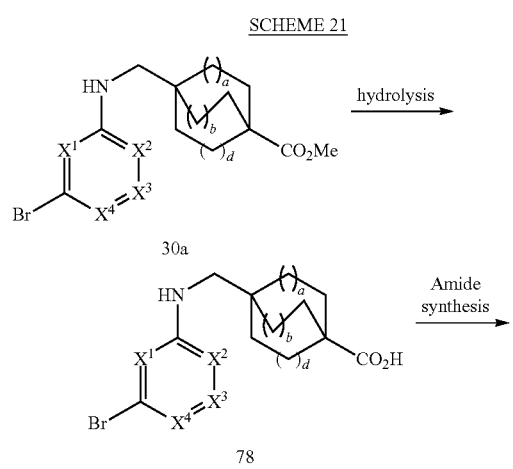

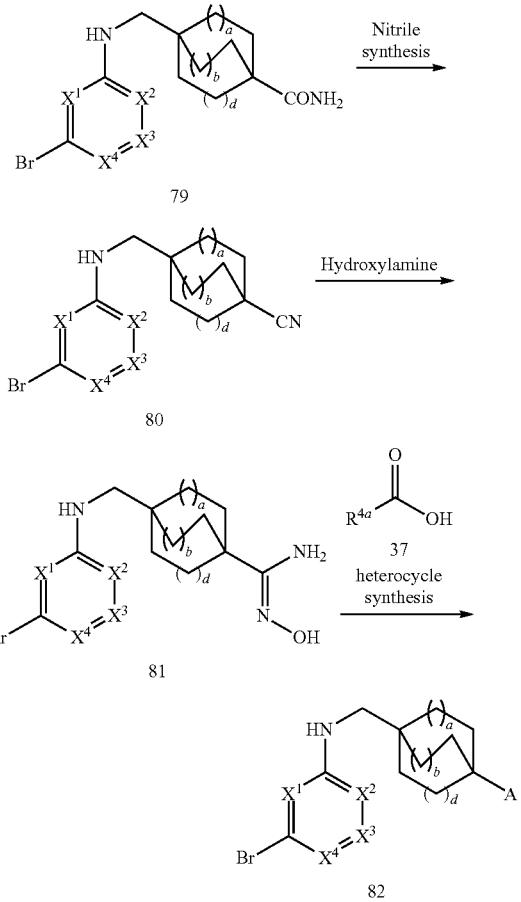

Scheme 21 describes the synthesis of intermediates 82 where A is 3-(5-substituted-1,2,4-oxadiazolyl) ring. Intermediate 30a (synthesized as described in Scheme 12) can be hydrolyzed with an alkali hydroxide base to afford intermediate 78. Intermediate 78 can be subjected to primary amide synthesis by activating acid with activation agent (BOP, CDI, HATU, etc.) in polar aprotic solvent (DCM, DMF, etc.) in presence of base (e.g. Et₃N, DIPEA, etc.) at ambient temperature in presence of ammonium chloride to afford intermediate 79. Intermediate 79 can be converted to intermediate 80 using various methods recognized by those skilled in the art including but not limited to the treatment with reagent (POCl₃, SOCl₂, TFAA, etc.) and base (imidazole, Et₃N, DIPEA, etc.). Intermediate 81 can be synthesized by reaction of intermediate 80 with hydroxylamine; see Hirawat, S., et al. WO 2006/110483. Intermediate 37 can be obtained from commercial sources or can be synthesized by known methods readily recognizable by one skilled in the art. Intermediates 37 can be coupled with intermediates 81 using an amide bond coupling reagent (e.g. CDI, BOP, EDC, etc.) in a polar aprotic solvent (e.g. THF, 1,4-dioxane, DMF, etc.) at room temperature. The acyclic intermediate can be subsequently cyclized at elevated temperatures (60° C. to 100° C.). Alternatively, in situ cyclization can be accomplished by conducting the coupling of intermediates 37 with intermediates 81 at elevated temperatures (60° C. to 100° C.) to afford oxadiazoles 82. Intermediates 82 can be converted to compounds of formula I via a sequential amide synthesis and coupling as described in Scheme 13.

SCHEME 22

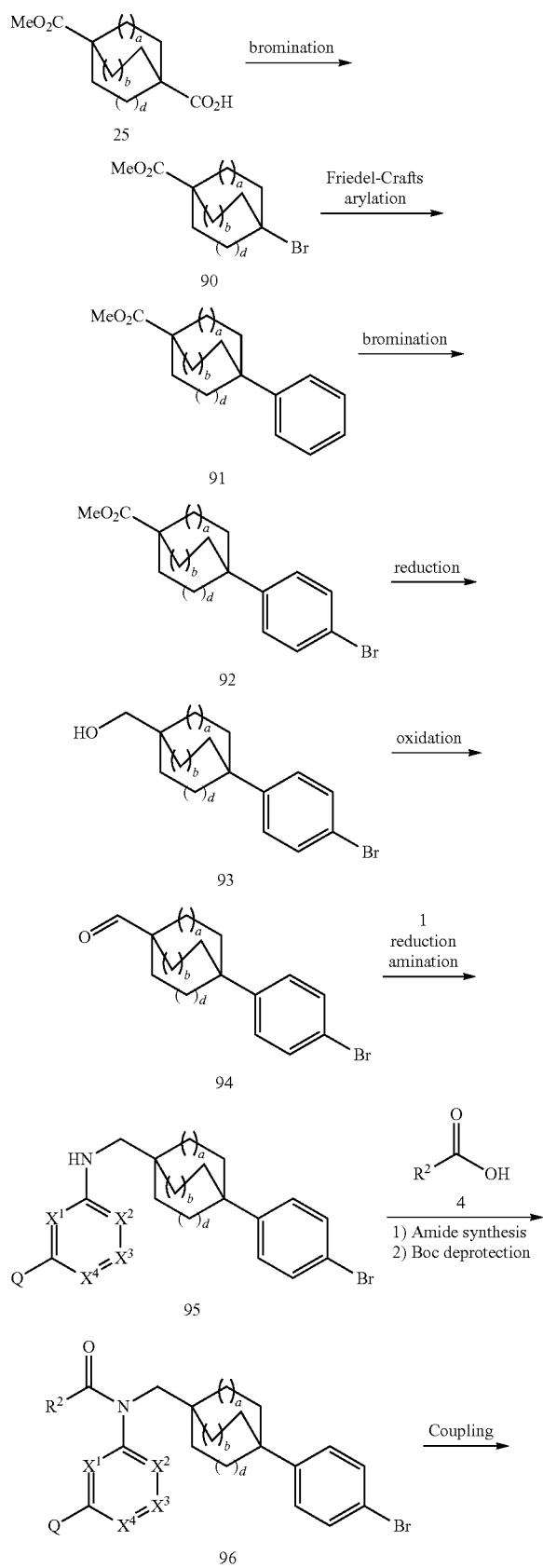

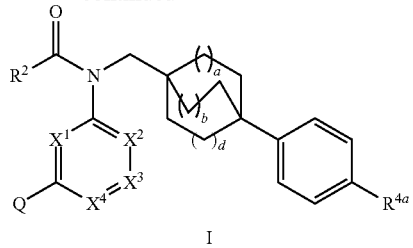

Scheme 22 describes synthesis of compounds of formula I (where 'A' is phenyl). Commercially available 4-(methoxycarbonyl)bicyclo[2.2.2]octane-1-carboxylic acid 25 can be subjected to bromination reaction with bromine in presence of mercuric oxide in dibromomethane as a solvent under heating conditions to afford intermediate 90 (as described by Owen et. al. PCT Int. Appl., 2014113485, 2014). Intermediate 90 can be converted to intermediate 91 in benzene in presence of $AlCl_3$ under conditions described by Piyasena et. al. PCT Int. Appl., 2015005901, 2015. Intermediate 91 can be subjected to bromination in presence of silver trifluoroacetate and bromine in $CHCl_3$ at room temperature to afford intermediate 92 (described by Piyasena et. al. PCT Int. Appl., 2015005901, 2015). Intermediate 92 can be subjected to reduction in presence of hydride based reducing agent (e.g. LAH, DIBAL-H, $NaBH_4$, etc.) to afford intermediate 93. The intermediate 93 can be oxidized to aldehyde 94, by methodologies recognized by one skilled in the art using oxidation conditions (e.g. Dess-Martin periodinane, Swern oxidation conditions, PDC or PCC, etc.). The intermediate 1 and intermediate 94 can be subjected to reductive amination, using numerous known methods recognizable by one skilled in the art, in presence of acid such as acetic acid in a suitable polar protic solvent (e.g. MeOH, EtOH, etc.) at room temperature or reflux temperature followed by reduction of imine with reducing agents (e.g. sodium cyanoborohydride, sodium triacetoxyborohydride, etc.) afforded intermediate 95. Intermediate 4 can be activated for acylation using any number of reagents recognizable by one skilled in the art (e.g. Thionyl chloride, phosphorus oxychloride, oxalyl chloride, methyl or ethylchloroformate, etc.), in a polar aprotic solvent (e.g. DCM, THF, etc.), at temperatures ranging between −30° C. to reflux temperatures. The activated acid intermediate can be reacted with intermediate 95 in presence of a base to generate intermediate 96. Intermediate 96 can be subjected to various metal catalyzed reactions (including but not limited to reactions such as Ullmann, Suzuki, Buchwald, Stille coupling, etc.) in presence of metal catalyst (e.g. CuBr, $Pd(OAc)_2$, $Pd_2(dba)_3$, $Pd(PPh_3)_4$, $Pd(PPh_3)_2Cl_2$, $Pd(dppf)Cl_2$, etc.) and appropriate ligand (including but not limited to ligands such as tricyclohexylphosphine, dppf, etc.) when necessary. The Ullmann and Buchwald coupling reactions of intermediate 96 can be carried out with various coupling partners such as alkyl or aryl or heteroaryl amines, thiols and alcohols, etc. The Suzuki, Stille coupling reaction of intermediate 96 can be carried out with various coupling partners such as alkenyl, aryl or heteroaryl boronic acids, boronic acid esters, organotin reagents, etc. The coupling reactions can be carried out in presence of base whenever necessary (including but not limited to $Na_2CO_3$, $K_2CO_3$, $NaHCO_3$, $K_3PO_4$, $NaO^tBu$, etc.) and solvent (e.g. dioxane, THF, DME, toluene, methanol, DMF, water, etc. or the mixture of two or three of these solvents) under heating conditions to afford compounds of formula I.

SCHEME 23

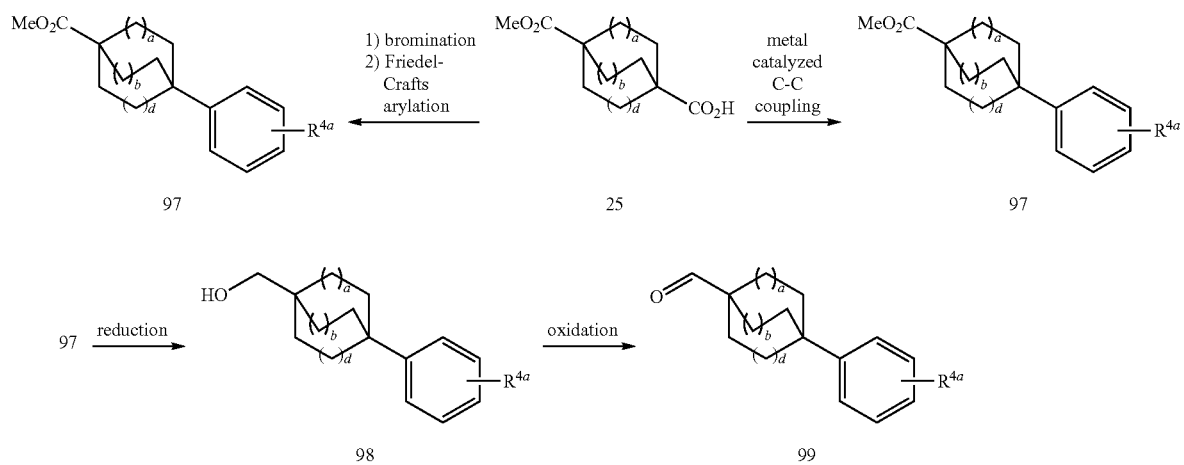

Scheme 23 describes the synthesis of intermediates 99. Commercially available 4-(methoxycarbonyl)bicyclo[2.2.2]octane-1-carboxylic acid 25 can be subjected to bromination followed by Friedel-Crafts arylation in presence of suitably substituted arenes as described in Scheme 22 to afford intermediate 97. Alternatively, intermediate 97 can be synthesized via decarboxylative Negishi- or Suzuki type cross coupling reactions. Intermediate 25 can be activated as N-hydroxyphthalimide ester or N-hydroxybenzotriazole ester, etc., as redox-active ester and can be treated with organozincs or organoboronic acids or Grignard reagents of variously substituted aryls in presence of metal catalysts (e.g. Fe(acac)$_3$, FeCl$_3$, NiCl$_2$·glyme, etc.) as described by Torriyama, F. et al *J. Am. Chem. Soc.* 2016, 138, 11132-11135 and references cited therein to afford intermediate 97. Intermediate 97 can be subjected to reduction in presence of hydride based reducing agent (e.g. LAH, DIBAL-H, NaBH$_4$, etc.) to afford intermediate 98. The intermediate 98 can be oxidized to aldehyde 99, by methodologies recognized by one skilled in the art using oxidation conditions (e.g. Dess-Martin periodinane, Swern oxidation conditions, PDC or PCC, etc.). Intermediate 99 can be converted to compounds of formula I (where 'A' is phenyl) by using steps described in Scheme 1.

SCHEME 24

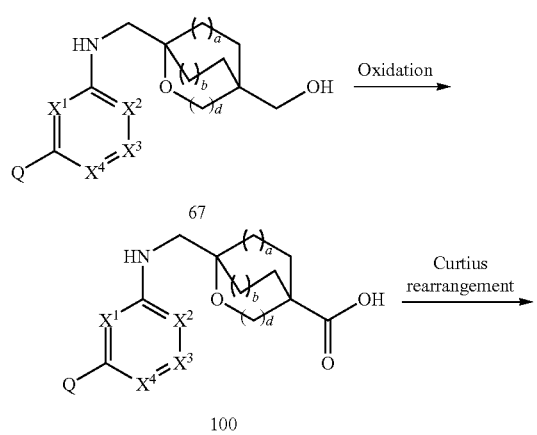

-continued

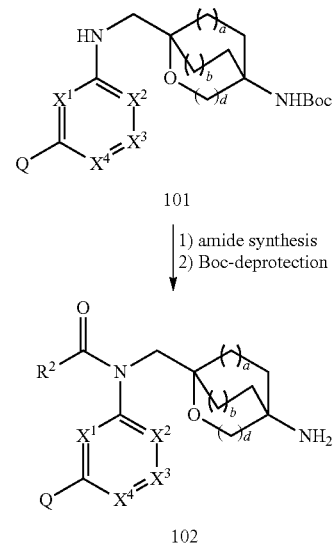

Scheme 24 describes alternative synthesis of compounds of formula I (where 'A' is amide, sulfonamide, urea or carbamate). Intermediate 67 (synthesized as described in Scheme 18A) can be oxidized by use of an oxidizing agent (NaClO$_2$, PCC or PDC, KMnO$_4$, etc.) to afford intermediate 100. Intermediate 100 can be converted to intermediate 101 via Curtius rearrangement (as described in Shioiri, T. et al. *J. Am. Chem. Soc.* 1972, 94, 6203-6205). Intermediates 101 can be subjected to sequential amide synthesis and boc-deprotection as described in Scheme 20 to afford the amine intermediate 102. Intermediate 102 can be subjected to a variety of different transformations using numerous known methods recognized by one skilled in the art, including but not limited to the methods described in Scheme 20 to afford variations of Formula I (where 'A' is amide, sulfonamide, urea or carbamate).

SCHEME 25

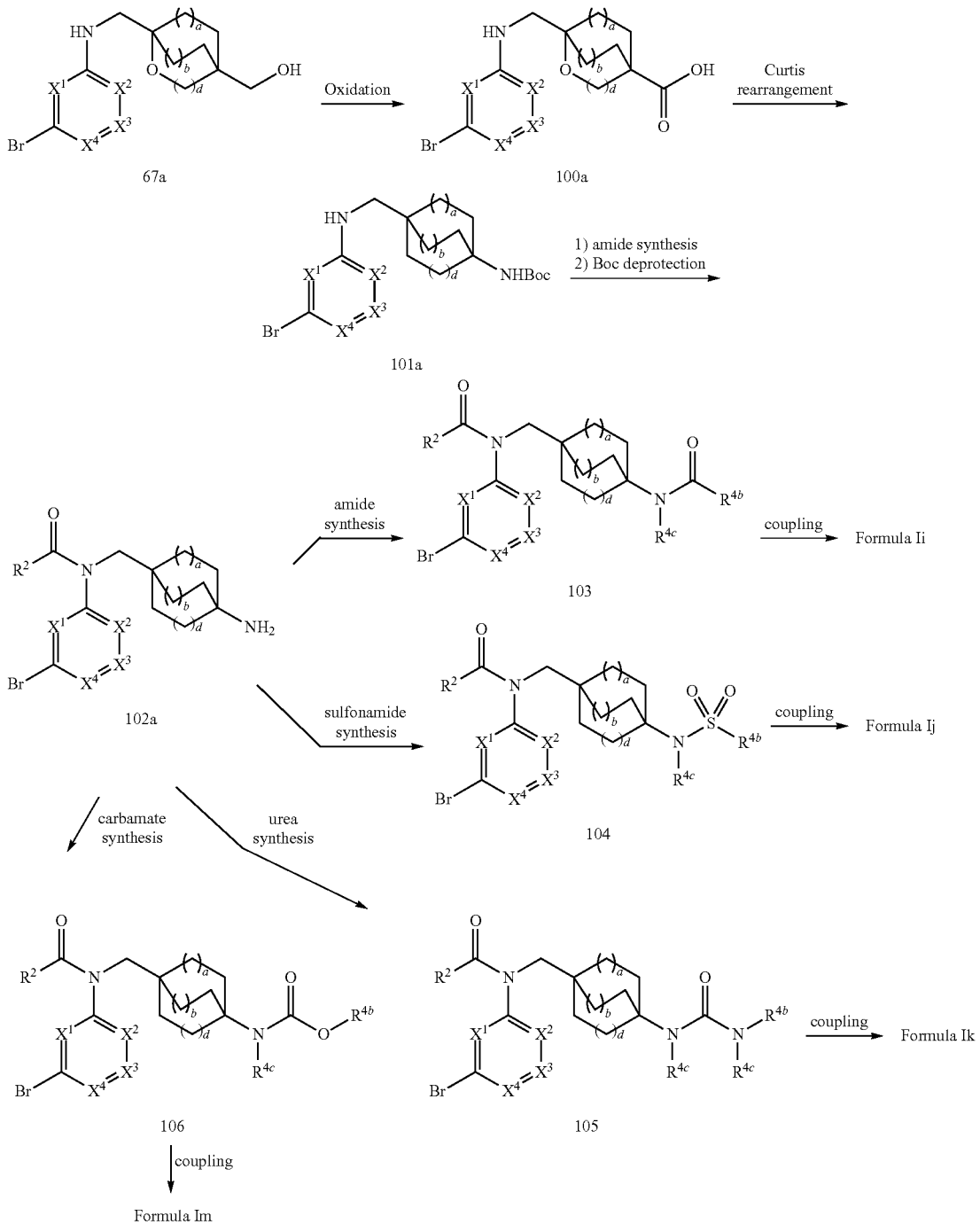

Scheme 25 describes synthesis of compounds of formula I(i,j,k,m) (where 'A' is amide, sulfonamide, urea or carbamate). Intermediate 67a (synthesized as described in Scheme 18B) can be oxidized by use of an oxidizing agent ($NaClO_2$, PCC or PDC, $KMnO_4$, etc.) to afford intermediate 100a. Intermediate 100a can be converted to intermediate 101a via Curtius rearrangement (as described in Shioiri, T. et al. *J. Am. Chem. Soc.* 1972, 94, 6203-6205). Intermediates 101a can be subjected to sequential amide synthesis and boc-deprotection as described in Scheme 20 to afford the amine intermediate 102a.

Intermediate 102a can be subjected to a variety of different transformations using numerous known methods recognized by one skilled in the art, including but not limited to the following methods to afford variations of Formula I:

Amides: Intermediate 102a can be reacted with activated acid intermediates in presence of base (e.g. pyridine, DMAP, 2-(dimethylamino)pyridine, N-methylmorpholine, etc.) in polar aprotic solvent (e.g. DCM, THF, etc.) to generate intermediate 103.

Sulfonamides: Intermediate 102a can be treated with sulfonyl chlorides in presence of a base (e.g. pyridine, DMAP, 2-(dimethylamino)pyridine, N-methylmorpholine, etc.) in a polar aprotic solvent (e.g. DCM, THF, etc.), at temperatures ranging between 0° C. to 90° C. to generate intermediate 104.

Ureas: Intermediate 102a can be subjected to treatment with isocyanates in presence of base (e.g. Et$_3$N, DIPEA, pyridine etc.) in polar aprotic solvent (e.g. DCM, DCE, etc.) at room temperature to afford intermediate 105. Alternatively, intermediate 102a can be activated by treatment with triphosgene in presence of base (e.g. Et$_3$N, DIPEA, etc.) in solvent (e.g. DCM, DCE, etc.) at 0° C. to room temperature. The activated intermediate 102a can then be treated with substituted alkyl or aryl or heteroaryl amine in presence of base (e.g. Et$_3$N, DIPEA, etc.) in solvent (e.g. DCM, DCE, etc.) at room temperature to afford intermediate 105.

Carbamates: Intermediate 102a can be treated with chloroformates (or alcohols, activated as carbonates) in presence of base (e.g. Et$_3$N, DIPEA, pyridine, t-BuOK etc.) in polar aprotic solvent (e.g. DCM, DCE, THF, etc.) at 0° C. to room temperature to afford intermediate 106.

Intermediates 103-106 can be subjected to metal catalyzed cross coupling reactions using numerous known methods recognized by the one skilled in the art including but not limited to the ones described in Metal-Catalyzed Cross-Coupling Reactions, Armin de Meijere, François Diederich, 2 Volumes, Second, Revised and Enlarged Edition, 2004, ISBN: 3-527-30518-1, Wiley-VCH and references cited therein. Intermediates 103-106 can be subjected to various metal catalyzed reactions (including but not limited to reactions such as Ullmann, Buchwald, Suzuki, Stille coupling, etc.) These coupling reactions can be carried out in presence of metal catalyst (e.g. CuBr, Pd(OAc)$_2$, Pd$_2$(dba)$_3$, Pd(PPh$_3$)$_4$, Pd(PPh$_3$)$_2$Cl$_2$, Pd(dppf)Cl$_2$, etc.) and appropriate ligand (including but not limited to ligands such as proline, 1,10-phenanthroline, tricyclohexylphosphine, dppf, etc.) as and when required. The Ullmann and Buchwald coupling reactions of intermediates 103-106 can be carried out with various coupling partners such as heterocyclyl or heteroaryl amines, etc. Intermediates 103-106 can be subjected to Suzuki, Stille, etc. cross couplings with coupling partners such as cycloalkyl or alkenyl or aryl or heteroaryl boronic acids, boronic acid esters, organotin reagents, etc. The coupling reactions can be carried out in presence of base as necessary (including but not limited to Na$_2$CO$_3$, K$_2$CO$_3$, NaHCO$_3$, K$_3$PO$_4$, NaO$^t$Bu, etc.) and solvent (e.g. dioxane, THF, DME, toluene, methanol, DMF, water, etc. or the mixture of two or three of these solvents) under heating conditions to afford compounds of formula I. Alternatively, intermediates 103-106 can be converted to organotin reagent using hexamethylditin in presence of a palladium catalyst and in solvent (e.g. Toluene, THF etc.) at reflux temperature, which upon coupling with suitable coupling partners such as cycloalkenyl, aryl or heteroaryl halides, triflates etc. in a Stille coupling (Sherer, B., et al. PCT Int. Appl., 2016/039734, 2016) afforded compounds represented by formula I. Intermediates 103-106 can be converted to organoboron reagent using bis(pinacolato)diboron, bis(neopentyl glycolato)diboron, etc in presence of a palladium catalyst such as Pd(dppf)Cl$_2$ and base such as potassium acetate in solvent (e.g. dioxane, DMSO etc.) at reflux temperature, which upon coupling with suitable coupling partners such as cycloalkenyl, aryl or heteroaryl halides, triflates etc. in a Suzuki coupling afforded compounds represented by formula I(i,j,k,m).

The sequence of the steps involving installation of groups 'Q' and 'A' can be interchangeably performed in the scheme as appropriate. The oxadiazole regio-isomers can be generated by using sequence described in schemes 11 and 14 attached to the oxabicyclo ring system.

Example 1

N-(3-chlorophenyl)-N-((4-(5-(1,1-difluoroethyl)-1,2,4-oxadiazol-3-yl) bicyclo[2.2.2]octan-1-yl)methyl)-3-fluorobicyclo[1.1.1]pentane-1-carboxamide (1)

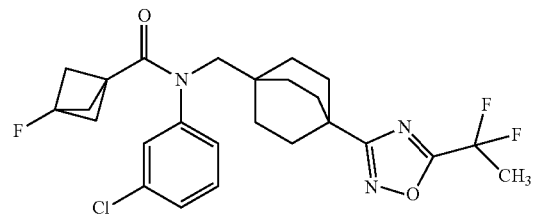

Step A. Intermediate 1A. Preparation of methyl 4-carbamoylbicyclo[2.2.2]octane-1-carboxylate

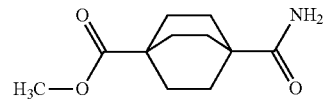

To a stirred solution of 4-(methoxycarbonyl)bicyclo [2.2.2]octane-1-carboxylic acid (0.5 g, 2.35 mmol) in DMF (10 mL) were added ammonium chloride (1.26 g, 23.56 mmol), TEA (1.3 mL, 9.42 mmol) and BOP (1.0 g, 2.35 mmol) under nitrogen atmosphere. The reaction mixture was stirred overnight at room temperature. The reaction mixture was poured into water (20 mL) and extracted with EtOAc (30 mL). The combined organic extracts were washed with brine solution (20 mL), dried over anhydrous sodium sulphate, filtered and concentrated under reduced pressure to afford the title compound (0.4 g, 1.89 mmol, 80% yield) as white solid. $^1$H NMR (400 MHz, DMSO-d$_6$) δ 6.95 (br. s., 1H), 6.74 (br. s., 1H), 3.57 (s, 3H), 1.74-1.61 (m, 12H). MS (ESI) 212 (M+H).

Step B. Intermediate 1B. Preparation of methyl 4-cyanobicyclo[2.2.2]octane-1-carboxylate

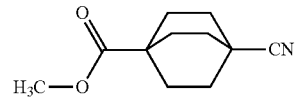

A stirred solution of Intermediate 1A (0.35 g, 1.65 mmol) in pyridine (7 mL) was cooled to 0° C. Trifluoroacetic anhydride (1.74 g, 8.28 mmol) was added drop wise and the reaction mixture was stirred at 0° C. for 30 min. The reaction mixture was quenched with aq. 10% NaHCO$_3$ solution, diluted with water (20 mL) and extracted with ethyl acetate (2×20 mL). The combined organic layers were washed with brine solution (20 mL), dried over anhydrous sodium sulphate, filtered and concentrated under reduced pressure. The crude material was purified by flash column chromatography (24 g silica gel cartridge; A=Hex, B=EtOAc; 30 min grad.; 0% B to 30% B; flow rate=24 mL/min). The pure fractions were combined, concentrated under reduced pressure and dried in vacuo to afford the title compound (0.25 g, 1.22 mmol, 74% yield) as off-white solid. $^1$H NMR (400 MHz, DMSO-d$_6$) δ 3.58 (s, 3H), 1.93-1.83 (m, 6H), 1.78-1.68 (m, 6H).

Step C. Intermediate 1C. Preparation of methyl 4-cyanobicyclo[2.2.2]octane-1-carboxylate

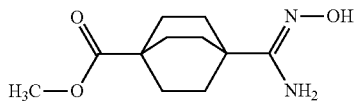

To a stirred solution of Intermediate 1B (0.25 g, 1.29 mmol) in ethanol (5 mL) was added hydroxylamine (50% aqueous solution, 0.32 mL, 5.17 mmol). The reaction mixture was refluxed at 80° C. for 2 h. The reaction mixture was cooled to room temperature, concentrated under reduced pressure and the residue was diluted with water (10 mL). The precipitated solid was filtered and dried in vacuo to afford the title compound (0.28 g, 1.18 mmol, 91% yield) as white solid. $^1$H NMR (400 MHz, Chloroform-d) δ 8.88 (s, 1H), 5.15 (s, 2H), 3.57 (s, 3H), 1.73-1.62 (m, 12H). MS (ESI) 227 (M+H).

Step D. Intermediate 1D. Preparation of methyl 4-(5-(1,1-difluoroethyl)-1,2,4-oxadiazol-3-yl)bicyclo[2.2.2]octane-1-carboxylate

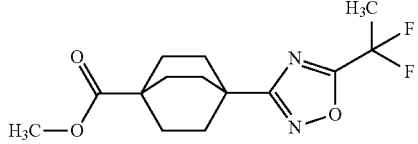

To a stirred solution of Intermediate 1C (5 g, 22.10 mmol) in DMF (100 mL) at room temperature were added 2,2-difluoropropanoic acid (3.16 g, 28.7 mmol), TEA (12.32 mL, 88 mmol) and BOP (10.75 g, 24.31 mmol). The reaction mixture was stirred at 110° C. overnight. The reaction mixture was cooled to room temperature and concentrated under reduced pressure. The residue was diluted with water (100 mL) and extracted with ethyl acetate (3×50 mL). The combined organic layers were washed with brine solution (20 mL), dried over anhydrous sodium sulphate, filtered and concentrated under reduced pressure. The crude material was purified by flash column chromatography (40 g silica gel cartridge; A=Hex, B=EtOAc; 30 min grad.; 0% B to 30% B; flow rate=24 mL/min). The pure fractions were combined, concentrated under reduced pressure and dried in vacuo to afford the title compound (4.2 g, 11.75 mmol, 53% yield) as colorless gummy solid. MS (ESI) 301 (M+H).

Step E. Intermediate 1E. Preparation of (4-(5-(1,1-difluoroethyl)-1,2,4-oxadiazol-3-yl) bicyclo[2.2.2]octan-1-yl)methanol

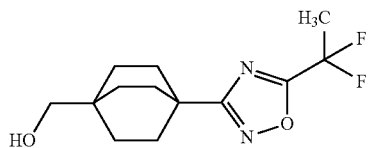

To a stirred solution of Intermediate 1D (4.2 g, 13.99 mmol) in THF (20 mL) was added DIBAL-H (35 mL, 35.0 mmol) drop wise at −78° C. The reaction mixture was stirred at −78° C. for 1 h. The reaction mixture was allowed to warm to 0° C. and quenched with aq. 1.5 N HCl solution (100 mL). The aqueous solution was extracted with ethyl acetate (2×50 mL). The combined organic layers were washed with brine solution (20 mL), dried over anhydrous sodium sulphate, filtered and concentrated under reduced pressure. The crude material was purified by flash column chromatography (40 g silica gel cartridge; A=Hex, B=EtOAc; 30 min grad.; 0% B to 40% B; flow rate=40 mL/min). The pure fractions were combined, concentrated under reduced pressure and dried in vacuo to afford the title compound (3 g, 10.58 mmol, 76% yield) as colorless liquid. MS (ESI) 273 (M+H).

Step F. Intermediate 1F. Preparation of 4-(5-(1,1-difluoroethyl)-1,2,4-oxadiazol-3-yl) bicyclo[2.2.2]octane-1-carbaldehyde

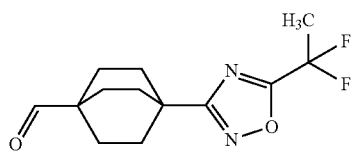 [SMILES: CC(F)(F)c1nc(C23CCC(C=O)(CC2)CC3)no1]

To a stirred solution of Intermediate 1E (3 g, 11.02 mmol) in DCM (70 mL) was added Dess-Martin periodinane (5.6 g, 13.22 mmol) at 0° C. The reaction mixture was stirred at 0° C. for 30 min. The reaction mixture was allowed to warm to room temperature, diluted with DCM (50 mL), washed with aq. 10% sodium bicarbonate solution (3×20 mL). The organic layer was washed with brine solution (20 mL), dried over anhydrous sodium sulphate, filtered and concentrated under reduced pressure. The crude material was purified by flash column chromatography (24 g silica gel cartridge; A=Hex, B=EtOAc; 30 min grad.; 0% B to 30% B; flow rate=24 mL/min). The pure fractions were combined, concentrated under reduced pressure and dried in vacuo to afford the title compound (2 g, 7.40 mmol, 67% yield) as colorless white gummy solid. $^1$H NMR (400 MHz, DMSO-d$_6$) δ 9.46 (br. s., 1H), 2.16 (t, J=19.6 Hz, 3H), 1.94-1.76 (m, 12H).

Step G. Intermediate 1G. Preparation of 3-chloro-N-((4-(5-(1,1-difluoroethyl)-1,2,4-oxadiazol-3-yl)bicyclo[2.2.2]octan-1-yl)methyl)aniline

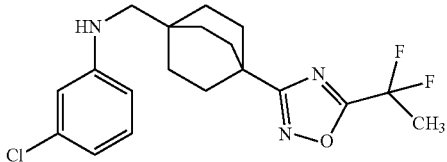 [SMILES: CC(F)(F)c1nc(C23CCC(CNc4cccc(Cl)c4)(CC2)CC3)no1]

To a stirred solution of Intermediate 1F (50 mg, 0.18 mmol) in MeOH (1 mL) were added 3-chloroaniline (23 mg, 0.18 mmol), AcOH (0.02 mL, 0.37 mmol) followed by 4 Å molecular sieves (5 mg). The reaction mixture was heated to 60° C. and stirred overnight. The reaction mixture was allowed to come to room temperature and then cooled to 0° C. Sodium cyanoborohydride (23.25 mg, 0.37 mmol) was added to the reaction mixture. The reaction mixture was allowed to warm to room temperature and stirred for 1 h. The reaction mixture was diluted with ethyl acetate (25 mL), washed with water (10 mL), brine solution (10 mL) and concentrated under reduced pressure. The crude material was purified by flash column chromatography (4 g silica gel cartridge; A=Hex, B=EtOAc; 30 min grad.; 0% B to 50% B; flow rate=24 mL/min). The pure fractions were combined, concentrated under reduced pressure and dried in vacuo to afford the title compound (60 mg, 0.14 mmol, 78% yield) as brown solid. MS (ESI) 382 (M+H).

Step H. Example 1. Preparation of N-(3-chlorophenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide To a stirred solution of Intermediate 1G (20 mg, 0.05 mmol) in DCM (1 mL) was added 3-fluorobicyclo[1.1.1]pentane-1-carboxylic acid (10.22 mg, 0.08 mmol) followed by pyridine (0.03 mL, 0.36 mmol) at room temperature. The reaction mixture was cooled to 0° C. and $POCl_3$ (0.02 mL, 0.16 mmol) was added. After stirring at 0° C. for 1 h, the reaction mixture was diluted with DCM (25 mL). The organic layer was washed with aq. 10% sodium bicarbonate solution (2×15 mL) followed by brine solution (15 mL), dried over anhydrous sodium sulphate, filtered and concentrated under reduced pressure. The crude material was purified via preparative LC/MS using following conditions: Column: Waters XBridge C18, 150 mm×19 mm, 5-μm particles; Mobile Phase A: 5:95 acetonitrile: water with 10-mM ammonium acetate; Mobile Phase B: 95:5 acetonitrile: water with 10 mM ammonium acetate; Gradient: a 2-minute hold at 30% B, 30-75% B over 25 minutes, then a 5-minute hold at 100% B; Flow Rate: 15 mL/min; Column Temperature: 25° C. Fraction collection was triggered by signals. Fractions containing the desired product were combined and dried via centrifugal evaporation to afford the title compound (4.8 mg, 9.72 μmol, 19% yield). $^1$H NMR (400 MHz, DMSO-$d_6$) δ 7.59 (s, 1H), 7.54-7.45 (m, 2H), 7.41 (dt, J=5.7, 2.7 Hz, 1H), 3.59 (br. s., 1H), 3.51 (br. s., 1H), 2.14 (t, J=19.7 Hz, 3H), 1.88 (br. s., 6H), 1.84-1.62 (m, 6H), 1.53-1.32 (m, 6H). FXR $EC_{50}$ (nM)=11. MS (ESI) 494 (M+H).

The following examples were prepared according to the method described for the synthesis of Example 1 (step H) by substituting Intermediate 1G and corresponding acids where appropriate:

| Ex. No. | Structure & Name | MS (ESI) (M + H) | FXR $EC_{50}$ (nM) |
|---|---|---|---|
| 2 | N-(3-chlorophenyl)-N-((4-(5-(1,1-difluoroethyl)-1,2,4-oxadiazol-3-yl)bicyclo[2.2.2]octan-1-yl)methyl)-3-hydroxy-3-(trifluoromethyl)cyclobutane-1-carboxamide | 548 | 64 |
| 3 | N-(3-chlorophenyl)-N-((4-(5-(1,1-difluoroethyl)-1,2,4-oxadiazol-3-yl)bicyclo[2.2.2]octan-1-yl)methyl)-4,4-difluorocyclohexane-1-carboxamide | 528 | 133 |

2  $^1$H NMR (400 MHz, DMSO-$d_6$) δ 7.59 (s, 1H), 7.51-7.32 (m, 3H), 6.54 (s, 1H), 3.61 (br. s., 2H), 2.74 (t, J = 8.8 Hz, 1H), 2.39-2.23 (m, 2H), 2.21-1.94 (m, 5H), 1.88-1.65 (m, 6H), 1.53-1.32 (m, 6H)

| Ex. No. | Structure & Name | MS (ESI) (M + H) | FXR EC$_{50}$ (nM) |
|---|---|---|---|
| 3 | $^1$H NMR (400 MHz, DMSO-d$_6$) δ 7.61 (br. s., 1H), 7.54-7.35 (m, 3H), 3.58 (br. s., 2H), 2.34 (dd, J = 3.8, 1.8 Hz, 1H), 2.24-2.05 (m, 3H), 1.97 (br. s., 2H), 1.83-1.67 (m, 8H), 1.67-1.47 (m, 4H), 1.47-1.31 (m, 6H). | | |

Example 4

N-(3-cyanophenyl)-N-((4-(5-(1,1-difluoroethyl)-1,2,4-oxadiazol-3-yl) bicyclo[2.2.2]octan-1-yl)methyl)-3-fluorobicyclo[1.1.1]pentane-1-carboxamide (4)

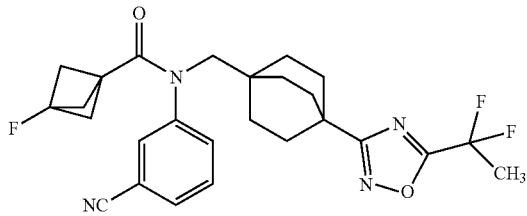

Step A. Intermediate 4A. Preparation of 3-(((4-(5-(1,1-difluoroethyl)-1,2,4-oxadiazol-3-yl)bicyclo[2.2.2]octan-1-yl)methyl)amino)benzonitrile

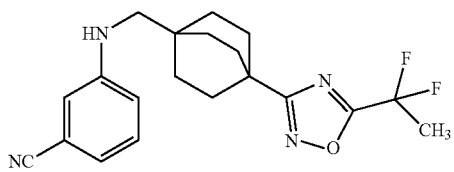 [SMILES: CC(F)(F)c1nc(C23CCC(CNc4cccc(C#N)c4)(CC2)CC3)no1]

The title compound was prepared according to method described for the synthesis of Intermediate 1G by substituting Intermediate 1F and 3-aminobenzonitrile where appropriate: (60 mg, 0.15 mmol, 86% yield). $^1$H NMR (400 MHz, DMSO-d$_6$) δ 7.24-7.18 (m, 1H), 6.97-6.92 (m, 2H), 6.85 (dt, J=7.5, 1.3 Hz, 1H), 6.01 (t, J=6.0 Hz, 1H), 2.86 (d, J=6.0 Hz, 2H), 2.15 (t, J=19.6 Hz, 3H), 1.91-1.82 (m, 6H), 1.61-1.53 (m, 6H). MS (ESI) 373 (M+H).

Step B. Example 4. Preparation of N-(3-cyanophenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide The title compound was prepared according to method described for the synthesis of Example 1 (Step H) by substituting Intermediate 4A where appropriate: (7 mg, 0.06 mmol, 28% yield). $^1$H NMR (400 MHz, DMSO-d$_6$) δ 8.05 (s, 1H), 7.88 (d, J=7.8 Hz, 1H), 7.84-7.77 (m, 1H), 7.71-7.59 (m, 1H), 3.58 (br. s, 2H), 2.14 (t, J=19.6 Hz, 3H), 1.87 (br. s., 6H), 1.84-1.66 (m, 6H), 1.53-1.30 (m, 6H). FXR EC$_{50}$ (nM)=12. MS (ESI) 485 (M+H).

The following examples were prepared according to the method described for the synthesis of Example 1 (step H) by substituting Intermediate 4A and corresponding acids where appropriate:

| Ex. No. | Structure & Name | MS (ESI) (M + H) | FXR EC$_{50}$ (nM) |
|---|---|---|---|
| 5 | N-(3-cyanophenyl)-N-((4-(5-(1,1-difluoroethyl)-1,2,4-oxadiazol-3-yl)bicyclo[2.2.2]octan-1-yl)methyl)-3-hydroxy-3-(trifluoromethyl)cyclobutane-1-carboxamide | 539 | 164 |

| Ex. No. | Structure & Name | MS (ESI) (M + H) | FXR EC$_{50}$ (nM) |
|---|---|---|---|
| 6 | ![structure]<br>N-(3-cyanophenyl)-N-((4-(5-(1,1-difluoroethyl)-1,2,4-oxadiazol-3-yl)bicyclo[2.2.2]octan-1-yl)methyl)-4,4-difluorocyclohexane-1-carboxamide | 519 | 106 |

| Ex. No. | |
|---|---|
| 5 | $^1$H NMR (400 MHz, DMSO-d$_6$) δ 8.04 (s, 1H), 7.81 (t, J = 6.5 Hz, 2H), 7.68-7.60 (m, 1H), 6.54 (s, 1H), 3.63 (br. s., 2H), 2.81-2.69 (m, 1H), 2.40-2.22 (m, 2H), 2.21-2.07 (m, 3H), 2.02 (t, J = 10.4 Hz, 2H), 1.87-1.66 (m, 6H), 1.52-1.29 (m, 6H) |
| 6 | $^1$H NMR (400 MHz, DMSO-d$_6$) δ 8.06 (br. s., 1H), 7.84 (d, J = 8.6 Hz, 2H), 7.66 (t, J = 7.8 Hz, 1H), 3.60 (br. s., 2H), 2.33 (d, J = 1.7 Hz, 1H), 2.22-2.08 (m, 3H), 1.94 (d, J = 6.4 Hz, 2H), 1.86-1.65 (m, 8H), 1.65-1.47 (m, 4H), 1.47-1.29 (m, 6H) |

Example 7

N-((4-(5-(1,1-difluoroethyl)-1,2,4-oxadiazol-3-yl) bicyclo[2.2.2]octan-1-yl)methyl)-3-fluoro-N-(3-fluorophenyl)bicyclo[1.1.1]pentane-1-carboxamide (7)

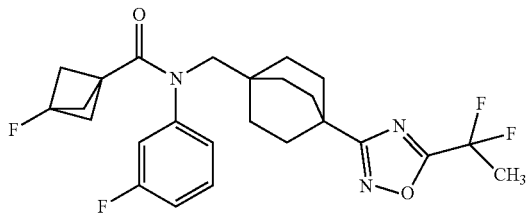

Step A. Intermediate 7A. Preparation of N-((4-(5-(1,1-difluoroethyl)-1,2,4-oxadiazol-3-yl)bicyclo[2.2.2]octan-1-yl)methyl)-3-fluoroaniline

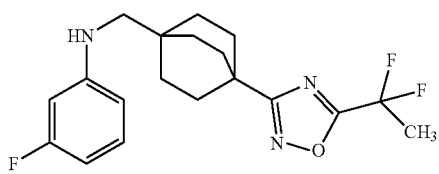 [SMILES: CC(F)(F)c1nc(C23CCC(CNc4cccc(F)c4)(CC2)CC3)no1]

The title compound was prepared according to method described for the synthesis of Intermediate 1G by substituting Intermediate 1F and 3-fluoroaniline where appropriate: (60 mg, 0.16 mmol, 89% yield). $^1$H NMR (400 MHz, DMSO-d$_6$) δ 7.05-6.98 (m, 1H), 6.43 (d, J=8.5 Hz, 1H), 6.39-6.33 (m, 1H), 6.25-6.18 (m, 1H), 5.78 (s, 1H), 2.81 (d, J=6.0 Hz, 2H), 2.21-2.09 (m, 3H), 1.90-1.83 (m, 6H), 1.60-1.53 (m, 6H). MS (ESI) 366 (M+H).

Step B. Example 7. Preparation of N-((4-(5-(1,1-difluoroethyl)-1,2,4-oxadiazol-3-yl) bicyclo[2.2.2]octan-1-yl)methyl)-3-fluoro-N-(3-fluorophenyl)bicyclo[1.1.1]pentane-1-carboxamide The title compound was prepared according to method described for the synthesis of Example 1 (Step H) by substituting Intermediate 7A where appropriate: (7 mg, 0.06 mmol, 27% yield). $^1$H NMR (400 MHz, DMSO-d$_6$) δ 7.50 (td, J=8.1, 6.7 Hz, 1H), 7.39 (dt, J=10.1, 2.1 Hz, 1H), 7.34-7.19 (m, 2H), 3.61 (br. s., 1H), 3.50 (br. s., 1H), 2.14 (t, J=19.7 Hz, 3H), 1.89 (br. s., 6H), 1.84-1.56 (m, 6H), 1.54-1.35 (m, 6H). FXR EC$_{50}$ (nM)=30. MS (ESI) 478 (M+H).

The following examples were prepared according to the method described for the synthesis of Example 1 (step H) by substituting Intermediate 7A and corresponding acids where appropriate:

| Ex. No. | Structure & Name | MS (ESI) (M + H) | FXR EC$_{50}$ (nM) |
|---|---|---|---|
| 8 | N-((4-(5-(1,1-difluoroethyl)-1,2,4-oxadiazol-3-yl)bicyclo[2.2.2]octan-1-yl)methyl)-N-(3-fluorophenyl)-3-hydroxy-3-(trifluoromethyl)cyclobutane-1-carboxamide | 532 | 462 |
| 9 | N-((4-(5-(1,1-difluoroethyl)-1,2,4-oxadiazol-3-yl)bicyclo[2.2.2]octan-1-yl)methyl)-4,4-difluoro-N-(3-fluorophenyl)cyclohexane-1-carboxamide | 519 | 451 |
| 8 | $^1$H NMR (400 MHz, DMSO-d$_6$) δ 7.54-7.44 (m, 1H), 7.40 (d, J = 9.8 Hz, 1H), 7.26 (d, J = 7.6 Hz, 1H), 7.20 (t, J = 8.4 Hz, 1H), 6.53 (br. s., 1H), 3.61 (s, 2H), 2.83-2.73 (m, 1H), 2.42-2.23 (m, 2H), 2.21-1.95 (m, 5H), 1.90-1.62 (m, 6H), 1.55-1.25 (m, 6H) | | |
| 9 | $^1$H NMR (400 MHz, DMSO-d$_6$) δ 7.55-7.45 (m, 1H), 7.43-7.40 (m, 1H), 7.23-7.19 (m, 1H), 7.05-6.9 (m, 1H), 3.59 (br. s., 2H), 2.39 (br. s., 1H), 2.24-2.05 (m, 3H), 1.96 (d, J = 7.6 Hz, 2H), 1.91-1.82 (m, 2H), 1.82-1.73 (m, 6H), 1.66-1.46 (m, 4H), 1.46-1.27 (m, 6H) | | |

Example 10

N-((4-(5-(1,1-difluoroethyl)-1,2,4-oxadiazol-3-yl)bicyclo[2.2.2]octan-1-yl)methyl)-N-(3,4-difluorophenyl)-3-fluorobicyclo[1.1.1]pentane-1-carboxamide (10)

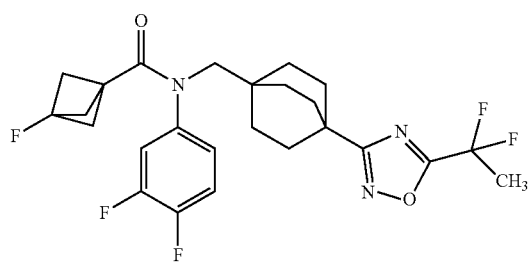

Step A. Intermediate 10A. Preparation of N-((4-(5-(1,1-difluoroethyl)-1,2,4-oxadiazol-3-yl)bicyclo[2.2.2]octan-1-yl)methyl)-3,4-difluoroaniline

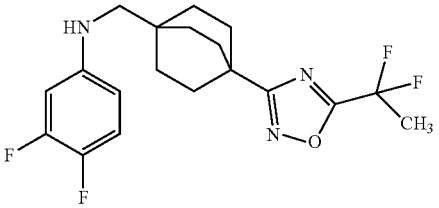 [SMILES: CC(F)(F)c1nc(C23CCC(CNc4ccc(F)c(F)c4)(CC2)CC3)no1]

The title compound was prepared according to method described for the synthesis of Intermediate 1G by substituting Intermediate 1F and 3,4-difluoroaniline where appropriate: (48 mg, 0.12 mmol, 68% yield). $^1$H NMR (300 MHz, DMSO-d$_6$) δ 7.13-7.00 (m, 1H), 6.62-6.50 (m, 1H), 6.38 (d, J=9.1 Hz, 1H), 5.66 (t, J=5.6 Hz, 1H), 2.78 (d, J=5.9 Hz, 2H), 2.25-2.07 (m, 3H), 1.95-1.80 (m, 6H), 1.66-1.46 (m, 6H). MS (ESI) 384 (M+H).

Step B. Example 10. Preparation of N-((4-(5-(1,1-difluoroethyl)-1,2,4-oxadiazol-3-yl) bicyclo[2.2.2]octan-1-yl)methyl)-N-(3,4-difluorophenyl)-3-fluorobicyclo[1.1.1]pentane-1-carboxamide The title compound was prepared according to method described for the synthesis of Example 1 (Step H) by substituting Intermediate 10A where appropriate: (4.0 mg, 15% yield). $^1$H NMR (400 MHz, DMSO-$d_6$) δ 7.78-7.63 (m, 1H), 7.59-7.45 (m, 1H), 7.39-7.22 (m, 1H), 3.59 (br. s., 1H), 3.45 (br. s., 1H), 2.14 (t, J=19.6 Hz, 3H), 1.91 (br. s., 6H), 1.86-1.58 (m, 6H), 1.57-1.32 (m, 6H). FXR $EC_{50}$ (nM)=124. MS (ESI) 496 (M+H).

Example 11

N-((4-(5-(1,1-difluoroethyl)-1,2,4-oxadiazol-3-yl) bicyclo[2.2.2]octan-1-yl)methyl)-N-(3,4-difluorophenyl)-4,4-difluorocyclohexane-1-carboxamide

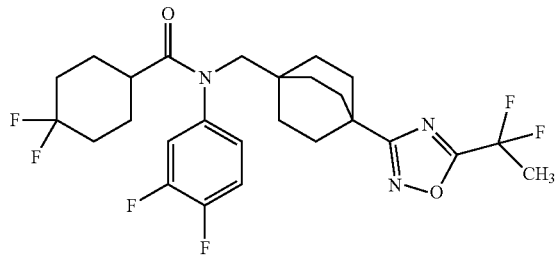

(11)

The title compound was prepared according to method described for the synthesis of Example 1 (Step H) by substituting Intermediate 10A where appropriate: (2 mg, 7% yield). $^1$H NMR (400 MHz, DMSO-$d_6$) δ 7.77-7.66 (m, 1H), 7.57-7.46 (m, 1H), 7.39-7.29 (m, 1H), 3.59-3.49 (m, 2H), 2.42-2.34 (m, 1H), 2.14 (t, J=19.7 Hz, 3H), 2.00-1.87 (m, 2H), 1.82-1.73 (m, 6H), 1.73-1.64 (m, 2H), 1.63-1.48 (m, 4H), 1.45-1.37 (m, 6H). FXR $EC_{50}$ (nM)=881. MS (ESI) 530 (M+H).

Example 12

N-((4-(5-(1,1-difluoroethyl)-1,2,4-oxadiazol-3-yl) bicyclo[2.2.2]octan-1-yl)methyl)-N-(3-(difluoromethoxy)phenyl)-3-fluorobicyclo[1.1.1]pentane-1-carboxamide

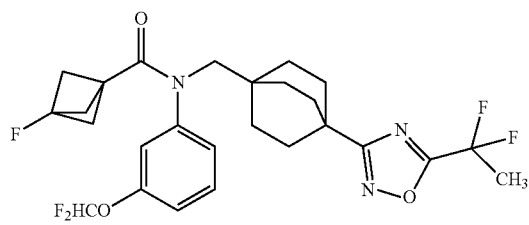

(12)

Step A. Intermediate 12A. Preparation of N-((4-(5-(1,1-difluoroethyl)-1,2,4-oxadiazol-3-yl)bicyclo[2.2.2]octan-1-yl)methyl)-3-(difluoromethoxy)aniline

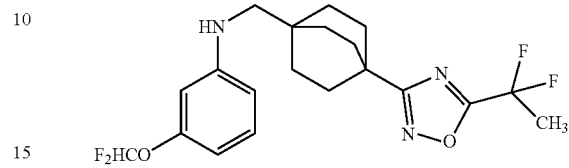

The title compound was prepared according to method described for the synthesis of Intermediate 1G by substituting Intermediate 1F and 3-(difluoromethoxy)aniline where appropriate: (50 mg, 0.12 mmol, 65% yield). MS (ESI) 414 (M+H).

Step B. Example 12. Preparation of N-((4-(5-(1,1-difluoroethyl)-1,2,4-oxadiazol-3-yl) bicyclo[2.2.2] octan-1-yl)methyl)-N-(3-(difluoromethoxy)phenyl)-3-fluorobicyclo[1.1.1]pentane-1-carboxamide The title compound was prepared according to method described for the synthesis of Example 1 (Step H) by substituting Intermediate 12A where appropriate: (9.0 mg, 0.02 mmol, 35% yield). $^1$H NMR (400 MHz, DMSO-$d_6$) δ 7.57-7.50 (m, 1H), 7.33-7.14 (m, 4H), 3.55 (d, J=16.1 Hz, 2H), 2.14 (t, J=19.7 Hz, 3H), 1.87 (br. s., 6H), 1.82-1.63 (m, 6H), 1.54-1.33 (m, 6H). FXR $EC_{50}$ (nM)=73. MS (ESI) 526 (M+H).

Example 13

N-((4-(5-(1,1-difluoroethyl)-1,2,4-oxadiazol-3-yl) bicyclo[2.2.2]octan-1-yl)methyl)-N-(3-(difluoromethoxy)phenyl)-3-hydroxy-3-(trifluoromethyl) cyclobutane-1-carboxamide

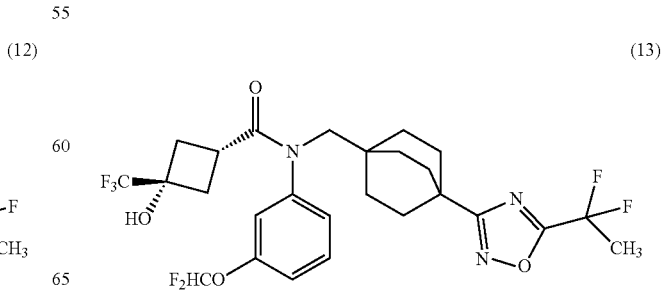

(13)

The title compound was prepared according to method described for the synthesis of Example 1 (Step H) by substituting Intermediate 12A where appropriate: (8 mg, 0.01 mmol, 28% yield). $^1$H NMR (400 MHz, DMSO-$d_6$) δ 7.51-7.13 (m, 5H), 6.53 (s, 1H), 3.62 (s, 2H), 2.76 (t, J=8.9 Hz, 1H), 2.35-2.26 (m, 2H), 2.21-1.99 (m, 5H), 1.87-1.69 (m, 6H), 1.54-1.31 (m, 6H). FXR EC$_{50}$ (nM)=302. MS (ESI) 580 (M+H).

Example 14

N-((4-(5-(1,1-difluoroethyl)-1,2,4-oxadiazol-3-yl)bicyclo[2.2.2]octan-1-yl)methyl)-3-fluoro-N-(3-(trifluoromethyl)phenyl)bicyclo[1.1.1]-pentane-1-carboxamide (14)

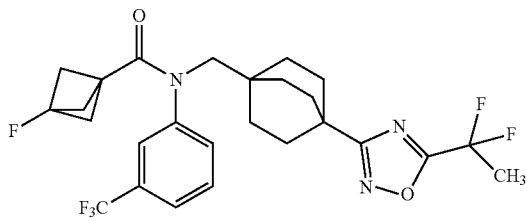

Step A. Intermediate 14A. Preparation of N-((4-(5-(1,1-difluoroethyl)-1,2,4-oxadiazol-3-yl)bicyclo[2.2.2]octan-1-yl)methyl)-3-(trifluoromethyl)aniline The title compound was prepared according to method described for the synthesis of Intermediate 1G by substituting Intermediate 1F and 3-(trifluoromethyl)aniline where appropriate: (65 mg, 0.13 mmol, 69% yield). MS (ESI) 416 (M+H).

Step B. Example 14. Preparation of N-((4-(5-(1,1-difluoroethyl)-1,2,4-oxadiazol-3-yl) bicyclo[2.2.2]octan-1-yl)methyl)-3-fluoro-N-(3-(trifluoromethyl)phenyl)bicyclo[1.1.1]pentane-1-carboxamide The title compound was prepared according to method described for the synthesis of Example 1 (Step H) by substituting Intermediate 14A where appropriate: (4 mg, 7.58 μmol, 16% yield). $^1$H NMR (400 MHz, DMSO-$d_6$) δ 7.86 (s, 1H), 7.81-7.74 (m, 2H), 7.71 (d, J=7.8 Hz, 1H), 3.67-3.48 (m, 2H), 2.14 (t, J=19.7 Hz, 3H), 1.90-1.72 (m, 12H), 1.50-1.36 (m, 6H). FXR EC$_{50}$ (nM)=29. MS (ESI) 528 (M+H).

The following examples were prepared according to the method described for the synthesis of Example 1 (step H) by substituting Intermediate 14A and corresponding acids where appropriate:

| Ex. No. | Structure & Name | MS (ESI) (M + H) | FXR EC$_{50}$ (nM) |
|---|---|---|---|
| 15 | N-((4-(5-(1,1-difluoroethyl)-1,2,4-oxadiazol-3-yl)bicyclo[2.2.2]octan-1-yl)methyl)-3-hydroxy-3-(trifluoromethyl)-N-(3-(trifluoromethyl)phenyl)cyclobutane-1-carboxamide | 582 | 176 |
| 16 | N-((4-(5-(1,1-difluoroethyl)-1,2,4-oxadiazol-3-yl)bicyclo[2.2.2]octan-1-yl)methyl)-4,4-difluoro-N-(3-(trifluoromethyl)phenyl)cyclohexane-1-carboxamide | 562 | 315 |

-continued

| Ex. No. | Structure & Name | MS (ESI) (M + H) | FXR EC$_{50}$ (nM) |
|---|---|---|---|
| 15 | $^1$H NMR (400 MHz, DMSO-d$_6$) δ 7.85 (s, 1H), 7.80-7.58 (m, 3H), 6.54 (s, 1H), 3.65 (s, 2H), 2.79-2.68 (m, 1H), 2.39-2.27 (m, 2H), 2.14 (t, J = 19.7 Hz, 3H), 2.00 (t, J = 11.1 Hz, 2H), 1.86-1.65 (m, 6H), 1.52-1.30 (m, 6H). | | |
| 16 | $^1$H NMR (400 MHz, DMSO-d$_6$) δ 7.88 (br s, 1H), 7.84-7.76 (m, 1H), 7.75-7.61 (m, 2H), 3.73-3.48 (m, 2H), 2.33-2.23 (m, 1H), 2.21-2.06 (m, 3H), 2.05-1.87 (m, 2H), 1.82-1.66 (m, 8H), 1.64-1.45 (m, 4H), 1.44-1.30 (m, 6H). | | |

Example 17

N-((4-(5-(1,1-difluoroethyl)-1,2,4-oxadiazol-3-yl)bicyclo[2.2.2]octan-1-yl)methyl)-3-fluoro-N-(2-methoxypyridin-4-yl)bicyclo[1.1.1]pentane-1-carboxamide (17)

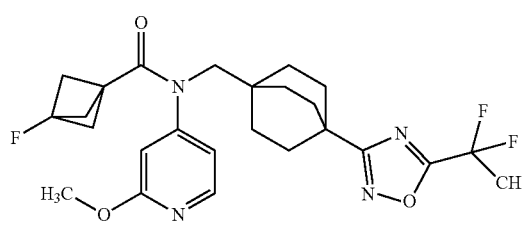

Step A. Intermediate 17A. Preparation of N-((4-(5-(1,1-difluoroethyl)-1,2,4-oxadiazol-3-yl)bicyclo[2.2.2]octan-1-yl)methyl)-2-methoxypyridin-4-amine

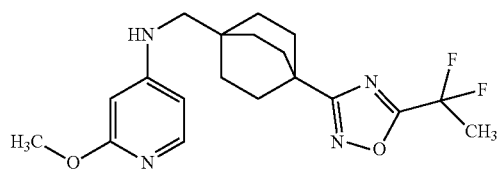 [SMILES: COc1cc(NCC23CCC(c4noc(C(C)(F)F)n4)(CC2)CC3)ccn1]

The title compound was prepared according to method described for the synthesis of Intermediate 1G by substituting Intermediate 1F and 2-methoxypyridin-4-amine where appropriate: (20 mg, 0.05 mmol, 28% yield). MS (ESI) 380.2 (M+H).

Step B. Example 17. Preparation of N-((4-(5-(1,1-difluoroethyl)-1,2,4-oxadiazol-3-yl) bicyclo[2.2.2]octan-1-yl)methyl)-3-fluoro-N-(2-methoxypyridin-4-yl) bicyclo[1.1.1]pentane-1-carboxamide The title compound was prepared according to method described for the synthesis of Example 1 (Step H) by substituting Intermediate 17A where appropriate: (2 mg, 3.80 μmol, 7% yield). $^1$H NMR (400 MHz, DMSO-d$_6$) δ 8.24 (d, J=5.6 Hz, 1H), 7.09 (dd, J=1.8, 5.5 Hz, 1H), 6.96 (d, J=1.7 Hz, 1H), 3.90 (s, 3H), 3.56 (s, 2H), 2.14 (t, J=19.6 Hz, 3H), 1.97 (d, J=2.4 Hz, 6H), 1.84-1.71 (m, 6H), 1.48-1.34 (m, 6H). FXR EC$_{50}$ (nM)=149. MS (ESI) 491 (M+H).

Example 18

N-(3-(N-cyclopropylsulfamoyl)phenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide (18)

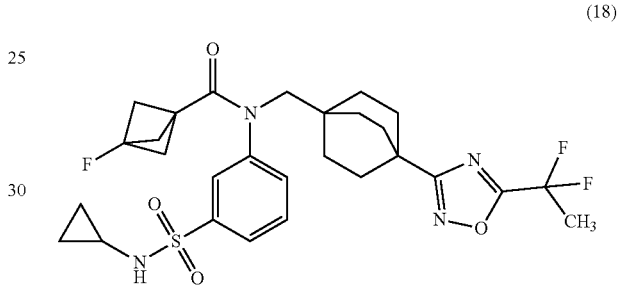

Step A. Intermediate 18A. Preparation of N-cyclopropyl-3-nitrobenzenesulfonamide

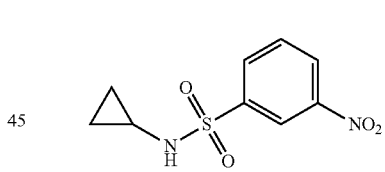

To a stirred solution of 3-nitrobenzenesulfonyl chloride (250 mg, 1.128 mmol) and TEA (0.472 mL, 3.38 mmol) in tetrahydrofuran (5 mL) at 0° C. was added cyclopropylamine (0.08 mL, 1.13 mmol). The reaction mixture was allowed to warm to room temperature and stirred for 2 h. The reaction mixture was poured into water (10 mL) and extracted with EtOAc (2×50 mL). The combined organic layers were washed with brine solution (20 mL), dried over anhydrous sodium sulphate, filtered and concentrated under reduced pressure. The crude material was purified by flash column chromatography (24 g silica gel cartridge; A=Hex, B=EtOAc; 30 min grad.; 0% B to 30% B; flow rate=24 mL/min). The pure fractions were combined, concentrated under reduced pressure and dried in vacuo to afford the title compound (200 mg, 0.82 mmol, 73% yield) as white solid. $^1$H NMR (400 MHz, DMSO-d$_6$) δ 8.56-8.49 (m, 2H), 8.30-8.20 (m, 2H), 7.94 (t, J=7.8 Hz, 1H), 2.18 (tt, J=6.8, 3.5 Hz, 1H), 0.55-0.48 (m, 2H), 0.43-0.36 (m, 2H).

Step B. Intermediate 18B. Preparation of 3-amino-N-cyclopropylbenzenesulfonamide

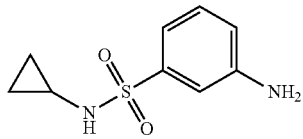 [SMILES: Nc1cccc(S(=O)(=O)NC2CC2)c1]

A stirred solution of Intermediate 18A (200 mg, 0.82 mmol) in methanol (5 mL) was degassed and back-filled with argon and 10% Pd-C (44 mg, 0.04 mmol) was added to the reaction mixture. After stirring overnight under hydrogen (1 atm, balloon), the reaction mixture was filtered over Celite pad and the filtrate was concentrated under reduced pressure to afford the title compound (150 mg, 0.67 mmol, 81% yield) as white solid. $^1$H NMR (400 MHz, DMSO-$d_6$) δ 7.72 (s, 1H), 7.24-7.16 (m, 1H), 7.01 (t, J=2.0 Hz, 1H), 6.93-6.87 (m, 1H), 6.76 (ddd, J=8.0, 2.0, 1.0 Hz, 1H), 5.57 (s, 2H), 2.08 (tt, J=6.8, 3.5 Hz, 1H), 0.52-0.36 (m, 4H).

Step C. Intermediate 18C. Preparation of N-cyclopropyl-3-(((4-(5-(1,1-difluoroethyl)-1,2,4-oxadiazol-3-yl)bicyclo[2.2.2]octan-1-yl)methyl)amino)benzenesulfonamide

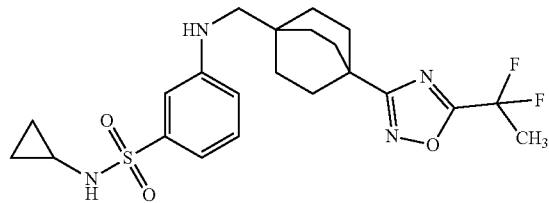 [SMILES: CC(F)(F)c1nc(C23CCC(CNc4cccc(S(=O)(=O)NC5CC5)c4)(CC2)CC3)no1]

The title compound was prepared according to method described for the synthesis of Intermediate 1G by substituting Intermediate 1F and Intermediate 18B where appropriate: (90 mg, 0.18 mmol, 71% yield). $^1$H NMR (400 MHz, DMSO-$d_6$) δ 7.73 (d, J=2.5 Hz, 1H), 7.27-7.20 (m, 1H), 7.04 (s, 1H), 6.90 (d, J=8.0 Hz, 1H), 6.85 (dd, J=8.3, 1.8 Hz, 1H), 6.03 (t, J=5.8 Hz, 1H), 2.86 (d, J=5.5 Hz, 2H), 2.22-2.09 (m, 3H), 2.09-2.03 (m, 1H), 1.92-1.80 (m, 6H), 1.65-1.54 (m, 4H), 1.49-1.42 (m, 2H), 0.51-0.37 (m, 4H). MS (ESI) 467 (M+H).

Step D. Example 18. Preparation of N-(3-(N-cyclopropylsulfamoyl)phenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide The title compound was prepared according to method described for the synthesis of Example 1 (Step H) by substituting Intermediate 18C where appropriate: (8 mg, 0.014 mmol, 34% yield). $^1$H NMR (400 MHZ, DMSO-$d_6$) δ 8.12 (d, J=3.2 Hz, 1H), 7.86-7.79 (m, 1H), 7.78-7.66 (m, 3H), 3.82-3.64 (m, 1H), 3.47 (br s, 1H), 2.14 (t, J=19.7 Hz, 4H), 1.99-1.82 (m, 6H), 1.78 (br t, J=7.8 Hz, 6H), 1.51-1.33 (m, 6H), 0.58-0.26 (m, 4H). FXR EC$_{50}$ (nM)=1563. MS (ESI) 579 (M+H).

The following examples were prepared according to the method described for the synthesis of Example 1 (step H) by substituting Intermediate 18C and corresponding acids where appropriate:

| Ex. No. | Structure & Name | MS (ESI) (M + H) | FXR EC$_{50}$ (nM) |
|---|---|---|---|
| 19 | (1S,3S)-N-(3-(N-cyclopropylsulfamoyl)phenyl)-N-((4-(5-(1,1-difluoroethyl)-1,2,4-oxadiazol-3-yl)bicyclo[2.2.2]octan-1-yl)methyl)-3-hydroxy-3-(trifluoromethyl)cyclobutane-1-carboxamide | 633 | 4000 |

| Ex. No. | Structure & Name | MS (ESI) (M + H) | FXR EC$_{50}$ (nM) |
|---|---|---|---|
| 20 | N-(3-(N-cyclopropylsulfamoyl)phenyl)-N-((4-(5-(1,1-difluoroethyl)-1,2,4-oxadiazol-3-yl)bicyclo[2.2.2]octan-1-yl)methyl)-4,4-difluorocyclohexane-1-carboxamide | 613 | 4000 |
| 19 | $^1$H NMR (400 MHz, DMSO-d$_6$) δ 8.03 (d, J = 3.2 Hz, 1H), 7.82-7.65 (m, 4H), 6.60 (s, 1H), 3.68-3.59 (m, 2H), 2.67-2.60 (m, 1H), 2.55 (s, 1H), 2.38-2.29 (m, 2H), 2.15-2.02 (m, 5H), 1.84-1.68 (m, 6H), 1.47-1.35 (m, 6H), 0.50-0.42 (m, 2H), 0.38-0.29 (m, 2H) | | |
| 20 | $^1$H NMR (400 MHz, DMSO-d$_6$) δ 8.02 (br d, J = 2.9 Hz, 1H), 7.86-7.62 (m, 4H), 3.69-3.53 (m, 2H), 2.34-2.28 (m, 1H), 2.20-2.05 (m, 5H), 2.02-1.86 (m, 2H), 1.82-1.72 (m, 6H), 1.71-1.52 (m, 5H), 1.50-1.31 (m, 6H), 0.51-0.43 (m, 2H), 0.36-0.24 (m, 2H) | | |

Example 21

N-((4-(5-(1,1-difluoroethyl)-1,2,4-oxadiazol-3-yl)bicyclo[2.2.2]octan-1-yl)methyl)-3-fluoro-N-(3-(N-methylsulfamoyl)phenyl)bicyclo[1.1.1]pentane-1-carboxamide (21)

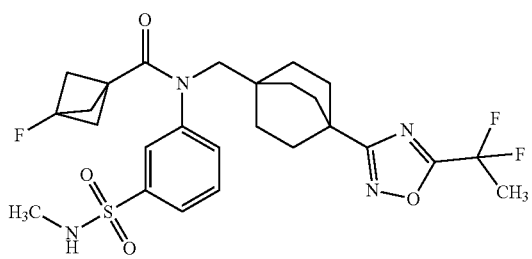

Step A. Intermediate 21A. Preparation of N-methyl-3-nitrobenzenesulfonamide

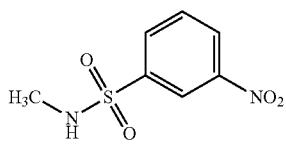

The title compound was prepared according to method described for the synthesis of Intermediate 18A by substituting 3-nitrobenzenesulfonyl chloride and methylamine hydrochloride where appropriate: (220 mg, 0.97 mmol, 86% yield). $^1$H NMR (400 MHz, DMSO-d$_6$) δ 8.53-8.48 (m, 2H), 8.23-8.19 (m, 1H), 7.96-7.90 (m, 1H), 7.84 (br. s., 1H), 2.47 (s, 3H).

Step B. Intermediate 21B. Preparation of 3-amino-N-methylbenzenesulfonamide

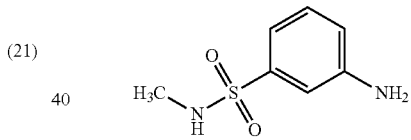

The title compound was prepared according to method described for the synthesis of Intermediate 18B by substituting Intermediate 21A where appropriate: (180 mg, 0.822 mmol, 81% yield). $^1$H NMR (400 MHz, DMSO-d$_6$) δ 7.28-7.17 (m, 2H), 6.96 (t, J=2.0 Hz, 1H), 6.88-6.83 (m, 1H), 6.76 (dt, J=8.0, 1.3 Hz, 1H), 5.57 (s, 2H), 2.39 (s, 3H).

Step C. Intermediate 21C. Preparation of 3-(((4-(5-(1,1-difluoroethyl)-1,2,4-oxadiazol-3-yl)bicyclo[2.2.2]octan-1-yl)methyl)amino)-N-methylbenzenesulfonamide

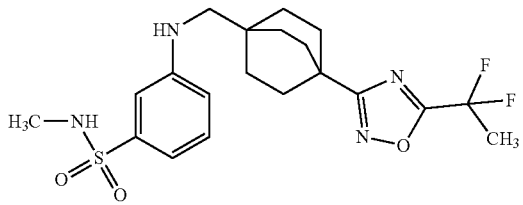 [SMILES: CNS(=O)(=O)c1cccc(NCC23CCC(c4noc(C(C)(F)F)n4)(CC2)CC3)c1]

The title compound was prepared according to method described for the synthesis of Intermediate 1G by substituting Intermediate 1F and Intermediate 21B where appropriate: (60 mg, 0.116 mmol, 45% yield). $^1$H NMR (400 MHz, DMSO-d$_6$) δ 7.27-7.20 (m, 2H), 7.00 (t, J=2.0 Hz, 1H), 6.88-6.82 (m, 2H), 6.02 (t, J=6.0 Hz, 1H), 2.85 (d, J=6.0 Hz, 2H), 2.40 (d, J=5.0 Hz, 3H), 2.21-2.09 (m, 3H), 1.93-1.83 (m, 6H), 1.65-1.54 (m, 6H). MS (ESI) 441 (M+H).

Step D. Example 21. Preparation of N-((4-(5-(1,1-difluoroethyl)-1,2,4-oxadiazol-3-yl) bicyclo[2.2.2]octan-1-yl)methyl)-3-fluoro-N-(3-(N-methylsulfamoyl)phenyl) bicyclo[1.1.1]pentane-1-carboxamide The title compound was prepared according to method described for the synthesis of Example 1 (Step H) by substituting Intermediate 21C where appropriate: (11 mg, 0.020 mmol, 59% yield). $^1$H NMR (400 MHz, DMSO-d$_6$) δ 7.83-7.78 (m, 1H), 7.76-7.62 (m, 4H), 3.77-3.59 (m, 1H), 3.56-3.42 (m, 1H), 2.43 (d, J=5.1 Hz, 3H), 2.14 (t, J=19.7 Hz, 3H), 1.97-1.82 (m, 6H), 1.81-1.69 (m, 6H), 1.50-1.33 (m, 6H). FXR EC$_{50}$ (nM)=4000. MS (ESI) 553 (M+H).

The following examples were prepared according to the method described for the synthesis of Example 1 (step H) by substituting Intermediate 21C and corresponding acids where appropriate:

Example 24

N-((4-(5-(1,1-difluoroethyl)-1,2,4-oxadiazol-3-yl) bicyclo[2.2.2]octan-1-yl)methyl)-N-(3-(dimethylphosphoryl)phenyl)-4,4-difluorocyclohexane-1-carboxamide (24)

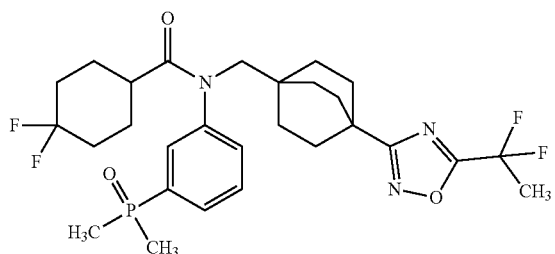

| Ex. No. | Structure & Name | MS (ESI) (M + H) | FXR EC$_{50}$ (nM) |
|---|---|---|---|
| 22 | (1S,3S)-N-((4-(5-(1,1-difluoroethyl)-1,2,4-oxadiazol-3-yl) bicyclo[2.2.2]octan-1-yl)methyl)-3-hydroxy-N-(3-(N-methylsulfamoyl)phenyl)-3-(trifluoromethyl)cyclobutane-1-carboxamide | 607 | 4000 |
| 23 | N-((4-(5-(1,1-difluoroethyl)-1,2,4-oxadiazol-3-yl) bicyclo[2.2.2]octan-1-yl)methyl)-4,4-difluoro-N-(3-(N-methylsulfamoyl)phenyl)cyclohexane-1-carboxamide | 587 | 4000 |

| 22 | $^1$H NMR (400 MHz, DMSO-d$_6$) δ 8.07-7.91 (m, 4H), 7.86 (q, J = 5.0 Hz, 1H), 6.85 (s, 1H), 3.96-3.84 (m, 2H), 3.02-2.90 (m, 1H), 2.68-2.55 (m, 5H), 2.47-2.25 (m, 5H), 2.11-1.96 (m, 6H), 1.74-1.59 (m, 6H) |
|---|---|
| 23 | $^1$H NMR (400 MHz, DMSO-d$_6$) δ 7.88-7.65 (m, 4H), 7.57 (br d, J = 4.9 Hz, 1H), 3.71-3.53 (m, 2H), 2.54 (s, 2H), 2.40 (d, J = 4.9 Hz, 3H), 2.32-2.23 (m, 1H), 2.13 (t, J = 19.7 Hz, 3H), 2.02-1.89 (m, 2H), 1.85-1.45 (m, 10H), 1.43-1.31 (m, 6H) |

Step A. Intermediate 24A. Preparation of dimethyl(3-nitrophenyl)phosphine oxide

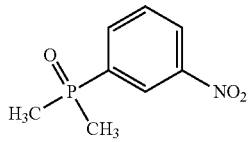

To a stirred suspension of 1-iodo-3-nitrobenzene (200 mg, 0.80 mmol) in dry 1,4-dioxane (2 mL) at room temperature were added dimethylphosphine oxide (62 mg, 0.80 mmol), XantPhos (465 mg, 0.80 mmol) and cesium carbonate (260 mg, 0.80 mmol). The reaction mixture was degassed and back-filled with argon three times. Bis(dibenzylideneacetone)palladium (462 mg, 0.803 mmol) was added to the reaction mixture and the reaction vial was sealed. The reaction mixture was heated to 90° C. and stirred for 4 h. The reaction mixture was cooled to room temperature and concentrated under reduced pressure. The crude material was purified by flash column chromatography (24 g silica gel cartridge; A=Hex, B=EtOAc; 30 min grad.; 0% B to 20% B; flow rate=24 mL/min). The pure fractions were combined, concentrated under reduced pressure and dried in vacuo to afford the title compound (150 mg, 0.72 mmol, 89% yield) as white solid. MS (ESI) 200 (M+H).

Step B. Intermediate 24B. Preparation of (3-aminophenyl)dimethylphosphine Oxide

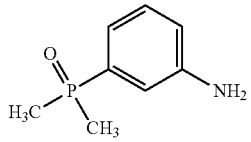

A solution of Intermediate 24A (200 mg, 1 mmol) in methanol (5 mL) was degassed and back-filled with nitrogen and 10% Pd-C (53 mg, 0.05 mmol) was added to the reaction. After stirring overnight under hydrogen (1 atm, balloon), the reaction mixture was filtered over a Celite pad and the filtrate was concentrated under reduced pressure to afford the title compound (150 mg, 0.84 mmol, 84% yield) as white solid. $^1$H NMR (400 MHz, DMSO-$d_6$) δ 7.13 (td, J=7.7, 3.8 Hz, 1H), 6.97-6.91 (m, 1H), 6.85-6.78 (m, 1H), 6.69 (dt, J=8.0, 1.0 Hz, 1H), 5.30 (s, 2H), 1.54 (s, 3H), 1.57 (s, 3H).

Step C. Intermediate 24C. Preparation of (3-(((4-(5-(1,1-difluoroethyl)-1,2,4-oxadiazol-3-yl)bicyclo[2.2.2]octan-1-yl)methyl)amino)phenyl)dimethylphosphine Oxide

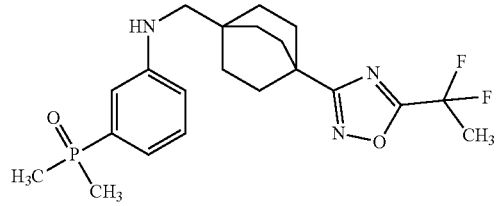 [SMILES: CC(F)(F)c1nc(C23CCC(CNc4cccc(P(C)(C)=O)c4)(CC2)CC3)no1]

The title compound was prepared according to method described for the synthesis of Intermediate 1G by substituting Intermediate 1F and Intermediate 24B where appropriate: (85 mg, 0.19 mmol, 74% yield). $^1$H NMR (400 MHz, DMSO-$d_6$) δ 7.17 (td, J=7.8, 3.5 Hz, 1H), 6.97-7.00 (m, 1H), 6.86-6.73 (m, 2H), 5.74 (t, J=5.8 Hz, 1H), 2.85 (d, J=5.5 Hz, 2H), 2.16 (t, J=19.6 Hz, 3H), 1.92-1.82 (m, 6H), 1.64-1.54 (m, 12H). MS (ESI) 424 (M+H).

Step D. Example 24. Preparation of N-((4-(5-(1,1-difluoroethyl)-1,2,4-oxadiazol-3-yl) bicyclo[2.2.2]octan-1-yl)methyl)-N-(3-(dimethylphosphoryl)phenyl)-4,4-difluorocyclohexane-1-carboxamide The title compound was prepared according to method described for the synthesis of Example 1 (Step H) by substituting Intermediate 24C where appropriate: (10 mg, 0.02 mmol, 36% yield). $^1$H NMR (400 MHz, DMSO-$d_6$) δ 7.84-7.71 (m, 2H), 7.67-7.55 (m, 2H), 3.61 (br d, J=1.0 Hz, 2H), 2.32-2.22 (m, 1H), 2.21-2.07 (m, 3H), 2.02-1.88 (m, 2H), 1.82-1.64 (m, 15H), 1.64-1.55 (m, 3H), 1.45-1.36 (m, 6H). FXR $EC_{50}$ (nM)=4000. MS (ESI) 570 (M+H).

The following examples were prepared according to the method described for the synthesis of Example 1 (step H) by substituting Intermediate 24C and corresponding acids where appropriate:

| Ex. No. | Structure & Name | MS (ESI) (M + H) | FXR $EC_{50}$ (nM) |
|---|---|---|---|
| 25 | N-((4-(5-(1,1-difluoroethyl)-1,2,4-oxadiazol-3-yl)bicyclo[2.2.2]octan-1-yl)methyl)-N-(3-(dimethylphosphoryl)phenyl)-3-fluorobicyclo[1.1.1]pentane-1-carboxamide | 536 | 4000 |

| Ex. No. | Structure & Name | MS (ESI) (M + H) | FXR EC$_{50}$ (nM) |
|---|---|---|---|
| 26 | (1S,3S)-N-((4-(5-(1,1-difluoroethyl)-1,2,4-oxadiazol-3-yl)bicyclo[2.2.2]octan-1-yl)methyl)-N-(3-(dimethylphosphoryl)phenyl)-3-hydroxy-3-(trifluoromethyl)cyclobutane-1-carboxamide | 590 | 4000 |
| 25 | $^{1}$H NMR (400 MHz, DMSO-d$_{6}$) δ 7.84-7.73 (m, 2H), 7.67-7.53 (m, 2H), 3.60-3.55 (m, 2H), 2.14 (t, J = 19.7 Hz, 3H), 1.94-1.75 (m, 12H), 1.70 (br d, J = 13.4 Hz, 6H), 1.51-1.38 (m, 6H) | | |
| 26 | $^{1}$H NMR (400 MHz, DMSO-d$_{6}$) δ 7.81-7.67 (m, 2H), 7.64-7.54 (m, 2H), 6.67-6.36 (m, 1H), 3.71-3.56 (m, 2H), 2.79-2.67 (m, 1H), 2.37-2.25 (m, 2H), 2.21-2.07 (m, 3H), 2.06-1.93 (m, 2H), 1.84-1.72 (m, 6H), 1.67 (d, J = 13.4 Hz, 6H), 1.49-1.34 (m, 6H) | | |

Example 27

Methyl 3-(N-((4-(5-(1,1-difluoroethyl)-1,2,4-oxadiazol-3-yl)bicyclo[2.2.2]octan-1-yl) methyl)-3-fluorobicyclo[1.1.1]pentane-1-carboxamido)benzoate (27)

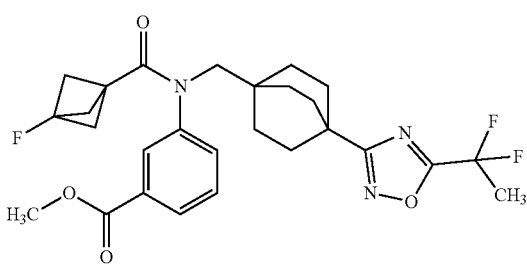

Step A. Intermediate 27A. Preparation of methyl 3-(((4-(5-(1,1-difluoroethyl)-1,2,4-oxadiazol-3-yl)bicyclo[2.2.2]octan-1-yl)methyl)amino)benzoate

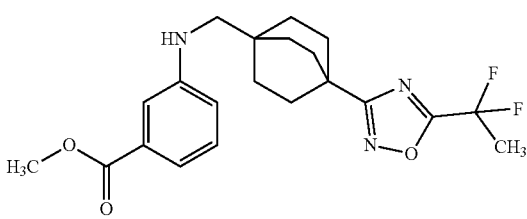 [SMILES: COC(=O)c1cccc(NCC23CCC(c4noc(C(C)(F)F)n4)(CC2)CC3)c1]

The title compound was prepared according to method described for the synthesis of Intermediate 1G by substituting Intermediate 1F and methyl 3-aminobenzoate where appropriate: (75 mg, 0.17 mmol, 68% yield). MS (ESI) 406.3 (M+H).

Step B. Example 27. Preparation of methyl 3-(N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamido)benzoate The title compound was prepared according to method described for the synthesis of Example 1 (Step H) by substituting Intermediate 27A where appropriate: (75 mg, 0.14 mmol, 77% yield). $^{1}$H NMR (400 MHz, DMSO-d$_{6}$) δ 7.97 (d, J=8.1 Hz, 1H), 7.91-7.86 (m, 1H), 7.77-7.70 (m, 1H), 7.66-7.57 (m, 1H), 3.90 (s, 3H), 3.66-3.50 (m, 2H), 2.14 (t, J=19.7 Hz, 3H), 1.84 (br s, 6H), 1.80-1.66 (m, 6H), 1.50-1.35 (m, 6H). FXR EC$_{50}$ (nM)=72. MS (ESI) 518.3 (M+H).

Example 28

N-((4-(5-(1,1-difluoroethyl)-1,2,4-oxadiazol-3-yl)bicyclo[2.2.2]octan-1-yl)methyl)-N-(3-(ethylcarbamoyl)phenyl)-3-fluorobicyclo[1.1.1]pentane-1-carboxamide (28)

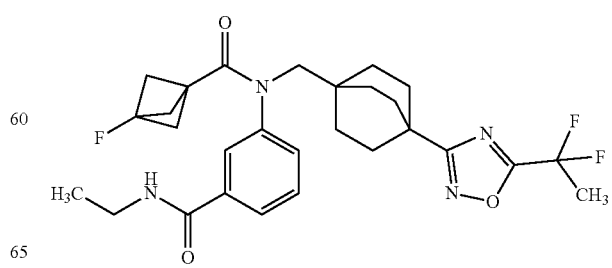

Step A. Intermediate 28A. Preparation of methyl 3-(((4-(5-(1,1-difluoroethyl)-1,2,4-oxadiazol-3-yl)bicyclo[2.2.2]octan-1-yl)methyl)amino)benzoate

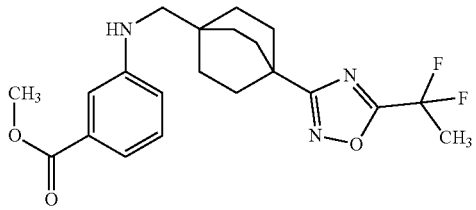 [SMILES: COC(=O)c1cccc(NCC23CCC(c4noc(C(C)(F)F)n4)(CC2)CC3)c1]

The title compound was prepared according to method described for the synthesis of Intermediate 1G by substituting Intermediate 1F and methyl 3-aminobenzoate where appropriate: (75 mg, 0.18 mmol, 68% yield). MS (ESI) 406 (M+H).

Step B. Intermediate 28B. Preparation of methyl 3-(N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamido)benzoate

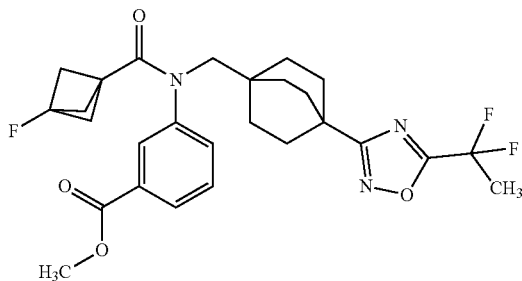 [SMILES: COC(=O)c1cccc(N(CC23CCC(c4noc(C(C)(F)F)n4)(CC2)CC3)C(=O)C23CC(F)(C2)C3)c1]

The title compound was prepared according to method described for the synthesis of Example 1 (Step H) by substituting Intermediate 28A where appropriate: (75 mg, 0.143 mmol, 77% yield). $^1$H NMR (400 MHz, DMSO-d$_6$) δ 7.97 (d, J=8.1 Hz, 1H), 7.91-7.86 (m, 1H), 7.77-7.70 (m, 1H), 7.66-7.57 (m, 1H), 3.90 (s, 3H), 3.66-3.50 (m, 2H), 2.14 (t, J=19.7 Hz, 3H), 1.84 (br s, 6H), 1.80-1.66 (m, 6H), 1.50-1.35 (m, 6H). MS (ESI) 518 (M+H).

Step C. Intermediate 28C. Preparation of 3-(N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamido)benzoic Acid

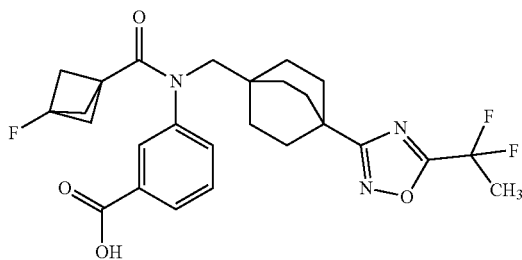 [SMILES: CC(F)(F)c1nc(C23CCC(CN(C(=O)C45CC(F)(C4)C5)c4cccc(C(=O)O)c4)(CC2)CC3)no1]

To a solution of Intermediate 28B (65 mg, 0.126 mmol) in methanol (1 mL) was added a solution of sodium hydroxide (20 mg, 0.502 mmol) in water (1 mL). The reaction mixture was stirred at room temperature for 1 h. The reaction mixture was concentrated under reduced pressure. The residue was diluted with water (5 mL), acidified with aq. 1.5 N HCl solution and extracted with EtOAc (2×20 mL). The combined organic layers were dried over anhydrous sodium sulphate, filtered and concentrated under reduced pressure to afford the title compound (50 mg, 0.01 mmol, 79% yield) as off-white solid. $^1$H NMR (400 MHz, DMSO-d$_6$) δ 7.94 (d, J=7.3 Hz, 1H), 7.83 (s, 1H), 7.70-7.62 (m, 1H), 7.61-7.54 (m, 1H), 3.58 (s, 2H), 2.13 (t, J=19.6 Hz, 3H), 1.83 (br s, 6H), 1.81-1.73 (m, 6H), 1.49-1.37 (m, 6H) (Exchangeable proton was buried under solvent peak.). MS (ESI) 504 (M+H).

Step D. Example 28. Preparation of N-((4-(5-(1,1-difluoroethyl)-1,2,4-oxadiazol-3-yl) bicyclo[2.2.2]octan-1-yl)methyl)-N-(3-(ethylcarbamoyl)phenyl)-3-fluorobicyclo[1.1.1]pentane-1-carboxamide To a stirred solution of Intermediate 28C (20 mg, 0.040 mmol) in DMF (1 mL) at room temperature were added ethanamine (0.06 mL, 0.12 mmol), TEA (0.02 mL, 0.16 mmol) followed by BOP (17.57 mg, 0.04 mmol). The reaction mixture was stirred at room temperature for 1 h. The reaction mixture was poured into water (10 mL) and extracted with EtOAc (2×10 mL). The combined organic layers were washed with brine (10 mL), dried over anhydrous sodium sulphate, filtered and concentrated under reduced pressure. The crude material was purified via preparative LC/MS using following conditions: Column: Waters XBridge C18, 150 mm×19 mm, 5 μm particles; Mobile Phase A: 5:95 acetonitrile: water with 10 mM ammonium acetate; Mobile Phase B: 95:5 acetonitrile: water with 10 mM ammonium acetate; Gradient: a 0-minute hold at 20% B, 20-59% B over 20 minutes, then a 5-minute hold at 100% B; Flow Rate: 15 mL/min; Column Temperature: 25° C. Fraction collection was triggered by signals. Fractions containing the desired product were combined and dried via centrifugal evaporation to afford the title compound (11 mg, 0.02 mmol, 49% yield). $^1$H NMR (400 MHz, DMSO-d$_6$) δ 8.58 (t, J=5.3 Hz, 1H), 7.90-7.85 (m, 1H), 7.84-7.80 (m, 1H), 7.61-7.49 (m, 2H), 3.68-3.50 (m, 2H), 3.32-3.26 (m, 2H), 2.14 (t, J=19.7 Hz, 3H), 1.84 (br s, 6H), 1.81-1.75 (m, 6H), 1.49-1.40 (m, 6H), 1.15 (t, J=7.2 Hz, 3H). FXR EC$_{50}$ (nM)=210. MS (ESI) 531 (M+H).

Example 29

N-(3-carbamoylphenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide (29)

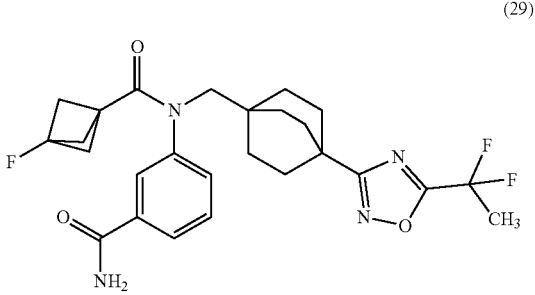 [SMILES: CC(F)(F)c1nc(C23CCC(CN(C(=O)C45CC(F)(C4)C5)c4cccc(C(N)=O)c4)(CC2)CC3)no1]

The title compound was prepared according to method described for the synthesis of Example 28 (Step D) by substituting Intermediate 28C and ammonium chloride where appropriate: (15 mg, 0.03 mmol, 75% yield). $^1$H NMR (400 MHz, DMSO-d$_6$) δ 8.12 (s, 1H), 7.93-7.87 (m, 1H), 7.86 (s, 1H), 7.62-7.49 (m, 3H), 3.67-3.50 (m, 2H), 2.14 (t, J=19.7 Hz, 3H), 1.88-1.70 (m, 12H), 1.53-1.35 (m, 6H). FXR EC$_{50}$ (nM)=902. MS (ESI) 503 (M+H).

Example 30

1-(3-bromophenyl)-1-((4-(5-(1,1-difluoroethyl)-1,2,4-oxadiazol-3-yl)bicyclo[2.2.2]octan-1-yl)methyl)-3-((1R,4R)-4-hydroxy-4-methylcyclohexyl)urea

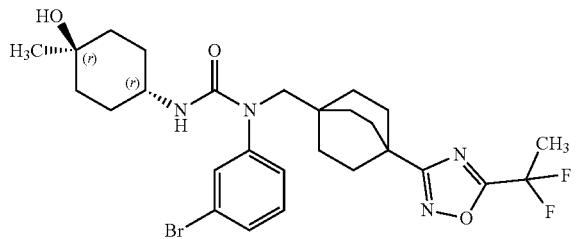

(30)

Step A. Intermediate 30A. Preparation of 3-bromo-N-((4-(5-(1,1-difluoroethyl)-1,2,4-oxadiazol-3-yl)bicyclo[2.2.2]octan-1-yl)methyl)aniline

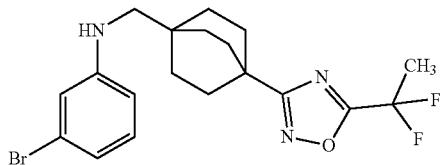 [SMILES: CC(F)(F)c1nc(C23CCC(CNc4cccc(Br)c4)(CC2)CC3)no1]

The title compound was prepared according to method described for the synthesis of Intermediate 1G by substituting Intermediate 1F and 3-bromoaniline where appropriate: (300 mg, 0.70 mmol, 86% yield). $^1$H NMR (400 MHz, DMSO-d$_6$) δ 7.01-6.93 (m, 1H), 6.78 (t, J=2.0 Hz, 1H), 6.65-6.57 (m, 2H), 5.81-5.73 (m, 1H), 2.81 (d, J=6.0 Hz, 2H), 2.16 (t, J=19.6 Hz, 3H), 1.93-1.81 (m, 6H), 1.62-1.52 (m, 6H). MS (ESI) 427.9 (M+H).

Step B. Example 30. Preparation of 1-(3-bromophenyl)-1-((4-(5-(1,1-difluoroethyl)-1,2,4-oxadiazol-3-yl)bicyclo[2.2.2]octan-1-yl)methyl)-3-((1R,4R)-4-hydroxy-4-methylcyclohexyl)urea A stirred solution of Intermediate 30A (15 mg, 0.035 mmol) and TEA (0.02 mL, 0.17 mmol) in DCM (3 mL) was cooled to 0° C. Triphosgene (10 mg, 0.03 mmol) as a solution in DCM (1 mL) was added to the reaction mixture. The reaction mixture was allowed to warm up to room temperature and stirred for 12 h. To the above reaction mixture, trans-4-Amino-1-methylcyclohexanol (5.46 mg, 0.04 mmol) was added and the reaction mixture was stirred at room temperature for 4 h. The reaction mixture was concentrated under reduced pressure. The crude compound was purified via preparative LC/MS using following conditions: Column: Waters XBridge C18, 150 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 2-minute hold at 18% B, 18-62% B over 25 minutes, then a 5-minute hold at 100% B; Flow Rate: 15 mL/min; Column Temperature: 25° C. Fraction collection was triggered by signals. Fractions containing the desired product were combined and dried via centrifugal evaporation to afford the title compound (6 mg, 10.84 μmol, 31% yield) as an off white solid. $^1$H NMR (400 MHz, DMSO-d$_6$) δ 7.54 (d, J=1.7 Hz, 1H), 7.44-7.38 (m, 1H), 7.37-7.27 (m, 2H), 5.44 (d, J=7.8 Hz, 1H), 4.20 (s, 1H), 3.53 (s, 2H), 3.49-3.42 (m, 1H), 2.14 (t, J=19.7 Hz, 3H), 1.82-1.68 (m, 6H), 1.65-1.53 (m, 2H), 1.45-1.23 (m, 12H), 1.06 (s, 3H). FXR EC$_{50}$ (nM)=150; MS (ESI) 581 (M+H).

Example 31

N-(3-bromophenyl)-N-((4-(5-(1,1-difluoroethyl)-1,2,4-oxadiazol-3-yl) bicyclo[2.2.2]octan-1-yl)methyl)-2,2-difluorocyclopropane-1-carboxamide (Racemate)

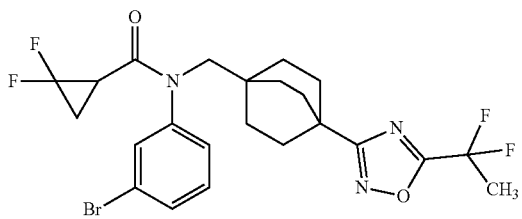

(31)

The title compound was prepared according to method described for the synthesis of Example 1 (Step H) by substituting Intermediate 30A where appropriate: (8 mg, 0.015 mmol, 21% yield). $^1$H NMR (400 MHz, DMSO-d$_6$) δ 7.75-7.65 (m, 1H), 7.59 (br d, J=7.1 Hz, 1H), 7.51-7.34 (m, 2H), 3.87 (br d, J=13.9 Hz, 1H), 3.47 (br d, J=14.4 Hz, 1H), 2.37-2.28 (m, 1H), 2.14 (t, J=19.7 Hz, 3H), 2.00-1.89 (m, 1H), 1.78 (br t, J=7.9 Hz, 7H), 1.49-1.30 (m, 6H). FXR EC$_{50}$ (nM)=261. MS (ESI) 530 (M+H).

Example 32

Tert-butyl (3-(N-((4-(5-(1,1-difluoroethyl)-1,2,4-oxadiazol-3-yl)bicyclo[2.2.2]octan-1-yl) methyl)-3-fluorobicyclo[1.1.1]pentane-1-carboxamido)phenyl) carbamate

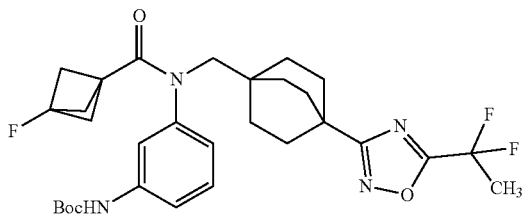

(32)

Step A. Intermediate 32A. Preparation of tert-butyl (3-nitrophenyl)carbamate

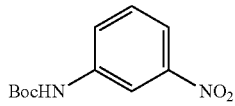

To a stirred solution of 3-nitroaniline (5 g, 36.2 mmol) in THF (50 mL) at room temperature was added boc-anhydride (8.40 mL, 36.2 mmol). The reaction mixture was cooled to 0° C. and DMAP (4.86 g, 39.8 mmol) was added portion wise. The reaction mixture was allowed to warm to room temperature and stirred overnight. The reaction mixture was diluted with ethyl acetate (100 mL) and the organic solution was washed with water (50 mL) followed by brine solution (2×50 mL). The organic layer was dried over anhydrous sodium sulphate, filtered and concentrated under reduced pressure. The crude material was purified by flash column chromatography (80 g silica gel cartridge; A=Hex, B=EtOAc; 30 min grad.; 0% B to 70% B; flow rate=40 mL/min). The pure fractions were combined, concentrated under reduced pressure and dried in vacuo to afford the title compound (8 g, 33.6 mmol, 93% yield) as brown solid. MS (ESI) 237 (M−H).

Step B. Intermediate 32B. Preparation of tert-butyl (3-aminophenyl)carbamate

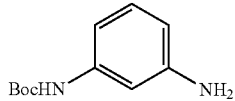

To a stirred solution of Intermediate 32A (1 g, 4.20 mmol) in ethanol (20 mL) and water (5 mL) at room temperature was added ammonium chloride (3.37 g, 63 mmol) followed by zinc (4.12 g, 63 mmol). After stirring overnight at room temperature, the reaction mixture was filtered over Celite pad and the filtrate was diluted with ethyl acetate (50 mL). The organic solution was then washed with brine solution (2×25 mL), dried over anhydrous sodium sulphate, filtered and concentrated under reduced pressure. The crude material was purified by flash column chromatography (40 g silica gel cartridge; A=Hex, B=EtOAc; 30 min grad.; 0% B to 60% B; flow rate=40 mL/min). The pure fractions were combined, concentrated under reduced pressure and dried in vacuo to afford the title compound (800 mg, 3.73 mmol, 89% yield) as brown solid. MS (ESI) 209 (M+H).

Step C. Intermediate 32C. Preparation of tert-butyl (3-(((4-(5-(1,1-difluoroethyl)-1,2,4-oxadiazol-3-yl) bicyclo[2.2.2]octan-1-yl)methyl)amino)phenyl)carbamate

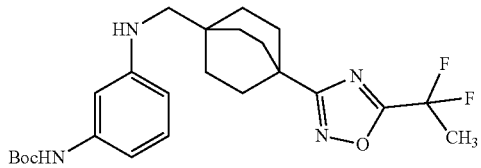 [SMILES: CC(C)(C)OC(=O)Nc1cccc(NCC23CCC(c4noc(C(C)(F)F)n4)(CC2)CC3)c1]

The title compound was prepared according to method described for the synthesis of Intermediate 1G by substituting Intermediate 1F and Intermediate 32B where appropriate: (40 mg, 0.08 mmol, 45% yield). MS (ESI) 463 (M+H).

Step D. Example 32. Preparation of tert-butyl (3-(N-((4-(5-(1,1-difluoroethyl)-1,2,4-oxadiazol-3-yl) bicyclo[2.2.2]octan-1-yl)methyl)-3-fluorobicyclo [1.1.1]pentane-1-carboxamido)phenyl)carbamate The title compound was prepared according to method described for the synthesis of Example 1 (Step H) by substituting Intermediate 32C where appropriate: (15 mg, 0.027 mmol, 62% yield). $^1$H NMR (400 MHz, DMSO-d$_6$) δ 9.52 (s, 1H), 7.47 (br d, J=8.6 Hz, 1H), 7.43 (t, J=1.8 Hz, 1H), 7.33 (t, J=7.9 Hz, 1H), 6.98 (dd, J=1.2, 7.8 Hz, 1H), 3.59-3.42 (m, 2H), 2.14 (t, J=19.7 Hz, 3H), 1.87 (br d, J=9.8 Hz, 6H), 1.82-1.71 (m, 6H), 1.49 (s, 9H), 1.47-1.36 (m, 6H). FXR EC$_{50}$ (nM)=62. MS (ESI) 575 (M+H).

Example 33

N-(3-bromophenyl)-N-((4-(5-(1,1-difluoroethyl)-1,2,4-oxadiazol-3-yl) bicyclo[2.2.2]octan-1-yl)methyl)-3-fluorobicyclo[1.1.1]pentane-1-carboxamide

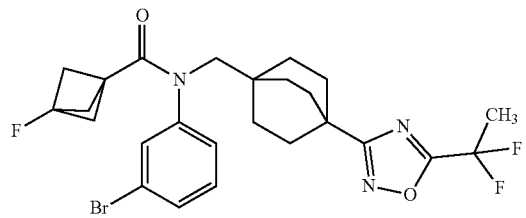

(33)

Step A. Intermediate 33A. Preparation of methyl 4-(hydroxymethyl) bicyclo[2.2.2]octane-1-carboxylate

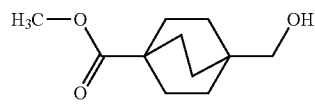

To a stirred solution of 4-(methoxycarbonyl)bicyclo [2.2.2]octane-1-carboxylic acid (10 g, 47.1 mmol) in THF (100 mL) at 0° C. was added BH$_3$·DMS (14.3 mL, 141 mmol) drop wise. The reaction mixture was allowed to warm to room temperature and stirred for 2 h. The reaction mixture was cooled to 0° C. and carefully quenched with methanol. The resulting solution was concentrated under reduced pressure and the residue was diluted with water (50 mL). The aqueous solution was extracted with ethyl acetate (2×50 mL). The combined organic layers were washed with brine solution (20 mL), dried over anhydrous sodium sulphate and concentrated under reduced pressure. The crude material was purified by flash column chromatography (80 g silica gel cartridge; A=Hex, B=EtOAc; 30 min grad.; 0% B to 70% B; flow rate=40 mL/min). The pure fractions were combined, concentrated under reduced pressure and dried in vacuo to afford the title compound (7 g, 35.3 mmol, 75% yield). $^1$H NMR (400 MHz, DMSO-$d_6$) δ 4.12 (dd, J=28.40, Hz, 1H), 3.65 (s, 3H), 3.29 (s, 2H), 1.82-1.77 (m, 6H), 1.47-1.42 (m, 6H).

Step B. Intermediate 33A. Preparation of methyl 4-formylbicyclo[2.2.2]octane-1-carboxylate

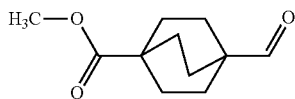

The title compound was prepared according to the method described for the synthesis of Intermediate 1F by substituting Intermediate 33A where appropriate. (900 mg, 4.59 mmol, 91% yield) as gummy liquid. $^1$H NMR (400 MHz, DMSO-$d_6$) δ 9.43 (s, 1H), 3.59 (s, 3H), 1.78-1.57 (m, 12H). MS (ESI) 197 (M+H).

Step C. Intermediate 33C. Preparation of methyl 4-(((3-bromophenyl)amino)methyl) bicyclo[2.2.2]octane-1-carboxylate

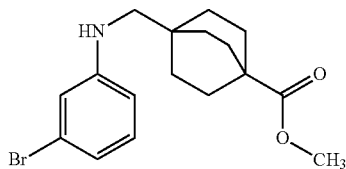 [SMILES: COC(=O)C12CCC(CNc3cccc(Br)c3)(CC1)CC2]

The title compound was prepared according to the method described for the synthesis of Intermediate 1G by substituting 3-bromoaniline and Intermediate 33B where appropriate. (6.4 g, 18.17 mmol, 79% yield) as brown gummy liquid. MS (ESI) 353 (M+H).

Step D. Intermediate 33D. Preparation of methyl 4-((N-(3-bromophenyl)-3-fluorobicyclo[1.1.1]pentane-1-carboxamido)methyl)bicyclo[2.2.2]octane-1-carboxylat

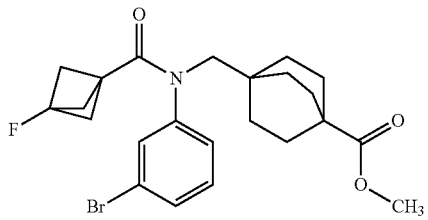 [SMILES: COC(=O)C12CCC(CN(C(=O)C34CC(F)(C3)C4)c3cccc(Br)c3)(CC1)CC2]

The title compound was prepared according to the method described for the synthesis of Example 1 (Step H) by substituting Intermediate 33C and corresponding acid where appropriate. (2.5 g, 5.38 mmol, 54% yield) as brown gummy liquid. MS (ESI) 464 (M+H).

Step E. Intermediate 33E. Preparation of 4-((N-(3-bromophenyl)-3-fluorobicyclo[1.1.1]pentane-1-carboxamido)methyl)bicyclo[2.2.2]octane-1-carboxylic Acid

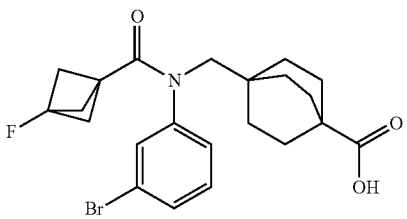 [SMILES: O=C(O)C12CCC(CN(C(=O)C34CC(F)(C3)C4)c3cccc(Br)c3)(CC1)CC2]

The title compound was prepared according to the method described for the synthesis of Intermediate 28C by substituting Intermediate 33D where appropriate. (2.1 g, 4.66 mmol, 98% yield) as brown gummy liquid. MS (ESI) 452 (M+H).

Step F. Intermediate 33F. Preparation of 4-((N-(3-bromophenyl)-3-fluorobicyclo[1.1.1]pentane-1-carboxamido)methyl)bicyclo[2.2.2]octane-1-carboxamide

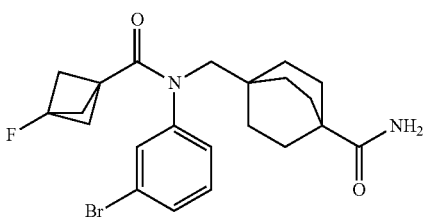 [SMILES: NC(=O)C12CCC(CN(C(=O)C34CC(F)(C3)C4)c3cccc(Br)c3)(CC1)CC2]

The title compound was prepared according to the method described for the synthesis of Intermediate 1A by substituting Intermediate 33E where appropriate. (1.6 g, 3.56 mmol, 97% yield). MS (ESI) 450 (M+H).

Step G. Intermediate 33G. Preparation of N-(3-bromophenyl)-N-((4-cyanobicyclo[2.2.2]octan-1-yl)methyl)-3-fluorobicyclo[1.1.1]pentane-1-carboxamide The title compound was prepared according to the method described for the synthesis of Intermediate 1B by substituting Intermediate 33F where appropriate. (850 mg, 1.97 mmol, 55% yield) as pale brown gummy liquid. MS (ESI) 431 (M+H).

Step H. Intermediate 33H. Preparation of (E)-N-(3-bromophenyl)-3-fluoro-N-((4-(N'-hydroxycarbamimidoyl)bicyclo[2.2.2]octan-1-yl)methyl)bicyclo[1.1.1]pentane-1-carboxamide

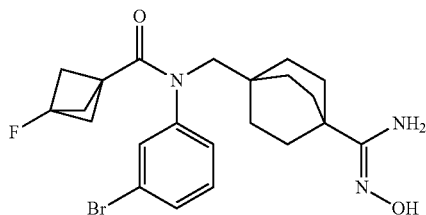 [SMILES: N/C(=N\O)C12CCC(CN(C(=O)C34CC(F)(C3)C4)c3cccc(Br)c3)(CC1)CC2]

The title compound was prepared according to the method described for the synthesis of Intermediate 1C by substituting Intermediate 33G where appropriate. (820 mg, 1.766 mmol, 92% yield) as white solid. MS (ESI) 464 (M+H).

Step I. Example 33. Preparation of N-(3-bromophenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide The title compound was prepared according to the method described for the synthesis of Intermediate 1D by substituting Intermediate 33H where appropriate. (9.6 mg, 0.017 mmol, 55% yield). $^1$H NMR (400 MHz, DMSO-d$_6$) δ 7.74-7.68 (m, 1H), 7.61 (dt, J=7.3, 1.7 Hz, 1H), 7.49-7.36 (m, 2H), 3.58 (br. s., 1H), 3.51 (br. s., 1H), 2.23-2.05 (m, 3H), 1.88 (br. s., 6H), 1.82-1.69 (m, 6H), 1.53-1.33 (m, 6H). FXR EC$_{50}$ (nM)=13. MS (ESI) 538 (M+H).

Example 34

N-(3-bromophenyl)-3-fluoro-N-((4-(5-(1-fluorocyclopropyl)-1,2,4-oxadiazol-3-yl) bicyclo[2.2.2]octan-1-yl)methyl)bicyclo[1.1.1]pentane-1-carboxamide (34)

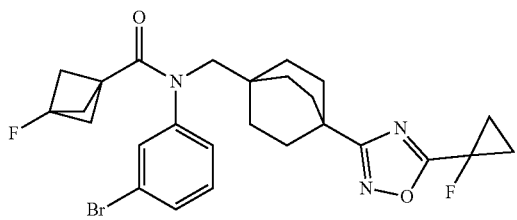

The title compound was prepared according to methods described for the synthesis of Intermediate 1D by substituting Intermediate 33H where appropriate: (450 mg, 0.845 mmol, 65% yield). $^1$H NMR (400 MHz, DMSO-d$_6$) δ 7.75-7.67 (m, 1H), 7.61 (dt, J=7.3, 1.7 Hz, 1H), 7.50-7.36 (m, 2H), 3.58 (br. s., 1H), 3.50 (br. s., 1H), 1.87 (br. s., 6H), 1.81-1.61 (m, 8H), 1.52-1.31 (m, 8H). FXR EC$_{50}$ (nM)=20. MS (ESI) 533 (M+H).

Example 35

N-(3-bromophenyl)-3-fluoro-N-((4-(5-(trifluoromethyl)-1,2,4-oxadiazol-3-yl) bicyclo[2.2.2]octan-1-yl)methyl)bicyclo[1.1.1]pentane-1-carboxamide (35)

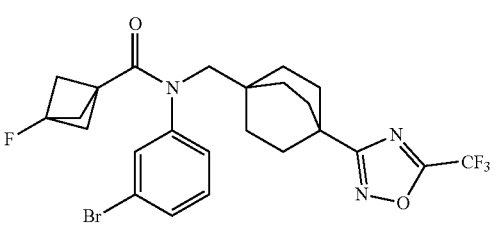

The title compound was prepared according to methods described for the synthesis of Intermediate 1D by substituting Intermediate 33H where appropriate: (1.2 g, 2.18 mmol, 78% yield). $^1$H NMR (400 MHz, DMSO-d$_6$) δ 7.71 (t, J=1.8 Hz, 1H), 7.61 (dt, J=7.6, 1.7 Hz, 1H), 7.50-7.37 (m, 2H), 3.59 (br. s., 1H), 3.52 (br. s., 1H), 1.88 (br. s., 6H), 1.84-1.67 (m, 6H), 1.54-1.35 (m, 6H). FXR EC$_{50}$ (nM)=42. MS (ESI) 543 (M+H).

Example 36

(1S,3S)—N-(3-bromophenyl)-N-((4-(3-(tert-butyl)-1,2,4-oxadiazol-5-yl) bicyclo[2.2.2]octan-1-yl)methyl)-3-hydroxy-3-(trifluoromethyl)cyclobutane-1-carboxamide (36)

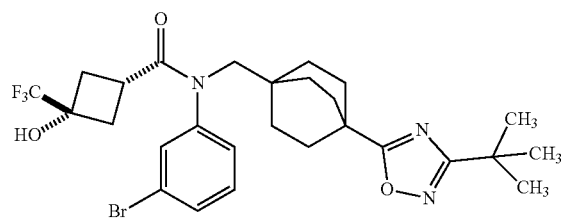

Step A. Intermediate 36A. Preparation of methyl 4-(3-(tert-butyl)-1,2,4-oxadiazol-5-yl) bicyclo[2.2.2]octane-1-carboxylate

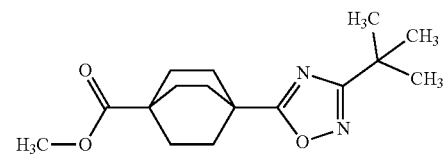

The title compound was prepared according to the method described for the synthesis of Intermediate 1D by substituting 4-(methoxycarbonyl)bicyclo[2.2.2]octane-1-carboxylic acid and N'-hydroxypivalimidamide where appropriate. (2.2 g, 7.52 mmol, 97% yield) as white solid. MS (ESI) 293

(M+H). ¹H NMR (400 MHz, DMSO-d₆) δ 3.61 (s, 3H), 1.96-1.87 (m, 6H), 1.87-1.79 (m, 6H), 1.29 (s, 9H).

Step B. Intermediate 36B. Preparation of (4-(3-(tert-butyl)-1,2,4-oxadiazol-5-yl) bicyclo[2.2.2]octan-1-yl)methanol

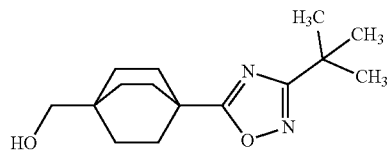 [SMILES: CC(C)(C)c1noc(C23CCC(CO)(CC2)CC3)n1]

The title compound was prepared according to the method described for the synthesis of Intermediate 1E by substituting Intermediate 36A where appropriate. (1.5 g, 5.62 mmol, 75% yield) as white solid. MS (ESI) 265 (M+H). ¹H NMR (400 MHz, DMSO-d₆) δ 4.43 (t, J=5.5 Hz, 1H), 3.09 (d, J=5.5 Hz, 2H), 1.94-1.79 (m, 6H), 1.52-1.39 (m, 6H), 1.29 (s, 9H).

Step C. Intermediate 36C. Preparation of 4-(3-(tert-butyl)-1,2,4-oxadiazol-5-yl) bicyclo[2.2.2]octane-1-carbaldehyde

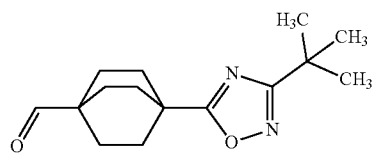 [SMILES: CC(C)(C)c1noc(C23CCC(C=O)(CC2)CC3)n1]

The title compound was prepared according to the method described for the synthesis of Intermediate 1F by substituting Intermediate 36B where appropriate. (1.1 g, 3.44 mmol, 60% yield) as white solid. MS (ESI) 263 (M+H). ¹H NMR (400 MHz, DMSO-d₆) δ 9.47 (s, 1H), 1.97-1.88 (m, 6H), 1.76-1.65 (m, 6H), 1.29 (s, 9H).

Step D. Intermediate 36D. Preparation of 3-bromo-N-((4-(3-(tert-butyl)-1,2,4-oxadiazol-5-yl)bicyclo[2.2.2]octan-1-yl)methyl)aniline

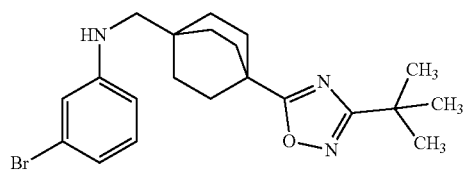 [SMILES: CC(C)(C)c1noc(C23CCC(CNc4cccc(Br)c4)(CC2)CC3)n1]

The title compound was prepared according to method described for the synthesis of Intermediate 1G by substituting Intermediate 36C and 3-bromoaniline where appropriate: (350 mg, 0.83 mmol, 72% yield). MS (ESI) 419 (M+H).

Step E. Example 36. Preparation of (1S,3S)—N-(3-bromophenyl)-N-((4-(3-(tert-butyl)-1,2,4-oxadiazol-5-yl)bicyclo[2.2.2]octan-1-yl)methyl)-3-hydroxy-3-(trifluoromethyl) cyclobutane-1-carboxamide The title compound was prepared according to the method described for the synthesis of Example 1 (Step H) by substituting Intermediate 36D where appropriate: (46.3 mg, 0.08 mmol, 55% yield). ¹H NMR (400 MHz, DMSO-d₆) δ 7.70 (s, 1H), 7.55 (d, J=7.6 Hz, 1H), 7.49-7.26 (m, 2H), 6.54 (s, 1H), 3.60 (br. s., 2H), 2.79-2.68 (m, 1H), 2.40-2.24 (m, 2H), 2.13-1.93 (m, 2H), 1.90-1.61 (m, 6H), 1.56-1.31 (m, 6H), 1.31-1.14 (m, 9H). FXR EC₅₀ (nM)=135. MS (ESI) 584 (M+H).

Example 37

N-(3-bromo-4-chlorophenyl)-N-((4-(3-(tert-butyl)-1,2,4-oxadiazol-5-yl) bicyclo[2.2.2]octan-1-yl) methyl)-3-fluorobicyclo[1.1.1]pentane-1-carboxamide (37)

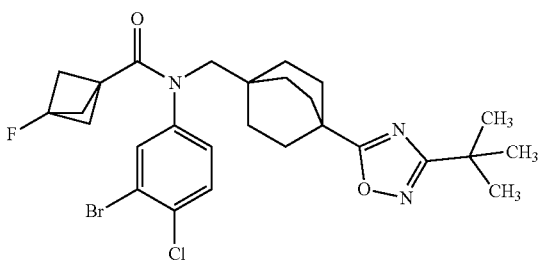

Step A. Intermediate 37A. Preparation of 3-bromo-N-((4-(3-(tert-butyl)-1,2,4-oxadiazol-5-yl)bicyclo[2.2.2]octan-1-yl)methyl)-4-chloroaniline

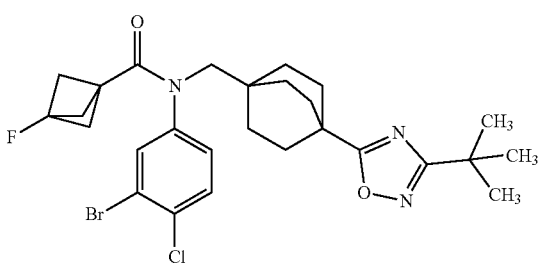 [SMILES: CC(C)(C)c1noc(C23CCC(CN(C(=O)C45CC(F)(C4)C5)c4ccc(Cl)c(Br)c4)(CC2)CC3)n1]

The title compound was prepared according to method described for the synthesis of Intermediate 1G by substituting Intermediate 36C and 3-bromo-4-chloroaniline where appropriate: (620 mg, 1.37 mmol, 81% yield). ¹H NMR (400 MHz, DMSO-d₆) δ 7.21 (d, J=8.5 Hz, 1H), 6.94 (d, J=2.5 Hz, 1H), 6.67-6.62 (m, 1H), 5.95 (t, J=5.8 Hz, 1H), 2.81 (d, J=6.0 Hz, 2H), 1.95-1.84 (m, 6H), 1.60-1.49 (m, 6H), 1.28 (s, 9H). MS (ESI) 452.2 (M+H).

Step B. Example 37. Preparation of N-(3-bromo-4-chlorophenyl)-N-((4-(3-(tert-butyl)-1,2,4-oxadiazol-5-yl)bicyclo[2.2.2]octan-1-yl)methyl)-3-fluorobicyclo[1.1.1]pentane-1-carboxamide The title compound was prepared according to the method described for the synthesis of Example 1 (Step H) by substituting Intermediate 37A where appropriate: (500 mg, 0.88 mmol, 65% yield). ¹H NMR (400 MHz, DMSO-d₆) δ 7.95 (d, J=2.4 Hz, 1H), 7.71 (d, J=8.3 Hz, 1H), 7.50 (dd, J=2.4, 8.6 Hz, 1H), 3.56 (br s, 2H), 1.91 (br s, 6H), 1.84-1.77 (m, 6H), 1.46-1.36 (m, 6H), 1.27 (s, 9H). FXR EC$_{50}$ (nM)=1078. MS (ESI) 564 (M+H).

Example 38

N-((4-(3-(tert-butyl)-1,2,4-oxadiazol-5-yl)bicyclo[2.2.2]octan-1-yl)methyl)-N-(3-cyanophenyl)-3-fluorobicyclo[1.1.1]pentane-1-carboxamide (38)

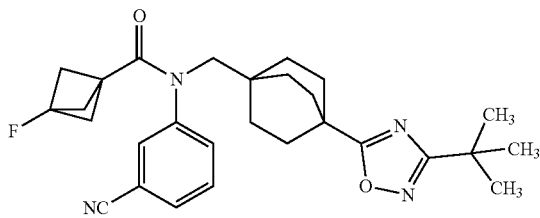

Step A. Intermediate 38A. Preparation of 3-(((4-(3-(tert-butyl)-1,2,4-oxadiazol-5-yl) bicyclo[2.2.2]octan-1-yl)methyl)amino)benzonitrile

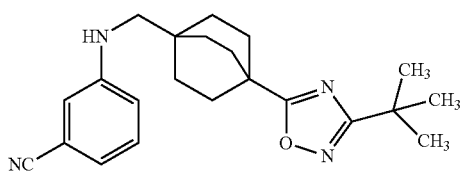 [SMILES: CC(C)(C)c1noc(C23CCC(CNc4cccc(C#N)c4)(CC2)CC3)n1]

The title compound was prepared according to method described for the synthesis of Intermediate 1G by substituting Intermediate 36C and 3-aminobenzonitrile where appropriate: (110 mg, 0.3 mmol, 78% yield). $^1$H NMR (300 MHz, DMSO-d$_6$) δ 7.25-7.16 (m, 1H), 6.98-6.90 (m, 2H), 6.88-6.81 (m, 1H), 6.03 (t, J=6.1 Hz, 1H), 2.86 (d, J=5.9 Hz, 2H), 1.95-1.81 (m, 6H), 1.61-1.49 (m, 6H), 1.28 (s, 9H). MS (ESI) 365.2 (M+H).

Step B. Example 38. Preparation of N-((4-(3-(tert-butyl)-1,2,4-oxadiazol-5-yl) bicyclo[2.2.2]octan-1-yl)methyl)-N-(3-cyanophenyl)-3-fluorobicyclo[1.1.1]pentane-1-carboxamide The title compound was prepared according to method described for the synthesis of Example 1 (Step H) by substituting Intermediate 38A where appropriate: (9 mg, 0.018 mmol, 33% yield). $^1$H NMR (400 MHz, DMSO-d$_6$) δ 8.04 (d, J=1.5 Hz, 1H), 7.88 (d, J=7.6 Hz, 1H), 7.82-7.77 (m, 1H), 7.70-7.62 (m, 1H), 3.65-3.49 (m, 2H), 1.87 (s, 6H), 1.82-1.74 (m, 6H), 1.47-1.34 (m, 6H), 1.27 (s, 9H). FXR EC$_{50}$ (nM)=142. MS (ESI) 477 (M+H).

The following examples were prepared according to the method described for the synthesis of Example 1 (step H) by substituting Intermediate 38A and corresponding acids where appropriate:

| Ex. No. | Structure & Name | MS (ESI) (M + H) | FXR EC$_{50}$ (nM) |
|---|---|---|---|
| 39 | (1S,3S)-N-((4-(3-(tert-butyl)-1,2,4-oxadiazol-5-yl)bicyclo[2.2.2]octan-1-yl)methyl)-N-(3-cyanophenyl)-3-hydroxy-3-(trifluoromethyl)cyclobutane-1-carboxamide | 531 | 568 |
| 40 | (1S,3S)-N-((4-(3-(tert-butyl)-1,2,4-oxadiazol-5-yl)bicyclo[2.2.2]octan-1-yl)methyl)-N-(3-cyanophenyl)-3-hydroxy-3-methylcyclobutane-1-carboxamide | 477 | 1260 |

| Ex. No. | Structure & Name | MS (ESI) (M + H) | FXR EC$_{50}$ (nM) |
|---|---|---|---|
| 41 | N-((4-(3-(tert-butyl)-1,2,4-oxadiazol-5-yl)bicyclo[2.2.2]octan-1-yl)methyl)-N-(3-cyanophenyl)-3,3-difluorocyclobutane-1-carboxamide | 483 | 171 |
| 42 | N-((4-(3-(tert-butyl)-1,2,4-oxadiazol-5-yl)bicyclo[2.2.2]octan-1-yl)methyl)-N-(3-cyanophenyl)-4,4-difluorocyclohexane-1-carboxamide | 511 | 1251 |
| 39 | $^1$H NMR (400 MHz, DMSO-d$_6$) δ 8.04 (s, 1H), 7.82 (t, J = 8.4 Hz, 2H), 7.70-7.59 (m, 1H), 6.56 (s, 1H), 3.71-3.52 (m, 2H), 2.79-2.69 (m, 1H), 2.36-2.27 (m, 2H), 2.07-1.94 (m, 2H), 1.87-1.74 (m, 6H), 1.47-1.34 (m, 6H), 1.26 (s, 9H) | | |
| 40 | $^1$H NMR (400 MHz, DMSO-d$_6$) δ 7.96 (s, 1H), 7.80 (br d, J = 7.8 Hz, 1H), 7.77-7.69 (m, 1H), 7.66-7.53 (m, 1H), 4.92 (br d, J = 2.2 Hz, 1H), 3.67-3.53 (m, 2H), 2.16-1.99 (m, 2H), 1.84-1.71 (m, 6H), 1.64-1.49 (m, 2H), 1.44-1.30 (m, 6H), 1.26 (s, 9H), 1.06-0.89 (m, 3H). 1H buried under moisture peak. | | |
| 41 | $^1$H NMR (400 MHz, DMSO-d$_6$) δ 8.02 (s, 1H), 7.89-7.74 (m, 2H), 7.71-7.58 (m, 1H), 3.63 (s, 2H), 2.97-2.85 (m, 1H), 2.81-2.65 (m, 2H), 2.38-2.23 (m, 2H), 1.84-1.75 (m, 6H), 1.44-1.34 (m, 6H), 1.26 (s, 9H) | | |
| 42 | $^1$H NMR (400 MHz, DMSO-d$_6$) δ 8.05 (br s, 1H), 7.91-7.76 (m, 2H), 7.72-7.58 (m, 1H), 3.67-3.55 (m, 2H), 2.35-2.30 (m, 1H), 2.03-1.89 (m, 2H), 1.83-1.75 (m, 6H), 1.73-1.48 (m, 6H), 1.43-1.33 (m, 6H), 1.26 (s, 9H) | | |

Example 43

N-((4-(3-(tert-butyl)-1,2,4-oxadiazol-5-yl)bicyclo[2.2.2]octan-1-yl)methyl)-N-(3-(dimethylphosphoryl)phenyl)-3-fluorobicyclo[1.1.1]pentane-1-carboxamide

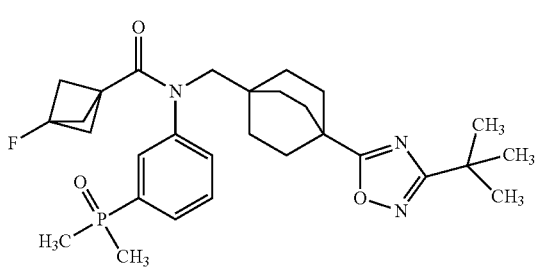

(43)

Step A. Intermediate 43A. Preparation of (3-(((4-(3-(tert-butyl)-1,2,4-oxadiazol-5-yl) bicyclo[2.2.2]octan-1-yl)methyl)amino)phenyl)dimethylphosphine Oxide

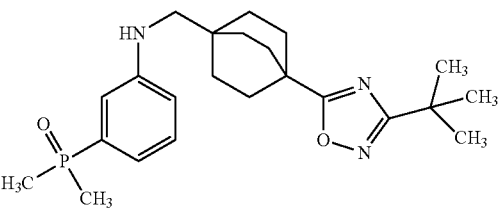 [SMILES: CC(C)(C)c1noc(C23CCC(CNc4cccc(P(C)(C)=O)c4)(CC2)CC3)n1]

The title compound was prepared according to method described for the synthesis of Intermediate 1G by substituting Intermediate 36C and Intermediate 24B where appropriate: (100 mg, 0.23 mmol, 77% yield). MS (ESI) 416 (M+H).

Step B. Example 43. Preparation of N-((4-(3-(tert-butyl)-1,2,4-oxadiazol-5-yl) bicyclo[2.2.2]octan-1-yl)methyl)-N-(3-(dimethylphosphoryl)phenyl)-3-fluorobicyclo[1.1.1]pentane-1-carboxamide The title compound was prepared according to method described for the synthesis of Example 1 (Step H) by substituting Intermediate 43A where appropriate: (16 mg, 0.03 mmol, 63% yield). $^1$H NMR (400 MHz, DMSO-d$_6$) δ 7.84-7.71 (m, 2H), 7.66-7.55 (m, 2H), 3.65-3.48 (m, 2H), 1.91-1.75 (m, 12H), 1.70 (br d, J=13.4 Hz, 6H), 1.50-1.35 (m, 6H), 1.31-1.20 (m, 9H). FXR EC$_{50}$ (nM)=4000. MS (ESI) 528 (M+H).

The following examples were prepared according to the method described for the synthesis of Example 1 (step H) by substituting Intermediate 43A and corresponding acids where appropriate:

| Ex. No. | Structure & Name | MS (ESI) (M + H) | FXR EC$_{50}$ (nM) |
|---|---|---|---|
| 44 | 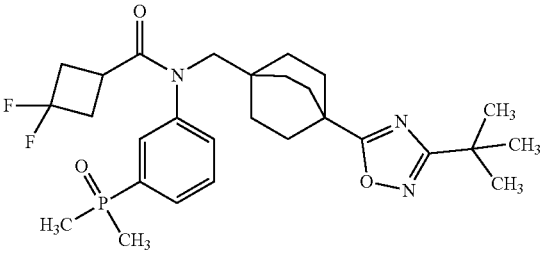 [SMILES: CC(C)(C)c1noc(C23CCC(CN(C(=O)C4CC(F)(F)C4)c4cccc(P(C)(C)=O)c4)(CC2)CC3)n1]<br>N-((4-(3-(tert-butyl)-1,2,4-oxadiazol-5-yl) bicyclo[2.2.2]octan-1-yl)methyl)-N-(3-(dimethylphosphoryl)phenyl)-3,3-difluorocyclobutane-1-carboxamide | 534 | 4000 |
| 45 | 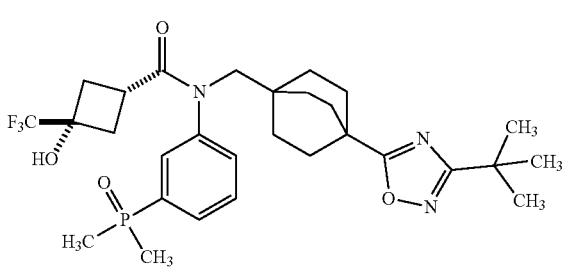 [SMILES: CC(C)(C)c1noc(C23CCC(CN(c4cccc(P(C)(C)=O)c4)C(=O)[C@H]4C[C@](O)(C(F)(F)F)C4)(CC2)CC3)n1]<br>(1S,3S)-N-((4-(3-(tert-butyl)-1,2,4-oxadiazol-5-yl) bicyclo[2.2.2]octan-1-yl)methyl)-N-(3-(dimethylphosphoryl)phenyl)-3-hydroxy-3-(trifluoromethyl)cyclobutane-1-carboxamide | 582 | 4000 |
| 46 | 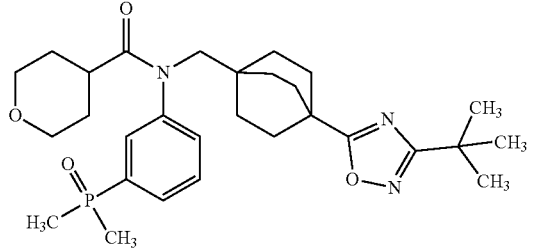 [SMILES: CC(C)(C)c1noc(C23CCC(CN(C(=O)C4CCOCC4)c4cccc(P(C)(C)=O)c4)(CC2)CC3)n1]<br>N-((4-(3-(tert-butyl)-1,2,4-oxadiazol-5-yl) bicyclo[2.2.2]octan-1-yl)methyl)-N-(3-(dimethylphosphoryl)phenyl)tetrahydro-2H-pyran-4-carboxamide | 528 | 4000 |

| Ex. No. | Structure & Name | MS (ESI) (M + H) | FXR EC$_{50}$ (nM) |
|---|---|---|---|
| 47 | N-((4-(3-(tert-butyl)-1,2,4-oxadiazol-5-yl)bicyclo[2.2.2]octan-1-yl)methyl)-N-(3-(dimethylphosphoryl)phenyl)tetrahydro-2H-thiopyran-4-carboxamide 1,1-dioxide | 576 | 4000 |

| 44 | $^1$H NMR (400 MHz, DMSO-d$_6$) δ 7.81-7.69 (m, 2H), 7.66-7.53 (m, 2H), 3.71-3.59 (m, 2H), 2.87-2.69 (m, 2H), 2.36-2.23 (m, 2H), 1.84-1.75 (m, 6H), 1.70 (s, 3H), 1.67 (s, 3H), 1.47-1.35 (m, 6H), 1.31-1.21 (m, 10H) |
|---|---|
| 45 | $^1$H NMR (400 MHz, DMSO-d$_6$) δ 7.80-7.68 (m, 2H), 7.63-7.54 (m, 2H), 6.55 (s, 1H), 3.70-3.58 (m, 2H), 2.79-2.69 (m, 1H), 2.36-2.25 (m, 2H), 2.07-1.91 (m, 2H), 1.83-1.74 (m, 6H), 1.68 (s, 3H), 1.65 (s, 3H), 1.47-1.36 (m, 6H), 1.30-1.22 (m, 9H) |
| 46 | $^1$H NMR (400 MHz, DMSO-d$_6$) δ 7.84-7.69 (m, 2H), 7.66-7.56 (m, 2H), 3.80-3.70 (m, 2H), 3.66-3.55 (m, 2H), 3.05-2.92 (m, 2H), 2.45-2.36 (m, 1H), 1.85-1.75 (m, 6H), 1.70 (s, 3H), 1.67 (s, 3H), 1.63-1.54 (m, 2H), 1.50-1.32 (m, 8H), 1.30-1.21 (m, 9H) |
| 47 | $^1$H NMR (400 MHz, DMSO-d$_6$) δ 7.84-7.70 (m, 2H), 7.62 (br d, J = 3.2 Hz, 2H), 3.04-2.87 (m, 5H), 2.74 (d, J = 0.7 Hz, 2H), 2.07-1.93 (m, 4H), 1.85-1.74 (m, 6H), 1.71 (s, 3H), 1.68 (s, 3H), 1.49-1.35 (m, 6H), 1.26 (s, 9H). |

Example 48

N-(3-bromophenyl)-N-((4-(5-(1,1-difluoroethyl)pyridin-2-yl)bicyclo[2.2.2]octan-1-yl) methyl)-3-fluorobicyclo[1.1.1]pentane-1-carboxamide

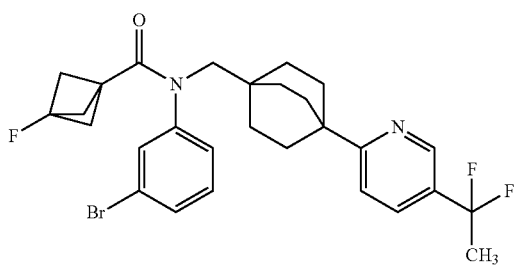

(48)

Step A. Intermediate 48A. Preparation of 3-(1,1-difluoroethyl)pyridine

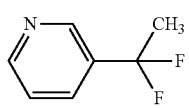

To a stirred solution of 1-(pyridin-3-yl)ethan-1-one (2 g, 16.51 mmol) in DCM (20 mL) at room temperature was added DAST (17.45 mL, 132 mmol). The reaction mixture was heated to 50° C. and stirred overnight. The reaction mixture was cooled to room temperature and poured drop wise into a cooled solution of aq. 2N NaOH (50 mL). The resulting solution was extracted with DCM (2×100 mL). The combined organic layers were washed with brine solution (100 mL), dried over anhydrous sodium sulphate, filtered and concentrated under reduced pressure. The crude material was purified by flash column chromatography (40 g silica gel cartridge; A=Hex, B=EtOAc; 30 min grad.; 0% B to 30% B; flow rate=40 mL/min). The pure fractions were combined, concentrated and dried in vacuo to afford the title compound (1.95 g, 13.35 mmol, 81% yield) as pale yellow liquid. Note: Rotary evaporation was done at 30° C. under reduced pressure. $^1$H NMR (400 MHz, DMSO-d$_6$) δ 8.80 (d, J=1.0 Hz, 1H), 8.72 (d, J=4.5 Hz, 1H), 8.00 (d, J=8.0 Hz, 1H), 7.58-7.51 (m, 1H), 2.10-1.97 (m, 3H). MS (ESI) 145.2 (M+H).

Step B. Intermediate 48B. Preparation of methyl 4-(5-(1,1-difluoroethyl)pyridin-2-yl) bicyclo[2.2.2]octane-1-carboxylate

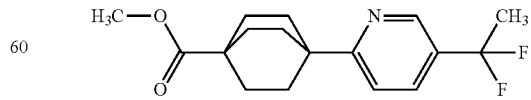

To a stirred solution of 4-(methoxycarbonyl)bicyclo[2.2.2]octane-1-carboxylic acid (2.3 g, 10.84 mmol) and Intermediate 48A (1.86 g, 13 mmol) in DCM (70 mL) and water (70 mL) at room temperature were added ammonium persulfate (2.47 g, 10.84 mmol) followed by silver nitrate (0.37 g, 2.16 mmol). The reaction mixture was stirred at room temperature for 48 h. The reaction mixture was diluted with DCM (25 mL) and filtered through Celite. The filtrate was washed with water (30 mL), dried over anhydrous sodium sulphate, filtered and concentrated under reduced pressure. The crude material was purified by flash column chromatography (40 g silica gel cartridge; A=Hex, B=EtOAc; 30 min grad.; 0% B to 60% B; flow rate=40 mL/min). The pure fractions were combined, concentrated under reduced pressure and dried in vacuo to afford the title compound (1.6 g, 5.12 mmol, 47% yield) as white solid. MS (ESI) 310 (M+H).

Step C. Intermediate 48C. Preparation of (4-(5-(1,1-difluoroethyl)pyridin-2-yl) bicyclo[2.2.2]octan-1-yl)methanol

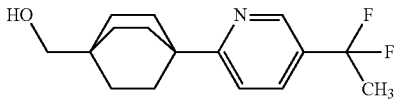

The title compound was prepared according to the method described for the synthesis of Intermediate 1E by substituting Intermediate 48B where appropriate, (1.4 g, 4.98 mmol, 96% yield) as brown gum. $^1$H NMR (400 MHz, DMSO-$d_6$) δ 8.70 (dd, J=2.5, 1.0 Hz, 1H), 7.89 (dd, J=8.0, 2.5 Hz, 1H), 7.45 (d, J=7.5 Hz, 1H), 4.36 (t, J=5.5 Hz, 1H), 3.10 (d, J=5.5 Hz, 2H), 2.08-1.93 (m, 3H), 1.89-1.79 (m, 6H), 1.52-1.42 (m, 6H).

Step D. Intermediate 48D. Preparation of 4-(5-(1,1-difluoroethyl)pyridin-2-yl) bicyclo[2.2.2]octane-1-carbaldehyde

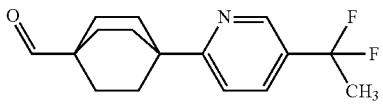

The title compound was prepared according to the method described for the synthesis of Intermediate 1F by substituting Intermediate 48C where appropriate, (0.9 g, 3.22 mmol, 64% yield) as white solid. $^1$H NMR (400 MHz, DMSO-$d_6$) δ 9.49 (s, 1H), 8.72 (dd, J=2.5, 1.0 Hz, 1H), 7.95-7.88 (m, 1H), 7.51-7.44 (m, 1H), 2.01 (t, J=19.1 Hz, 3H), 1.94-1.85 (m, 6H), 1.76-1.67 (m, 6H).

Step E. Intermediate 48E. Preparation of 3-bromo-N-((4-(5-(1,1-difluoroethyl)pyridin-2-yl)bicyclo[2.2.2]octan-1-yl)methyl)aniline

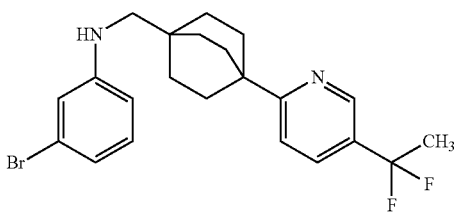 [SMILES: CC(F)(F)c1ccc(C23CCC(CNc4cccc(Br)c4)(CC2)CC3)nc1]

The title compound was prepared according to methods described for the synthesis of Intermediate 1G by substituting Intermediate 48D and 3-bromoaniline where appropriate: (300 mg, 0.60 mmol, 68% yield). MS (ESI) 435 (M+H).

Step F. Example 48. Preparation of N-(3-bromophenyl)-N-((4-(5-(1,1-difluoroethyl) pyridin-2-yl) bicyclo[2.2.2]octan-1-yl)methyl)-3-fluorobicyclo[1.1.1]pentane-1-carboxamide The title compound was prepared according to method described for the synthesis of Example 1 (Step H) by substituting Intermediate 48E where appropriate: (300 mg, 0.548 mmol, 95% yield). $^1$H NMR (400 MHz, DMSO-$d_6$) δ 8.72-8.61 (m, 1H), 7.87 (dd, J=2.4, 8.6 Hz, 1H), 7.70 (t, J=1.7 Hz, 1H), 7.61 (td, J=1.8, 7.2 Hz, 1H), 7.49-7.35 (m, 3H), 3.68-3.56 (m, 1H), 3.55-3.43 (m, 1H), 1.99 (t, J=19.1 Hz, 3H), 1.88 (br s, 6H), 1.81-1.68 (m, 6H), 1.52-1.35 (m, 6H). FXR EC$_{50}$ (nM)=288. MS (ESI) 549 (M+H).

Example 49

N-(3-cyanophenyl)-N-((4-(5-(1,1-difluoroethyl)pyridin-2-yl)bicyclo[2.2.2]octan-1-yl)methyl)-3-fluorobicyclo[1.1.1]pentane-1-carboxamide (49)

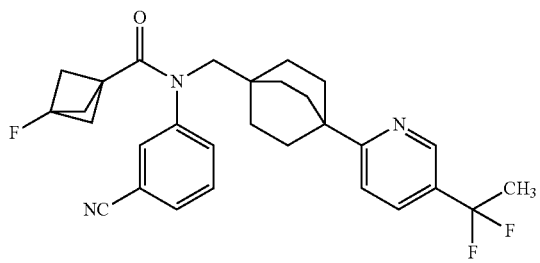

Step A. Intermediate 49A. Preparation of 3-(((4-(5-(1,1-difluoroethyl)pyridin-2-yl) bicyclo[2.2.2]octan-1-yl)methyl)amino)benzonitrile

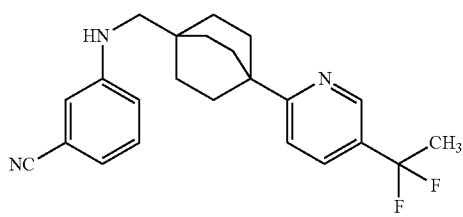 [SMILES: CC(F)(F)c1ccc(C23CCC(CNc4cccc(C#N)c4)(CC2)CC3)nc1]

The title compound was prepared according to method described for the synthesis of Intermediate 1G by substituting Intermediate 48D and 3-aminobenzonitrile where appropriate: (150 mg, 0.32 mmol, 90% yield). $^1$H NMR (300 MHz, DMSO-$d_6$) δ 8.70 (d, J=1.7 Hz, 1H), 7.89 (dd, J=8.3, 2.3 Hz, 1H), 7.46 (d, J=8.6 Hz, 1H), 7.26-7.16 (m, 1H), 6.98-6.91 (m, 2H), 6.88-6.82 (m, 1H), 6.01 (t, J=5.4 Hz, 1H), 2.86 (d, J=5.9 Hz, 2H), 2.08-1.92 (m, 3H), 1.91-1.81 (m, 6H), 1.62-1.52 (m, 6H). MS (ESI) 382 (M+H).

Step B. Example 49. Preparation of N-(3-cyanophenyl)-N-((4-(5-(1,1-difluoroethyl) pyridin-2-yl)bicyclo[2.2.2]octan-1-yl)methyl)-3-fluorobicyclo[1.1.1]pentane-1-carboxamide The title compound was prepared according to method described for the synthesis of Example 1 (Step H) by substituting Intermediate 49A where appropriate: (12.8 mg, 0.026 mmol, 40% yield). $^1$H NMR (400 MHz, DMSO-$d_6$) δ 8.68 (d, J=1.5 Hz, 1H), 8.05 (s, 1H), 7.91-7.84 (m, 2H), 7.83-7.78 (m, 1H), 7.70-7.62 (m, 1H), 7.40 (d, J=8.6 Hz, 1H), 3.68-3.44 (m, 2H), 1.99 (t, J=19.1 Hz, 3H), 1.92-1.68 (m, 12H), 1.51-1.29 (m, 6H). FXR EC$_{50}$ (nM)=327. MS (ESI) 494 (M+H).

The following examples were prepared according to the method described for the synthesis of Example 1 (step H) by substituting Intermediate 49A and corresponding acids where appropriate:

Example 52

N-((4-(3-cyclopropyl-1,2,4-oxadiazol-5-yl)bicyclo[2.2.2]octan-1-yl)methyl)-N-(3-ethoxyphenyl)-3-fluorobicyclo[1.1.1]pentane-1-carboxamide (52)

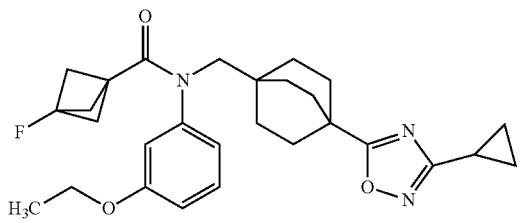

| Ex. No. | Structure & Name | MS (ESI) (M + H) | FXR EC$_{50}$ (nM) |
|---|---|---|---|
| 50 | (1S,3S)-N-(3-cyanophenyl)-N-((4-(5-(1,1-difluoroethyl)pyridin-2-yl)bicyclo[2.2.2]octan-1-yl)methyl)-3-hydroxy-3-methylcyclobutane-1-carboxamide | 494 | 1185 |
| 51 | (1S,3S)-N-(3-cyanophenyl)-N-((4-(5-(1,1-difluoroethyl)pyridin-2-yl)bicyclo[2.2.2]octan-1-yl)methyl)-3-hydroxy-3-(trifluoromethyl)cyclobutane-1-carboxamide | 548 | 1333 |
| 50 | $^1$H NMR (400 MHz, DMSO-$d_6$) δ 8.67 (d, J = 1.5 Hz, 1H), 7.97 (s, 1H), 7.88 (dd, J = 2.3, 8.4 Hz, 1H), 7.83-7.78 (m, 1H), 7.75 (br d, J = 8.6 Hz, 1H), 7.69-7.57 (m, 1H), 7.40 (d, J = 8.3 Hz, 1H), 2.97-2.89 (m, 1H), 2.15-2.05 (m, 2H), 1.99 (t, J = 19.1 Hz, 3H), 1.83-1.70 (m, 6H), 1.64-1.50 (m, 2H), 1.45-1.31 (m, 6H). | | |
| 51 | $^1$H NMR (400 MHz, DMSO-$d_6$) δ 8.67 (dd, J = 0.9, 2.3 Hz, 1H), 8.05 (s, 1H), 7.87 (dd, J = 2.4, 8.6 Hz, 1H), 7.84-7.75 (m, 2H), 7.70-7.59 (m, 1H), 7.40 (d, J = 8.3 Hz, 1H), 6.56 (s, 1H), 3.72-3.56 (m, 2H), 2.81-2.70 (m, 1H), 2.36-2.27 (m, 2H), 2.08-1.89 (m, 5H), 1.82-1.70 (m, 6H), 1.46-1.33 (m, 6H). | | |

Step A. Intermediate 52A. Preparation of methyl 4-(3-cyclopropyl-1,2,4-oxadiazol-5-yl) bicyclo[2.2.2]octane-1-carboxylate

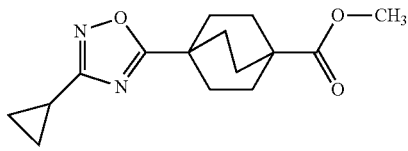 [SMILES: COC(=O)C12CCC(c3nc(C4CC4)no3)(CC1)CC2]

The title compound was prepared according to the method described for the synthesis of Intermediate 1D by substituting 4-(methoxycarbonyl)bicyclo[2.2.2]octane-1-carboxylic acid and (Z)—N'-hydroxycyclopropanecarboximidamide (commercially available) where appropriate. (490 mg, 1.66 mmol, 71% yield). MS (ESI) 277 (M+H).

Step B. Intermediate 52B. Preparation of (4-(3-cyclopropyl-1,2,4-oxadiazol-5-yl) bicyclo[2.2.2]octan-1-yl)methanol

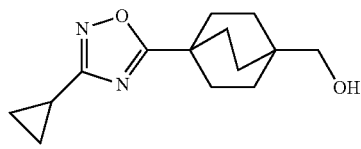 [SMILES: OCC12CCC(c3nc(C4CC4)no3)(CC1)CC2]

The title compound was prepared according to the method described for the synthesis of Intermediate 1E by substituting Intermediate 52A where appropriate. (500 mg, 1.08 mmol, 61% yield). MS (ESI) 249 (M+H).

Step C. Intermediate 52C. Preparation of 4-(3-cyclopropyl-1,2,4-oxadiazol-5-yl) bicyclo[2.2.2]octane-1-carbaldehyde

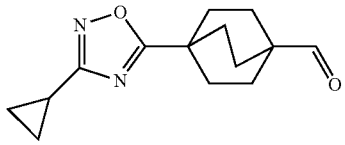 [SMILES: O=CC12CCC(c3nc(C4CC4)no3)(CC1)CC2]

The title compound was prepared according to the method described for the synthesis of Intermediate 1F by substituting Intermediate 52B where appropriate. (350 mg, 1.421 mmol, 71% yield). MS (ESI) 247 (M+H).

Step D. Intermediate 52D. Preparation of N-((4-(3-cyclopropyl-1,2,4-oxadiazol-5-yl) bicyclo[2.2.2]octan-1-yl)methyl)-3-ethoxyaniline

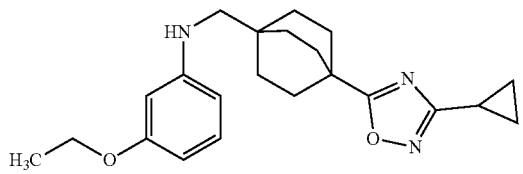 [SMILES: CCOc1cccc(NCC23CCC(c4nc(C5CC5)no4)(CC2)CC3)c1]

The title compound was prepared according to method described for the synthesis of Intermediate 1G by substituting Intermediate 52C and 3-ethoxyaniline where appropriate: (120 mg, 0.31 mmol, 76% yield). $^1$H NMR (400 MHz, DMSO-$d_6$) δ 6.90 (t, J=8.0 Hz, 1H), 6.18 (dd, J=8.0, 1.5 Hz, 1H), 6.14 (t, J=2.0 Hz, 1H), 6.04 (dd, J=7.5, 2.5 Hz, 1H), 5.39 (t, J=6.0 Hz, 1H), 3.91 (q, J=7.0 Hz, 2H), 2.78 (d, J=6.0 Hz, 2H), 2.06 (tt, J=8.3, 4.8 Hz, 1H), 1.91-1.79 (m, 6H), 1.59-1.48 (m, 6H), 1.28 (t, J=7.0 Hz, 3H), 1.06-0.98 (m, 2H), 0.89-0.81 (m, 2H). MS (ESI) 368.3 (M+H).

Step E. Example 52. Preparation of N-((4-(3-cyclopropyl-1,2,4-oxadiazol-5-yl) bicyclo[2.2.2]octan-1-yl)methyl)-N-(3-ethoxyphenyl)-3-fluorobicyclo[1.1.1]pentane-1-carboxamide The title compound was prepared according to method described for the synthesis of Example 1 (Step H) by substituting Intermediate 52D where appropriate: (8 mg, 0.017 mmol, 30% yield). $^1$H NMR (400 MHz, DMSO-$d_6$) δ 7.38-7.29 (m, 1H), 7.00-6.88 (m, 3H), 4.13-3.99 (m, 2H), 3.63-3.55 (m, 1H), 3.49-3.41 (m, 1H), 2.09-2.01 (m, 1H), 1.94-1.81 (m, 6H), 1.81-1.71 (m, 6H), 1.49-1.38 (m, 6H), 1.34 (t, J=7.0 Hz, 3H), 1.05-0.97 (m, 2H), 0.86-0.79 (m, 2H). FXR EC$_{50}$ (nM)=102. MS (ESI) 480 (M+H).

The following examples were prepared according to the method described for the synthesis of Example 1 (step H) by substituting Intermediate 52D and corresponding acids where appropriate:

| Ex. No. | Structure & Name | MS (ESI) (M + H) | FXR EC$_{50}$ (nM) |
|---|---|---|---|
| 53 | N-((4-(3-cyclopropyl-1,2,4-oxadiazol-5-yl)bicyclo[2.2.2]octan-1-yl)methyl)-N-(3-ethoxyphenyl)-3,3-difluorocyclobutane-1-carboxamide | 486 | 441 |

| Ex. No. | Structure & Name | MS (ESI) (M + H) | FXR EC₅₀ (nM) |
|---|---|---|---|
| 54 | N-((4-(3-cyclopropyl-1,2,4-oxadiazol-5-yl)bicyclo[2.2.2]octan-1-yl)methyl)-N-(3-ethoxyphenyl)-3-hydroxy-3-(trifluoromethyl)cyclobutane-1-carboxamide | 534 | 938 |
| 55 | N-((4-(3-cyclopropyl-1,2,4-oxadiazol-5-yl)bicyclo[2.2.2]octan-1-yl)methyl)-N-(3-ethoxyphenyl)tetrahydro-2H-pyran-4-carboxamide | 480 | 320 |
| 56 | N-((4-(3-cyclopropyl-1,2,4-oxadiazol-5-yl)bicyclo[2.2.2]octan-1-yl)methyl)-N-(3-ethoxyphenyl)tetrahydro-2H-thiopyran-4-carboxamide 1,1-dioxide | 528 | 4000 |

| | |
|---|---|
| 53 | $^{1}$H NMR (400 MHz, DMSO-d₆) δ 7.33 (t, J = 8.1 Hz, 1H), 7.01-6.82 (m, 3H), 4.12-3.99 (m, 2H), 3.59 (br s, 2H), 2.95-2.84 (m, 1H), 2.80-2.65 (m, 2H), 2.38-2.23 (m, 2H), 2.08-1.99 (m, 1H), 1.82-1.68 (m, 6H), 1.45-1.37 (m, 6H), 1.33 (t, J = 7.0 Hz, 3H), 1.05-0.98 (m, 2H), 0.87-0.79 (m, 2H) |
| 54 | $^{1}$H NMR (400 MHz, DMSO-d₆) δ 7.32 (t, J = 8.1 Hz, 1H), 6.96-6.87 (m, 3H), 6.53 (s, 1H), 4.05 (q, J = 7.1 Hz, 2H), 3.58 (br s, 2H), 3.47-3.36 (m, 1H), 2.49-2.27 (m, 2H), 2.12-1.99 (m, 3H), 1.81-1.71 (m, 6H), 1.44-1.30 (m, 9H), 1.04-0.97 (m, 2H), 0.88-0.77 (m, 2H) |
| 55 | $^{1}$H NMR (400 MHz, DMSO-d₆) δ 7.34 (t, J = 8.3 Hz, 1H), 7.00-6.83 (m, 3H), 4.05 (q, J = 7.0 Hz, 2H), 3.75 (br dd, J = 2.7, 11.0 Hz, 2H), 3.66-3.43 (m, 2H), 3.09-2.92 (m, 2H), 2.11-2.00 (m, 1H), 1.82-1.72 (m, 6H), 1.66-1.53 (m, 2H), 1.48-1.36 (m, 9H), 1.33 (t, J = 6.8 Hz, 3H), 1.05-0.97 (m, 2H), 0.86-0.79 (m, 2H) |
| 56 | $^{1}$H NMR (400 MHz, DMSO-d₆) δ 7.38-7.29 (m, 1H), 7.00-6.86 (m, 3H), 4.10-4.02 (m, 2H), 3.55 (br t, J = 5.3 Hz, 2H), 3.05-2.90 (m, 4H), 2.69-2.65 (m, 1H), 2.09-1.90 (m, 5H), 1.82-1.68 (m, 6H), 1.46-1.24 (m, 9H), 1.06-0.97 (m, 2H), 0.87-0.78 (m, 2H) |

Example 57

(1S,3S)—N-((4-(3-cyclopropyl-1,2,4-oxadiazol-5-yl)bicyclo[2.2.2]octan-1-yl)methyl)-3-hydroxy-N-(3-methoxyphenyl)-3-(trifluoromethyl)cyclobutane-1-carboxamide (57)

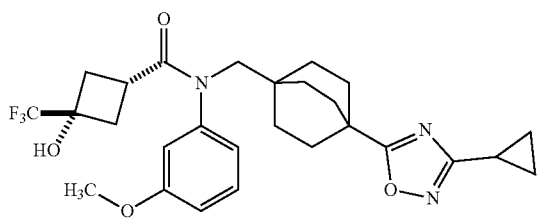

Step A. Intermediate 57A. Preparation of N-((4-(3-cyclopropyl-1,2,4-oxadiazol-5-yl) bicyclo[2.2.2]octan-1-yl)methyl)-3-methoxyaniline

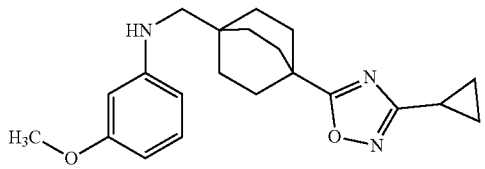 [SMILES: COc1cccc(NCC23CCC(c4nc(C5CC5)no4)(CC2)CC3)c1]

The title compound was prepared according to method described for the synthesis of Intermediate 1G by substituting Intermediate 52C and 3-methoxyaniline where appropriate: (85 mg, 0.23 mmol, 56% yield). $^1$H NMR (400 MHz, DMSO-$d_6$) δ 6.92 (t, J=8.0 Hz, 1H), 6.20 (dd, J=8.3, 1.3 Hz, 1H), 6.16 (t, J=2.0 Hz, 1H), 6.06 (dd, J=8.0, 2.5 Hz, 1H), 5.44 (t, J=6.0 Hz, 1H), 3.66 (s, 3H), 2.78 (d, J=6.0 Hz, 2H), 2.11-2.02 (m, 1H), 1.90-1.81 (m, 6H), 1.59-1.50 (m, 6H), 1.06-1.00 (m, 2H), 0.89-0.83 (m, 2H). MS (ESI) 354.3 (M+H).

Step B. Example 57. Preparation of (1S,3S)—N-(4-(3-cyclopropyl-1,2,4-oxadiazol-5-yl) bicyclo[2.2.2]octan-1-yl)methyl)-3-hydroxy-N-(3-methoxyphenyl)-3-(trifluoromethyl) cyclobutane-1-carboxamide The title compound was prepared according to method described for the synthesis of Example 1 (Step H) by substituting Intermediate 57A where appropriate: (1 mg, 1.92 μmol, 5% yield). $^1$H NMR (400 MHz, DMSO-$d_6$) δ 7.37-7.29 (m, 1H), 6.98-6.86 (m, 3H), 6.51 (s, 1H), 3.77 (s, 3H), 3.63-3.53 (m, 2H), 2.98-2.88 (m, 1H), 2.79-2.71 (m, 1H), 2.13-2.00 (m, 4H), (br dd, J=7.1, 8.3 Hz, 6H), 1.44-1.34 (m, 6H), 1.04-0.98 (m, 2H), 0.88-0.77 (m, 2H). FXR EC$_{50}$ (nM)=304. MS (ESI) 520 (M+H).

The following examples were prepared according to the method described for the synthesis of Example 1 (step H) by substituting Intermediate 57A and corresponding acids where appropriate:

| Ex. No. | Structure & Name | MS (ESI) (M + H) | FXR EC$_{50}$ (nM) |
|---|---|---|---|
| 58 | N-((4-(3-cyclopropyl-1,2,4-oxadiazol-5-yl)bicyclo[2.2.2]octan-1-yl)methyl)-3-fluoro-N-(3-methoxyphenyl)bicyclo[1.1.1]pentane-1-carboxamide | 466 | 345 |
| 59 | N-((4-(3-cyclopropyl-1,2,4-oxadiazol-5-yl)bicyclo[2.2.2]octan-1-yl)methyl)-3,3-difluoro-N-(3-methoxyphenyl)cyclobutane-1-carboxamide | 472 | 673 |

| Ex. No. | Structure & Name | MS (ESI) (M + H) | FXR EC$_{50}$ (nM) |
|---|---|---|---|
| 60 | N-((4-(3-cyclopropyl-1,2,4-oxadiazol-5-yl) bicyclo[2.2.2]octan-1-yl)methyl)-N-(3-methoxyphenyl)tetrahydro-2H-pyran-4-carboxamide | 466 | 902 |
| 61 | N-((4-(3-cyclopropyl-1,2,4-oxadiazol-5-yl) bicyclo[2.2.2]octan-1-yl)methyl)-N-(3-methoxyphenyl) tetrahydro-2H-thiopyran-4-carboxamide 1,1-dioxide | 514 | 4000 |
| 58 | $^1$H NMR (400 MHz, DMSO-d$_6$) δ 7.41-7.29 (m, 1H), 7.03-6.86 (m, 3H), 3.79 (s, 3H), 3.59 (br s, 1H), 3.48-3.41 (m, 1H), 2.09-2.00 (m, 1H), 1.95-1.81 (m, 6H), 1.81-1.66 (m, 6H), 1.50-1.34 (m, 6H), 1.06-0.97 (m, 2H), 0.87-0.77 (m, 2H) | | |
| 59 | $^1$H NMR (400 MHz, DMSO-d$_6$) δ 7.35 (t, J - 7.9 Hz, 1H), 7.03-6.88 (m, 3H), 3.79 (s, 3H), 3.67-3.51 (m, 2H), 2.95-2.83 (m, 1H), 2.80-2.66 (m, 2H), 2.40-2.26(m, 2H), 2.09-1.98 (m, 1H), 1.81-1.69 (m, 6H), 1.46-1.32 (m, 6H), 1.05-0.98 (m, 2H), 0.87-0.79 (m, 2H) | | |
| 60 | $^1$H NMR (400 MHz, DMSO-d$_6$) δ 7.40-7.30 (m, 1H), 7.01-6.85 (m, 3H), 3.84-3.68 (m, 5H), 3.65-3.43 (m, 2H), 3.09-2.93 (m, 2H), 2.09-1.98 (m, 1H), 1.85-1.68 (m, 7H), 1.66-1.53 (m, 2H), 1.49-1.29 (m, 8H), 1.07-0.98 (m, 2H), 0.87-0.79 (m, 2H) | | |
| 61 | $^1$H NMR (400 MHz, DMSO-d$_6$) δ 7.36 (t, J = 8.2 Hz, 1H), 7.03-6.96 (m, 2H), 6.96-6.89 (m, 1H), 3.79 (s, 3H), 3.56 (br s, 2H), 3.06-2.88 (m, 4H), 2.69-2.65 (m, 1H), 2.10-1.93 (m, 5H), 1.81-1.71 (m, 6H), 1.44-1.35 (m, 6H), 1.05-0.98 (m, 2H), 0.86-0.80 (m, 2H) | | |

Example 62

N-(3-cyano-5-fluorophenyl)-N-((4-(3-cyclopropyl-1,2,4-oxadiazol-5-yl) bicyclo[2.2.2]octan-1-yl)methyl)-3-fluorobicyclo[1.1.1]pentane-1-carboxamide (62)

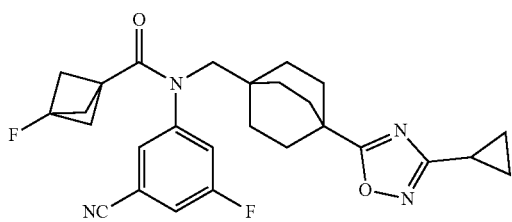

Step A. Intermediate 62A. Preparation of 3-(((4-(3-cyclopropyl-1,2,4-oxadiazol-5-yl) bicyclo[2.2.2]octan-1-yl)methyl)amino)-5-fluorobenzonitrile

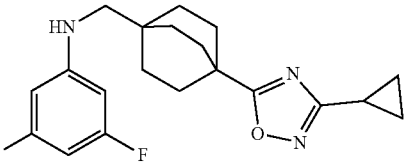

The title compound was prepared according to method described for the synthesis of Intermediate 1G by substituting Intermediate 52C and 3-amino-5-fluorobenzonitrile where appropriate: (90 mg, 0.246 mmol, 48% yield). $^1$H NMR (400 MHz, DMSO-d$_6$) δ 6.85 (s, 1H), 6.80-6.71 (m, 1H), 6.66-6.60 (m, 1H), 6.40-6.35 (m, 1H), 2.87 (d, J=6.0 Hz, 2H), 2.11-2.03 (m, 1H), 1.90-1.82 (m, 6H), 1.57-1.50 (m, 6H), 1.06-1.00 (m, 2H), 0.88-0.82 (m, 2H). MS (ESI) 367.2 (M+H).

Step B. Example 62. Preparation of N-(3-cyano-5-fluorophenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide The title compound was prepared according to method described for the synthesis of Example 1 (Step H) by substituting Intermediate 62A where appropriate: (7.1 mg). $^1$H NMR (400 MHz, DMSO-d$_6$) δ 7.97 (d, J=1.2 Hz, 1H), 7.95-7.84 (m, 2H), 3.66-3.45 (m, 2H), 2.05 (tt, J=4.7, 8.3 Hz, 1H), 1.98-1.84 (m, 6H), 1.82-1.69 (m, 6H), 1.48-1.30 (m, 6H), 1.06-0.96 (m, 2H), 0.87-0.76 (m, 2H). FXR EC$_{50}$ (nM)=185. MS (ESI) 479 (M+H).

The following examples were prepared according to the method described for the synthesis of Example 1 (step H) by substituting Intermediate 62A and corresponding acids where appropriate:

Example 65

N-((4-(3-cyclopropyl-1,2,4-oxadiazol-5-yl)bicyclo[2.2.2]octan-1-yl)methyl)-3,3-difluoro-N-(3-(methylsulfonamido)phenyl)cyclobutane-1-carboxamide (65)

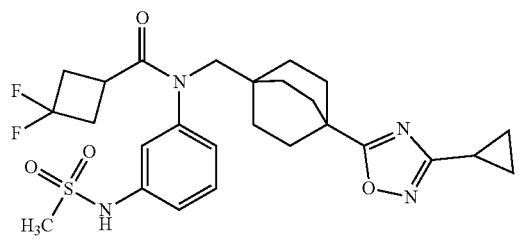

| Ex. No. | Structure & Name | MS (ESI) (M + H) | FXR EC$_{50}$ (nM) |
|---|---|---|---|
| 63 | 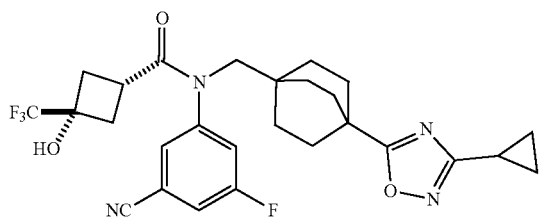 [SMILES: N#Cc1cc(F)cc(N(CC23CCC(c4nc(C5CC5)no4)(CC2)CC3)C(=O)[C@H]2C[C@](O)(C(F)(F)F)C2)c1]<br>(1S,3S)-N-(3-cyano-5-fluorophenyl)-N-((4-(3-cyclopropyl 1,2,4-oxadiazol-5-yl)bicyclo[2.2.2]octan-1-yl)methyl)-3-hydroxy-3-(trifluoromethyl)cyclobutane-1-carboxamide | 533 | 1047 |
| 64 | 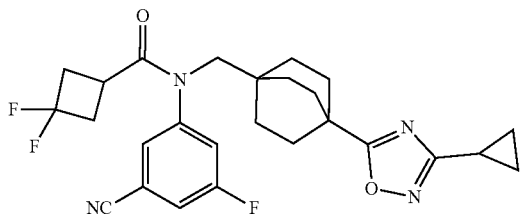 [SMILES: N#Cc1cc(F)cc(N(CC23CCC(c4nc(C5CC5)no4)(CC2)CC3)C(=O)C2CC(F)(F)C2)c1]<br>N-(3-cyano-5-fluorophenyl)-N-((4-(3-cyclopropyl-1,2,4-oxadiazol-5-yl)bicyclo[2.2.2]octan-1-yl)methyl)-3,3-difluorocyclobutane-1-carboxamide | 485 | 528 |
| 63 | $^1$H NMR (400 MHz, DMSO-d$_6$) δ 8.01-7.93 (m, 1H), 7.93-7.80 (m, 2H), 6.65-6.48 (m, 1H), 3.67-3.56 (m, 2H), 2.91-2.73 (m, 1H), 2.35-2.25 (m, 2H), 2.05 (tt, J = 4.8, 8.3 Hz, 3H), 1.84-1.69 (m, 6H), 1.46-1.30 (m, 6H), 1.09-0.96 (m, 2H), 0.89-0.78 (m, 2H) | | |
| 64 | $^1$H NMR (400 MHz, DMSO-d$_6$) δ 7.96-7.91 (m, 1H), 7.91-7.80 (m, 2H), 3.61 (s, 2H), 3.08-2.94 (m, 1H), 2.82-2.65 (m, 2H), 2.43-2.29 (m, 2H), 2.11-1.99 (m, 1H), 1.86-1.65 (m, 6H), 1.45-1.32 (m, 6H), 1.07-0.96 (m, 2H), 0.89-0.78 (m, 2H) | | |

Step A. Intermediate 65A. Preparation of tert-butyl (3-(((4-(3-cyclopropyl-1,2,4-oxadiazol-5-yl)bicyclo[2.2.2]octan-1-yl)methyl)amino)phenyl)carbamate

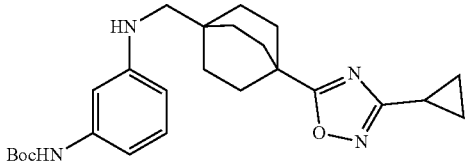 [SMILES: CC(C)(C)OC(=O)Nc1cccc(NCC23CCC(c4nc(C5CC5)no4)(CC2)CC3)c1]

The title compound was prepared according to method described for the synthesis of Intermediate 1G by substituting Intermediate 32B and Intermediate 52C where appropriate: (360 mg, 0.82 mmol, 68% yield). $^1$H NMR (400 MHz, DMSO-d$_6$) δ 8.97 (s, 1H), 6.91-6.78 (m, 2H), 6.54 (d, J=7.5 Hz, 1H), 6.22 (dd, J=8.3, 1.8 Hz, 1H), 5.38 (t, J=5.8 Hz, 1H), 2.75 (d, J=6.0 Hz, 2H), 2.10-2.01 (m, 1H), 1.91-1.80 (m, 6H), 1.59-1.49 (m, 6H), 1.46 (s, 9H), 1.06-0.97 (m, 2H), 0.89-0.80 (m, 2H). MS (ESI) 439 (M+H).

Step B. Intermediate 65B. Preparation of N1-((4-(3-cyclopropyl-1,2,4-oxadiazol-5-yl) bicyclo[2.2.2]octan-1-yl)methyl)benzene-1,3-diamine

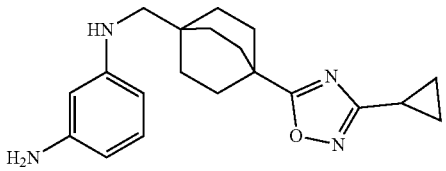 [SMILES: Nc1cccc(NCC23CCC(c4nc(C5CC5)no4)(CC2)CC3)c1]

To a stirred solution of Intermediate 65A (60 mg, 0.13 mmol) in DCM (2 mL) at 0° C. was added 4 M HCl in dioxane (0.10 mL, 0.41 mmol). The reaction mixture was allowed to warm to room temperature and stirred for 1 h. The reaction mixture was concentrated under reduced pressure and the residue was basified with aq. 10% sodium bicarbonate solution (2 mL). The resulting aqueous solution was extracted with ethyl acetate (2×5 mL). The combined organic layers were washed with brine solution (10 mL), dried over anhydrous sodium sulphate, filtered and concentrated under reduced pressure to afford the title compound (40 mg, 0.118 mmol, 86% yield). $^1$H NMR (400 MHz, DMSO-d$_6$) δ 6.71-6.64 (m, 1H), 5.87-5.82 (m, 2H), 5.80-5.74 (m, 1H), 5.01 (t, J=6.0 Hz, 1H), 4.68 (br. s., 2H), 2.73 (d, J=6.0 Hz, 2H), 2.11-2.02 (m, 1H), 1.90-1.80 (m, 6H), 1.58-1.48 (m, 6H), 1.07-0.99 (m, 2H), 0.89-0.82 (m, 2H). MS (ESI) 339 (M+H).

Step C. Intermediate 65C. Preparation of N-(3-(((4-(3-cyclopropyl-1,2,4-oxadiazol-5-yl) bicyclo[2.2.2]octan-1-yl)methyl)amino)phenyl)methanesulfonamide

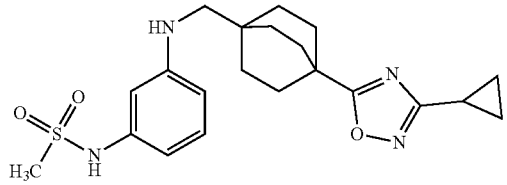 [SMILES: CS(=O)(=O)Nc1cccc(NCC23CCC(c4nc(C5CC5)no4)(CC2)CC3)c1]

To a stirred solution of Intermediate 65B (60 mg, 0.17 mmol) in DCM (2 mL) at 0° C. was added TEA (0.08 mL, 0.53 mmol) followed by methanesulfonyl chloride (30 mg, 0.26 mmol). The reaction mixture was allowed to warm to room temperature and stirred for 2 h. The reaction mixture was diluted with DCM (5 mL), washed with water (5 mL), brine solution (5 mL), dried over anhydrous sodium sulphate, filtered and concentrated under reduced pressure to afford the title compound (100 mg, crude) as brown solid. MS (ESI) 417 (M+H).

Step D. Example 65. Preparation of N-((4-(3-cyclopropyl-1,2,4-oxadiazol-5-yl) bicyclo[2.2.2]octan-1-yl)methyl)-3,3-difluoro-N-(3-(methylsulfonamido)phenyl) cyclobutane-1-carboxamide The title compound was prepared according to method described for the synthesis of Example 1 (Step H) by substituting Intermediate 65C where appropriate: (17 mg, 0.03 mmol, 68% yield). $^1$H NMR (400 MHz, DMSO-d$_6$) δ 9.90 (s, 1H), 7.46-7.37 (m, 1H), 7.22-7.08 (m, 3H), 3.58 (s, 2H), 3.03 (s, 3H), 2.91-2.83 (m, 1H), 2.79-2.63 (m, 2H), 2.45-2.35 (m, 2H), 2.09-2.00 (m, 1H), 1.84-1.68 (m, 6H), 1.48-1.27 (m, 6H), 1.07-0.97 (m, 2H), 0.86-0.80 (m, 2H). FXR EC$_{50}$ (nM)=1279. MS (ESI) 535 (M+H).

The following examples were prepared according to the method described for the synthesis of Example 1 (step H) by substituting Intermediate 65C and corresponding acids where appropriate:

| Ex. No. | Structure & Name | MS (ESI) (M + H) | FXR EC$_{50}$ (nM) |
|---|---|---|---|
| 66 | ![structure] N-((4-(3-cyclopropyl-1,2,4-oxadiazol-5-yl) bicyclo[2.2.2]octan-1-yl)methyl)-3-fluoro-N-(3-(methylsulfonamido)phenyl)bicyclo[1.1.1]pentane-1-carboxamide | 529 | 4000 |

| Ex. No. | Structure & Name | MS (ESI) (M + H) | FXR EC$_{50}$ (nM) |
|---|---|---|---|
| 67 | (1S,3S)-N-((4-(3-cyclopropyl-1,2,4-oxadiazol-5-yl)bicyclo[2.2.2]octan-1-yl)methyl)-3-hydroxy-N-(3-(methylsulfonamido)phenyl)-3-(trifluoromethyl)cyclobutane-1-carboxamide | 583 | 4000 |

66  $^1$H NMR (400 MHz, DMSO-d$_6$) δ 9.94 (s, 1H), 7.46-7.38 (m, 1H), 7.21 (d, J = 7.8 Hz, 1H), 7.18-7.09 (m, 2H), 3.60-3.44 (m, 2H), 3.04 (s, 3H), 2.10-2.02 (m, 1H), 1.88 (br s, 6H), 1.81-1.73 (m, 6H), 1.46-1.37 (m, 6H), 1.05-0.98 (m, 2H), 0.87-0.80 (m, 2H)

67  $^1$H NMR (400 MHz, DMSO-d$_6$) δ 9.88 (s, 1H), 7.45-7.36 (m, 1H), 7.21-7.04 (m, 3H), 6.56 (s, 1H), 3.66-3.50 (m, 2H), 2.98 (s, 3H), 2.74-2.65 (m, 1H), 2.37-2.28 (m, 2H), 2.18-2.02 (m, 3H), 1.86-1.69 (m, 6H), 1.45-1.32 (m, 6H), 1.05-0.97 (m, 2H), 0.87-0.79 (m, 2H)

Example 68

N-((4-(3-cyclopropyl-1,2,4-oxadiazol-5-yl)bicyclo[2.2.2]octan-1-yl)methyl)-3-fluoro-N-(3-(methylsulfonyl)phenyl)bicyclo[1.1.1]pentane-1-carboxamide

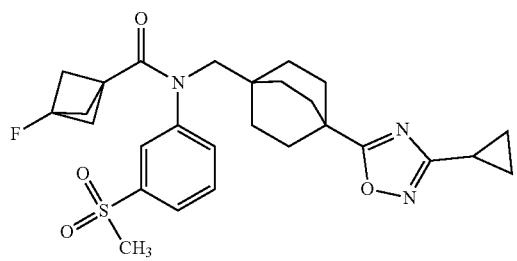

(68)

Step A. Intermediate 68A. Preparation of N-((4-(3-cyclopropyl-1,2,4-oxadiazol-5-yl) bicyclo[2.2.2]octan-1-yl)methyl)-3-(methylsulfonyl)aniline

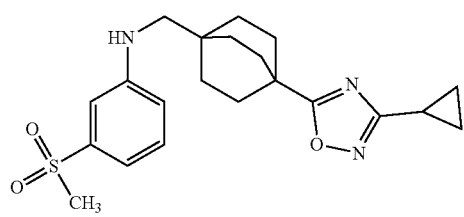 [SMILES: CS(=O)(=O)c1cccc(NCC23CCC(c4nc(C5CC5)no4)(CC2)CC3)c1]

The title compound was prepared according to the method described for the synthesis of Intermediate 1G by substituting Intermediate 52C and 3-(methylsulfonyl) aniline where appropriate: (110 mg, 0.25 mmol, 63% yield). $^1$H NMR (400 MHz, DMSO-d$_6$) δ 7.31-7.25 (m, 1H), 7.09 (t, J=2.0 Hz, 1H), 6.97 (d, J=6.0 Hz, 1H), 6.91 (dd, J=7.5, 2.5 Hz, 1H), 6.11 (t, J=5.8 Hz, 1H), 3.12 (s, 3H), 2.87 (d, J=5.5 Hz, 2H), 2.11-2.03 (m, 1H), 1.90-1.84 (m, 6H), 1.61-1.53 (m, 6H), 1.06-1.00 (m, 2H), 0.88-0.83 (m, 2H). MS (ESI) 402 (M+H).

Step B. Example 68. Preparation of N-((4-(3-cyclopropyl-1,2,4-oxadiazol-5-yl) bicyclo[2.2.2]octan-1-yl)methyl)-3-fluoro-N-(3-(methylsulfonyl)phenyl) bicyclo[1.1.1]pentane-1-carboxamide The title compound was prepared according to the method described for the synthesis of Example 1 (Step H) by substituting Intermediate 68A where appropriate: (7 mg, 0.014 mmol, 23% yield). $^1$H NMR (400 MHz, DMSO-d$_6$) δ 7.97 (d, J=1.7 Hz, 1H), 7.94 (d, J=8.1 Hz, 1H), 7.84-7.78 (m, 1H), 7.77-7.70 (m, 1H), 3.58 (s, 2H), 3.31 (s, 3H), 2.09-2.00 (m, 1H), 1.85 (br s, 6H), 1.80-1.70 (m, 6H), 1.47-1.33 (m, 6H), 1.06-0.98 (m, 2H), 0.86-0.79 (m, 2H). FXR EC$_{50}$ (nM)=1488. MS (ESI) 534 (M+H).

The following examples were prepared according to the method described for the synthesis of Example 1 (step H) by substituting Intermediate 68A and corresponding acids where appropriate:

| Ex. No. | Structure & Name | MS (ESI) (M + H) | FXR EC$_{50}$ (nM) |
|---|---|---|---|
| 69 | 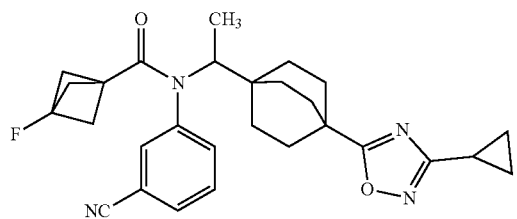<br>N-((4-(3-cyclopropyl-1,2,4-oxadiazol-5-yl)bicyclo[2.2.2]octan-1-yl)methyl)-4,4-difluoro-N-(3-(methylsulfonyl)phenyl)cyclohexane-1-carboxamide | 548 | 4000 |
| 70 | $^1$H NMR (400 MHz, DMSO-d$_6$) δ 7.99 (br s, 1H), 7.90 (br d, J = 6.8 Hz, 1H), 7.86-7.79 (m, 1H), 7.77-7.66 (m, 1H), 3.69-3.57 (m, 2H), 3.30 (s, 3H), 2.32-2.24 (m, 1H), 2.09-2.00 (m, 1H), 2.00-1.84 (m, 2H), 1.82-1.66 (m, 8H), 1.65-1.47 (m, 4H), 1.43-1.32 (m, 6H), 1.05-0.97 (m, 2H), 0.86-0.78 (m, 2H) | | |

Example 70

N-(3-cyanophenyl)-N-(1-(4-(3-cyclopropyl-1,2,4-oxadiazol-5-yl)bicyclo[2.2.2]octan-1-yl)ethyl)-3-fluorobicyclo[1.1.1]pentane-1-carboxamide (70)

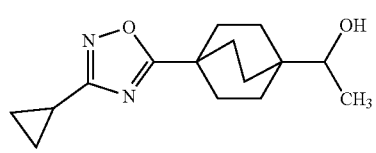

Step A. Intermediate 70A. Preparation of 1-(4-(3-cyclopropyl-1,2,4-oxadiazol-5-yl) bicyclo[2.2.2]octan-1-yl)ethan-1-ol

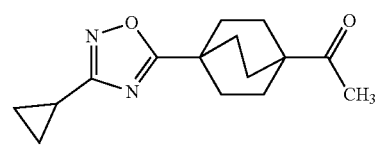 [SMILES: CC(=O)C12CCC(c3nc(C4CC4)no3)(CC1)CC2]

To a solution of Intermediate 52C (1.5 g, 6.09 mmol) in dry tetrahydrofuran (15 mL) at −78° C. was added 3 M solution of methylmagnesium bromide in diethyl ether (3 mL, 9.13 mmol) under argon atmosphere. The reaction mixture was allowed to warm to room temperature and stirred for 1 h. The reaction mixture was cooled to 0° C., quenched with satd. NH$_4$Cl solution and extracted with EtOAc (2×50 mL). The combined organic layers were washed with brine solution (20 mL), dried over anhydrous sodium sulphate and concentrated under reduced pressure. The crude material was purified by flash column chromatography (40 g silica gel cartridge; A=Hex, B=EtOAc; 30 min grad.; 0% B to 50% B; flow rate=40 mL/min). The pure fractions were combined, concentrated under reduced pressure and dried in vacuo to afford the title compound (1.25 g, 4.53 mmol, 74% yield) as oil. $^1$H NMR (400 MHz, DMSO-d$_6$) δ 4.29 (d, J=6.80 Hz, 1H), 3.25-3.21 (m, 1H), 2.10-2.00 (m, 1H), 1.98-1.78 (m, 6H), 1.53-1.37 (m, 6H), 1.04-0.99 (m, 2H), 0.94 (d, J=8.40 Hz, 3H), 0.87-0.85 (m, 2H).

Step B. Intermediate 70B. Preparation of 1-(4-(3-cyclopropyl-1,2,4-oxadiazol-5-yl) bicyclo[2.2.2]octan-1-yl)ethan-1-one The title compound was prepared according to the method described for the synthesis of Intermediate 1F by substituting Intermediate 70A where appropriate. (1 g, 3.65 mmol, 80% yield). $^1$H NMR (400 MHz, DMSO-d$_6$) δ 2.09-2.05 (m, 4H), 1.99-1.85 (m, 6H), 1.76-1.71 (m, 6H), 1.06-1.00 (m, 2H), 0.87-0.84 (m, 2H).

Step C. Intermediate 70C. Preparation of 3-((1-(4-(3-cyclopropyl-1,2,4-oxadiazol-5-yl) bicyclo[2.2.2]octan-1-yl)-1l3-ethyl)amino)benzonitrile

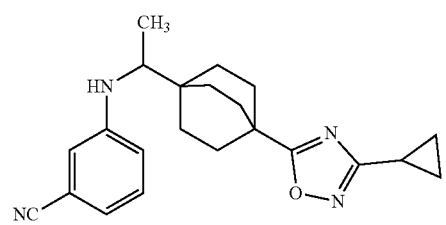 [SMILES: CC(Nc1cccc(C#N)c1)C12CCC(c3nc(C4CC4)no3)(CC1)CC2]

To a stirred solution of Intermediate 70B (198 mg, 0.762 mmol) in methanol (2 mL) at room temperature was added 3-aminobenzonitrile (90 mg, 0.76 mmol). The reaction mixture was stirred for 1 h at room temperature. Triethylsilane (177 mg, 1.524 mmol) and indium (III) chloride (16.85 mg, 0.076 mmol) were added to the reaction. The resulting reaction mixture was stirred overnight at room temperature. The reaction mixture was concentrated under reduced pressure. And the residue was dissolved in EtOAc (20 mL). The organic solution was washed with water (10 mL) followed by brine solution (10 mL), dried over anhydrous sodium sulphate, filtered and concentrated under reduced pressure. The crude material was purified by flash column chromatography (12 g silica gel cartridge; A=Hex, B=EtOAc; 30 min grad.; 0% B to 50% B; flow rate=24 mL/min). The pure fractions were combined, concentrated and dried in vacuo to afford the title compound (110 mg, 0.30 mmol, 40% yield) as brown solid. $^1$H NMR (300 MHz, DMSO-$d_6$) δ 7.27-7.17 (m, 1H), 6.96-6.82 (m, 3H), 3.25 (d, J=6.6 Hz, 1H), 2.09-20.05 (d, J=9.6 Hz, 1H), 1.92-1.71 (m, 6H), 1.50 (d, J=7.3 Hz, 3H), 1.42 (br. s., 3H), 1.04 (dd, J=8.4, 2.5 Hz, 2H), 0.96 (d, J=6.6 Hz, 3H), 0.85 (dd, J=4.8, 2.5 Hz, 2H). MS (ESI) 363 (M+H).

Step D. Example 70. Preparation of N-(3-cyanophenyl)-N-(1-(4-(3-cyclopropyl-1,2,4-oxadiazol-5-yl)bicyclo[2.2.2]octan-1-yl)ethyl)-3-fluorobicyclo[1.1.1]pentane-1-carboxamide The title compound was prepared according to method described for the synthesis of Example 1 (Step H) by substituting Intermediate 70C where appropriate: (0.5 mg, 1.0 μmol, 1% yield). $^1$H NMR (400 MHz, DMSO-$d_6$) δ 7.97-7.85 (m, 2H), 7.67 (t, J=5.5 Hz, 1H), 3.18 (br d, J=5.5 Hz, 1H), 4.80-4.70 (m, 1H), 2.10-2.03 (m, 1H), 1.88-1.66 (m, 12H), 1.58-1.40 (m, 6H), 1.06-0.91 (m, 5H), 0.88-0.80 (m, 2H). FXR $EC_{50}$ (nM)=2000. MS (ESI) 475 (M+H).

Example 72

N-(3-cyanophenyl)-N-((4-(3-cyclopropyl-1-methyl-1H-pyrazol-5-yl)bicyclo[2.2.2]octan-1-yl)methyl)-3-fluorobicyclo[1.1.1]pentane-1-carboxamide (72)

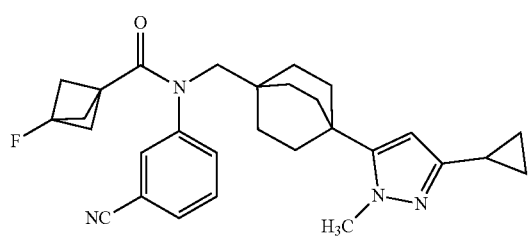

Step A. Intermediate 72A. Preparation of methyl 4-(chlorocarbonyl)bicyclo[2.2.2]octane-1-carboxylate

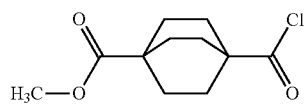

A solution of 4-(methoxycarbonyl)bicyclo[2.2.2]octane-1-carboxylic acid (2 g) in $SOCl_2$ (15 mL) was heated at reflux for 2 h. The progress of the reaction mixture was monitored by TLC (small amount of reaction mixture was quenched with MeOH and checked TLC). After TLC showed completion of reaction, the reaction mixture was concentrated under reduced pressure. The crude material was co-distilled twice with DCM and dried in vacuo to afford the title compound (1.8 g, 7.80 mmol) as an off-white solid which was taken to next step without further purification.

Step B. Intermediate 72B. Preparation of methyl 4-(3-cyclopropyl-3-oxopropanoyl)bicyclo[2.2.2]octane-1-carboxylate

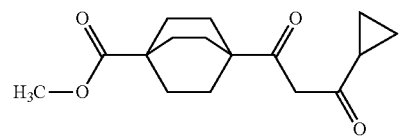 [SMILES: COC(=O)C12CCC(C(=O)CC(=O)C3CC3)(CC1)CC2]

To a stirred solution of 1M LiHMDS in THF (9.10 mL, 9.10 mmol) at −78° C. was added 1-cyclopropylethan-1-one (0.38 g, 4.55 mmol). The reaction mixture was stirred for 45 min at −78° C. A solution of Intermediate 72A (1 g, 4.33 mmol) in tetrahydrofuran (10 mL) was added to the reaction mixture at −78° C. and stirred for 1 h. The reaction mixture was allowed to warm to 0° C., quenched with saturated aqueous ammonium chloride solution (10 mL) and extracted with EtOAc (3×10 mL). The combined organic layers were washed with brine solution (20 mL), dried over anhydrous sodium sulphate, filtered and concentrated under reduced pressure. The crude material was purified by flash column chromatography (24 g silica gel cartridge; A=Hex, B=EtOAc; 30 min grad.; 0% B to 30% B; flow rate=24 mL/min). The pure fractions were combined, concentrated under reduced pressure and dried in vacuo to afford the title compound (800 mg, 2.73 mmol, 63% yield) as oily liquid. MS (ESI) 279 (M+H).

Step C. Intermediate 72C1 and 72C2. Preparation of methyl 4-(5-cyclopropyl-1-methyl-1H-pyrazol-3-yl)bicyclo[2.2.2]octane-1-carboxylate and methyl 4-(3-cyclopropyl-1-methyl-1H-pyrazol-5-yl)bicyclo[2.2.2]octane-1-carboxylate

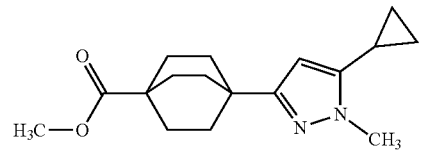

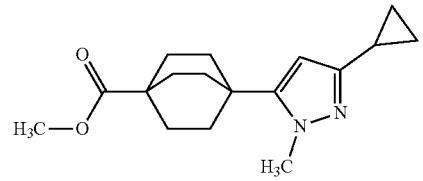

To a stirred solution of Intermediate 72B (800 mg, 2.87 mmol) in methanol (10 mL) at room temperature was added methylhydrazine sulphate (1 g, 7.19 mmol). The reaction mixture was heated to 80° C. and stirred overnight. The reaction mixture was cooled to room temperature and concentrated under reduced pressure. The residue was diluted with water (30 mL) and extracted with EtOAc (3×25 mL). The combined organic layers were washed with brine solution (20 mL), dried over anhydrous sodium sulphate, filtered and concentrated under reduced pressure. The crude material was purified by flash column chromatography (24 g silica gel cartridge; A=Hex, B=EtOAc; 30 min grad.; 0% B to 30% B; flow rate=24 mL/min). The pure fractions were combined, concentrated under reduced pressure and dried in vacuo to afford the title compound as a mixture of regioisomers. The regioisomers were separated by prep-HPLC to offered first eluting isomer (RT=4.31 min, peak-1) Intermediate 72C1 (270 mg, 0.89 mmol, 30% yield), $^1$H NMR (400 MHz, DMSO-d$_6$) δ 5.65 (s, 1H), 3.71 (s, 3H), 3.57 (s, 3H), 1.69-1.81 (m, 13H), 0.88-0.91 (m, 2H), 0.52-0.57 (m, 2H) and the second eluting isomer (RT=4.90 min, peak-2) Intermediate 72C2 (320 mg, 1.054 mmol, 37% yield), $^1$H NMR (400 MHz, DMSO-d$_6$) δ 5.67 (s, 1H), 3.76 (s, 3H), 3.59 (s, 3H), 1.75-1.83 (m, 12H), 1.69-1.74 (m, 1H), 0.73-0.78 (m, 2H), 0.56-0.57 (m, 2H). MS (ESI) 289 (M+H).

Step D. Intermediate 72D. Preparation of (4-(3-cyclopropyl-1-methyl-1H-pyrazol-5-yl) bicyclo[2.2.2]octan-1-yl)methanol

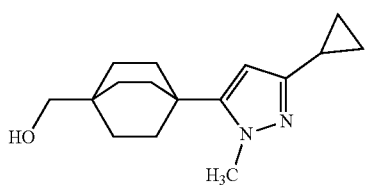 [SMILES: Cn1nc(C2CC2)cc1C12CCC(CO)(CC1)CC2]

The title compound was prepared according to the method described for the synthesis of Intermediate 1E by substituting Intermediate 72C2 where appropriate. (120 mg, 0.44 mmol, 42% yield) as pale yellow oil. $^1$H NMR (400 MHz, DMSO-d$_6$) δ 5.65 (s, 1H), 3.75 (s, 3H), 3.05 (s, 2H), 1.68-1.79 (m, 7H), 1.35-1.44 (m, 6H), 0.72-0.78 (m, 2H), 0.50-0.56 (m, 2H).

Step E. Intermediate 72E. Preparation of 4-(3-cyclopropyl-1-methyl-1H-pyrazol-5-yl) bicyclo[2.2.2]octane-1-carbaldehyde

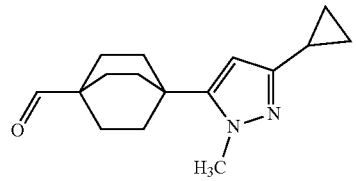

The title compound was prepared according to the method described for the synthesis of Intermediate 1F by substituting Intermediate 72D where appropriate. (90 mg, 0.35 mmol, 76% yield) as an off-white solid. $^1$H NMR (400 MHz, DMSO-d$_6$) δ 9.45 (s, 1H), 5.69 (s, 1H), 3.77 (s, 3H), 1.68-1.79 (m, 7H), 1.55-1.61 (m, 6H), 0.73-0.79 (m, 2H), 0.53-0.58 (m, 2H).

Step F. Intermediate 72F. Preparation of 3-(((4-(3-cyclopropyl-1-methyl-1H-pyrazol-5-yl)bicyclo[2.2.2]octan-1-yl)methyl)amino)benzonitrile

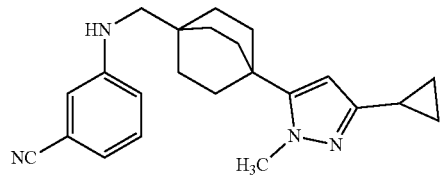 [SMILES: Cn1nc(C2CC2)cc1C12CCC(CNc3cccc(C#N)c3)(CC1)CC2]

The title compound was prepared according to the method described for the synthesis of Intermediate 1G by substituting Intermediate 72E and 3-aminobenzonitrile where appropriate: (70 mg, 0.184 mmol, 79% yield). $^1$H NMR (400 MHz, DMSO-d$_6$) δ 7.24-7.17 (m, 1H), 6.97-6.89 (m, 2H), 6.87-6.81 (m, 1H), 6.01 (t, J=5.8 Hz, 1H), 3.76 (s, 3H), 2.83 (d, J=6.0 Hz, 2H), 1.86-1.76 (m, 6H), 1.72 (tt, J=8.5, 5.0 Hz, 1H), 1.59-1.49 (m, 6H), 0.80-0.72 (m, 2H), 0.58-0.52 (m, 2H). MS (ESI) 361 (M+H).

Step G. Example 72. Preparation of N-(3-cyanophenyl)-N-((4-(3-cyclopropyl-1-methyl-1H-pyrazol-5-yl)bicyclo[2.2.2]octan-1-yl)methyl)-3-fluorobicyclo[1.1.1]pentane-1-carboxamide The title compound was prepared according to method described for the synthesis of Example 1 (Step H) by substituting Intermediate 72F where appropriate: (12 mg, 0.025 mmol, 61% yield). $^1$H NMR (400 MHz, DMSO-d$_6$) δ 8.04 (s, 1H), 7.87 (d, J=7.8 Hz, 1H), 7.79 (td, J=1.0, 8.0 Hz, 1H), 7.70-7.61 (m, 1H), 5.64 (s, 1H), 3.73 (s, 5H), 1.96-1.77 (m, 6H), 1.76-1.63 (m, 7H), 1.47-1.31 (m, 6H), 0.80-0.72 (m, 2H), 0.59-0.50 (m, 2H). FXR EC$_{50}$ (nM)=993. MS (ESI) 473 (M+H).

The following examples were prepared according to the method described for the synthesis of Example 1 (step H) by substituting Intermediate 72F and corresponding acids where appropriate:

| Ex. No. | Structure & Name | MS (ESI) (M + H) | FXR EC$_{50}$ (nM) |
|---|---|---|---|
| 73 | N-(3-cyanophenyl)-N-((4-(3-cyclopropyl-1-methyl-1H-pyrazol-5-yl)bicyclo[2.2.2]octan-1-yl)methyl)-4,4-difluorocyclohexane-1-carboxamide | 507 | 2131 |
| 74 | (1S,3S)-N-(3-cyanophenyl)-N-((4-(3-cyclopropyl-1-methyl-1H-pyrazol-5-yl)bicyclo[2.2.2]octan-1-yl)methyl)-3-hydroxy-3-methylcyclobutane-1-carboxamide | 473 | 1346 |
| 75 | (1S,3S)-N-(3-cyanophenyl)-N-((4-(3-cyclopropyl-1-methyl-1H-pyrazol-5-yl)bicyclo[2.2.2]octan-1-yl)methyl)-3-hydroxy-3-(trifluoromethyl)cyclobutane-1-carboxamide | 527 | 1376 |
| 73 | $^1$H NMR (400 MHz, DMSO-d$_6$) δ 8.09-7.98 (m, 1H), 7.89-7.76 (m, 2H), 7.68-7.61 (m, 1H), 5.62 (s, 1H), 3.72 (s, 3H), 3.61-3.53 (m, 2H), 2.36-2.29 (m, 1H), 2.03-1.87 (m, 2H), 1.79-1.65 (m, 8H), 1 63-1.45 (m, 4H), 1.40-1.29 (m, 6H), 1.26-1.20 (m, 1H), 0.78-0.70 (m, 2H), 0.56-0.49 (m, 2H) | | |
| 74 | $^1$H NMR (400 MHz, DMSO-d$_6$) δ 7.94 (br s, 1H), 7.78 (br dd, J = 1.7, 7.3 Hz, 1H), 7.74-7.69 (m, 1H), 7.65-7.57 (m, 1H), 5.61 (s, 1H), 4.89 (s, 1H), 3.71 (s, 3H), 3.61-3.53 (m, 2H), 2.14-2.02 (m, 2H), 1.78-1.63 (m, 7H), 1.61-1.47 (m, 2H), 1.42-1.27 (m, 6H), 1.25-1.11 (m, 2H), 1.04-0.95 (m, 2H), 0.77-0.69 (m, 2H), 0.56-0.48 (m, 2H) | | |
| 75 | $^1$H NMR (400 MHz, DMSO-d$_6$) δ 8.03 (d, J = 1.5 Hz, 1H), 7.87-7.74 (m, 2H), 7.68-7.60 (m, 1H), 6.55 (br s, 1H), 5.64 (s, 1H), 3.73 (s, 3H), 3.60 (br s, 2H), 2.78-2.69 (m, 1H), 2.34-2.27 (m, 2H), 2.10-1.96 (m, 2H), 1.77-1.56 (m, 7H), 1.43-1.30 (m, 6H), 0.79-0.71 (m, 2H), 0.60-0.48 (m, 2H) | | |

Example 76

(1S,3S)—N-((4-(3-cyclopropyl-1-methyl-1H-pyrazol-5-yl)bicyclo[2.2.2]octan-1-yl) methyl)-3-hydroxy-N-(3-(methylsulfonyl)phenyl)-3-(trifluoromethyl)cyclobutane-1-carboxamide (76)

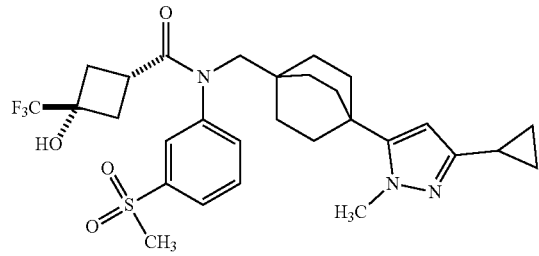

STEP A. Intermediate 76A. Preparation of N-((4-(3-cyclopropyl-1-methyl-1H-pyrazol-5-yl)bicyclo[2.2.2]octan-1-yl)methyl)-3-(methylsulfonyl) aniline

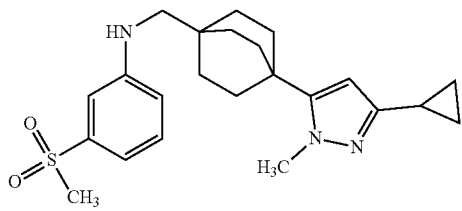 [SMILES: Cn1nc(C2CC2)cc1C12CCC(CNc3cccc(S(C)(=O)=O)c3)(CC1)CC2]

The title compound was prepared according to method described for the synthesis of Intermediate 1G by substituting Intermediate 72E and 3-(methylsulfonyl) aniline where appropriate: (20 mg, crude). MS (ESI) 414 (M+H).

Step B. Example 76. Preparation of (1s, 3s)-N-((4-(3-cyclopropyl-1-methyl-1H-pyrazol-5-yl)bicyclo[2.2.2]octan-1-yl)methyl)-3-hydroxy-N-(3-(methylsulfonyl)phenyl)-3-(trifluoromethyl)cyclobutane-1-carboxamide The title compound was prepared according to method described for the synthesis of Example 1 (Step H) by substituting Intermediate 76A where appropriate: (17 mg, 0.03 mmol, 59% yield). $^1$H NMR (400 MHz, DMSO-d$_6$) δ 7.95 (s, 1H), 7.88 (d, J=7.8 Hz, 1H), 7.83-7.77 (m, 1H), 7.75-7.68 (m, 1H), 6.57 (s, 1H), 5.62 (s, 1H), 3.72 (s, 3H), 3.68-3.59 (m, 2H), 3.27 (s, 3H), 2.78-2.68 (m, 1H), 2.38-2.26 (m, 2H), 2.10-1.98 (m, 2H), 1.79-1.60 (m, 7H), 1.45-1.29 (m, 6H), 0.78-0.70 (m, 2H), 0.57-0.48 (m, 2H). FXR EC$_{50}$ (nM)=4000. MS (ESI) 580 (M+H).

Example 77

N-((4-(3-cyclopropyl-1-methyl-1H-pyrazol-5-yl) bicyclo[2.2.2]octan-1-yl)methyl)-4,4-difluoro-N-(3-(methylsulfonyl) phenyl) cyclohexane-1-carboxamide (77)

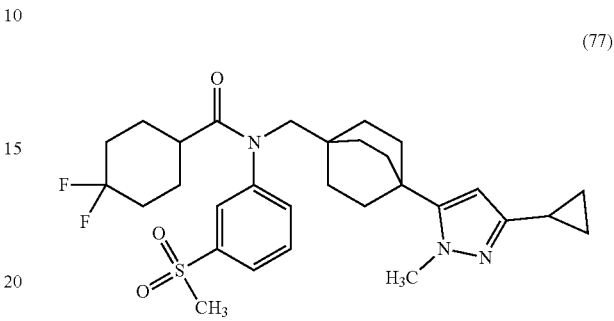

The title compound was prepared according to method described for the synthesis of Example 1 (Step H) by substituting Intermediate 76A where appropriate: (4 mg, 7.15 μmol, 15% yield). $^1$H NMR (400 MHz, DMSO-d$_6$) δ 8.02-7.94 (m, 1H), 7.92-7.86 (m, 1H), 7.85-7.79 (m, 1H), 7.77-7.68 (m, 1H), 5.62 (s, 1H), 3.72 (s, 3H), 3.61 (br s, 2H), 3.30 (s, 3H), 2.58-2.53 (m, 5H), 2.31-2.23 (m, 1H), 2.03-1.89 (m, 2H), 1.78-1.44 (m, 8H), 1.36 (br dd, J=7.2, 8.4 Hz, 6H), 0.79-0.68 (m, 2H), 0.58-0.48 (m, 2H). FXR EC$_{50}$ (nM)=4000. MS (ESI) 560 (M+H).

Example 78

N-((4-(3-cyclopropyl-1-methyl-1H-pyrazol-5-yl) bicyclo[2.2.2]octan-1-yl)methyl)-3-fluoro-N-(3-(methylsulfonyl) phenyl)bicyclo[1.1.1]pentane-1-carboxamide (78)

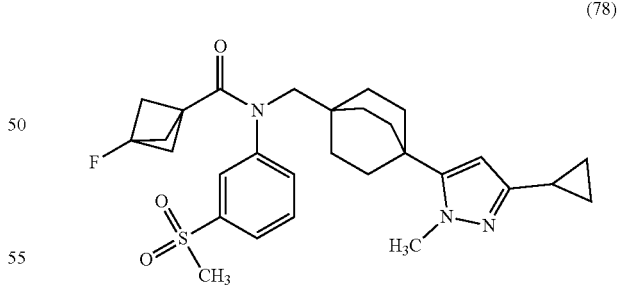

The title compound was prepared according to method described for the synthesis of Example 1 (Step H) by substituting Intermediate 76A where appropriate: (11 mg, 0.019 mmol, 40% yield). $^1$H NMR (400 MHz, DMSO-d$_6$) δ 8.02-7.88 (m, 2H), 7.83-7.78 (m, 1H), 7.75 (d, J=7.6 Hz, 1H), 5.62 (s, 1H), 3.72 (s, 3H), 3.63-3.48 (m, 2H), 3.31 (s, 3H), 1.94-1.79 (m, 6H), 1.77-1.63 (m, 7H), 1.47-1.34 (m, 6H), 0.77-0.69 (m, 2H), 0.57-0.49 (m, 2H). FXR EC$_{50}$ (nM)=4000. MS (ESI) 526 (M+H).

Example 79

Methyl 2-(3-(N-((4-(3-chloro-4-(dimethylamino)phenyl)bicyclo[2.2.2]octan-1-yl) methyl)cyclohexanecarboxamido) phenoxy) acetate

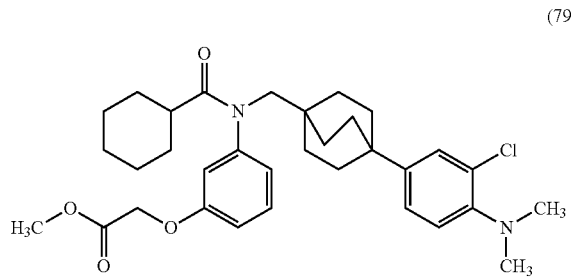

(79)

Step A. Intermediate 79A. Preparation of methyl 4-bromobicyclo[2.2.2]octane-1-carboxylate

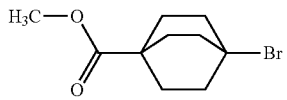

To a stirred solution of 4-(methoxycarbonyl)bicyclo[2.2.2]octane-1-carboxylic acid (1 g, 4.71 mmol) in $CH_2Br_2$ (10 mL) at room temperature was added mercuric oxide (1.73 g, 8.01 mmol). The reaction mixture was heated to 80° C. and $Br_2$ (0.36 mL, 7.07 mmol) was added drop wise to the reaction mixture and stirring continued for 3 h. The reaction mixture was cooled to room temperature and filtered through Celite pad. The filtrate was concentrated under reduced pressure to afford the title compound (1 g, 4.05 mmol, 86% yield). This compound was taken to the next step without further purification. $^1$H NMR (300 MHz, DMSO-$d_6$) δ 3.56 (s, 3H), 2.25-2.15 (m, 6H), 1.94-1.85 (m, 6H).

Step B. Intermediate 79B. Preparation of methyl 4-phenylbicyclo[2.2.2]octane-1-carboxylate

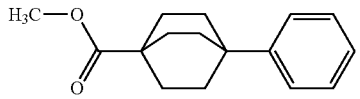 [SMILES: COC(=O)C12CCC(c3ccccc3)(CC1)CC2]

Benzene (12 mL, 142 mmol) was cooled to −10° C. and aluminum chloride (2.70 g, 20.23 mmol) was added under nitrogen atmosphere. The solution was stirred for 5 min at −10° C. and a solution of Intermediate 79A (1 g, 4.0 mmol) in benzene (12 mL) was added. The reaction mixture was allowed to warm to room temperature and stirred for 12 h. The reaction mixture was poured into crushed ice and diluted with water (50 mL). The organic layer was separated, washed with water (2×10 mL), dried over $MgSO_4$ and concentrated under reduced pressure to afford the title compound (0.82 g, 2.10 mmol, 52% yield). This compound was taken to the next step without further purification. $^1$H NMR (300 MHz, Chloroform-d) δ 7.34-7.30 (m, 4H), 7.21 (dt, J=5.8, 2.6 Hz, 1H), 3.73 (s, 3H), 1.99-1.84 (m, 12H). MS (ESI) 445 (M+H).

Step C. Intermediate 79C. Preparation of methyl 4-(4-bromophenyl)bicyclo[2.2.2]octane-1-carboxylate

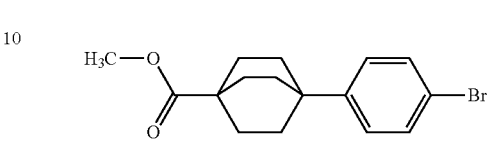

A solution of Intermediate 79B (0.8 g, 3.27 mmol) and silver trifluoro acetate (0.86 g, 3.93 mmol) was stirred at room temperature for 5 min under nitrogen atmosphere. A solution of $Br_2$ (0.17 mL, 3.27 mmol) in $CHCl_3$ (40 mL) was added to the reaction mixture and stirred for 2 h. The reaction mixture was filtered through Celite pad and the filtrate was evaporated under reduced pressure. The residue was triturated with n-hexane and dried in vacuo to afford the title compound (0.74 g, 1.58 mmol, 48% yield). $^1$H NMR (300 MHz, Chloroform-d) δ 7.43 (d, J=8.7 Hz, 2H), 7.20 (d, J=8.7 Hz, 2H), 3.69 (s, 3H), 1.99-1.78 (m, 12H). MS (ESI) 323 (M+H).

Step D. Intermediate 79D. Preparation of (4-(4-bromophenyl)bicyclo[2.2.2]octan-1-yl)methanol

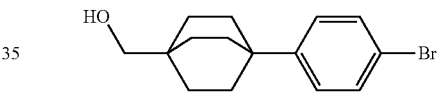

A solution of Intermediate 79C (0.65 g, 2.011 mmol) in DCM (5 mL) was cooled to −78° C. and DIBAL-H (4.0 mL, 4.02 mmol) was added to the reaction mixture. The reaction mixture was allowed to warm to room temperature and stirred for 2 h. The reaction mixture was poured into crushed ice and diluted with water (10 mL). The aqueous layer was extracted with ethyl acetate (2×20 mL). The combined organic layers were dried over anhydrous sodium sulphate, filtered and concentrated under reduced pressure. The crude material was purified by flash chromatography (24 g silica gel cartridge; A=Hex, B=EtOAc; 30 min grad.; 0% B to 40% B; flow rate=30 mL/min). The pure fractions were combined, concentrated under reduced pressure and dried in vacuo to afford the title compound (0.59 g, 1.9 mmol, 99% yield.). $^1$H NMR (300 MHz, DMSO-$d_6$) δ 7.44 (d, J=8.7 Hz, 2H), 7.28 (d, J=8.7 Hz, 2H), 4.35 (t, J=5.3 Hz, 1H), 3.08 (d, J=5.3 Hz, 2H), 1.78-1.66 (m, 6H), 1.51-1.39 (m, 6H).

Step E. Intermediate 79E. Preparation of (4-(4-(dimethylamino) phenyl)bicyclo[2.2.2]octan-1-yl)methanol

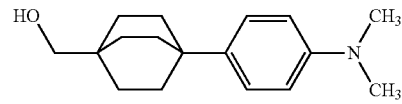

To a stirred solution of Intermediate 79D (200 mg, 0.677 mmol) in toluene (5 mL) at room temperature were added dimethylamine (10 mL, 10.16 mmol), 2-di-tert-butylphosphino-2',4',6'-triisopropylbiphenyl (28 mg, 0.068 mmol) and sodium tert-butoxide (195 mg, 2.032 mmol). The reaction mixture was degassed and back-filled with argon three times and Pd₂(dba)₃ (31.0 mg, 0.034 mmol) was added to the reaction mixture and the vial was sealed (Pressure release vial). The reaction mixture was heated to 80° C. and stirred for 4 h. The reaction mixture was cooled to room temperature and concentrated under reduced pressure. The residue was diluted with water (10 mL) and extracted with ethyl acetate (2×10 mL). The combined organic layers were dried over anhydrous sodium sulphate, filtered and concentrated under reduced pressure. The crude material was purified by flash chromatography (4 g silica gel cartridge; A=Hex, B=EtOAc; 30 min grad.; 0% B to 20% B; flow rate=30 mL/min). The pure fractions were combined, concentrated under reduced pressure and dried in vacuo to afford the title compound (130 mg, 0.501 mmol, 74% yield) as white solid. ¹H NMR (400 MHz, DMSO-d₆) δ 7.11 (dd, J=2.00, 6.80 Hz, 2H), 6.64 (dd, J=2.00, 6.80 Hz, 2H), 4.31 (t, J=5.60 Hz, 1H), 3.07 (d, J=5.60 Hz, 2H), 2.77 (s, 6H), 1.66-1.72 (m, 6H), 1.40-1.43 (m, 6H).

Step F. Intermediate 79F. Preparation of 4-(3-chloro-4-(dimethylamino)phenyl)bicyclo [2.2.2]octane-1-carbaldehyde

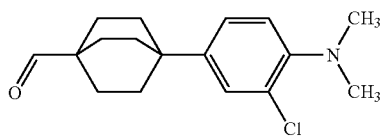

To a stirred solution of oxalyl chloride (0.053 mL, 0.601 mmol) in anhydrous DCM (1.5 mL) at −78° C. was added a solution of DMSO (0.10 mL, 1.50 mmol) in anhydrous DCM (1.5 mL) under nitrogen atmosphere. The reaction mixture was stirred at −78° C. for 15 min. A solution of Intermediate 79E (0.13 g, 0.50 mmol) in DCM (2.5 mL) was added to the reaction mixture over a period of 10 min. The reaction mixture was stirred at −78° C. for 3 h. TEA (0.42 mL, 3.01 mmol) was added to the reaction and continued stirring for another 5 min. The reaction mixture was allowed to warm to room temperature and stirred for 1 h. The reaction mixture was diluted with DCM (10 mL), washed with water (2×20 mL), brine solution (2×10 mL), dried over anhydrous sodium sulphate, filtered and concentrated under reduced pressure to afford the title compound (0.11 g, 0.28 mmol, 57% yield) as colorless gummy liquid. MS (ESI) 292 (M+H).

Step G. Intermediate 79G. Preparation of methyl 2-(3-nitrophenoxy) acetate

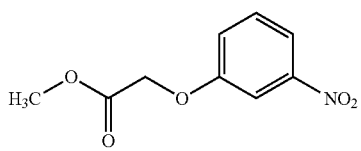

To a stirred solution of 3-nitrophenol (2 g, 14.38 mmol) in acetone (40 mL) at room temperature was added K₂CO₃ (3.97 g, 28.8 mmol) followed by methyl 2-bromoacetate (3.30 g, 21.57 mmol). The reaction mixture was heated to 60° C. and stirred for 7 h. The reaction mixture was diluted with ethyl acetate (50 mL) and filtered through Celite pad. The filtrate was concentrated under reduced pressure and the crude material was purified by flash chromatography (40 g silica gel cartridge; A=Hex, B=EtOAc; 30 min grad.; 0% B to 20% B; flow rate=30 mL/min). The pure fractions were combined, concentrated under reduced pressure and dried in vacuo to afford the title compound (3 g, 14.21 mmol, 99% yield) as white solid. MS (ESI) 229 (M+18, NH₃ adduct).

Step H. Intermediate 79H. Preparation of methyl 2-(3-aminophenoxy) acetate

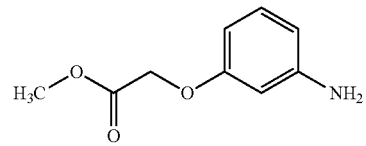

A stirred solution of Intermediate 79G (1 g, 4.74 mmol) in methanol (15 mL) was degassed and back-filled with argon and 10% Pd/C (150 mg, 0.141 mmol) was added. The resulting solution was stirred overnight under hydrogen atmosphere (balloon pressure, 1 atm). The reaction mixture was filtered through Celite pad and the filtrate was concentrated under reduced pressure to afford the title compound (0.8 g, 4.42 mmol, 93% yield) as colorless gummy liquid. MS (ESI) 189 (M+H).

Step I. Intermediate 79I. Preparation of methyl 2-(3-(((4-(3-chloro-4-(dimethylamino) phenyl)bicyclo[2.2.2]octan-1-yl)methyl) amino) phenoxy) acetate

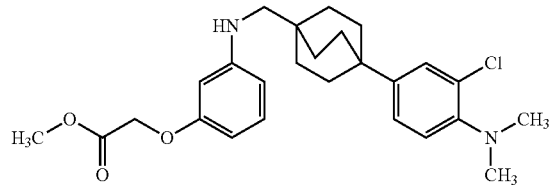

The title compound was prepared according to the method described for the synthesis of Intermediate 1G by substituting Intermediate 79D and Intermediate 79H. (120 mg, 0.20 mmol, 59% yield) as yellow liquid. MS (ESI) 457 (M+H).

Step J. Example 79. Preparation of methyl 2-(3-(N-((4-(3-chloro-4-(dimethylamino) phenyl)bicyclo [2.2.2]octan-1-yl) methyl) cyclohexanecarboxamido) phenyl) acetate To a stirred solution of Intermediate 79I (0.12 g, 0.263 mmol) in DCM (5 mL) at 0° C. were added TEA (0.146 mL, 1.050 mmol) followed by cyclohexanecarbonyl chloride (0.05 mL, 0.39 mmol). After stirring at room temperature for 2 h, the reaction mixture was diluted with DCM (20 mL). The organic solution was washed with water (10 mL), dried over anhydrous sodium sulphate, filtered and concentrated under reduced pressure. The crude material was purified via preparative LC/MS with the following conditions: Column: Waters XBridge C18, 19×150 mm, 5-μm particles; Mobile Phase A: 10-mM ammonium acetate; Mobile Phase B: acetonitrile; Gradient: 10-45% B over 25 minutes, then a 5-minute hold at 100% B; Flow: 15 mL/min. Fractions containing the desired product were combined and dried via centrifugal evaporation to obtain the title compound (23 mg, 0.04 mmol, 15% yield). $^1$H NMR (400 MHz, DMSO-$d_6$) δ 7.34 (t, J=8.0 Hz, 1H), 7.21 (d, J=2.0 Hz, 1H), 7.19-7.11 (m, 1H), 7.04 (d, J=8.5 Hz, 1H), 7.00-6.83 (m, 3H), 4.86 (s, 2H), 3.69 (s, 3H), 3.54 (s, 2H), 2.71-2.61 (m, 6H), 1.73-1.54 (m, 10H), 1.49 (br. s., 1H), 1.43-1.18 (m, 8H), 1.09 (d, J=12.5 Hz, 1H), 0.90 (d, J=13.1 Hz, 2H). FXR EC50 (nM)=1,044. MS (ESI) 567 (M+H).

Example 80

Methyl 2-(3-(N-((4-(4-(dimethylamino) phenyl) bicyclo[2.2.2]octan-1-yl)methyl) cyclohexanecarboxamido) phenoxy) acetate

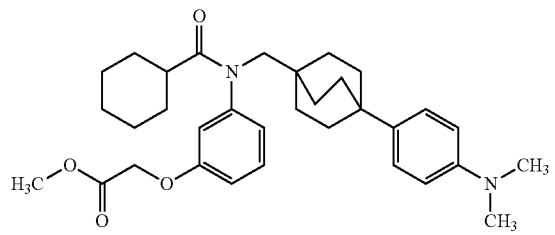

(80)

A stirred solution of Example 79 (30 mg, 0.053 mmol) in methanol (10 mL) was degassed and back-filled with nitrogen and 10% Pd/C (10 mg, 0.094 mmol) was added. The resulting solution was stirred overnight under hydrogen atmosphere (balloon pressure, 1 atm). The reaction mixture was filtered through Celite pad and the filtrate was concentrated under reduced pressure. The crude material was purified via preparative LC/MS using following conditions: (Column: Waters XBridge C18, 19×150 mm, 5-μm particles; Mobile Phase A: 10-mM ammonium acetate; Mobile Phase B: acetonitrile; Gradient: 40-80% B over 20 minutes, then a 5-minute hold at 100% B; Flow: 20 mL/min). Fractions containing the desired product were combined and dried via centrifugal evaporation to afford the title compound (6 mg, 0.011 mmol, 21% yield) as an off-white solid. $^1$H NMR (400 MHz, DMSO-$d_6$) δ 7.34 (t, J=7.9 Hz, 1H), 7.06 (d, J=9.0 Hz, 2H), 7.00-6.80 (m, 3H), 6.62 (d, J=8.8 Hz, 2H), 3.69 (s, 3H), 3.53 (s, 2H), 2.87-2.77 (m, 6H), 2.23 (br. s., 1H), 1.71-1.54 (m, 10H), 1.49 (br. s., 1H), 1.43-1.19 (m, 8H), 1.15-1.02 (m, 1H), 0.90 (d, J=11.7 Hz, 2H). FXR $EC_{50}$ (nM) 1,597; MS (ESI) 533 (M+H).

Example 81

Methyl 2-(3-(N-((1-(1-methyl-1H-indazol-5-yl)-2-oxabicyclo[2.2.2]octan-4-yl)methyl) tetrahydro-2H-pyran-4-carboxamido) phenoxy) acetate

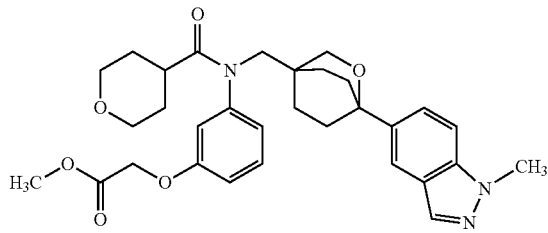

(81)

Step A. Intermediate 81A1 & 81A2. Preparation of (5-bromo-1-methyl-1H-indazole & 5-bromo-2-methyl-2H-indazole

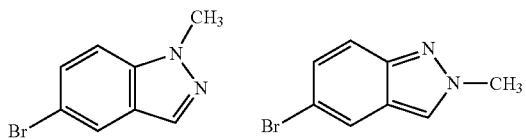

To a stirred solution of 5-bromo-1H-indazole (2 g, 10.15 mmol) in DMSO (20 mL) at room temperature was added methyl iodide (0.82 mL, 13.20 mmol) followed by potassium carbonate (7.0 g, 50.8 mmol). The reaction mixture was stirred overnight at room temperature. The reaction mixture was diluted with water (50 mL) and the aqueous solution was extracted with EtOAc (3×50). The combined organic layers were dried over anhydrous sodium sulphate, filtered and concentrated under reduced pressure. The crude material was purified by flash chromatography (40 g silica gel cartridge; A=Hex, B=EtOAc; 30 min grad.; 0% B to 40% B; flow rate=30 mL/min). The pure fractions were combined, concentrated under reduced pressure and dried in vacuo to afford Intermediate 81A1 (1.2 g, 5.40 mmol, 53% yield) as a white solid and Intermediate 81A2 (0.6 g, 2.70 mmol, 27% yield) as an off-white solid. The required compound was confirmed NOE studies. MS (ESI) 213(M+H).

Step B. Intermediate 81B. Preparation of 5-iodo-1-methyl-1H-indazole

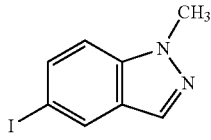

To a solution of Intermediate 81A1 (1 g, 4.74 mmol) in 1,4-dioxane (5 mL) at room temperature were added sodium iodide (1.42 g, 9.48 mmol), copper(I) iodide (0.05 g, 0.237 mmol) and (1r,2r)-N,N'-dimethyl-1,2-cyclohexanediamine (0.07 g, 0.474 mmol) under argon atmosphere. The reaction mixture was heated to 110° C. and stirred overnight. The reaction mixture was cooled to room temperature and diluted with water (30 mL). The aqueous solution was extracted with DCM (3×20 mL). The combined organic layers were dried over anhydrous sodium sulphate, filtered and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (1 g, 3.60 mmol, 76% yield) as an off-white crystalline solid. MS (ESI) 259 (M+H).

Step C. Intermediate 81C. Preparation of (4-hydroxy-4-(1-methyl-1H-indazol-5-yl) cyclohexane-1,1-diyl) bis (methylene) bis (4-methylbenzenesulfonate)

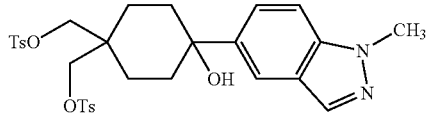 [SMILES: Cc1ccc(S(=O)(=O)OCC2(COS(=O)(=O)c3ccc(C)cc3)CCC(O)(c3ccc4c(cnn4C)c3)CC2)cc1]

A stirred solution of Intermediate 81B (0.3 g, 1.163 mmol) in tetrahydrofuran (5 mL) was cooled to −78° C. and n-BuLi (0.93 mL, 2.33 mmol) in hexane was added drop wise to the reaction mixture. The reaction mixture was stirred at −78° C. for 1 h. A solution of (4-oxocyclohexane-1,1-diyl)bis(methylene) bis(4-methylbenzenesulfonate) (see ACS Med. Chem. Lett., 5(5), 609-614; 2014) (0.70 g, 1.511 mmol) in 2 mL dry THF was added to the reaction. The reaction mixture was allowed to warm to room temperature over 1 h. The reaction mixture was quenched with aq. saturated ammonium chloride solution (10 mL) and the aqueous solution was extracted with EtOAc (2×20 mL). The combined organic layers were dried over anhydrous sodium sulphate, filtered and concentrated under reduced pressure. The crude material was purified by flash chromatography (24 g silica gel cartridge; A=Hex, B=EtOAc; 30 min grad.; 0% B to 100% B; flow rate=30 mL/min). The pure fractions were combined, concentrated under reduced pressure and dried in vacuo to afford the title compound (0.25 g, 0.4 mmol, 34% yield) as an off-white solid. MS (ESI) 599 (M+H).

Step D. Intermediate 81D. Preparation of (1-(1-methyl-1H-indazol-5-yl)-2-oxabicyclo [2.2.2]octan-4-yl)methyl 4-methylbenzenesulfonate

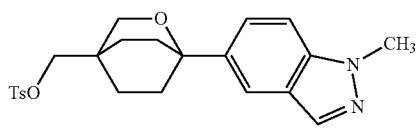 [SMILES: Cc1ccc(S(=O)(=O)OCC23CCC(c4ccc5c(cnn5C)c4)(CC2)OC3)cc1]

To a stirred solution of Intermediate 81C (0.25 g, 0.418 mmol) in anhydrous 1,2-dimethoxyethane (10 mL) at 0° C. was added sodium hydride (0.050 g, 1.253 mmol) under nitrogen atmosphere. The reaction mixture was stirred at 0° C. for 30 min. and then heated at reflux for 12 h. The reaction mixture was cooled to 0° C., quenched with aq. saturated ammonium chloride solution (5 mL) and extracted with EtOAc (2×10 mL). The combined organic layers were dried over anhydrous sodium sulphate, filtered and concentrated under reduced pressure. The crude material was purified by flash chromatography (24 g silica gel cartridge; A=Hex, B=EtOAc; 30 min grad.; 0% B to 50% B; flow rate=30 mL/min). The pure fractions were combined, concentrated under reduced pressure and dried in vacuo to afford the title compound (0.18 g, 0.401 mmol, 96% yield) as white solid. MS (ESI) 427 (M+H).

Step E. Intermediate 81E. Preparation of (1-(1-methyl-1H-indazol-5-yl)-2-oxabicyclo[2.2.2]octan-4-yl)methyl Acetate

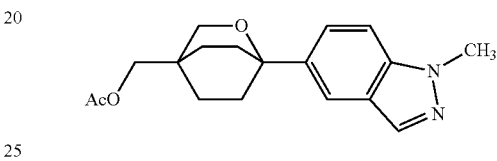

To a solution of Intermediate 81D (2.5 g, 5.86 mmol) in DMF (30 mL) in a pressure tube was added sodium acetate (2.88 g, 35.2 mmol). The reaction mixture was heated to 120° C. and stirred overnight. The reaction mixture was cooled to room temperature and diluted with water (50 mL). The aqueous solution was extracted with EtOAc (2×30 mL). The combined organic layers were dried over anhydrous sodium sulphate and concentrated under reduced pressure. The crude material was purified by flash chromatography (40 g silica gel cartridge; A=Hex, B=EtOAc; 30 min grad.; 0% B to 50% B; flow rate=30 mL/min). The pure fractions were combined, concentrated under reduced pressure and dried in vacuo to afford the title compound (0.6 g, 1.813 mmol, 31% yield) as an off-white solid. MS (ESI) 315 (M+H).

Step F. Intermediate 81F. Preparation of (1-(1-methyl-1H-indazol-5-yl)-2-oxabicyclo[2.2.2]octan-4-yl)methanol

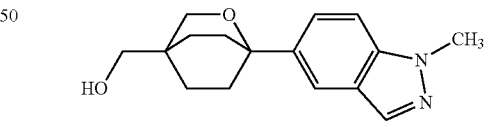

To a stirred solution of Intermediate 81E (0.6 g, 1.909 mmol) in methanol (10 mL) at 0° C. was added a solution of potassium carbonate (1.32 g, 9.54 mmol) in water (15 mL). The reaction mixture was allowed to warm to room temperature and stirred for 2 h. The solvent was removed under reduced pressure and the residue was diluted with water (15 mL). The aqueous solution was extracted with EtOAc (2×20 mL). The combined organic layers were dried over anhydrous sodium sulphate, filtered and concentrated under reduced pressure to afford the title compound (0.45 g, 1.57 mmol, 82% yield) as white solid. MS (ESI) 273 (M+H).

Step G. Intermediate 81G. Preparation of 1-(1-methyl-1H-indazol-5-yl)-2-oxabicyclo[2.2.2]octane-4-carbaldehyde

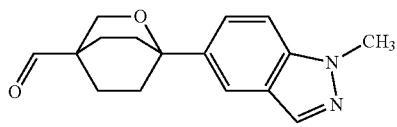

To a stirred solution of Intermediate 81F (0.4 g, 1.47 mmol) in dichloromethane (2 mL) at 0° C. was added Dess-Martin periodinane (0.748 g, 1.76 mmol). The reaction mixture was allowed to warm to room temperature and stirred for 2 h. The reaction mixture was diluted with DCM (30 mL) and the organic solution was washed with water (10 mL), and aq. 10% sodium bicarbonate solution (10 mL). The organic layer was dried over anhydrous sodium sulphate, filtered and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (0.4 g, 1.40 mmol, 96% yield) as semi solid. $^1$H NMR (400 MHz, DMSO-$d_6$) δ 9.53 (s, 1H), 7.98 (s, 1H), 7.87 (d, J=7.5 Hz, 1H), 7.74-7.71 (m, 1H), 7.57-7.53 (m, 1H), 4.03 (s, 2H), 4.01 (s, 3H), 2.23-2.12 (m, 2H), 2.01-1.85 (m, 6H).

Step H. Intermediate 81H. Preparation of methyl 2-(3-(((1-(1-methyl-1H-indazol-5-yl)-2-oxabicyclo[2.2.2]octan-4-yl)methyl)amino)phenoxy)acetate

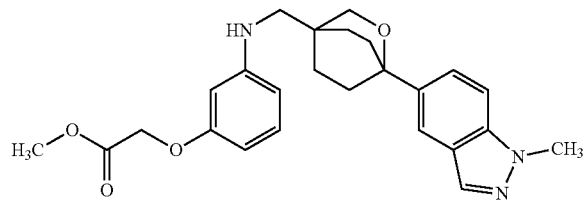

The title compound was prepared according to the method described for the synthesis of Intermediate 1G by substituting Intermediate 81G and Intermediate 79H where appropriate. (0.19 g, 0.41 mmol, 56% yield) as pale yellow solid. MS (ESI) 436 (M+H).

Step I. Example 81. Preparation of methyl 2-(3-(N-((1-(1-methyl-1H-indazol-5-yl)-2-oxabicyclo[2.2.2]octan-4-yl)methyl)tetrahydro-2H-pyran-4-carboxamido)phenoxy) acetate The title compound was prepared according to the method described for the synthesis of Example 79 (step J) by substituting Intermediate 81H and corresponding acid where appropriate. (8 mg, 0.013 mmol, 22% yield). $^1$H NMR (400 MHz, DMSO-$d_6$) δ 7.94 (s, 1H), 7.65 (s, 1H), 7.50 (d, J=8.8 Hz, 1H), 7.44-7.30 (m, 2H), 7.10-6.98 (m, 2H), 6.95 (d, J=7.1 Hz, 1H), 4.88 (s, 2H), 3.99 (s, 3H), 3.76 (d, J=8.1 Hz, 2H), 3.70-3.64 (m, 6H), 3.59 (s, 2H), 3.02 (t, J=11.7 Hz, 2H), 2.11-1.95 (m, 2H), 1.90-1.74 (m, 2H), 1.70-1.49 (m, 6H), 1.44 (d, J=13.2 Hz, 2H). FXR $EC_{50}$ (nM) 4355; MS (ESI) 548 (M+H).

Example 82

3-(N-((4-(3-methyl-1,2,4-oxadiazol-5-yl)bicyclo[2.2.2]octan-1-yl)methyl) cyclohexanecarboxamido)-N-(thiazol-2-yl)benzamide (82)

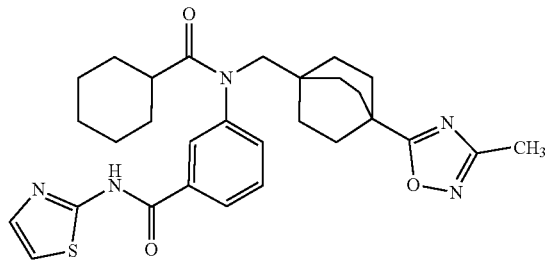

Step A. Intermediate 82A. Preparation of 3-nitro-N-(thiazol-2-yl)benzamide

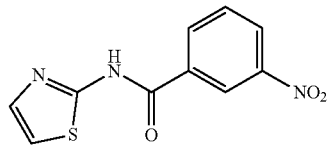 [SMILES: Nc1cccc(C(=O)Nc2nccs2)c1]

To a stirred solution of thiazol-2-amine (0.27 g, 2.69 mmol) in dichloromethane (10 mL) at 0° C. was added TEA (1.12 mL, 8.08 mmol) followed by 3-nitrobenzoyl chloride (0.5 g, 2.69 mmol). The reaction mixture was allowed to warm to room temperature and stirred for 12 h. The reaction mixture was concentrated under reduced pressure and the residue was diluted with EtOAc (30 mL). The organic solution was washed with water (20 mL), brine solution (10 mL), dried over anhydrous sodium sulphate, filtered and concentrated under reduced pressure to afford the title compound (0.35 g, 1.334 mmol, 49% yield) as an off-white solid. MS (ESI) 250 (M+H).

Step B. Intermediate 82B. Preparation of 3-amino-N-(thiazol-2-yl)benzamide

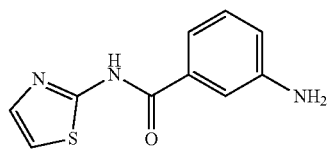

To a stirred solution of Intermediate 82A (0.35 g, 1.40 mmol) in ethanol (10 mL) at room temperature was added tin(II) chloride (1.06 g, 5.62 mmol). The reaction mixture was heated to 90° C. and stirred for 12 h. The reaction mixture was cooled to room temperature and concentrated under reduced pressure. The crude material was dissolved in EtOAc (20 mL) and the resulting solution was washed with aq. 10% NaHCO$_3$ solution (10 mL), and brine solution (10 mL). The organic layer was dried over anhydrous sodium sulphate, filtered and concentrated under reduced pressure. The crude material was purified by flash chromatography (12 g silica gel cartridge; A=Hex, B=EtOAc; 30 min grad.; 0% B to 60% B; flow rate=30 mL/min). The pure fractions were combined, concentrated under reduced pressure and dried in vacuo to afford the title compound (0.15 g, 0.616 mmol, 43% yield) as an off-white solid. MS (ESI) 220 (M+H).

Step C. Intermediate 82C. Preparation of methyl 4-(3-methyl-1,2,4-oxadiazol-5-yl) bicyclo[2.2.2]octane-1-carboxylate

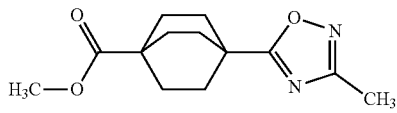

To a stirred solution of 4-(methoxycarbonyl)bicyclo[2.2.2]octane-1-carboxylic acid (2 g, 9.42 mmol) in DMF (20 mL) at room temperature were added (E)-N'-hydroxyacetimidamide (1.4 g, 18.85 mmol), BOP (4.17 g, 9.42 mmol) and TEA (4 mL, 28.3 mmol). The reaction mixture was stirred at room temperature for 2 h and heated at 110° C. overnight. The reaction mixture was cooled to room temperature, diluted with water (50 mL) and extracted with EtOAc (2×30 mL). The combined organic layers were dried over anhydrous sodium sulphate, filtered and concentrated under reduced pressure. The crude material was purified by flash chromatography (40 g silica gel cartridge; A=Hex, B=EtOAc; 30 min grad.; 0% B to 40% B; flow rate=30 mL/min). The pure fractions were combined, concentrated under reduced pressure and dried in vacuo to afford the title compound (0.6 g, 2.27 mmol, 24% yield) as white solid. $^1$H NMR (400 MHz, DMSO-d$_6$) δ 3.60 (s, 3H), 2.29 (s, 3H), 1.95-1.86 (m, 6H), 1.86-1.78 (m, 6H).

Step D. Intermediate 82D. Preparation of methyl 4-(3-methyl-1,2,4-oxadiazol-5-yl) bicyclo[2.2.2]octane-1-carboxylate

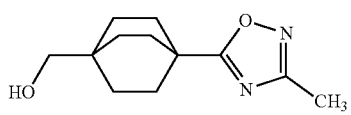

To a stirred solution of Intermediate 82C (0.6 g, 2.397 mmol) in tetrahydrofuran (20 mL) at −78° C. was added DIBAL-H (6 mL, 5.99 mmol) under nitrogen atmosphere. The reaction mixture was allowed to warm to room temperature and stirred for 1 h. The reaction mixture was cooled to 0° C., quenched with aq. 1.5 N HCl solution (30 mL) and extracted with EtOAc (2×25 mL). The combined organic layers were dried over anhydrous sodium sulphate, filtered and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (0.58 g, 2.35 mmol, 98% yield) as an off-white solid. $^1$H NMR (400 MHz, DMSO-d$_6$) δ 4.41 (br. s., 1H), 3.08 (s, 2H), 2.29 (s, 3H), 1.90-1.80 (m, 6H), 1.50-1.40 (m, 6H).

Step E. Intermediate 82E. Preparation of 4-(3-methyl-1,2,4-oxadiazol-5-yl) bicyclo[2.2.2]octane-1-carbaldehyde

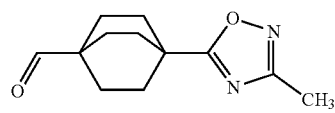

To a stirred solution of Intermediate 82D (0.58 g, 2.61 mmol) in dichloromethane (10 mL) at 0° C. was added Dess-Martin periodinane (2.2 g, 5.22 mmol) under nitrogen atmosphere. The reaction mixture was stirred at 0° C. for 1 h. The reaction mixture was allowed to warm to room temperature, diluted with DCM (20 mL) and filtered through Celite. The filtrate was washed with aq. 10% sodium bicarbonate solution (2×20 mL). The organic layer was dried over anhydrous sodium sulphate, filtered and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (0.46 g, 1.98 mmol, 76% yield) as white solid. $^1$H NMR (400 MHz, DMSO-d$_6$) δ 9.46 (s, 1H), 2.30 (s, 3H), 1.96-1.84 (m, 6H), 1.73-1.66 (m, 6H).

Step C. Intermediate 82C. Preparation of 3-(((4-(3-methyl-1,2,4-oxadiazol-5-yl) bicyclo[2.2.2]octan-1-yl)methyl)amino)-N-(thiazol-2-yl)benzamide

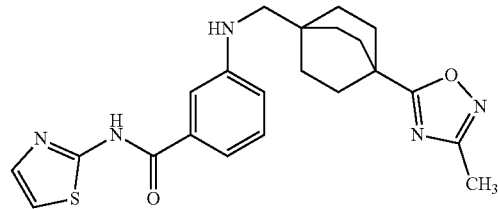 [SMILES: Cc1noc(C23CCC(CNc4cccc(C(=O)Nc5nccs5)c4)(CC2)CC3)n1]

The title compound was prepared according to the method described for the synthesis of Intermediate 1G by substituting Intermediate 82B and Intermediate 82E where appropriate. (40 mg, 0.09 mmol, 39% yield) as pale yellow solid. MS (ESI) 424 (M+H).

Step D. Example 82. Preparation of 3-(N-((4-(3-methyl-1,2,4-oxadiazol-5-yl) bicyclo[2.2.2]octan-1-yl)methyl)cyclohexanecarboxamido)-N-(thiazol-2-yl)benzamide The title compound was prepared according to the method described for the synthesis of Example 79 (step J) by substituting Intermediate 82C and cyclohexanecarbonyl chloride. (32 mg, 0.06 mmol, 72% yield). $^1$H NMR (400 MHz, DMSO-d$_6$) δ 12.68 (s, 1H), 8.15 (s, 1H), 8.06 (d, J=7.6 Hz, 1H), 7.73-7.66 (m, 1H), 7.66-7.51 (m, 2H), 7.31 (d, J=3.7 Hz, 1H), 3.67 (br. s., 2H), 2.27 (s, 3H), 2.21 (br. s., 1H), 1.88-1.73 (m, 6H), 1.61 (br. s., 4H), 1.49 (br. s., 1H), 1.46-1.27 (m, 8H), 1.10 (d, J=13.2 Hz, 1H), 0.90 (br. s., 2H). FXR EC$_{50}$ (nM)=3011; MS (ESI) 534 (M+H).

Example 83

N-((4-(3-(tert-butyl)-1,2,4-oxadiazol-5-yl)bicyclo[2.2.2]octan-1-yl)methyl)-N-(3-((4-ethoxyphenyl)amino)phenyl)-3-fluorobicyclo[1.1.1]pentane-1-carboxamide

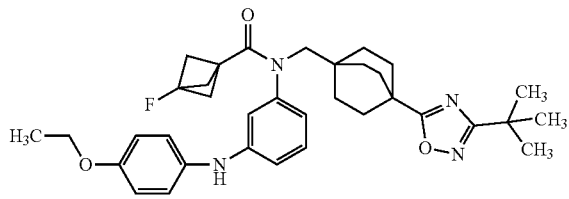

(83)

Step A. Intermediate 83A: Preparation of N-(3-bromophenyl)-N-((4-(3-(tert-butyl)-1,2,4-oxadiazol-5-yl)bicyclo[2.2.2]octan-1-yl)methyl)-3-fluorobicyclo[1.1.1]pentane-1-carboxamide

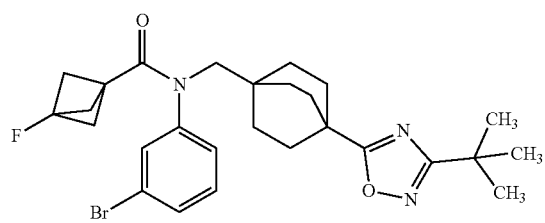 [SMILES: CC(C)(C)c1noc(C23CCC(CN(C(=O)C45CC(F)(C4)C5)c4cccc(Br)c4)(CC2)CC3)n1]

The title compound was synthesized according to the method described for the synthesis of Intermediate 1D by substituting Intermediate 33E and (Z)—N'-hydroxypivalimidamide where appropriate. (200 mg, 0.377 mmol, 68% yield) as brown gummy solid. MS (ESI) 530 (M+H).

Step B. Example 83: Preparation of N-((4-(3-(tert-butyl)-1,2,4-oxadiazol-5-yl) bicyclo[2.2.2]octan-1-yl)methyl)-N-(3-((4-ethoxyphenyl)amino)phenyl)-3-fluorobicyclo [1.1.1]pentane-1-carboxamide To a stirred solution of Intermediate 83A (30 mg, 0.057 mmol) in 1,4-dioxane (2 mL) at room temperature were added 4-ethoxyaniline (8 mg, 0.057 mmol), cesium carbonate (46 mg, 0.141 mmol) and Xantphos (4 mg, 5.66 μmol). The reaction mixture was degassed and back-filled with argon three times and bis(dibenzylideneacetone) palladium (2 mg, 2.83 μmol) was added. The reaction vial was sealed. The reaction mixture was heated to 110° C. and stirred overnight. The reaction mixture was concentrated under reduced pressure to afford a residue. The crude material was purified via preparative LC/MS with the following conditions: Column: Waters XBridge C18, 150 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 40% B, 40-84% B over 20 minutes, then a 5-minute hold at 100% B; Flow Rate: 15 mL/min; Column Temperature: 25° C. Fraction collection was triggered by MS signals. Fractions containing the product were combined and dried via centrifugal evaporation to obtain the title compound (12 mg, 0.019 mmol, 34% yield). $^1$H NMR (400 MHz, DMSO-d$_6$) δ 8.01 (s, 1H), 7.22 (t, J=7.9 Hz, 1H), 7.05 (d, J=8.8 Hz, 2H), 6.96-6.80 (m, 3H), 6.79-6.70 (m, 1H), 6.67 (d, J=7.6 Hz, 1H), 3.99 (q, J=6.9 Hz, 2H), 3.49 (d, J=4.9 Hz, 2H), 1.90 (s, 6H), 1.87-1.67 (m, 6H), 1.55-1.37 (m, 6H), 1.35-1.17 (m, 12H); FXR EC$_{50}$ (nM)=1131; MS (ESI) 587 (M+H).

Example 84

N-((4-(5-(tert-butyl)-1,2,4-oxadiazol-3-yl)bicyclo[2.2.2]octan-1-yl)methyl)-N-(3-((4-(difluoromethoxy)phenyl)amino)phenyl)-3-fluorobicyclo[1.1.1]pentane-1-carboxamide

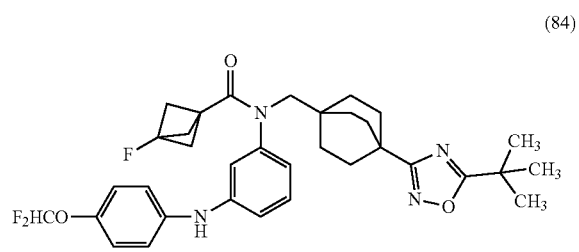 [SMILES: CC(C)(C)c1nc(C23CCC(CN(C(=O)C45CC(F)(C4)C5)c4cccc(Nc5ccc(OC(F)F)cc5)c4)(CC2)CC3)no1]

(84)

Step A. Intermediate 84A: Preparation of N-(3-bromophenyl)-N-((4-(5-(tert-butyl)-1,2,4-oxadiazol-3-yl)bicyclo[2.2.2]octan-1-yl)methyl)-3-fluorobicyclo[1.1.1]pentane-1-carboxamide

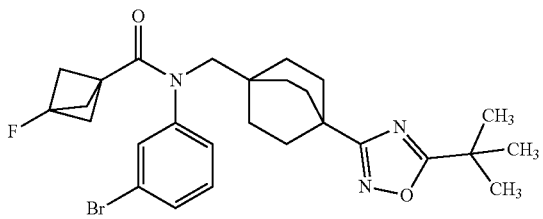

The title compound was synthesized according to the method described for the synthesis of Intermediate 1D by substituting Intermediate 33H and corresponding acid where appropriate. (190 mg, 0.358 mmol, 83% yield) as pale yellow solid. MS (ESI) 530 (M+H).

Step B. Intermediate 84B: Preparation of N-((4-(5-(tert-butyl)-1,2,4-oxadiazol-3-yl) bicyclo[2.2.2]octan-1-yl)methyl)-N-(3-((4-(difluoromethoxy)phenyl)amino)phenyl)-3-fluorobicyclo[1.1.1]pentane-1-carboxamide The title compound was synthesized according to the method described for the synthesis of Example 83 (step B) by substituting Intermediate 84A and 4-(difluoromethoxy)aniline where appropriate. (0.4 mg, 0.61 μmol, 2% yield). $^1$H NMR (400 MHz, DMSO-d$_6$) δ 8.37 (s, 1H), 7.34-6.86 (m, 8H), 6.80 (d, J=7.8 Hz, 1H), 3.63-3.40 (m, 2H), 1.91 (br. s., 6H), 1.82-1.70 (m, 6H), 1.55-1.39 (m, 6H), 1.34 (s, 9H); FXR EC$_{50}$ (nM)=84; MS (ESI) 609 (M+H).

The following examples were synthesized according to the method described for the synthesis of Example 83 by substituting Intermediate 84A and the corresponding Aryl/hetero aryl amines where appropriate.

| Ex. No. | Structure & Name | MS (ESI) (M + H) | FXR EC$_{50}$ (nM) |
|---|---|---|---|
| 85 | 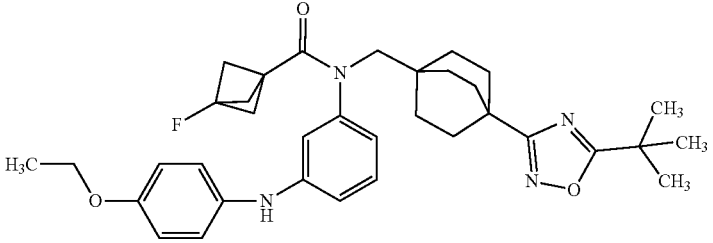 [SMILES: CCOc1ccc(Nc2cccc(N(CC34CCC(c5noc(C(C)(C)C)n5)(CC3)CC4)C(=O)C34CC(F)(C3)C4)c2)cc1]<br>N-((4-(5-(tert-butyl)-1,2,4-oxidial-3-yl)bicyclo[2.2.2]octan-1-yl)methyl)-N-(3-((4-ethoxyphenyl)amino)phenyl)-3-fluorobicyclo[1.1.1]pentane-1-carboxamide | 587 | 608 |
| 86 | 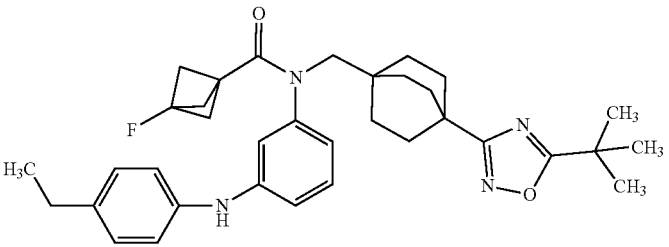 [SMILES: CCc1ccc(Nc2cccc(N(CC34CCC(c5noc(C(C)(C)C)n5)(CC3)CC4)C(=O)C34CC(F)(C3)C4)c2)cc1]<br>N-((4-(5-(tert-butyl)-1,2,4-oxadiazol-3-yl)bicyclo[2.2.2]octan-1-yl)methyl)-N-(3-((4-ethylphenyl)amino)phenyl)-3-fluorobicyclo[1.1.]pentane-1-carboxamide | 571 | 519 |
| 87 | 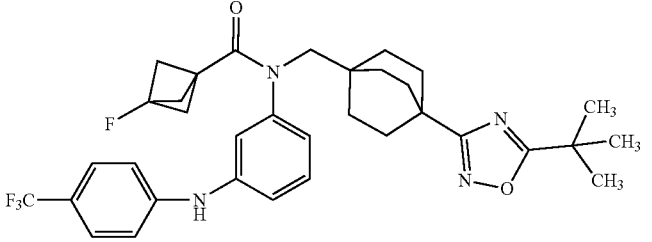 [SMILES: CC(C)(C)c1nc(C23CCC(CN(C(=O)C45CC(F)(C4)C5)c4cccc(Nc5ccc(C(F)(F)F)cc5)c4)(CC2)CC3)no1]<br>N-((4-(5-(tert-butyl)-1,2,4-oxadiazol-3-yl)bicyclo[2.2.2]octan-1-yl)methyl)-3-fluoro-N-(3-((4-(trifluoromethyl)phenyl)amino)phenyl)bicyclo[1.1.1]pentane-1-carboxamide | 611 | 2000 |
| 88 | 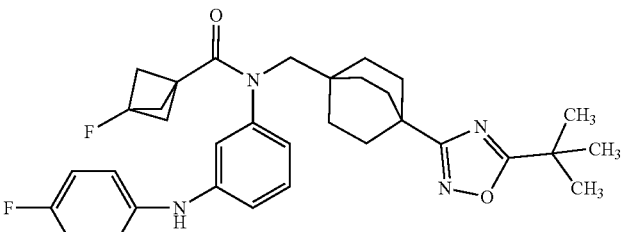<br>N-((4-(5-(tert-butyl)-1,2,4-oxadiazol-3-yl)bicyclo[2.2.2]octan-1-yi)methyl)-3-fluoro-N-(3-((4-fluorophenyl)amino)phenyl)bicyclo[1.1.1]pentane-1-carboxamide | 561 | 179 |
| 85 | $^1$H NMR (400 MHz, DMSO-d$_6$) δ 8.01 (s, 1H), 7.22 (t, J = 7.9 Hz, 1H), 7.12-6.99 (m, 2H), 6.96-6.82 (m, 3H), 6.76 (t, J = 2.1 Hz, 1H), 6.71-6.61 (m, 1H), 3.99 (q, J = 7.1 Hz, 2H), 3.48 (s, 2H), 2.03-1.81 (m, 6H), 1.81-1.62 (m, 6H), 1.54-1.38 (m, 6H), 1.37-1.27 (m, 12H), | | |

| Ex. No. | Structure & Name | MS (ESI) (M + H) | FXR EC$_{50}$ (nM) |
|---|---|---|---|
| 86 | $^1$H NMR (400 MHz, DMSO-d$_6$) δ 8.22 (s, 1H), 7.26 (t, J = 7.9 Hz, 1H), 7.18-7.09 (m, 2H), 7.08-6.93 (m, 3H), 6.89 (t, J = 2.1 Hz, 1H), 6.74 (dd, J = 7.6, 1.0 Hz, 1H), 3.50 (s, 2H), 2.60-2.53 (m, 2H), 1.90 (br. s., 6H), 1.82-1.59 (m, 6H), 1.58-1.38 (m, 6H), 1.34 (s, 9H), 1.16 (t, J = 7.6 Hz, 3H) | | |
| 87 | $^1$H NMR (400 MHz, DMSO-d$_6$) δ 8.84 (s, 1H), 7.57 (d, J = 8.6 Hz, 2H), 7.44-7.31 (m, 1H), 7.24-7.11 (m, 3H), 7.09 (t, J = 2.0 Hz, 1H), 6.97 (d, J = 7.6 Hz, 1H), 3.53 (d, J = 18.8 Hz, 2H), 1.92 (br. s., 6H), 1.83-1.54 (m, 6H), 1.54-1.39 (m, 6H), 1.39-1.25 (m, 9H) | | |
| 88 | $^1$H NMR (400 MHz, DMSO-d$_6$) δ 8.28 (s, 1H), 7.27 (t, J = 7.9 Hz, 1H), 7.19-7.07 (m, 4H), 7.01(dd, J = 8.3, 1.5 Hz, 1H), 6.87 (t, J = 2.1 Hz, 1H), 6.77 (dd, J = 7.6, 1.2 Hz, 1H), 3.50 (d, J = 13.9 Hz, 2H), 1.91 (br. s., 6H), 1.82-1.65 (m, 6H), 1.56-1.38 (m, 6H), 1.38-1.25 (m, 9H) | | |

Example 89

Methyl 3-(3-(N-((4-(4-(dimethylamino)phenyl)bicyclo[2.2.2]octan-1-yl)methyl) cyclohexanecarboxamido)phenyl)propanoate

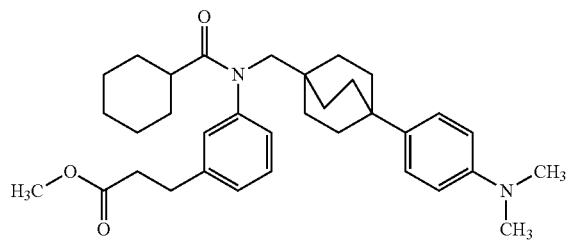

(89)

Step A. Intermediate 89A. Preparation of 4-(4-bromophenyl)bicyclo[2.2.2]octane-1-carbaldehyde

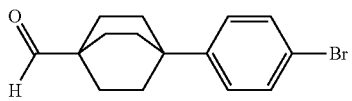

To a stirred solution of oxalyl chloride (0.12 mL, 1.219 mmol) in anhydrous DCM (3 mL) at −78° C. was added a solution of DMSO (0.21 mL, 3.05 mmol) in anhydrous DCM (2.5 mL) drop wise under nitrogen atmosphere. The reaction mixture was stirred at −78° C. for 15 min. A solution of Intermediate 79D (0.3 g, 1.016 mmol) in DCM (5 mL) was added to the above reaction mixture over a period of 10 min. The reaction mixture was further stirred at −78° C. for 3 h. Et$_3$N (0.85 mL, 6.10 mmol) was added to the reaction and continued stirring for another 5 min. at −78° C. The reaction mixture was allowed to warm to 0° C. and stirred for 1 h. The reaction mixture was diluted with DCM (10 mL) and poured onto crushed ice. The organic layer was separated and the aqueous layer was extracted with DCM (2×10 mL). The combined organic layers were dried over anhydrous sodium sulphate and concentrated under reduced pressure to afford the title compound (220 mg, 0.75 mmol, 74% yield). $^1$H NMR (300 MHz, Chloroform-d) δ 9.53 (s, 1H), 7.44 (d, J=8.7 Hz, 2H), 7.20 (d, J=8.7 Hz, 2H), 1.95-1.73 (m, 12H).

Step B. Intermediate 89B. Preparation of methyl (E)-3-(3-nitrophenyl)acrylate

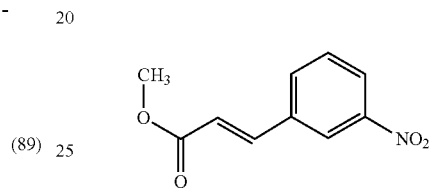

To a stirred solution of methyl 2-(dimethoxyphosphoryl) acetate (1.3 mL, 7.94 mmol) in water (6 mL) at room temperature were added K$_2$CO$_3$ (1.82 g, 13.23 mmol) followed by 3-nitrobenzaldehyde (1 g, 6.62 mmol). The reaction mixture was stirred at room temperature for 30 min. The reaction mixture was diluted with water (10 mL) and extracted with EtOAc (2×25 mL). The combined organic layers were dried over anhydrous sodium sulphate, filtered and concentrated under reduced pressure to afford the title compound (1 g, 4.83 mmol, 73% yield). $^1$H NMR (300 MHz, DMSO-d$_6$) δ 8.56 (t, J=1.7 Hz, 1H), 8.27-8.18 (m, 2H), 7.81 (d, J=16.2 Hz, 1H), 7.71 (t, J=8.1 Hz, 1H), 6.87 (d, J=16.2 Hz, 1H), 3.75 (s, 3H).

Step C. Intermediate 89C. Preparation of methyl (E)-3-(3-aminophenyl)acrylate

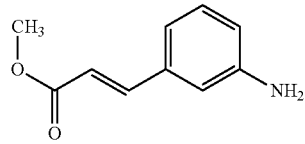

To a stirred solution of Intermediate 89B (1.300 g, 6.27 mmol) in water (15 mL) at room temperature was added tin(II) chloride dihydrate (8.50 g, 37.6 mmol). The reaction mixture was heated at 80° C. for 3 h. The reaction mixture was allowed to warm to room temperature. The reaction volume was reduced to half under reduced pressure and the remaining solution was poured onto crushed ice. The aqueous solution was neutralized (pH~7) using aq. saturated Na$_2$CO$_3$ solution and extracted with ethyl acetate (2×30 mL). The combined organic layers were dried over anhydrous sodium sulphate, filtered and concentrated under reduced pressure to afford the title compound (1 g, 3.84 mmol, 61% yield) as a light yellow solid. $^1$H NMR (400 MHz, DMSO-d$_6$) δ 7.49 (d, J=15.6 Hz, 1H), 7.12-7.01 (m, 1H), 6.87-6.77 (m, 2H), 6.67-6.59 (m, 1H), 6.41 (d, J=16.1 Hz, 1H), 5.18 (s, 2H), 3.71 (s, 3H). MS (ESI) 178 (M+H).

Step D. Intermediate 89D. Preparation of methyl (E)-3-(3-(((4-(4-bromophenyl) bicyclo[2.2.2]octan-1-yl)methyl)amino)phenyl)acrylate

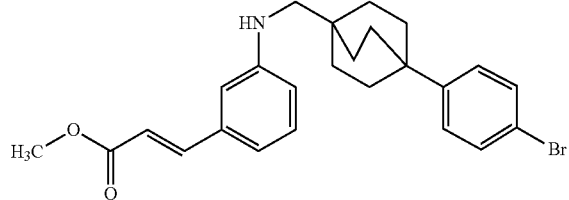 [SMILES: COC(=O)/C=C/c1cccc(NCC23CCC(c4ccc(Br)cc4)(CC2)CC3)c1]

The title compound was prepared according to the method described for the synthesis of Intermediate 1G by substituting Intermediate 89C and Intermediate 89A where appropriate. (100 mg, 0.178 mmol, 35% yield). $^1$H NMR (400 MHz, DMSO-$d_6$) δ 7.53 (d, J=16.1 Hz, 1H), 7.46 (d, J=8.00 Hz, 2H), 7.30 (d, J=8.00 Hz, 2H), 7.09 (t, J=7.8 Hz, 1H), 6.89 (s, 1H), 6.85-6.79 (m, 1H), 6.72 (d, J=8.3 Hz, 1H), 6.50 (d, J=15.9 Hz, 1H), 5.60-5.54 (m, 1H), 3.72 (s, 3H), 3.18 (d, J=5.4 Hz, 2H), 1.80-1.72 (m, 6H), 1.63-1.53 (m, 6H). MS (ESI) 455 (M+H).

Step E. Intermediate 89E. Preparation of methyl (E)-3-(3-(N-((4-(4-bromophenyl) bicyclo[2.2.2]octan-1-yl)methyl)cyclohexanecarboxamido)phenyl)acrylate

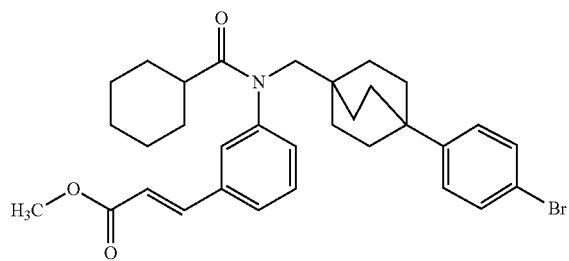 [SMILES: COC(=O)/C=C/c1cccc(N(CC23CCC(c4ccc(Br)cc4)(CC2)CC3)C(=O)C2CCCCC2)c1]

The title compound was prepared according to the method described for the synthesis of Example 79 (step J) by substituting Intermediate 89D and corresponding acid where appropriate. (120 mg, 0.172 mmol, 78% yield). MS (ESI) 564 (M+H).

Step F. Intermediate 89F1 and 89F2. Preparation of methyl (E)-3-(3-(N-((4-(4-(dimethylamino)phenyl) bicyclo[2.2.2]octan-1-yl)methyl)cyclohexanecarboxamido) phenyl)acrylate & (E)-3-(3-(N-((4-(4-(dimethylamino)phenyl)bicyclo[2.2.2]octan-1-yl)methyl) cyclohexanecarboxamido)phenyl)acrylic acid

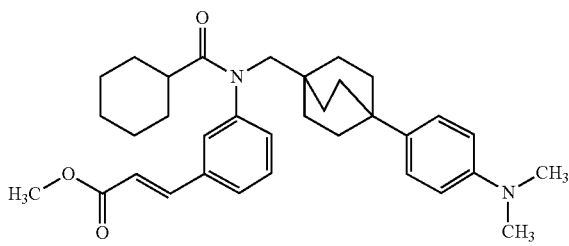

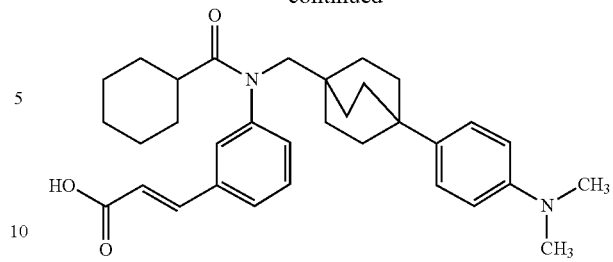

To a stirred solution of Intermediate 89E (100 mg, 0.177 mmol) in toluene (5 mL) at room temperature were added dimethylamine (0.09 mL, 1.771 mmol), 2-di-tert-butylphosphino-2',4',6'-triisopropylbiphenyl (8 mg, 0.018 mmol) and sodium tert-butoxide (50 mg, 0.53 mmol). The reaction mixture was degassed and back-filled with argon three times and Pd$_2$(dba)$_3$ (8 mg, 8.86 µmol) was added to the reaction mixture and the vial was sealed (Pressure release vial). The reaction mixture was heated to 80° C. and stirred for 12 h. The reaction mixture was diluted with water (10 mL) and extracted with EtOAc (2×50 mL). The combined organic layers were dried over anhydrous sodium sulphate and concentrated under reduced pressure. The crude material was purified via preparative HPLC using following conditions: (Column: waters XBridge C18, 19×150 mm, 5-µm particles; Mobile Phase A: 10-mM ammonium acetate; Mobile Phase B: acetonitrile; Gradient: 40-80% B over 20 minutes, then a 5-minute hold at 100% B; Flow: 15 mL/min). Fractions containing the desired product were combined and dried via centrifugal evaporation to afford the title compound (Intermediate 89F1) (9 mg, 0.016 mmol, 9% yield); $^1$H NMR (400 MHz, DMSO-$d_6$) δ 7.79 (s, 1H), 7.75-7.66 (m, 2H), 7.53-7.37 (m, 2H), 7.10-7.00 (m, J=8.8 Hz, 2H), 6.76 (d, J=16.1 Hz, 1H), 6.65-6.58 (m, J=8.8 Hz, 2H), 3.74 (s, 3H), 3.58 (br. s., 2H), 2.81 (s, 6H), 1.66-1.53 (m, 12H), 1.42-1.28 (m, 8H), 0.86 (d, J 6.1 Hz, 3H). FXR EC$_{50}$ (nM) 78; MS (ESI) 529 (M+H). Intermediate 89F2 (3 mg, 4.98 µmol, 3% yield); $^1$H NMR (400 MHz, DMSO-$d_6$) δ 12.44 (br. s., 1H), 7.74 (s, 1H), 7.68-7.62 (m, 2H), 7.60 (s, 1H), 7.47 (t, J=7.8 Hz, 1H), 7.40 (d, J=7.8 Hz, 1H), 7.06 (d, J=9.0 Hz, 2H), 6.61 (d, J=9.0 Hz, 2H), 3.58 (br. s., 2H), 2.81 (s, 6H), 2.20 (br. s., 1H), 1.65-1.54 (m, 8H), 1.49 (d, J 12.2 Hz, 2H), 1.41-1.33 (m, 7H), 1.32 (br. s., 1H), 1.24 (s, 1H), 1.08 (d, J=7.1 Hz, 1H), 0.94-0.79 (m, 2H). FXR EC$_{50}$ (nM) 1517, MS (ESI) 515 (M+H).

Step G. Intermediate 89G. Preparation of 3-(3-(N-((4-(4-(dimethylamino)phenyl) bicyclo[2.2.2]octan-1-yl)methyl)cyclohexanecarboxamido)phenyl) propionic acid

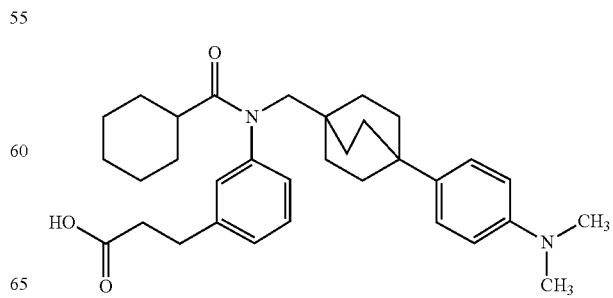

A solution of Intermediate 89F2 (50 mg, 0.097 mmol) in MeOH (3 mL) at room temperature was degassed and back-filled with nitrogen three times. To the above reaction, 10% Pd—C (20 mg, 0.019 mmol) was added and the reaction mixture was stirred overnight under hydrogen (1 atm, balloon). The reaction mixture was filtered through Celite and the filtrate was concentrated under reduced pressure to afford crude product (35 mg). MS (ESI) 517 (M+H).

Step H. Example 89. Preparation of methyl 3-(3-(N-((4-(4-(dimethylamino)phenyl) bicyclo[2.2.2]octan-1-yl)methyl)cyclohexanecarboxamido)phenyl)propionate To a stirred solution of Intermediate 89G (35 mg, 0.068 mmol) in DCM (2 mL) at room temperature was added (trimethylsilyl)diazomethane (0.07 mL, 0.135 mmol, 2 M solution in hexane) under nitrogen atmosphere. The reaction mixture was stirred at room temperature for 4 h. The reaction was quenched by adding acetic acid (0.5 mL). The reaction mixture was concentrated under reduced pressure. The crude material was purified via preparative LC/MS using following conditions: (Column: Waters XBridge C18, 19×150 mm, 5-μm particles; Mobile Phase A: 10-mM ammonium acetate; Mobile Phase B: acetonitrile; Gradient: 10-45% B over 20 minutes, then a 5-minute hold at 100% B; Flow: 15 mL/min). Fractions containing the desired product were combined and dried via centrifugal evaporation to afford the title compound (3 mg, 4.33 μmol, 6% yield). $^1$H NMR (400 MHz, DMSO-$d_6$) δ 7.38-7.29 (m, 1H), 7.25-7.13 (m, 3H), 7.11-7.03 (m, 2H), 6.64 (d, J=8.8 Hz, 2H), 3.55 (s, 3H), 3.53 (s, 2H), 2.93-2.86 (m, 2H), 2.82 (s, 6H), 2.71-2.62 (m, 3H), 2.19 (t, J=11.5 Hz, 1H), 1.71-1.53 (m, 10H), 1.48 (br. s., 1H), 1.42-1.20 (m, 8H), 1.08 (d, J=13.2 Hz, 1H), 0.95-0.78 (m, 2H); FXR $EC_{50}$ (nM) 1118; MS (ESI) 531 (M+H).

Example 90

(1S,3S)—N-((4-(3-cyclopropyl-1,2,4-oxadiazol-5-yl)bicyclo[2.2.2]octan-1-yl)methyl)-3-hydroxy-N-(3-(methylsulfonyl)phenyl)-3-(trifluoromethyl)cyclobutane-1-carboxamide (90)

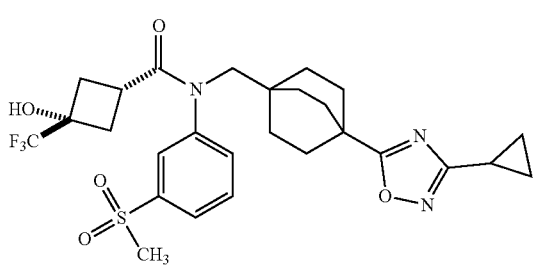

The title compound was prepared according to method described for the synthesis of Example 1 (Step H) by substituting Intermediate 68A and corresponding acid where appropriate: (2 mg, 3.45 μmol, 6% yield). $^1$H NMR (400 MHz, DMSO-$d_6$) δ 7.97-7.92 (m, 1H), 7.89-7.85 (m, 1H), 7.82-7.77 (m, 1H), 7.75-7.68 (m, 1H), 6.57-6.52 (m, 1H), 3.67-3.63 (m, 2H), 3.26 (s, 1H), 2.09-1.99 (m, 2H), 1.80-1.69 (m, 2H), 1.42-1.34 (m, 6H), 1.24 (s, 9H), 1.05-0.97 (m, 2H), 0.89-0.79 (m, 2H). FXR $EC_{50}$ (nM)=4000. MS (ESI) 568 (M+H).

Example 91

(1S,3S)—N-(3-((4-(1-cyanocyclopropyl)phenyl)amino)phenyl)-N-((4-(5-(1-fluorocyclopropyl)-1,2,4-oxadiazol-3-yl)bicyclo[2.2.2]octan-1-yl)methyl)-3-hydroxy-3-(trifluoromethyl)cyclobutane-1-carboxamide (91)

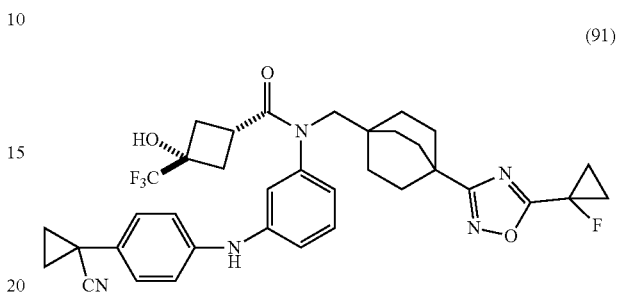

Step A. Intermediate 91A. Preparation of methyl 4-(5-(1-fluorocyclopropyl)-1,2,4-oxadiazol-3-yl)bicyclo[2.2.2]octane-1-carboxylate

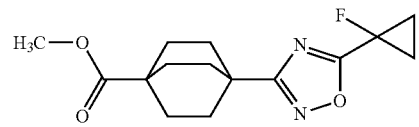 [SMILES: COC(=O)C12CCC(c3noc(C4(F)CC4)n3)(CC1)CC2]

The title compound as prepared according to the method described for the synthesis of Intermediate 1D by substituting Intermediate 1C and corresponding acid where appropriate. (2.4 g, 8.07 mmol, 91% yield). MS (ESI) 295 (M+H).

Step B. Intermediate 91B. Preparation of (4-(5-(1-fluorocyclopropyl)-1,2,4-oxadiazol-3-yl)bicyclo[2.2.2]octan-1-yl)methanol

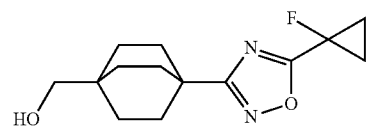 [SMILES: OCC12CCC(c3noc(C4(F)CC4)n3)(CC1)CC2]

The title compound was prepared according to the method described for the synthesis of Intermediate 1E by substituting Intermediate 91A and corresponding acid where appropriate. (1.6 g, 6.01 mmol, 80% yield). MS (ESI) 267 (M+H).

Step C. Intermediate 91C. Preparation of 4-(5-(1-fluorocyclopropyl)-1,2,4-oxadiazol-3-yl)bicyclo[2.2.2]octane-1-carbaldehyde

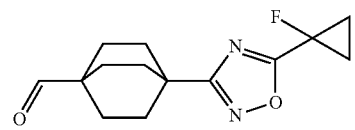 [SMILES: O=CC12CCC(c3noc(C4(F)CC4)n3)(CC1)CC2]

The title compound was prepared according to the method described for the synthesis of Intermediate 1F by substituting Intermediate 91B where appropriate. (1.6 g, 6.05 mmol, 77% yield) MS (ESI) 265 (M+H).

Step D. Intermediate 91D. Preparation of tert-butyl (3-(((4-(5-(1-fluorocyclopropyl)-1,2,4-oxadiazol-3-yl)bicyclo[2.2.2]octan-1-yl)methyl)amino)phenyl)carbamate

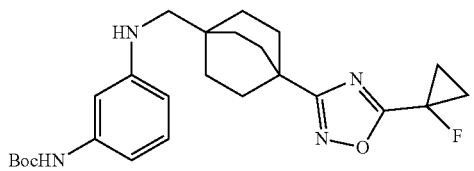 [SMILES: CC(C)(C)OC(=O)Nc1cccc(NCC23CCC(c4noc(C5(F)CC5)n4)(CC2)CC3)c1]

The title compound was prepared according to the method described for the synthesis of Intermediate 1G by substituting Intermediate 91C and tert-butyl (3-aminophenyl)carbamate where appropriate. (350 mg, 0.767 mmol, 68% yield). MS (ESI) 457 (M+H).

Step E. Intermediate 91E. Preparation of tert-butyl (3-((1S,3S)—N-((4-(5-(1-fluorocyclopropyl)-1,2,4-oxadiazol-3-yl)bicyclo[2.2.2]octan-1-yl)methyl)-3-hydroxy-3-(trifluoromethyl)cyclobutane-1-carboxamido)phenyl)carbamate

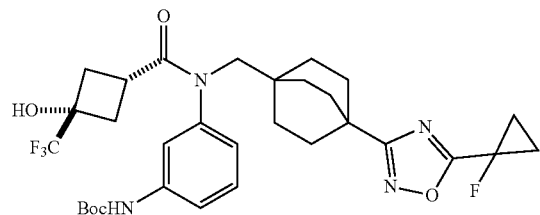

The title compound was prepared according to method described for the synthesis of Example 1 (Step H) by substituting Intermediate 91D and corresponding acid where appropriate. (240 mg, 0.366 mmol, 84% yield). MS (ESI) 623 (M+H).

Step F. Intermediate 91F. Preparation of (1S,3S)—N-(3-aminophenyl)-N-((4-(5-(1-fluorocyclopropyl)-1,2,4-oxadiazol-3-yl)bicyclo[2.2.2]octan-1-yl)methyl)-3-hydroxy-3-(trifluoromethyl)cyclobutane-1-carboxamide

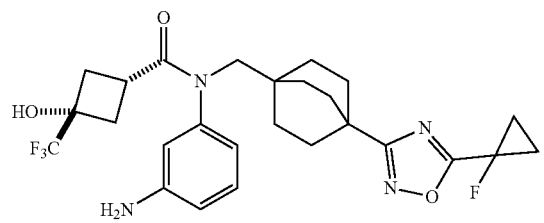

To a stirred solution of Intermediate 91E (125 mg, 0.201 mmol) in 1,4-dioxane (2 mL) was added 4M HCl in 1,4 dioxane (2.00 mL, 8.00 mmol) and stirred at room temperature for 4 h. The reaction mixture was concentrated under reduced pressure and the residue was diluted with ethyl acetate (15 mL). The resulting solution was washed with aq. 10% sodium bicarbonate solution (10 mL) followed by brine solution (10 mL). The organic layer was dried over anhydrous sodium sulfate, filtered and concentrated under reduced pressure to afford the title compound (95 mg, 0.178 mmol, 89% yield) as brown solid. MS (ESI) 523 (M+H).

Step G. Example 91. Preparation of (1S,3S)—N-(3-((4-(1-cyanocyclopropyl)phenyl) amino)phenyl)-N-((4-(5-(1-fluorocyclopropyl)-1,2,4-oxadiazol-3-yl) bicyclo[2.2.2]octan-1-yl)methyl)-3-hydroxy-3-(trifluoromethyl)cyclobutane-1-carboxamide The title compound was prepared according to method described for the synthesis of Example 102 by substituting Intermediate 91F and corresponding aryl halide where appropriate: (6.2 mg, 8.87 µmol, 16% yield). $^1$H NMR (400 MHz, DMSO-d$_6$) δ 8.40 (s, 1H), 7.33-7.18 (m, 3H), 7.09-6.90 (m, 4H), 6.82 (br d, J=8.1 Hz, 1H), 6.53 (s, 1H), 3.68-3.46 (m, 2H), 2.87-2.73 (m, 1H), 2.41-2.27 (m, 2H), 2.22-2.05 (m, 2H), 1.86-1.59 (m, 10H), 1.53-1.31 (m, 10H). FXR EC$_{50}$ (nM)=2191. MS (ESI) 664 (M+H).

Example 92

(1S,3S)—N-(3-((4-((2-cyanopropan-2-yl)oxy)phenyl)amino)phenyl)-N-((4-(5-(1,1-difluoroethyl)pyridin-2-yl)bicyclo[2.2.2]octan-1-yl)methyl)-3-hydroxy-3-(trifluoromethyl)cyclobutane-1-carboxamide (92)

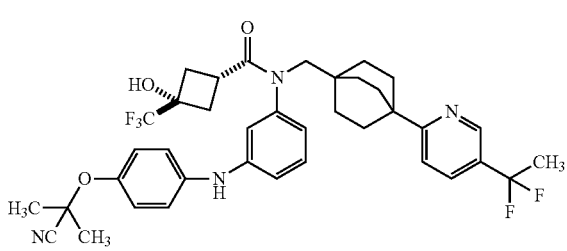

Step A. Intermediate 92A. Preparation of tert-butyl (3-(((4-(5-(1,1-difluoroethyl) pyridin-2-yl)bicyclo[2.2.2]octan-1-yl)methyl)amino)phenyl)carbamate

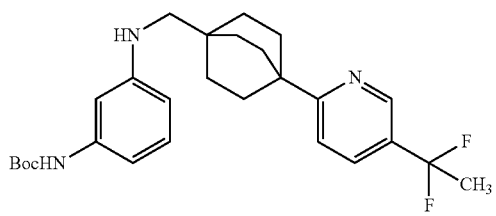 [SMILES: CC(C)(C)OC(=O)Nc1cccc(NCC23CCC(c4ccc(C(C)(F)F)cn4)(CC2)CC3)c1]

The title compound was prepared according to the method described for the synthesis of Intermediate 1G by substituting Intermediate 48D and tert-butyl (3-aminophenyl)carbamate where appropriate. (400 mg, 0.831 mmol, 77% yield). MS (ESI) 471 (M+H).

Step B. Intermediate 92B. Preparation of tert-butyl (3-((1S,3S)—N-((4-(5-(1,1-difluoroethyl)pyridin-2-yl)bicyclo[2.2.2]octan-1-yl)methyl)-3-hydroxy-3-(trifluoromethyl)cyclobutane-1-carboxamido)phenyl)carbamate

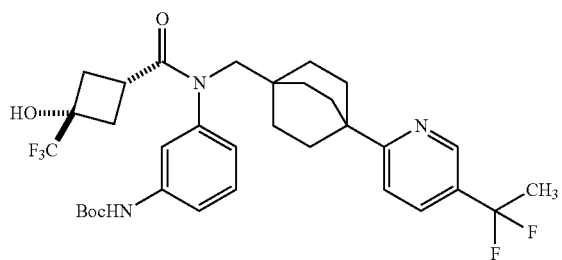

The title compound was prepared according to method described for the synthesis of Example 1 (Step H) by substituting Intermediate 92A and corresponding acid where appropriate. (250 mg, 0.369 mmol, 87% yield). MS (ESI) 637 (M+H).

Step C. Intermediate 92C. Preparation of (1S,3S)—N-(3-aminophenyl)-N-((4-(5-(1,1-difluoroethyl)pyridin-2-yl)bicyclo[2.2.2]octan-1-yl)methyl)-3-hydroxy-3-(trifluoromethyl)cyclobutane-1-carboxamide

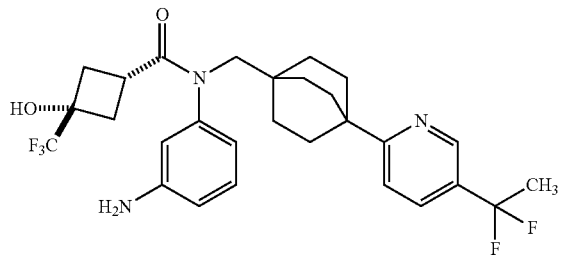

The title compound was prepared according to method described for the synthesis of Intermediate 91F by substituting Intermediate 92B where appropriate. (100 mg, 0.180 mmol, 96% yield) as brown solid. MS (ESI) 537 (M+H).

Step D. Intermediate 92D. Preparation of 2-(4-bromophenoxy)-2-methylpropanenitrile

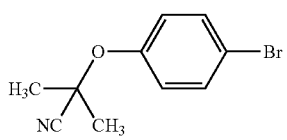

To a stirred solution of 2-(4-bromophenoxy)-2-methylpropanoic acid (2.0 g, 7.72 mmol) and ammonium chloride (2.064 g, 38.6 mmol) in DCM (20 mL) at room temperature was added BOP (5.12 g, 11.58 mmol). The reaction mixture was cooled (0-5° C.) and TEA (3.23 mL, 23.16 mmol) was added dropwise. The reaction mixture was warmed up to room temperature and stirred for 1 h. The reaction mixture was then diluted with water (20 mL) and the aqueous solution was extracted with DCM (3×50 mL). The combined organic layers were dried over anhydrous sodium sulfate, filtered, and concentrated under reduced pressure to afford a residue. The residue was dissolved in pyridine (20 mL) and the solution was cooled to 0° C. To the above reaction mixture was added trifluoroacetic anhydride (2.432 g, 11.58 mmol) and the reaction mixture was allowed to warm up to room temperature and stirred for 2 h. The reaction mixture was diluted with water (30 mL) and extracted with Ethyl acetate (3×20 mL). The combined organic layers were washed with 1.5 N aqueous HCl (2×50 mL), followed by saturated brine solution (2×20 mL). The organic layer was dried over anhydrous sodium sulfate, filtered and concentrated under reduced pressure. The crude material was purified by flash chromatography (24 g silica gel cartridge; A=Hex, B=EtOAc; 30 min grad.; 0% B to 80% B; flow rate=30 mL/min). The pure fractions were combined, concentrated under reduced pressure and dried in vacuo to afford the title compound (750 mg, 3.12 mmol, 41% yield) as brown oil. $^1$H NMR (400 MHz, DMSO-$d_6$) δ 7.59-7.57 (m, 2H), 7.15-7.13 (m, 2H), 1.69 (s, 6H).

Step E. Example 92. Preparation of (1S,3S)—N-(3-((4-((2-cyanopropan-2-yl)oxy)phenyl) amino)phenyl)-N-((4-(5-(1,1-difluoroethyl)pyridin-2-yl)bicyclo[2.2.2]octan-1-yl) methyl)-3-hydroxy-3-(trifluoromethyl)cyclobutane-1-carboxamide The title compound was prepared according to method described for the synthesis of Example 102 by substituting Intermediate 92C and Intermediate 92D where appropriate: (11.8 mg, 0.015 mmol, 28% yield). $^1$H NMR (400 MHz, DMSO-$d_6$) δ 8.67 (s, 1H), 8.29 (s, 1H), 7.86 (dd, J=2.4, 8.3 Hz, 1H), 7.40 (d, J=8.3 Hz, 1H), 7.28 (t, J=7.9 Hz, 1H), 7.08 (s, 4H), 7.02-6.97 (m, 1H), 6.92 (s, 1H), 6.78 (d, J=8.6 Hz, 1H), 6.54 (s, 1H), 3.59 (s, 2H), 2.81 (t, J=9.0 Hz, 1H), 2.41-2.27 (m, 2H), 2.22-2.11 (m, 2H), 1.99 (t, J=19.1 Hz, 3H), 1.84-1.74 (m, 6H), 1.67 (s, 6H), 1.51-1.40 (m, 6H). FXR EC$_{50}$ (nM)=2035. MS (ESI) 697 (M+H).

Example 93

(1S,3S)—N-(3-((4-(1-cyanocyclopropyl)phenyl) amino)phenyl)-N-((4-(5-(1,1-difluoroethyl) pyridin-2-yl)bicyclo[2.2.2]octan-1-yl)methyl)-3-hydroxy-3-(trifluoromethyl)cyclobutane-1-carboxamide (93)

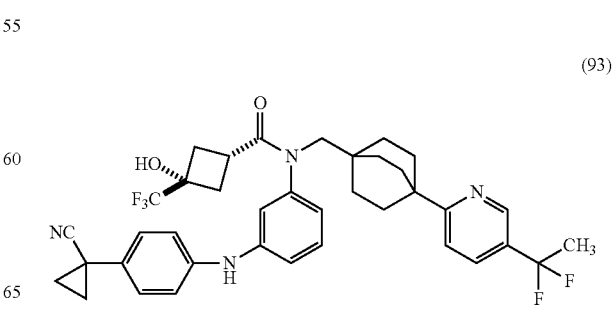

The title compound was prepared according to method described for the synthesis of Example 102 by substituting Intermediate 92C and corresponding aryl halide where appropriate: (8.1 mg, 0.011 mmol, 20% yield). $^1$H NMR (400 MHz, DMSO-d$_6$) δ 8.68 (s, 1H), 8.41 (s, 1H), 7.86 (dd, J=2.1, 8.4 Hz, 1H), 7.40 (d, J=8.3 Hz, 1H), 7.30 (t, J=8.1 Hz, 1H), 7.23 (d, J=8.6 Hz, 2H), 7.06 (d, J=8.6 Hz, 2H), 7.01 (br d, J=8.1 Hz, 1H), 6.97 (s, 1H), 6.82 (d, J=7.3 Hz, 1H), 6.53 (s, 1H), 3.60 (br s, 2H), 2.87-2.75 (m, 1H), 2.40-2.28 (m, 2H), 2.21-2.10 (m, 2H), 1.99 (t, J=19.1 Hz, 3H), 1.85-1.71 (m, 6H), 1.70-1.64 (m, 2H), 1.52-1.35 (m, 8H). FXR EC$_{50}$ (nM)=1419. MS (ESI) 679 (M+H).

Example 94

N-((4-(3-(tert-butyl)-1,2,4-oxadiazol-5-yl)bicyclo[2.2.2]octan-1-yl)methyl)-N-(5-cyanopyridin-3-yl)-3-fluorobicyclo[1.1.1]pentane-1-carboxamide (94)

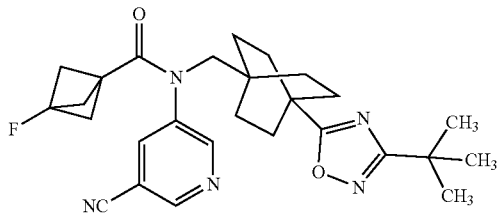

Step A. Intermediate 94A. Preparation of 5-(((4-(3-(tert-butyl)-1,2,4-oxadiazol-5-yl) bicycle[2.2.2]octan-1-yl)methyl)amino)nicotinonitrile

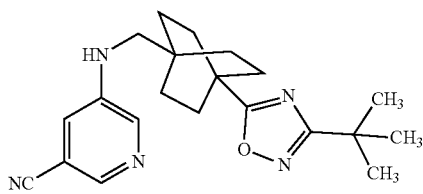 [SMILES: CC(C)(C)c1noc(C23CCC(CNc4cncc(C#N)c4)(CC2)CC3)n1]

The title compound was prepared according to method described for the synthesis of Intermediate 1G by substituting Intermediate 36C and commercially available 5-aminonicotinonitrile where appropriate: (200 mg, 0.547 mmol, 33% yield). MS (ESI) 366 (M+H).

Step B. Example 94. Preparation of N-((4-(3-(tert-butyl)-1,2,4-oxadiazol-5-yl) bicyclo[2.2.2]octan-1-yl)methyl)-N-(5-cyanopyridin-3-yl)-3-fluorobicyclo[1.1.1]pentane-1-carboxamide The title compound was prepared according to method described for the synthesis of Example 1 (Step H) by substituting Intermediate 94A where appropriate: (2 mg, 4.09 μmol, 3% yield). $^1$H NMR (400 MHz, DMSO-d$_6$) δ 9.04 (d, J=1.7 Hz, 1H), 9.00 (d, J=2.4 Hz, 1H), 8.58 (t, J=2.1 Hz, 1H), 3.77-3.42 (m, 2H), 2.01-1.66 (m, 12H), 1.47-1.33 (m, 6H), 1.27 (s, 9H). FXR EC$_{50}$ (nM)=1319. MS (ESI) 478 (M+H).

Example 95

1-(3-cyanophenyl)-1-((4-(5-(2-fluoropropan-2-yl)-1,2,4-oxadiazol-3-yl) bicyclo[2.2.2]octan-1-yl)methyl)-3-((1R,4R)-4-hydroxy-4-methylcyclohexyl)urea (95)

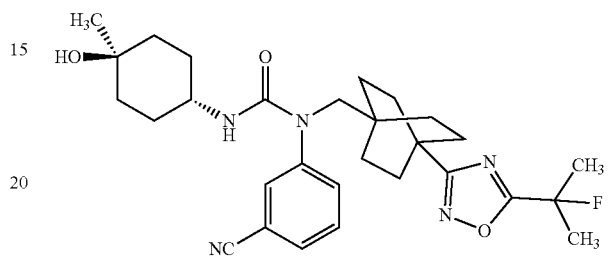

Step A. Intermediate 95A. Preparation of methyl 4-(5-(2-fluoropropan-2-yl)-1,2,4-oxadiazol-3-yl)bicyclo[2.2.2]octane-1-carboxylate

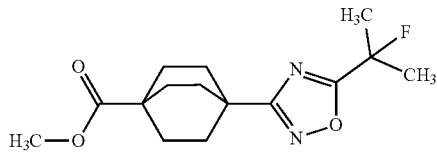

The title compound was prepared according to method described for the synthesis of Intermediate 1D by substituting Intermediate 1C and commercially available 2-fluoro-2-methylpropanoic acid where appropriate: (8.2 g, 27.7 mmol, 63% yield) colorless gummy solid. MS (ESI) 297 (M+H).

Step B. Intermediate 95B. Preparation of (4-(5-(2-fluoropropan-2-yl)-1,2,4-oxadiazol-3-yl)bicyclo[2.2.2]octan-1-yl)methanol

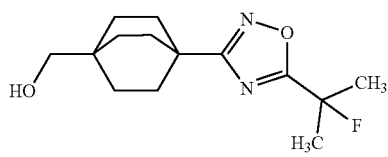 [SMILES: CC(C)(F)c1nc(C23CCC(CO)(CC2)CC3)no1]

The title compound was prepared according to method described for the synthesis of Intermediate 1E by substituting Intermediate 95A where appropriate: (6.5 g, 24.22 mmol, 96% yield) as colorless liquid. MS (ESI) 269 (M+H).

Step C. Intermediate 95C. Preparation of 4-(5-(2-fluoropropan-2-yl)-1,2,4-oxadiazol-3-yl)bicyclo[2.2.2]octane-1-carbaldehyde

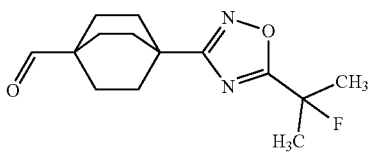 [SMILES: CC(C)(F)c1nc(C23CCC(C=O)(CC2)CC3)no1]

The title compound was prepared according to method described for the synthesis of Intermediate 1F by substituting Intermediate 95B where appropriate: (1.9 g, 7.13 mmol, 64% yield) as colorless white gummy solid. $^1$H NMR (400 MHz, DMSO-d$_6$) δ 9.50-9.40 (m, 1H), 1.97-1.50 (m, 18H).

Step D. Intermediate 95D. Preparation of 3-(((4-(5-(2-fluoropropan-2-yl)-1,2,4-oxadiazol-3-yl)bicyclo[2.2.2]octan-1-yl)methyl)amino)benzonitrile

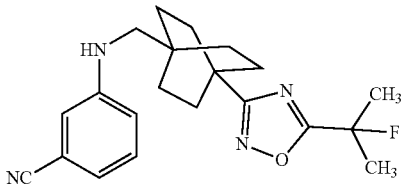 [SMILES: CC(C)(F)c1nc(C23CCC(CNc4cccc(C#N)c4)(CC2)CC3)no1]

The title compound was prepared according to method described for the synthesis of Intermediate 1G by substituting Intermediate 95C and commercially available 3-aminobenzonitrile where appropriate: (75 mg, 0.204 mmol, 72% yield). MS (ESI) 369 (M+H).

Step E. Example 95. Preparation of 1-(3-cyanophenyl)-1-((4-(5-(2-fluoropropan-2-yl)-1,2,4-oxadiazol-3-yl)bicyclo[2.2.2]octan-1-yl)methyl)-3-((1R,4R)-4-hydroxy-4-methylcyclohexyl)urea The title compound was prepared according to method described for the synthesis of Example 30 (Step B) by substituting Intermediate 95D and commercially available trans-4-Amino-1-methylcyclohexanol where appropriate: (15.8 mg, 0.030 mmol, 45% yield). $^1$H NMR (400 MHz, DMSO-d$_6$) δ 7.81 (s, 1H), 7.70-7.62 (m, 2H), 7.59-7.49 (m, 1H), 5.65-5.56 (m, 1H), 4.20 (d, J=2.4 Hz, 1H), 3.57 (s, 2H), 3.50-3.39 (m, 1H), 1.80 (s, 3H), 1.77-1.67 (m, 9H), 1.64-1.53 (m, 2H), 1.47-1.18 (m, 12H), 1.07 (s, 3H). FXR EC$_{50}$ (nM)=181. MS (ESI) 524 (M+H).

Example 96

1-(3-cyanophenyl)-1-((4-(5-(2-fluoropropan-2-yl)-1,2,4-oxadiazol-3-yl) bicyclo[2.2.2]octan-1-yl) methyl)-3-((1R,4R)-4-hydroxycyclohexyl)urea

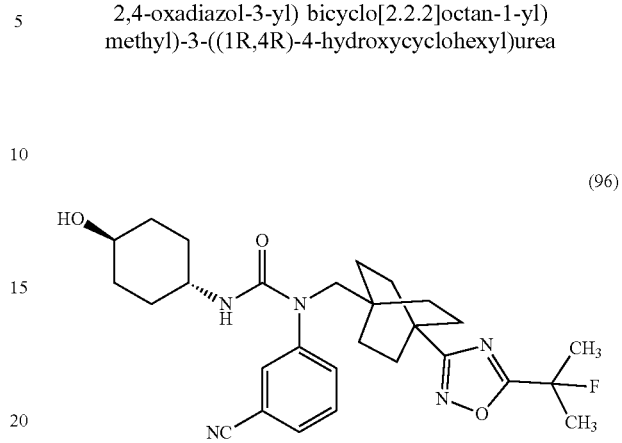

(96)

The title compound was prepared according to method described for the synthesis of Example 30 (Step B) by substituting Intermediate 95D and commercially available (1R,4R)-4-aminocyclohexan-1-ol where appropriate: (16.9 mg, 0.033 mmol, 15% yield). $^1$H NMR (400 MHz, DMSO-d$_6$) δ 7.81 (s, 1H), 7.70-7.62 (m, 2H), 7.59-7.49 (m, 1H), 5.65-5.56 (m, 1H), 4.20 (d, J=2.4 Hz, 1H), 3.57 (s, 2H), 3.50-3.39 (m, 1H), 1.80 (s, 3H), 1.77-1.67 (m, 9H), 1.64-1.53 (m, 2H), 1.47-1.18 (m, 12H), 1.07 (s, 3H). FXR EC$_{50}$ (nM)=181. MS (ESI) 524 (M+H).

Example 97

1-(3-cyanophenyl)-1-((4-(5-(2-fluoropropan-2-yl)-1,2,4-oxadiazol-3-yl)bicyclo[2.2.2]octan-1-yl)methyl)-3-(3-hydroxy-2,2-dimethylpropyl)urea

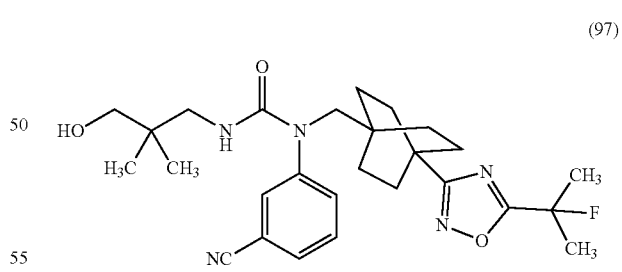

(97)

The title compound was prepared according to method described for the synthesis of Example 30 (Step B) by substituting Intermediate 95D and commercially available 3-amino-2,2-dimethylpropan-1-ol where appropriate: (18.4 mg, 0.037 mmol, 55% yield). $^1$H NMR (400 MHz, DMSO-d$_6$) δ 7.87 (br d, J=1.0 Hz, 1H), 7.74-7.67 (m, 2H), 7.63-7.56 (m, 1H), 5.92 (br s, 1H), 4.59-4.53 (m, 2H), 3.57 (s, 3H), 3.04 (d, J=6.1 Hz, 2H), 2.89 (br d, J=5.4 Hz, 3H), 1.80 (s, 3H), 1.78-1.68 (m, 6H), 1.42-1.33 (m, 6H), 0.73 (s, 6H). FXR EC$_{50}$ (nM)=1003. MS (ESI) 498 (M+H).

Example 98

1-(3-cyanophenyl)-1-((4-(5-(1,1-difluoroethyl)-1,2,4-oxadiazol-3-yl)bicyclo[2.2.2]octan-1-yl)methyl)-3-((1R,4R)-4-hydroxycyclohexyl)urea

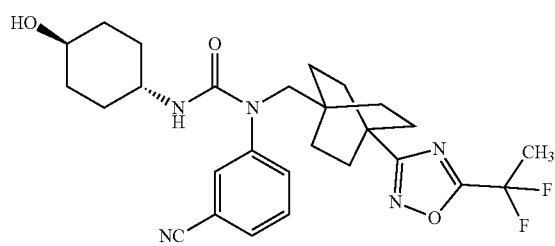

(98)

Step A. Intermediate 98A. Preparation of 3-(((4-(5-(1,1-difluoroethyl)-1,2,4-oxadiazol-3-yl)bicyclo[2.2.2]octan-1-yl)methyl)amino)benzonitrile

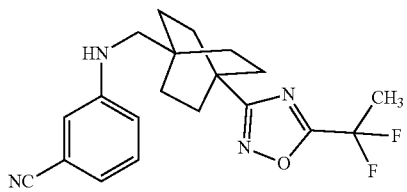 [SMILES: CC(F)(F)c1nc(C23CCC(CNc4cccc(C#N)c4)(CC2)CC3)no1]

The title compound was prepared according to method described for the synthesis of Intermediate 1G by substituting Intermediate 1F and commercially available 3-aminobenzonitrile where appropriate: (75 mg, 0.201 mmol, 73% yield). MS (ESI) 373 (M+H).

Step B. EXAMPLE 98. Preparation of 1-(3-cyanophenyl)-1-((4-(5-(1,1-difluoroethyl)-1,2,4-oxadiazol-3-yl)bicyclo[2.2.2]octan-1-yl)methyl)-3-((1R,4R)-4-hydroxycyclohexyl) urea The title compound was prepared according to method described for the synthesis of Example 30 (Step B) by substituting Intermediate 98A and commercially available (1R,4R)-4-aminocyclohexan-1-ol where appropriate: (25 mg, 0.049 mmol, 23% yield). $^1$H NMR (400 MHz, DMSO-$d_6$) δ 7.80 (s, 1H), 7.64 (d, J=8.3 Hz, 2H), 7.58-7.47 (m, 1H), 5.68-5.61 (m, 1H), 4.52-4.39 (m, 1H), 3.56 (s, 2H), 3.40-3.27 (m, 2H, merged with water), 2.13 (t, J=19.7 Hz, 3H), 1.81-1.64 (m, 10H), 1.38 (br dd, J=6.4, 9.3 Hz, 6H), 1.26-1.09 (m, 4H). FXR EC$_{50}$ (nM)=230. MS (ESI) 514 (M+H).

Example 99

1-(3-cyanophenyl)-1-((4-(5-(1,1-difluoroethyl)-1,2,4-oxadiazol-3-yl)bicyclo[2.2.2]octan-1-yl)methyl)-3-((1R,4R)-4-hydroxy-4-methylcyclohexyl)urea

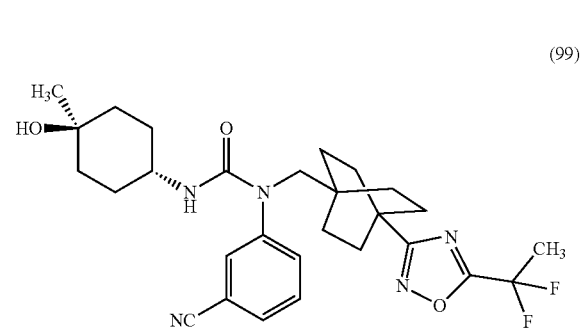 [SMILES: CC(F)(F)c1nc(C23CCC(CN(C(=O)N[C@H]4CC[C@](C)(O)CC4)c4cccc(C#N)c4)(CC2)CC3)no1]

(99)

The title compound was prepared according to method described for the synthesis of Example 30 (Step B) by substituting Intermediate 98A and commercially available trans-4-Amino-1-methylcyclohexanol where appropriate: (19.1 mg, 0.036 mmol, 53% yield). $^1$H NMR (400 MHz, DMSO-$d_6$) δ 7.82 (s, 1H), 7.68-7.62 (m, 2H), 7.61-7.51 (m, 1H), 5.62 (br d, J=7.6 Hz, 1H), 4.20 (s, 1H), 3.57 (s, 2H), 3.51-3.40 (m, 1H), 2.13 (t, J=19.6 Hz, 3H), 1.82-1.67 (m, 6H), 1.65-1.53 (m, 2H), 1.47-1.21 (m, 12H), 1.07 (s, 3H) FXR EC$_{50}$ (nM)=391. MS (ESI) 528 (M+H).

Example 100

1-(3-cyanophenyl)-1-((4-(5-(1,1-difluoroethyl)-1,2,4-oxadiazol-3-yl)bicyclo[2.2.2]octan-1-yl)methyl)-3-(3-hydroxy-2,2-dimethylpropyl)urea

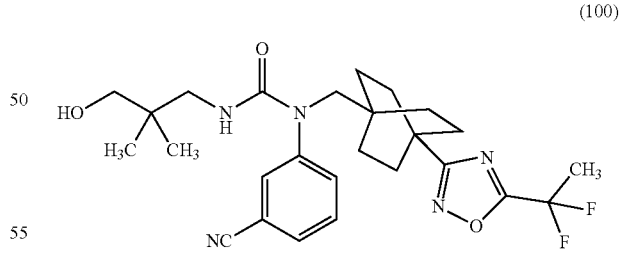

(100)

The title compound was prepared according to method described for the synthesis of Example 30 (Step B) by substituting Intermediate 98A and commercially available 3-amino-2,2-dimethylpropan-1-ol where appropriate: (25.4 mg, 0.050 mmol, 74% yield). $^1$H NMR (400 MHz, DMSO-$d_6$) δ 7.87 (s, 1H), 7.70 (t, J=6.8 Hz, 2H), 7.64-7.54 (m, 1H), 5.92 (t, J=5.5 Hz, 1H), 4.56 (t, J=5.7 Hz, 1H), 3.64-3.51 (m, 2H), 3.04 (d, J=5.9 Hz, 2H), 2.89 (d, J=5.9 Hz, 2H), 2.14 (t, J=19.7 Hz, 3H), 1.84-1.71 (m, 6H), 1.47-1.30 (m, 6H), 0.73 (s, 6H). FXR EC$_{50}$ (nM)=1479. MS (ESI) 502 (M+H).

Example 101

1-(3-bromo-4-fluorophenyl)-1-((4-(5-(2-fluoropropan-2-yl)-1,2,4-oxadiazol-3-yl) bicyclo[2.2.2]octan-1-yl)methyl)-3-((1R,4R)-4-hydroxycyclohexyl)urea

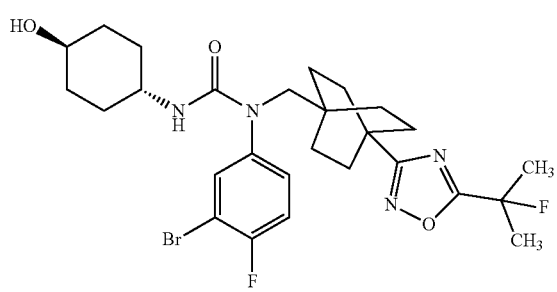

(101)

Step A. Intermediate 101A. Preparation of 3-bromo-4-fluoro-N-((4-(5-(2-fluoropropan-2-yl)-1,2,4-oxadiazol-3-yl)bicyclo[2.2.2]octan-1-yl)methyl)aniline

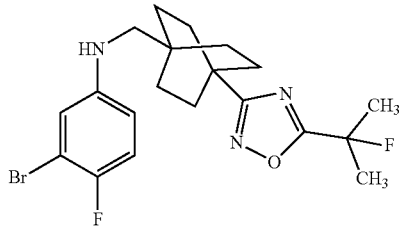 [SMILES: CC(C)(F)c1nc(C23CCC(CNc4ccc(F)c(Br)c4)(CC2)CC3)no1]

The title compound was prepared according to method described for the synthesis of Intermediate 1G by substituting Intermediate 95C and commercially available 3-bromo-4-fluoroaniline where appropriate: (170 mg, 0.386 mmol, 59% yield). MS (ESI) 440 (M+H).

Step B. Example 101. 1-(3-bromo-4-fluorophenyl)-1-((4-(5-(2-fluoropropan-2-yl)-1,2,4-oxadiazol-3-yl)bicyclo[2.2.2]octan-1-yl)methyl)-3-((1R,4R)-4-hydroxycyclohexyl)urea The title compound was prepared according to method described for the synthesis of Example 30 (Step B) by substituting Intermediate 101A and commercially available (1R,4R)-4-aminocyclohexan-1-ol where appropriate: (13.2 mg, 0.022 mmol, 23% yield). $^1$H NMR (400 MHz, DMSO-$d_6$) δ 7.65 (dd, J=1.8, 6.2 Hz, 1H), 7.44-7.24 (m, 2H), 5.46 (d, J=7.8 Hz, 1H), 4.46 (d, J=4.4 Hz, 1H), 3.49 (s, 2H), 3.43-3.36 (m, 1H), 3.29-3.20 (m, 1H), 1.86-1.60 (m, 16H), 1.47-1.31 (m, 6H), 1.27-1.10 (m, 4H). FXR $EC_{50}$ (nM)=1520. MS (ESI) 581 (M+H).

Example 102

N-((4-(5-(tert-butyl)-1,2,4-oxadiazol-3-yl)bicyclo[2.2.2]octan-1-yl)methyl)-N-(3-((5-(difluoromethoxy)pyrimidin-2-yl)amino)phenyl)-3-fluorobicyclo[1.1.1]pentane-1-carboxamide

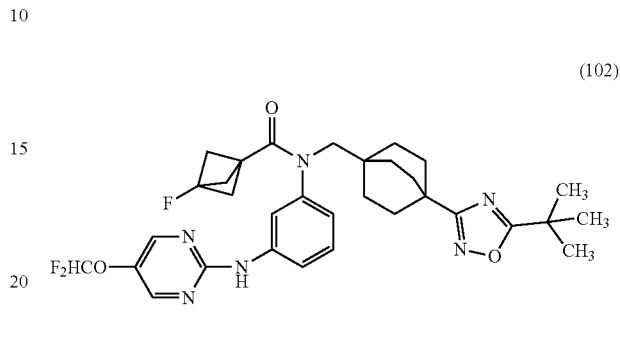

(102)

Step A. Intermediate 102A. Preparation of methyl 4-(5-(tert-butyl)-1,2,4-oxadiazol-3-yl)bicyclo[2.2.2]octane-1-carboxylate

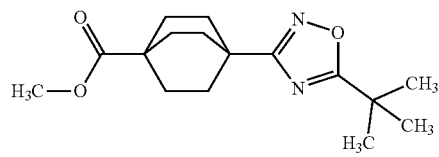 [SMILES: COC(=O)C12CCC(c3noc(C(C)(C)C)n3)(CC1)CC2]

The title compound was prepared according to the method described for the synthesis of Intermediate 1D by substituting Intermediate 1C and corresponding acid where appropriate. (650 mg, 2.22 mmol, 95% yield) as gummy mass. MS (ESI) 293 (M+H).

Step B. Intermediate 102B. Preparation of (4-(5-(tert-butyl)-1,2,4-oxadiazol-3-yl) bicyclo[2.2.2]octan-1-yl)methanol

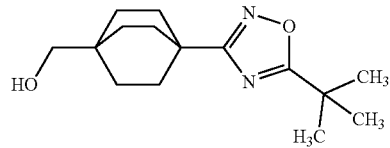

The title compound was prepared according to the method described for the synthesis of Intermediate 1E by substituting Intermediate 102A where appropriate. (500 mg, 1.89 mmol, 89% yield) as white solid. MS (ESI) 265 (M+H).

Step C. Intermediate 102C. Preparation of 4-(5-(tert-butyl)-1,2,4-oxadiazol-3-yl)bicyclo[2.2.2]octane-1-carbaldehyde

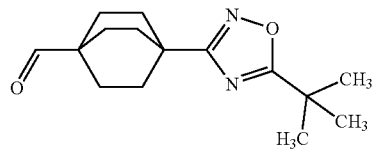

The title compound was prepared according to the method described for the synthesis of Intermediate 1F by substituting Intermediate 102B where appropriate. (390 mg, 1.487 mmol, 82% yield) as pale yellow solid. $^1$H NMR (400 MHz, DMSO-$d_6$) δ 9.45 (s, 1H), 1.88-1.84 (m, 6H), 1.70-1.66 (m, 6H), 1.35 (s, 9H).

Step C. Intermediate 102C. Preparation of tert-butyl (3-(((4-(5-(tert-butyl)-1,2,4-oxadiazol-3-yl)bicyclo[2.2.2]octan-1-yl)methyl)amino)phenyl)carbamate

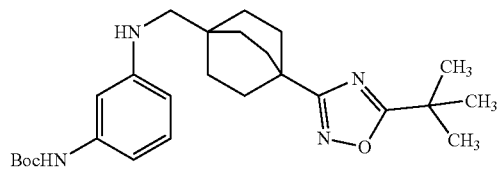 [SMILES: CC(C)(C)OC(=O)Nc1cccc(NCC23CCC(c4noc(C(C)(C)C)n4)(CC2)CC3)c1]

The title compound was prepared according to the method described for the synthesis of Intermediate 1G by substituting Intermediate 102C and tert-butyl (3-aminophenyl)carbamate where appropriate. (160 mg, 0.345 mmol, 53% yield) as brown solid. MS (ESI) 455 (M+H).

Step D. Intermediate 102D. Preparation of tert-butyl (3-(N-((4-(5-(tert-butyl)-1,2,4-oxadiazol-3-yl)bicyclo[2.2.2]octan-1-yl)methyl)-3-fluorobicyclo[1.1.1]pentane-1-carboxamido)phenyl)carbamate

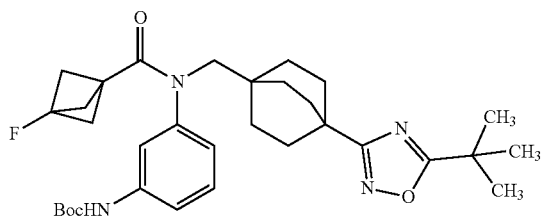 [SMILES: CC(C)(C)OC(=O)Nc1cccc(N(CC23CCC(c4noc(C(C)(C)C)n4)(CC2)CC3)C(=O)C23CC(F)(C2)C3)c1]

The title compound was prepared according to the method described for the synthesis of Example 1 by substituting Intermediate 102C and corresponding acid where appropriate. (120 mg, 0.184 mmol, 52% yield) as white solid. MS (ESI) 567 (M+H).

Step E. Intermediate 102E. Preparation of N-(3-aminophenyl)-N-((4-(5-(tert-butyl)-1,2,4-oxadiazol-3-yl)bicyclo[2.2.2]octan-1-yl)methyl)-3-fluorobicyclo[1.1.1]pentane-1-carboxamide

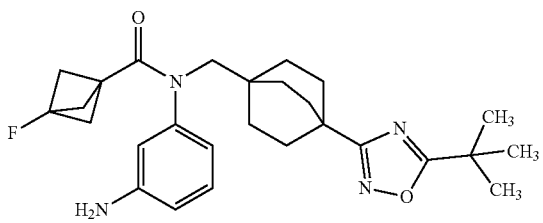 [SMILES: CC(C)(C)c1nc(C23CCC(CN(C(=O)C45CC(F)(C4)C5)c4cccc(N)c4)(CC2)CC3)no1]

The title compound was prepared according to the method described for the synthesis of Intermediate 91F by substituting Intermediate 102D where appropriate (95 mg, 0.20 mmol, 95% yield) as brown gummy solid. MS (ESI) 467 (M+H).

Step F. Example 102. Preparation of N-((4-(5-(tert-butyl)-1,2,4-oxadiazol-3-yl) bicyclo[2.2.2]octan-1-yl)methyl)-N-(3-((5-(difluoromethoxy)pyrimidin-2-yl)amino) phenyl)-3-fluorobicyclo[1.1.1]pentane-1-carboxamide To a stirred solution of Intermediate 102E (30 mg, 0.064 mmol) in 1,4-dioxane (1.5 mL) at room temperature were added 2-chloro-5-(difluoromethoxy)pyrimidine (17.41 mg, 0.096 mmol) and sodium tert-butoxide (18.54 mg, 0.193 mmol). The reaction mixture was purged with argon for 5 minutes and XantPhos (3.72 mg, 6.43 μmol) was added followed by Pd$_2$(dba)$_3$ (1.849 mg, 3.21 μmol). The reaction mixture was heated to 110° C. and stirred overnight. The reaction mixture was cooled down to room temperature and concentrated under reduced pressure. The crude material was purified via preparative LC/MS with the following conditions: Column: Waters XBridge C18, 150 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 40% B, 40-76% B over 15 minutes, then a 5-minute hold at 100% B; Flow Rate: 15 mL/min; Column Temperature: 25° C. Fraction collection was triggered by MS signals. Fractions containing the desired product were combined and dried via centrifugal evaporation to afford the title compound (4.4 mg, 7.21 μmol, 11% yield). $^1$H NMR (400 MHz, DMSO-$d_6$) δ 9.98 (s, 1H), 8.50 (s, 2H), 7.76 (s, 1H), 7.70 (d, J=7.8 Hz, 1H), 7.43-6.92 (m, 3H), 3.69-3.57 (m, 1H), 3.51-3.40 (m, 1H), 1.93-1.89 (m, 6H), 1.74 (t, J=7.6 Hz, 6H), 1.45 (d, J=7.6 Hz, 6H), 1.37-1.26 (m, 9H). FXR EC$_{50}$ (nM)=183. MS (ESI) 611 (M+H).

The following examples were synthesized according to the method described for the synthesis of Example 102 by substituting Intermediate 102E and the corresponding aryl halides where appropriate.

| Ex. No. | Structure & Name | MS (ESI) (M + H) | FXR EC$_{50}$ (nM) |
|---|---|---|---|
| 103 | N-((4-(5-(tert-butyl)-1,2,4-oxadiazol-3-yl)bicyclo[2.2.2]octan-1-yl)methyl)-N-(3-((2-cyclopropylpyrimidin-5-yl)amino)phenyl)-3-fluorobicyclo[1.1.1]pentane-1-carboxamide | 585 | 187 |
| 104 | N-((4-(5-(tert-butyl)-1,2,4-oxadiazol-3-yl)bicyclo[2.2.2]octan-1-yl)methyl)-N-(3-((5-(difluoromethoxy)pyridin-2-yl)amino)phenyl)-3-fluorobicyclo[1.1.1]pentane-1-carboxamide | 610 | 221 |
| 103 | $^1$H NMR (400 MHz, DMSO-d$_6$) δ 9.67 (s, 1H), 8.32 (s, 2H), 7.80 (t, J = 2.0 Hz, 1H), 7.70 (d, J = 8.1 Hz, 1H), 7.33 (t, J = 8.1 Hz, 1H), 6.91 (d, J = 7.8 Hz, 1H), 3.62 (d, J = 14.9 Hz, 1H), 3.44 (d, J = 13.0 Hz, 1H), 2.02-1.80 (m, 6H), 1.74 (t, J = 7.7 Hz, 6H), 1.56-1.37 (m, 6H), 1.33 (s, 9H), 0.96-0.87 (m, 2H), 0.78-0.66 (m, 2H) | | |
| 104 | $^1$H NMR (400 MHz, DMSO-d$_6$) δ 9.34 (s, 1H), 8.08 (d, J = 2.9 Hz, 1H), 7.72 (t, J = 2.1 Hz, 1H), 7.59 (dd, J = 8.2, 1.1 Hz, 1H), 7.54 (dd, J = 9.0, 2.9 Hz, 1H), 7.42-7.20 (m, 1H), 7.11 (s, 1H), 6.96-6.80 (m, 2H), 3.66-3.59 (m, 1H), 3.51-3.41 (m, 1H), 1.90 (s, 3H), 1.94 (s, 3H), 1.74 (t, J = 7.9 Hz, 6H), 1.46 (d, J = 7.3 Hz, 6H), 1.37-1.29 (m, 9H) | | |

Example 105

N-(3-((5-cyclopropylpyrimidin-2-yl)amino)phenyl)-3-fluoro-N-((4-(5-(trifluoromethyl)pyridin-2-yl)bicyclo[2.2.2]octan-1-yl)methyl)bicyclo[1.1.1]pentane-1-carboxamide (105)

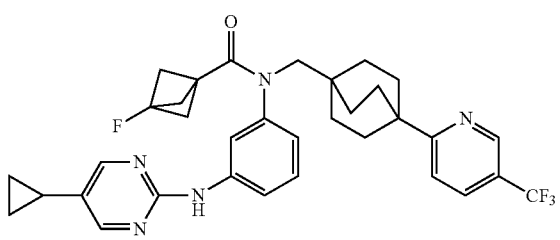

Step A. Intermediate 105A. Preparation of methyl 4-(5-(trifluoromethyl)pyridin-2-yl) bicyclo[2.2.2]octane-1-carboxylate

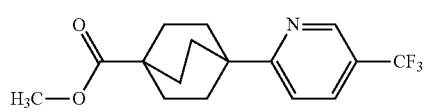

To a stirred solution of 4-(methoxycarbonyl)bicyclo[2.2.2]octane-1-carboxylic acid (3 g, 14.13 mmol) and 3-(trifluoromethyl)pyridine (2.495 g, 16.96 mmol) in DCM (90 mL) and water (90 mL) at room temperature was added ammonium persulfate (3.23 g, 14.13 mmol) followed by silver nitrate (0.480 g, 2.83 mmol). After stirring overnight at room temperature, the reaction mixture was diluted with DCM (25 mL) and filtered through celite. The organic layer was separated and washed with brine solution (25 mL), dried over anhydrous sodium sulphate, filtered and concentrated under reduced pressure. The crude material was purified by flash chromatography (40 g silica gel cartridge; A=Hex, B=EtOAc; 30 min grad.; 0% B to 50% B). The pure fractions were combined, concentrated under reduced pressure and dried in vacuo to afford the title compound (2.2 g, 6.95 mmol, 49% yield) as white solid. MS (ESI) 314 (M+H).

Step B. Intermediate 105B. Preparation of (4-(5-(trifluoromethyl)pyridin-2-yl)bicyclo [2.2.2]octan-1-yl)methanol

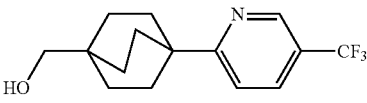 [SMILES: OCC12CCC(c3ccc(C(F)(F)F)cn3)(CC1)CC2]

The title compound was synthesized according to the method described for the synthesis of Intermediate 1E by substituting Intermediate 105A where appropriate: (1.6 g, 5.05 mmol, 79% yield) as white solid. MS (ESI) 286 (M+H).

Step C. Intermediate 105C. Preparation of 4-(5-(trifluoromethyl)pyridin-2-yl) bicyclo[2.2.2]octane-1-carbaldehyde

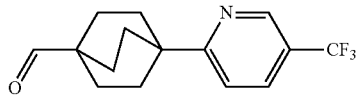

The title compound was synthesized according to the method described for the synthesis of Intermediate 1F by substituting Intermediate 105B where appropriate. (1.2 g, 4.24 mmol, 78% yield) as a white solid. MS (ESI) 284 (M+H). $^1$H NMR (400 MHz, DMSO-$d_6$) δ 9.48 (s, 1H), 8.89 (dd, J=2.5, 1.0 Hz, 1H), 8.18-8.07 (m, 1H), 7.60 (d, J=8.5 Hz, 1H), 1.98-1.83 (m, 6H), 1.76-1.65 (m, 6H).

Step D. Intermediate 105D. Preparation of tert-butyl (3-(((4-(5-(trifluoromethyl)pyridin-2-yl)bicyclo[2.2.2]octan-1-yl)methyl)amino)phenyl)carbamate

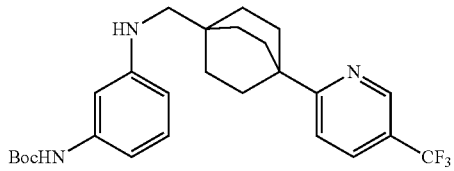 [SMILES: CC(C)(C)OC(=O)Nc1cccc(NCC23CCC(c4ccc(C(F)(F)F)cn4)(CC2)CC3)c1]

The title compound was prepared according to the method described for the synthesis of Intermediate 1G by substituting Intermediate 105C and tert-butyl (3-aminophenyl)carbamate where appropriate. (300 mg, 0.618 mmol, 88% yield) as brown solid. MS (ESI) 476 (M+H).

Step E. Intermediate 105E. Preparation of tert-butyl (3-(3-fluoro-N-((4-(5-(trifluoromethyl)pyridin-2-yl)bicyclo[2.2.2]octan-1-yl)methyl)bicyclo[1.1.1]pentane-1-carboxamido)phenyl)carbamate

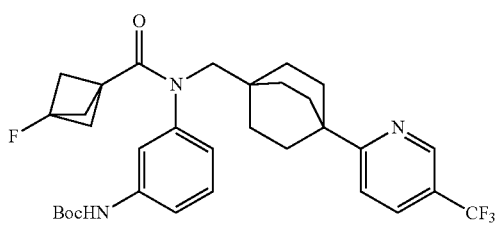 [SMILES: CC(C)(C)OC(=O)Nc1cccc(N(CC23CCC(c4ccc(C(F)(F)F)cn4)(CC2)CC3)C(=O)C23CC(F)(C2)C3)c1]

The title compound was prepared according to the method described for the synthesis of Example 1 by substituting Intermediate 105D and corresponding acid where appropriate. (300 mg, 0.510 mmol, 81% yield) as white solid. MS (ESI) 588 (M+H).

Step F. Intermediate 105F. Preparation of N-(3-aminophenyl)-3-fluoro-N-((4-(5-(trifluoromethyl)pyridin-2-yl)bicyclo[2.2.2]octan-1-yl)methyl)bicyclo[1.1.1]pentane-1-carboxamide

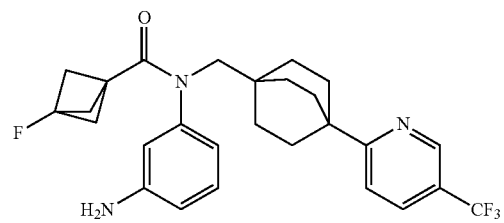 [SMILES: Nc1cccc(N(CC23CCC(c4ccc(C(F)(F)F)cn4)(CC2)CC3)C(=O)C23CC(F)(C2)C3)c1]

The title compound was prepared according to the method described for the synthesis of Intermediate 91F by substituting Intermediate 105E and corresponding acid where appropriate. (200 mg, 0.410 mmol, 80% yield) as brown gummy solid. MS (ESI) 488 (M+H).

Step G. Example 105: Preparation of N-(3-((5-cyclopropylpyrimidin-2-yl)amino) phenyl)-3-fluoro-N-((4-(5-(trifluoromethyl)pyridin-2-yl)bicyclo[2.2.2]octan-1-yl)methyl) bicyclo[1.1.1]pentane-1-carboxamide The title compound was prepared according to the method described for the synthesis Example 102 by substituting Intermediate 105F where appropriate. (7.4 mg, 0.012 mmol, 20% yield). $^1$H NMR (400 MHz, DMSO-$d_6$) δ 9.67 (s, 1H), 8.85 (s, 1H), 8.32 (s, 2H), 8.07 (dd, J=8.9, 2.1 Hz, 1H), 7.82 (s, 1H), 7.70 (d, J=8.6 Hz, 1H), 7.53 (d, J=8.6 Hz, 1H), 7.33 (t, J=7.9 Hz, 1H), 6.91 (d, J=7.3 Hz, 1H), 3.64 (d, J=11.0 Hz, 1H), 3.47 (d, J=11.5 Hz, 1H), 1.95 (br. s., 3H), 1.92-1.69 (m, 10H), 1.48 (d, J=6.8 Hz, 6H), 0.98-0.88 (m, 2H), 0.78-0.67 (m, 2H). FXR EC$_{50}$ (nM)=292. MS (ESI) 606 (M+H).

The following examples were synthesized according to the method described for the synthesis of Example 102 by substituting Intermediate 105F and the corresponding aryl halides where appropriate.

| Ex. No. | Structure & Name | MS (ESI) (M + H) | FXR EC$_{50}$ (nM) |
|---|---|---|---|
| 106 | 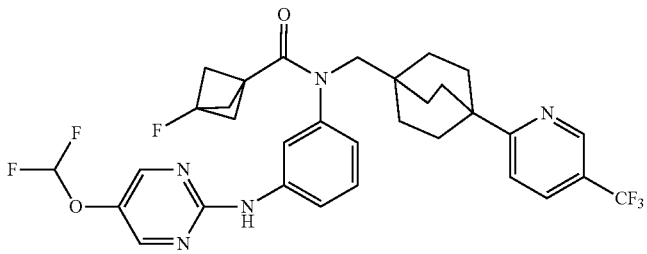 [SMILES: O=C(N(CC12CCC(c3ccc(C(F)(F)F)cn3)(CC1)CC2)c1cccc(Nc2ncc(OC(F)F)cn2)c1)C12CC(F)(C1)C2]<br>N-(3-((5-(difluoromethoxy)pyrimidin-2-yl)amino)phenyl)-3-fluoro-N-((4-(5-(trifluoromethyl)pyridin-2-yl)bicyclo[.2.2.2]octan-1-yl)methyl)bicyclo[1.1.1]pentane-1-carboxamide | 632 | 132 |
| 107 | 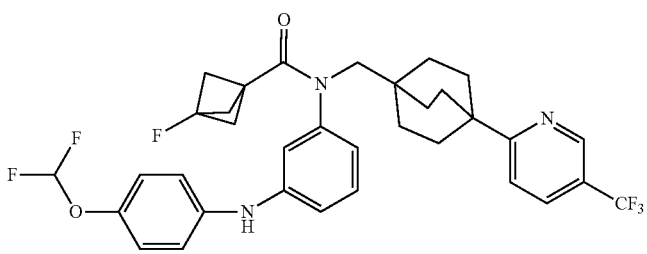 [SMILES: O=C(N(CC12CCC(c3ccc(C(F)(F)F)cn3)(CC1)CC2)c1cccc(Nc2ccc(OC(F)F)cc2)c1)C12CC(F)(C1)C2]<br>N-(3-((4-(difluoromethoxy)phenyl)amino)phenyl)-3-fluoro-N-((4-(5-(trifluoromethyl)pyridin-2-yl)bicyclo[2.2.2]octan-1-yl)methyl)bicyclo[1.1.1]pentane-1-carboxamide | 630 | 484 |
| 108 | 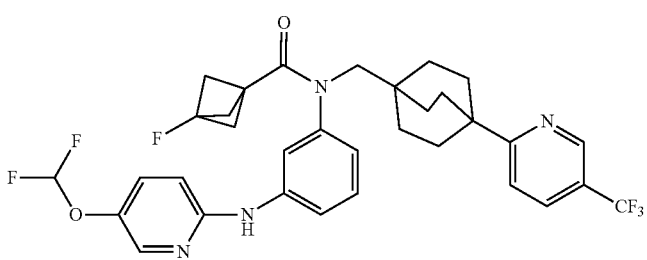<br>N-(3-((5-(difluoromethoxy)pyridin-2-yl)amino)phenyl)-3-fluoro-N-((4-(5-(trifluoromethyl)pyridin-2-yl)bicyclo[2.2.2]octan-1-yl)methyl)bicyclo[1.1.1]pentane-1-carboxamide | 631 | 629 |
| 109 | 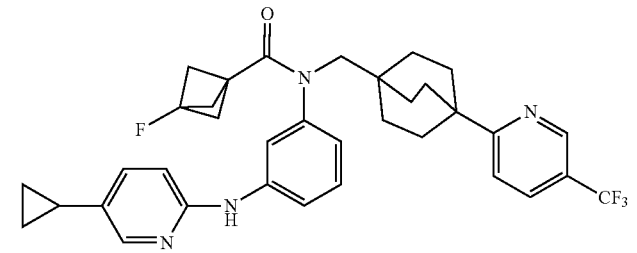 [SMILES: O=C(N(CC12CCC(c3ccc(C(F)(F)F)cn3)(CC1)CC2)c1cccc(Nc2ccc(C3CC3)cn2)c1)C12CC(F)(C1)C2]<br>N-(3-((5-cyclopropylpyridin-2-yl)amino)phenyl)-3-fluoro-N-((4-(5-(trifluoromethyl)pyridin-2-yl)bicyclo[2..2.2]octan-1-yl)methyl)bicyclo[1.1.1]pentane-1-carboxamide | 605 | 292 |
| 106 | $^1$H NMR (400 MHz, DMSO-d$_6$) δ 9.99 (s, 1H), 8.85 (s, 1H), 8.50 (s, 2H), 8.07 (dd, J = 8.6, 2.2 Hz, 1H), 7.78 (s, 1H), 7.71 (d, J = 8.3 Hz, 1H), 7.53 (d, J = 8.3 Hz, 1H), 7.40-7.26 (m, 1H), 7.16(s, 1H), 7.07-6.92 (m, 1H), 3.65 (d, J = 13.9 Hz, 1H), 3.48 (d, J = 13.2 Hz, 1H), 1.90 (s, 3H), 1.94(s, 3H), 1.80 (t, J = 7.8 Hz, 6H), 1.48 (d, J = 6.4 Hz, 6H) | | |
| 107 | $^1$H NMR (400 MHz, DMSO-d$_6$) δ 8.86 (s, 1H), 8.38 (s, 1H), 8.08 (dd, J = 8.4, 2.1 Hz, 1H), 7.54 (d, J = 8.6 Hz, 1H), 7.34-7.24 (m, 1H), 7.21-7.07 (m, 5H), 7.05 (d, J = 6.1 Hz, 1H), 6.97-6.88 (m, 1H), 6.81 (d, J = 7.8 Hz, 1H), 3.56 (br. s., 1H), 3.51 (br. s., 1H), 1.92 (br. s., 6H), 1.88-1.61 (m, 6H), 1.59-1.35 (m, 6H) | | |

| Ex. No. | Structure & Name | MS (ESI) (M + H) | FXR EC$_{50}$ (nM) |
|---|---|---|---|
| 108 | $^1$H NMR (400 MHz, DMSO-d$_6$) δ 9.35 (s, 1H), 8.85 (d, J = 2.4 Hz, 1H), 8.14-7.97 (m, 2H), 7.74 (t, J = 2.1 Hz, 1H), 7.59 (dd, J = 8.2, 1.3 Hz, 1H), 7.56-7.46 (m, 2H), 7.34 (t, J = 8.1 Hz, 1H), 7.11(s, 1H), 7.02-6.86 (m, 2H), 3.65 (d, J = 14.2 Hz, 1H), 3.48 (d, J = 13.9 Hz, 1H), 1.91 (s, 3H), 1.95 (s, 3H), 1.81 (t, J = 7.8 Hz, 6H), 1.49 (d, J = 6.8 Hz, 6H) | | |
| 109 | $^1$H NMR (400 MHz, DMSO-d$_6$) δ 9.08 (s, 1H), 8.85 (s, 1H), 8.07 (dd, J = 8.4, 2.1 Hz, 1H), 8.03 (d, J = 2.2 Hz, 1H), 7.81-7.73 (m, 1H), 7.61-7.46 (m, 2H), 7.36-7.19 (m, 2H), 6.83 (d, J = 9.0 Hz, 1H), 6.77 (d, J = 8.6 Hz, 1H), 3.66 (d, J = 12.7 Hz, 1H), 3.46 (d, J = 13.7 Hz, 1H), 1.96 (br. s., 3H), 1.93-1.65 (m, 10H), 1.49 (d, J = 7.6 Hz, 6H), 0.94-0.82 (m, 2H), 0.68-0.55 (m, 2H) | | |

Example 110

N-((4-(5-(tert-butyl)-1,2,4-oxadiazol-3-yl)bicyclo[2.2.2]octan-1-yl)methyl)-3-fluoro-N-(3-hydroxyphenyl)bicyclo[1.1.1]pentane-1-carboxamide

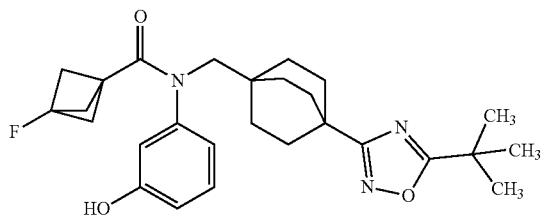

(110)

Step A. Intermediate 110A. Preparation of 3-((tert-butyldimethylsilyl)oxy)aniline

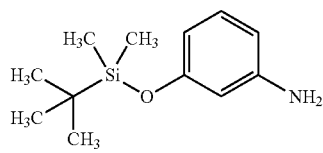

To a stirred solution of 3-aminophenol (2 g, 18.33 mmol) and imidazole (1.560 g, 22.91 mmol) in THF (50 mL) at room temperature was added TBDMS-Cl (3.45 g, 22.91 mmol). After stirring overnight at room temperature, the reaction mixture was diluted with ethyl acetate (50 mL). The resulting solution was washed with aq. 10% sodium bicarbonate solution (2×50 mL) followed by brine solution (50 mL). The organic layer was dried over anhydrous sodium sulfate, filtered and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated under reduced pressure and dried in vacuo to afford 3-((tert-butyldimethylsilyl)oxy)aniline (3.5 g, 15.51 mmol, 85% yield) as brown oil. MS (ESI) 224 (M+H).

Step B. Intermediate 110B. Preparation of N-((4-(5-(tert-butyl)-1,2,4-oxadiazol-3-yl) bicyclo[2.2.2]octan-1-yl)methyl)-3-((tert-butyldimethylsilyl)oxy)aniline

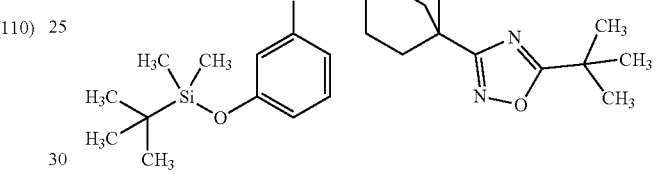

The title compound was prepared according to the method described for the synthesis of Example 1G by substituting Intermediate 110A and Intermediate 102C where appropriate. (170 mg, 0.362 mmol, 63% yield) as gummy solid. MS (ESI) 470 (M+H).

Step C. Intermediate 110C. Preparation of N-((4-(5-(tert-butyl)-1,2,4-oxadiazol-3-yl) bicyclo[2.2.2]octan-1-yl)methyl)-N-(3-((tert-butyldimethylsilyl)oxy)phenyl)-3-fluorobicyclo[1.1.1]pentane-1-carboxamide

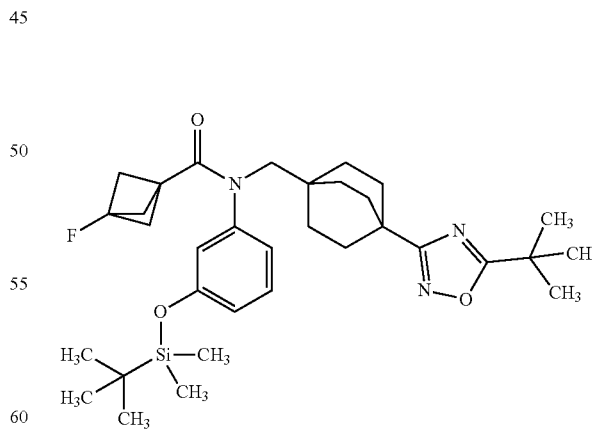

The title compound was prepared according to the method described for the synthesis of Example 1 by substituting Intermediate 110B and corresponding acid where appropriate. (170 mg, 0.280 mmol, 78% yield) as white solid. MS (ESI) 582 (M+H).

Step D. Example 110. Preparation of N-((4-(5-(tert-butyl)-1,2,4-oxadiazol-3-yl) bicyclo[2.2.2]octan-1-yl)methyl)-3-fluoro-N-(3-hydroxyphenyl)bicyclo[1.1.1]pentane-1-carboxamide To a stirred solution of Intermediate 110C (170 mg, 0.292 mmol) in THF (3 mL) at room temperature was added TBAF (0.584 mL, 0.584 mmol). After stirring for 1 h, the reaction mixture was diluted with water (10 mL) and extracted with EtOAc (2×10 mL). The combined organic layers were dried over anhydrous sodium sulphate, filtered, and concentrated under reduced pressure. The crude material was purified via preparative LC/MS with the following conditions: Column: Waters XBridge C18, 150 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 2-minute hold at 15% B, 15-57% B over 25 minutes, then a 5-minute hold at 100% B; Flow Rate: 15 mL/min; Column Temperature: 25° C. Fraction collection was triggered by signals. Fractions containing the desired product were combined and dried via centrifugal evaporation to afford the title compound (120 mg, 0.257 mmol, 88% yield) as white solid. $^1$H NMR (400 MHz, DMSO-$d_6$) δ 9.75 (s, 1H), 7.23 (t, J=7.9 Hz, 1H), 6.78 (td, J=2.2, 8.1 Hz, 2H), 6.73-6.67 (m, 1H), 3.56-3.45 (m, 2H), 1.87 (d, J=2.4 Hz, 6H), 1.78-1.67 (m, 6H), 1.47-1.37 (m, 6H) 1.34 (s. 9H). FXR $EC_{50}$ (nM)=65. MS (ESI) 468 (M+H).

Example 111

N-((4-(5-(tert-butyl)-1,2,4-oxadiazol-3-yl)bicyclo[2.2.2]octan-1-yl)methyl)-N-(3-(cyanomethoxy)phenyl)-3-fluorobicyclo[1.1.1]pentane-1-carboxamide

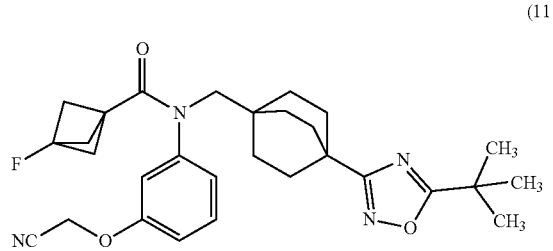

(111)

To a stirred solution of Example 110 (20 mg, 0.043 mmol) in DMF (1 mL) at room temperature was added 2-bromoacetonitrile (6.16 mg, 0.051 mmol) followed by $K_2CO_3$ (14.78 mg, 0.107 mmol). The reaction mixture was heated to 110° C. and stirred for 2 h. The reaction mixture was diluted with water (5 mL) and extracted with ethyl acetate (2×10 mL). The combined organic layers were dried over anhydrous sodium sulfate, filtered and concentrated under reduced pressure. The crude material was purified via preparative LC/MS with the following conditions: Column: Waters XBridge C18, 150 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 2-minute hold at 18% B, 18-62% B over 25 minutes, then a 5-minute hold at 100% B; Flow Rate: 15 mL/min; Column Temperature: 25° C. Fraction collection was triggered by signals. Fractions containing the desired product were combined and dried via centrifugal evaporation to afford the title compound (21.3 mg, 0.042 mmol, 97% yield). $^1$H NMR (400 MHz, DMSO-$d_6$) δ 7.47-7.39 (m, 1H), 7.18 (t, J=2.2 Hz, 1H), 7.10 (td, J=2.0, 8.2 Hz, 2H), 5.25 (s, 2H), 3.61-3.47 (m, 2H), 1.96-1.81 (m, 6H), 1.78-1.68 (m, 6H), 1.47-1.38 (m, 6H), 1.33 (s, 9H). FXR $EC_{50}$ (nM)=618. MS (ESI) 507 (M+H).

Example 112

N-((4-(5-(tert-butyl)-1,2,4-oxadiazol-3-yl)bicyclo[2.2.2]octan-1-yl)methyl)-3-fluoro-N-(3-(2-hydroxy-2-methylpropoxy)phenyl)bicyclo[1.1.1]pentane-1-carboxamide

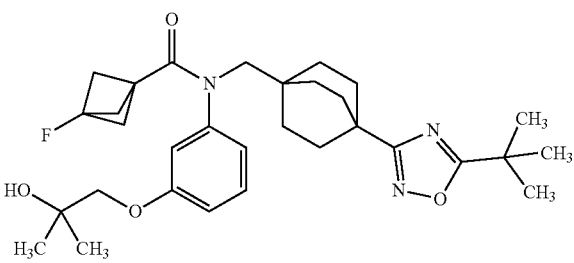

(112)

Step A. Intermediate 112A. Preparation of ethyl 2-(3-(N-((4-(5-(tert-butyl)-1,2,4-oxadiazol-3-yl)bicyclo[2.2.2]octan-1-yl)methyl)-3-fluorobicyclo[1.1.1]pentane-1-carboxamido)phenoxy)acetate

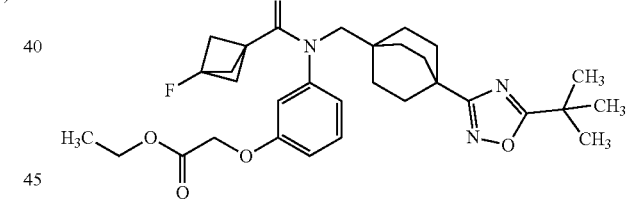

The title compound was prepared according to the method described for the synthesis of Example 111 by substituting Example 110 and ethyl bromoacetate where appropriate. (60 mg, 0.108 mmol, 75% yield) as white solid. MS (ESI) 554 (M+H).

Step B. Example 112. Preparation of N-((4-(5-(tert-butyl)-1,2,4-oxadiazol-3-yl) bicyclo[2.2.2]octan-1-yl)methyl)-3-fluoro-N-(3-(2-hydroxy-2-methylpropoxy)phenyl) bicyclo[1.1.1]pentane-1-carboxamide The title compound was prepared according to the method described for the synthesis of Example 128 by substituting Intermediate 112A where appropriate. (6.2 mg, 0.011 mmol, 31% yield). $^1$H NMR (400 MHz, DMSO-$d_6$) δ 7.39-7.29 (m, 1H), 7.02-6.85 (m, 3H), 4.64 (s, 1H), 3.77 (d, J=3.2 Hz, 2H), 3.66-3.57 (m, 1H), 3.54-3.39 (m, 1H), 1.87 (br d, J=8.3 Hz, 6H), 1.79-1.66 (m, 6H), 1.47-1.37 (m, 6H), 1.33 (s, 9H), 1.21 (s, 6H). FXR $EC_{50}$ (nM)=63. MS (ESI) 540 (M+H).

Example 113

2-(3-(N-((4-(5-(tert-butyl)-1,2,4-oxadiazol-3-yl)bicyclo[2.2.2]octan-1-yl)methyl)-3-fluorobicyclo[1.1.1]pentane-1-carboxamido)phenoxy)-2-methylpropanoic acid (113)

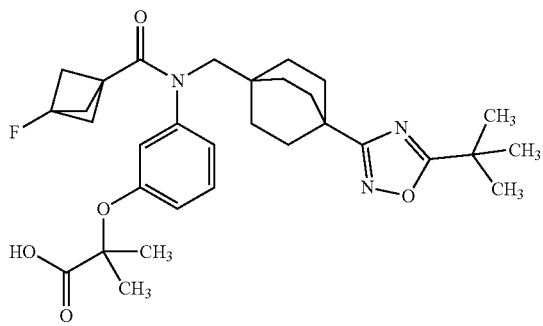

Step A. Intermediate 113A: Preparation of ethyl 2-(3-(N-((4-(5-(tert-butyl)-1,2,4-oxadiazol-3-yl)bicyclo[2.2.2]octan-1-yl)methyl)-3-fluorobicyclo[1.1.1]pentane-1-carboxamido)phenoxy)-2-methylpropanoate

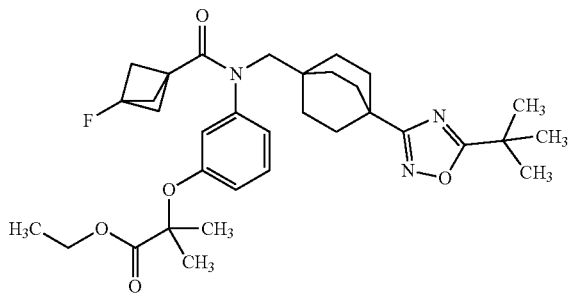 [SMILES: CCOC(=O)C(C)(C)Oc1cccc(N(CC23CCC(c4noc(C(C)(C)C)n4)(CC2)CC3)C(=O)C23CC(F)(C2)C3)c1]

The title compound was prepared according to the method described for the synthesis of Example 111 by substituting Example 110 where appropriate. (50 mg, 0.086 mmol, 67% yield) as white solid. MS (ESI) 582 (M+H).

Step B. Example 113: Preparation of 2-(3-(N-((4-(5-(tert-butyl)-1,2,4-oxadiazol-3-yl) bicyclo[2.2.2]octan-1-yl)methyl)-3-fluorobicyclo[1.1.1]pentane-1-carboxamido) phenoxy)-2-methylpropanoic Acid The title compound was prepared according to the method described for the synthesis of Intermediate 28C by substituting Intermediate 113A where appropriate. (19.7 mg, 0.036 mmol, 83% yield). $^1$H NMR (400 MHz, DMSO-$d_6$) δ 7.35 (t, J=8.1 Hz, 1H), 7.01 (d, J=7.6 Hz, 1H), 6.89 (dd, J=2.2, 8.1 Hz, 1H), 6.81-6.70 (m, 1H), 3.49 (br d, J=3.2 Hz, 2H), 1.93-1.79 (m, 6H), 1.78-1.64 (m, 6H), 1.59-1.47 (m, 6H), 1.45-1.37 (m, 6H), 1.34 (s, 9H). FXR $EC_{50}$ (nM)=2000. MS (ESI) 554 (M+H).

Example 114

N-(3-cyanophenyl)-3-fluoro-N-((4-(5-(trifluoromethyl)-1,2,4-oxadiazol-3-yl) bicyclo[2.2.2]octan-1-yl)methyl)bicyclo[1.1.1]pentane-1-carboxamide (114)

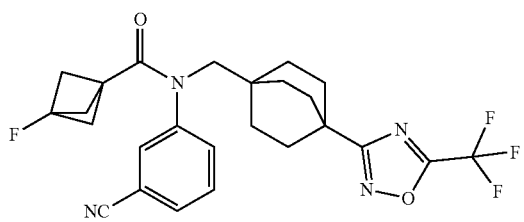

Step A. Intermediate 114A: Preparation of methyl 4-(5-(trifluoromethyl)-1,2,4-oxadiazol-3-yl)bicyclo[2.2.2]octane-1-carboxylate

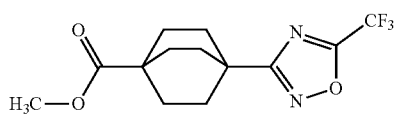

To a stirred solution of Intermediate 1C (5.0 g, 22.10 mmol) in DMF (50 mL) at 0° C. was added pyridine (8.90 mL, 110 mmol) followed by 2,2,2-trifluoroacetic anhydride (4.65 mL, 33.1 mmol). The reaction mixture was allowed to warm up to room temperature and stirred overnight. The reaction mixture was diluted with cold water (50 mL) and extracted with ethyl acetate (2×50 mL). The combined organic layers were dried over anhydrous sodium sulfate, filtered and concentrated under reduced pressure. The crude material was purified by flash chromatography (40 g silica gel cartridge; A=Hex, B=EtOAc; 30 min grad.; 0% B to 30% B). The pure fractions were combined, concentrated under reduced pressure and dried in vacuo to afford methyl 4-(5-(trifluoromethyl)-1,2,4-oxadiazol-3-yl)bicyclo[2.2.2]octane-1-carboxylate (4.8 g, 15.78 mmol, 71% yield) as gummy solid. MS (ESI) 305 (M+H).

Step B: Intermediate 114B: Preparation of (4-(5-(trifluoromethyl)-1,2,4-oxadiazol-3-yl) bicyclo[2.2.2]octan-1-yl)methanol

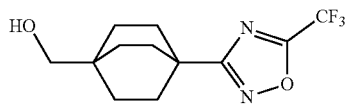 [SMILES: OCC12CCC(c3noc(C(F)(F)F)n3)(CC1)CC2]

The title compound was prepared according to the method described for the synthesis of Intermediate 1E by substituting Intermediate 114A where appropriate. (2.1 g, 7.60 mmol, 48% yield) as gummy liquid. MS (ESI) 277 (M+H).

Step C: Intermediate 114C: Preparation of 4-(5-(trifluoromethyl)-1,2,4-oxadiazol-3-yl) bicyclo[2.2.2]octane-1-carbaldehyde

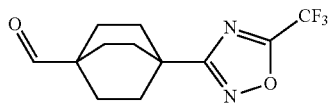 [SMILES: O=CC12CCC(c3noc(C(F)(F)F)n3)(CC1)CC2]

The title compound was prepared according to the method described for the synthesis of Intermediate 1F by substituting Intermediate 114B where appropriate. (1.3 g, 4.74 mmol, 66% yield) as white solid. MS (ESI) 275 (M+H).

Step D: Intermediate 114D: Preparation of 3-(((4-(5-(trifluoromethyl)-1,2,4-oxadiazol-3-yl)bicyclo[2.2.2]octan-1-yl)methyl)amino)benzonitrile

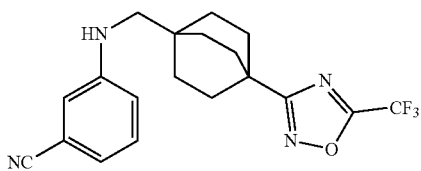 [SMILES: N#Cc1cccc(NCC23CCC(c4noc(C(F)(F)F)n4)(CC2)CC3)c1]

The title compound was prepared according to the method described for the synthesis of Intermediate 1G by substituting Intermediate 114C where appropriate (180 mg, 0.478 mmol, 87% yield) as white gummy solid. MS (ESI) 377 (M+H).

Step E. Example 114: Preparation of N-(3-cyanophenyl)-3-fluoro-N-((4-(5-(trifluoromethyl)-1,2,4-oxadiazol-3-yl)bicyclo[2.2.2]octan-1-yl)methyl)bicyclo[1.1.1]pentane-1-carboxamide The title compound was prepared according to the method described for the synthesis of Example 1 by substituting Intermediate 114D and corresponding acid where appropriate. (9.3 mg, 0.019 mmol, 36% yield). $^1$H NMR (400 MHz, DMSO-$d_6$) δ 8.05 (s, 1H), 7.88 (d, J=7.8 Hz, 1H), 7.81 (dd, J=1.5, 7.3 Hz, 1H), 7.71-7.61 (m, 1H), 3.66-3.47 (m, 2H), 1.87 (br s, 6H), 1.82-1.71 (m, 6H), 1.49-1.34 (m, 6H). FXR $EC_{50}$ (nM)=80. MS (ESI) 489 (M+H).

The following examples were synthesized according to the method described for the synthesis of Example 1 by substituting Intermediate 114D and the corresponding aryl halides where appropriate.

| Ex. No. | Structure & Name | MS (ESI) (M + H) | FXR $EC_{50}$ (nM) |
|---|---|---|---|
| 115 | (1S,3S)-N-(3-cyanophenyl)-3-hydroxy-3-(trifluoromethyl)-N-((4-(5-(trifluoromethyl)-1,2,4-oxadiazol-3-yl)bicyclo[2.2.2]octan-1-yl)methyl)cyclobutane-1-carboxamide | 543 | 436 |
| 116 | N-(3-cyanophenyl)-N-((4-(5-(trifluoromethyl)-1,2,4-oxadiazol-3-yl)bicyclo[2.2.2]octan-1-yl)methyl)tetrahydro-2H-pyran-4-carboxamide | 489 | 518 |
| 117 | (1S,3S)-N-(3-cyanophenyl)-3-hydroxy-3-methyl-N-((4-(5-(trifluoromethyl)-1,2,4-oxadiazol-3-yl)bicyclo[2.2.2]octan-1-yl)methyl)cyclobutane-1-carboxamide | 489 | 1353 |

| Ex. No. | Structure & Name | MS (ESI) (M + H) | FXR EC$_{50}$ (nM) |
|---|---|---|---|
| 115 | $^1$HNMR (400 MHz, DMSO-d$_6$) δ 8.05 (s, 1H), 7.87-7.76 (m, 2H), 7.68-7.59 (m, 1H), 6.56 (s, 1H), 3.69-3.57 (m, 2H), 2.78-2.69 (m, 1H), 2.35-2.26 (m, 2H), 2.07-1.93 (m, 2H), 1.85-1.73 (m, 6H), 1.48-1.35 (m, 6H) | | |
| 116 | $^1$H NMR (400 MHz, DMSO-d$_6$) δ 8.12-8.00 (m, 1H), 7.90-7.75 (m, 2H), 7.66 (br t, J = 7.8 Hz, 1H), 3.81-3.68 (m, 2H), 3.66-3.54 (m, 2H), 3.09-2.94 (m, 2H), 2.47-2.35 (m, 1H), 1.86-1.71 (m, 6H), 1.66-1.51 (m, 2H), 1.50-1.33 (m, 8H) | | |
| 117 | $^1$H NMR (400 MHz, DMSO-d$_6$) δ 7.97 (s, 1H), 7.80 (br d, J = 7.1 Hz, 1H), 7.78-7.70 (m, 1H), 7.66-7.58 (m, 1H), 4.91 (s, 1H), 3.61 (s, 2H), 2.16-2.01 (m, 2H), 1.84-1.73 (m, 6H), 1.64-1.50 (m, 2H), 1.46-1.31 (m, 6H), 1.06-0.89 (m, 3H) | | |

NOTE:
One proton buried under solvent peak

Example 118

N-((4-(5-(tert-butyl)-1,2,4-oxadiazol-3-yl)bicyclo [2.2.2]octan-1-yl)methyl)-N-(3-((5-(difluoromethoxy)pyrimidin-2-yl)oxy)phenyl)-3-fluorobicyclo[1.1.1]pentane-1-carboxamide

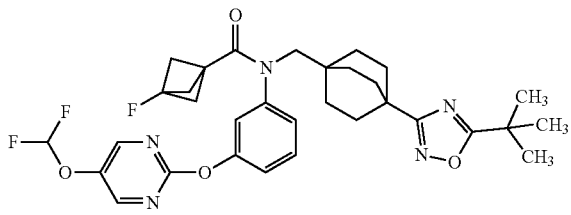

(118)

Step A. Intermediate 118A. Preparation of N-((4-(5-(tert-butyl)-1,2,4-oxadiazol-3-yl) bicyclo[2.2.2] octan-1-yl)methyl)-N-(3-(5,5-dimethyl-1,3,2-dioxaborinan-2-yl)phenyl)-3-fluorobicyclo[1.1.1]pentane-1-carboxamide

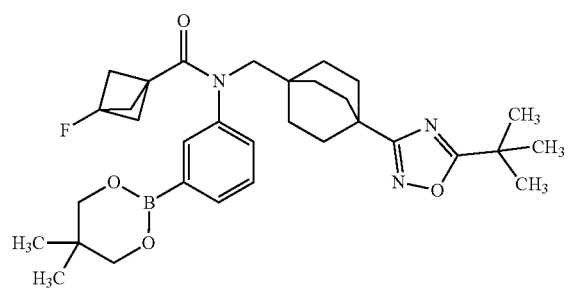 [SMILES: CC1(C)COB(c2cccc(N(CC34CCC(c5noc(C(C)(C)C)n5)(CC3)CC4)C(=O)C34CC(F)(C3)C4)c2)OC1]

To a stirred solution of Intermediate 84A (180 mg, 0.339 mmol) in 1,4-dioxane (5 mL) at room temperature was added bis(neopentyl glycolato)diboron (153 mg, 0.679 mmol) followed by potassium acetate (150 mg, 1.527 mmol). The reaction mixture was purged with argon for 10 minutes and Pd(dppf)$_2$Cl$_2$ (12.41 mg, 0.017 mmol) was added. The reaction mixture was heated to 110° C. and stirred for 4 h. The reaction mixture was cooled to room temperature and poured into water (10 mL) and extracted with EtOAc (2×25 mL). The combined organic layers were washed with brine (10 mL), dried over anhydrous sodium sulfate, filtered and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (90 mg, 0.152 mmol, 45% yield) as white solid. MS (ESI) 496 (M+H) (Boronic acid fragment of parent boronate).

Step B. Intermediate 118B. Preparation of N-((4-(5-(tert-butyl)-1,2,4-oxadiazol-3-yl) bicyclo[2.2.2]octan-1-yl)methyl)-3-fluoro-N-(3-hydroxyphenyl)bicyclo[1.1.1]pentane-1-carboxamide

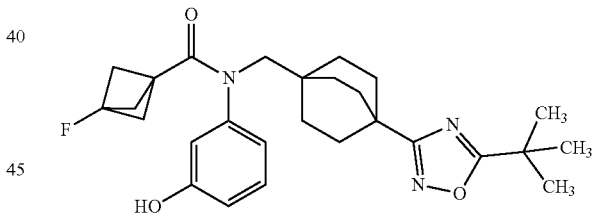

A solution of Intermediate 118A (80 mg, 0.142 mmol) in DCM (3 mL) was cooled to 0° C. and m-CPBA (29.4 mg, 0.170 mmol) was added. The reaction mixture was allowed to warm up to room temperature and stirred for 1 h. The reaction mixture was concentrated under reduced pressure. The crude was poured into water (5 mL) and extracted with EtOAc (2×10 mL). The combined organic layers were washed with brine (10 mL), dried over anhydrous sodium sulfate, filtered and concentrated under reduced pressure. The crude material was purified by flash chromatography (4 g silica gel cartridge; A=Hex, B=EtOAc; 30 min grad.; 0% B to 60% B). The pure fractions were combined, concentrated under reduced pressure and dried in vacuo to afford the title compound (60 mg, 0.122 mmol, 86% yield) as white solid. MS (ESI) 468 (M+H).

Step C. EXAMPLE 118. Preparation of N-((4-(5-(tert-butyl)-1,2,4-oxadiazol-3-yl) bicyclo[2.2.2]octan-1-yl)methyl)-N-(3-((5-(difluoromethoxy)pyrimidin-2-yl)oxy) phenyl)-3-fluorobicyclo[1.1.1]pentane-1-carboxamide To a solution Intermediate 118B (25 mg, 0.053 mmol) and 2-chloro-5-(difluoromethoxy)pyrimidine (9.65 mg, 0.053 mmol) in acetonitrile (1 mL) at room temperature was added potassium carbonate (7.39 mg, 0.053 mmol) and stirred overnight at 90° C. The reaction mixture was filtered through a filter disc. Filtrate was concentrated under reduced pressure. The crude material was purified via preparative LC/MS with the following conditions: Column: Waters XBridge C18, 150 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 2-minute hold at 15% B, 15-57% B over 25 minutes, then a 5-minute hold at 100% B; Flow Rate: 15 mL/min; Column Temperature: 25° C. Fraction collection was triggered by signals. Fractions containing the desired product were combined and dried via centrifugal evaporation to afford the title compound (18.3 mg, 0.030 mmol, 56% yield). $^1$H NMR (400 MHz, DMSO-$d_6$) δ 8.62 (s, 2H), 7.58-7.48 (m, 1H), 7.37 (d, J=2.0 Hz, 1H), 7.34-7.17 (m, 3H), 3.60 (br. s., 1H), 3.47 (br. s., 1H), 1.94 (br. s., 6H), 1.81-1.65 (m, 6H), 1.43 (d, J=4.9 Hz, 6H), 1.34 (s, 9H). FXR $EC_{50}$ (nM)=361. MS (ESI) 612 (M+H)

Example 119

N-((4-(5-(tert-butyl)-1,2,4-oxadiazol-3-yl)bicyclo[2.2.2]octan-1-yl)methyl)-N-(3-((5-(difluoromethoxy)pyridin-2-yl)oxy)phenyl)-3-fluorobicyclo[1.1.1]pentane-1-carboxamide (119)

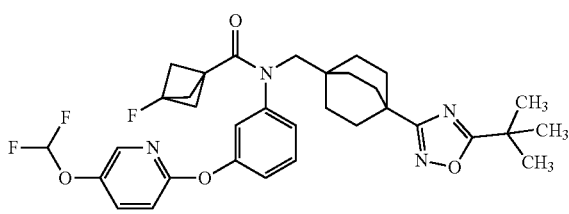

The title compound was synthesized according to the method described for the synthesis of Example 118 by substituting Intermediate 118B and 2-bromo-5-(difluoromethoxy)pyridine where appropriate. (8.3 mg, 0.013 mmol, 31% yield). $^1$H NMR (400 MHz, DMSO-$d_6$) δ 8.01 (d, J=2.9 Hz, 1H), 7.81 (dd, J=9.0, 2.9 Hz, 1H), 7.56-7.43 (m, 1H), 7.33-7.10 (m, 5H), 3.59 (br. s., 1H), 3.47 (br. s., 1H), 1.93 (br. s., 6H), 1.81-1.58 (m, 6H), 1.43 (br. s., 6H), 1.34 (s, 9H). FXR $EC_{50}$ (nM)=536. MS (ESI) 611 (M+H).

Example 120

3-(N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamido)benzoic acid (120)

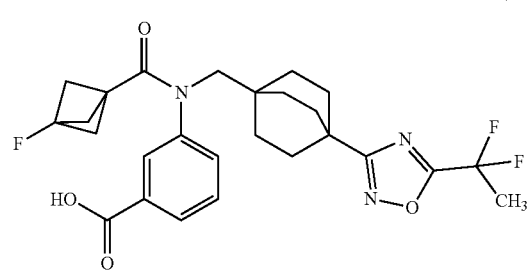

Step A. Intermediate 120A. Preparation of methyl 3-(((4-(5-(1,1-difluoroethyl)-1,2,4-oxadiazol-3-yl)bicyclo[2.2.2]octan-1-yl)methyl)amino)benzoate

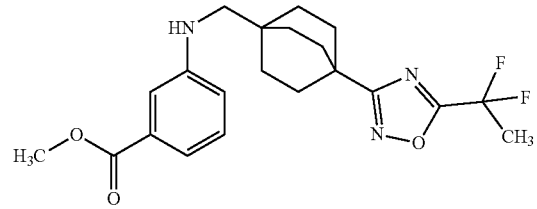 [SMILES: COC(=O)c1cccc(NCC23CCC(c4noc(C(C)(F)F)n4)(CC2)CC3)c1]

The title compound was synthesized according to the method described for the synthesis of Intermediate 1G by substituting Intermediate 1F and methyl 3-aminobenzoate where appropriate. (75 mg, 0.176 mmol, 68% yield) as pale yellow oil. MS (ESI) 406 (M+H).

Step B. Intermediate 120B. Preparation of methyl 3-(N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamido)benzoate

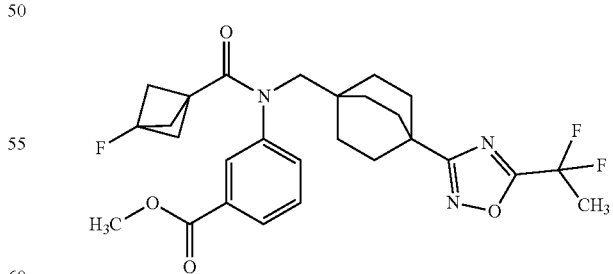

The title compound was synthesized according to the method described for the synthesis of Example 1 by substituting Intermediate 120A and corresponding acid where appropriate. (75 mg, 0.143 mmol, 77% yield). $^1$H NMR (400 MHz, DMSO-$d_6$) δ 7.97 (d, J=8.1 Hz, 1H), 7.91-7.86 (m, 1H), 7.77-7.70 (m, 1H), 7.66-7.57 (m, 1H), 3.90 (s, 3H), 3.66-3.50 (m, 2H), 2.14 (t, J=19.7 Hz, 3H), 1.84 (br s, 6H), 1.80-1.66 (m, 6H), 1.50-1.35 (m, 6H). MS (ESI) 518 (M+H).

Step C. Example 120. Preparation of 3-(N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamido)benzoic Acid The title compound was synthesized according to the method described for the synthesis of Intermediate 28C by substituting Intermediate 120B where appropriate. (50 mg, 0.099 mmol, 79% yield) as off-white solid. $^1$H NMR (400 MHz, DMSO-d$_6$) δ 7.94 (d, J=7.3 Hz, 1H), 7.83 (s, 1H), 7.70-7.62 (m, 1H), 7.61-7.54 (m, 1H), 3.58 (s, 2H), 2.13 (t, J=19.6 Hz, 3H), 1.83 (br s, 6H), 1.81-1.73 (m, 6H), 1.49-1.37 (m, 6H). FXR EC$_{50}$ (nM)=4000. MS (ESI) 504 (M+H).

Example 121

N-((4-(3-(tert-butyl)-1,2,4-oxadiazol-5-yl)bicyclo[2.2.2]octan-1-yl)methyl)-N-(3-carbamoyl-4-fluorophenyl)-3-fluorobicyclo[1.1.1]pentane-1-carboxamide

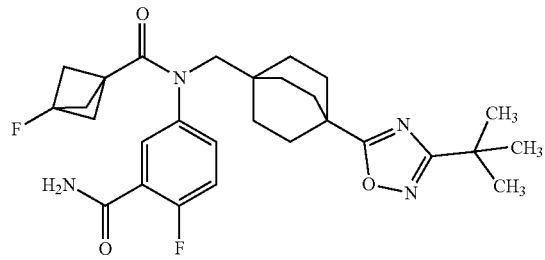 [SMILES: CC(C)(C)c1noc(C23CCC(CN(C(=O)C45CC(F)(C4)C5)c4ccc(F)c(C(N)=O)c4)(CC2)CC3)n1]

Step A. Intermediate 121A. Preparation of methyl 5-(((4-(3-(tert-butyl)-1,2,4-oxadiazol-5-yl)bicyclo[2.2.2]octan-1-yl)methyl)amino)-2-fluorobenzoate

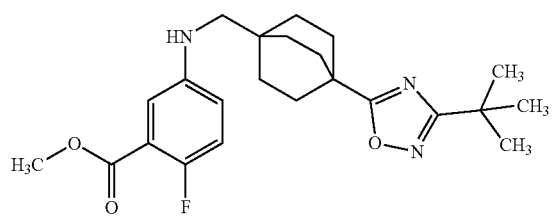 [SMILES: COC(=O)c1cc(NCC23CCC(c4nc(C(C)(C)C)no4)(CC2)CC3)ccc1F]

The title compound was synthesized according to the method described for the synthesis of Intermediate 1G by substituting Intermediate 36C where appropriate. (280 mg, 0.674 mmol, 88% yield) as off-white solid. MS (ESI) 416 (M+H).

Step B. Intermediate 121B. Preparation of methyl 5-(N-((4-(3-(tert-butyl)-1,2,4-oxadiazol-5-yl)bicyclo[2.2.2]octan-1-yl)methyl)-3-fluorobicyclo[1.1.1]pentane-1-carboxamido)-2-fluorobenzoate

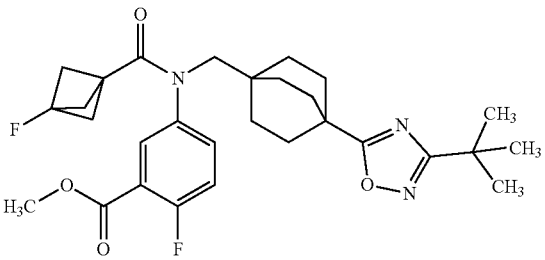 [SMILES: COC(=O)c1cc(N(CC23CCC(c4nc(C(C)(C)C)no4)(CC2)CC3)C(=O)C23CC(F)(C2)C3)ccc1F]

The title compound was synthesized according to the method described for the synthesis of Example 1 by substituting Intermediate 121A and corresponding acid where appropriate. (200 mg, 0.360 mmol, 75% yield) as off-white solid. MS (ESI) 528 (M+H).

Step C. Intermediate 121C Preparation of 5-(N-((4-(3-(tert-butyl)-1,2,4-oxadiazol-5-yl)bicyclo[2.2.2]octan-1-yl)methyl)-3-fluorobicyclo[1.1.1]pentane-1-carboxamido)-2-fluorobenzoic Acid

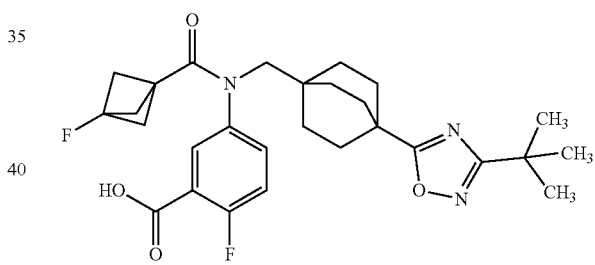

The title compound was synthesized according to the method described for the synthesis of Intermediate 28C by substituting Intermediate 121B where appropriate. (55 mg, 0.096 mmol, 78% yield) as solid. MS (ESI) 514 (M+H).

Step D. Example 121. Preparation of N-((4-(3-(tert-butyl)-1,2,4-oxadiazol-5-yl) bicyclo[2.2.2]octan-1-yl)methyl)-N-(3-carbamoyl-4-fluorophenyl)-3-fluorobicyclo[1.1.1]pentane-1-carboxamide The title compound was synthesized according to the method described for the synthesis of Intermediate 1A by substituting Intermediate 121C where appropriate. (10 mg, 0.020 mmol, 50% yield). $^1$H NMR (400 MHz, DMSO-d$_6$) δ 7.87-7.75 (m, 2H), 7.64-7.51 (m, 2H), 7.37 (t, J=9.3 Hz, 1H), 3.60-3.48 (m, 2H), 1.88 (br s, 6H), 1.84-1.75 (m, 6H), 1.48-1.36 (m, 6H), 1.27 (s, 9H). FXR EC$_{50}$ (nM)=412. MS (ESI) 513 (M+H).

Example 122

N-((4-(3-(tert-butyl)-1,2,4-oxadiazol-5-yl)bicyclo[2.2.2]octan-1-yl)methyl)-N-(3-(ethylcarbamoyl)-4-fluorophenyl)-3-fluorobicyclo[1.1.1]pentane-1-carboxamide

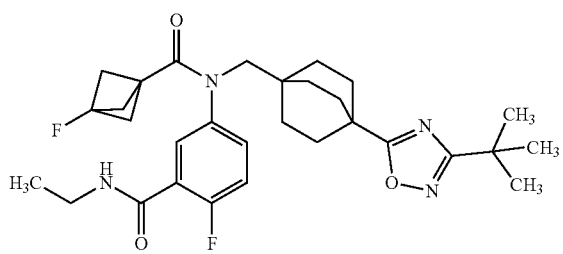

(122)

The title compound was synthesized according to the method described for the synthesis of Intermediate 1A by substituting Intermediate 121C and ethanamine where appropriate. (20 mg, 0.037 mmol, 95% yield). $^1$H NMR (400 MHz, DMSO-d$_6$) δ 8.47-8.34 (m, 1H), 7.61-7.50 (m, 2H), 7.42-7.32 (m, 1H), 3.57 (br s, 1H), 3.53-3.44 (m, 1H), 3.31-3.23 (m, 2H), 1.88 (br s, 6H), 1.84-1.70 (m, 6H), 1.50-1.35 (m, 6H), 1.27 (s, 9H), 1.14 (t, J=7.1 Hz, 3H). FXR EC$_{50}$ (nM)=123. MS (ESI) 540 (M+H).

Example 123

(1S,3S)—N-((4-(3-(tert-butyl)-1,2,4-oxadiazol-5-yl)bicyclo[2.2.2]octan-1-yl)methyl)-3-hydroxy-N-(3-isopropoxyphenyl)-3-(trifluoromethyl)cyclobutane-1-carboxamide

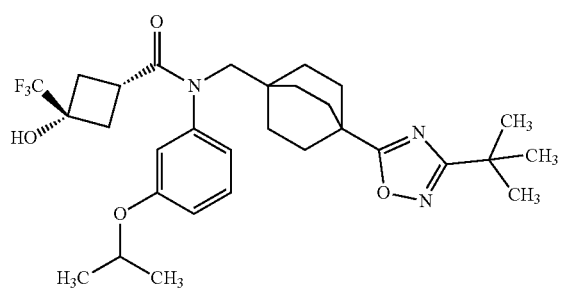

(123)

Step A. Intermediate 123A. Preparation of N-((4-(3-(tert-butyl)-1,2,4-oxadiazol-5-yl) bicyclo[2.2.2]octan-1-yl)methyl)-3-isopropoxyaniline

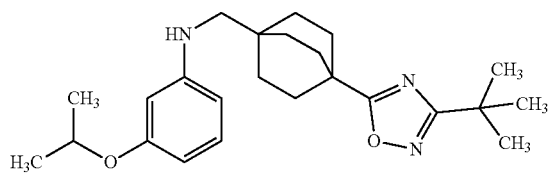 [SMILES: CC(C)Oc1cccc(NCC23CCC(c4nc(C(C)(C)C)no4)(CC2)CC3)c1]

The title compound was synthesized according to the method described for the synthesis of Intermediate 1G by substituting Intermediate 36C and 3-isopropoxyaniline where appropriate. (70 mg, 0.158 mmol, 69% yield) as off-white solid. MS (ESI) 398 (M+H).

Step B. Example 123. Preparation of (1S,3S)—N-((4-(3-(tert-butyl)-1,2,4-oxadiazol-5-yl)bicyclo[2.2.2]octan-1-yl)methyl)-3-hydroxy-N-(3-isopropoxyphenyl)-3-(trifluoromethyl)cyclobutane-1-carboxamide The title compound was synthesized according to the method described for the synthesis of Example 1 by substituting Intermediate 123A and corresponding acid where appropriate. (14 mg, 0.024 mmol, 47% yield). $^1$H NMR (400 MHz, DMSO-d$_6$) δ 7.36-7.25 (m, 1H), 6.98-6.92 (m, 1H), 6.92-6.80 (m, 2H), 6.53 (s, 1H), 4.72-4.62 (m, 1H), 3.59 (s, 2H), 2.85-2.73 (m, 1H), 2.36-2.25 (m, 2H), 2.09-2.00 (m, 2H), 1.85-1.74 (m, 6H), 1.47-1.38 (m, 6H), 1.29-1.22 (m, 15H). FXR EC$_{50}$ (nM)=2000. MS (ESI) 564 (M+H).

Example 124

N-((4-(3-(tert-butyl)-1,2,4-oxadiazol-5-yl)bicyclo[2.2.2]octan-1-yl)methyl)-3-fluoro-N-(3-isopropoxyphenyl)bicyclo[1.1.1]pentane-1-carboxamide

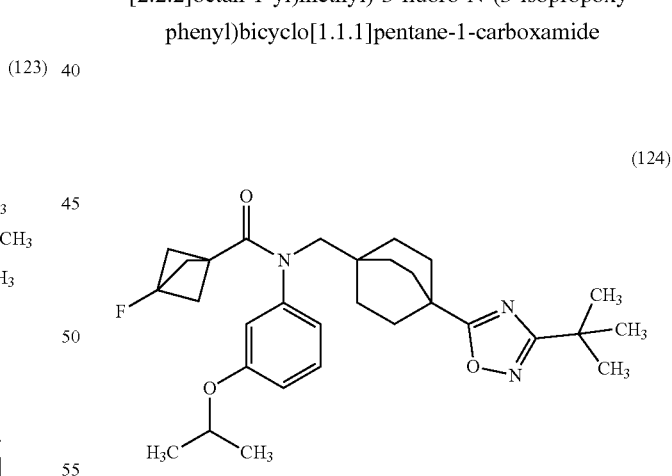

(124)

The title compound was synthesized according to the method described for the synthesis of Example 1 by substituting Intermediate 123A and corresponding acid where appropriate. (12 mg, 0.024 mmol, 47% yield). $^1$H NMR (400 MHz, DMSO-d$_6$) δ 7.37-7.28 (m, 1H), 6.99-6.85 (m, 3H), 4.68 (quin, J=6.0 Hz, 1H), 3.59 (br s, 1H), 3.48-3.40 (m, 1H), 1.94-1.71 (m, 12H), 1.53-1.36 (m, 6H), 1.27 (s, 15H). FXR EC$_{50}$ (nM)=2000. MS (ESI) 510 (M+H).

Example 125

(1S,3S)—N-((4-(5-(1,1-difluoroethyl)-1,2,4-oxadiazol-3-yl)bicyclo[2.2.2]octan-1-yl) methyl)-3-hydroxy-N-(3-isopropoxyphenyl)-3-methylcyclobutane-1-carboxamide (125)

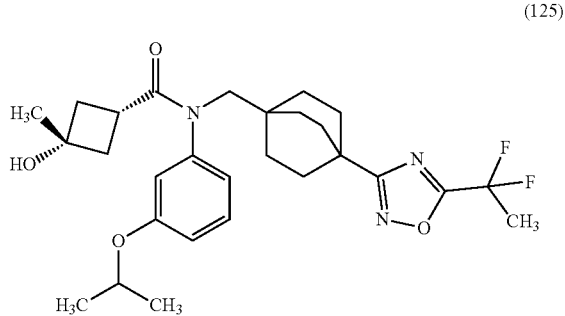 [SMILES: CC(C)Oc1cccc(N(CC23CCC(c4noc(C(C)(F)F)n4)(CC2)CC3)C(=O)[C@H]2C[C@@](C)(O)C2)c1]

Step A. Intermediate 125A Preparation of N-((4-(5-(1,1-difluoroethyl)-1,2,4-oxadiazol-3-yl)bicyclo[2.2.2]octan-1-yl)methyl)-3-isopropoxyaniline

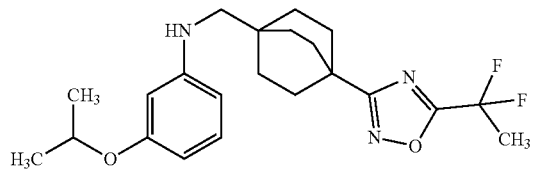 [SMILES: CC(C)Oc1cccc(NCC23CCC(c4noc(C(C)(F)F)n4)(CC2)CC3)c1]

The title compound was synthesized according to the method described for the synthesis of Intermediate 1G by substituting Intermediate 1F and 3-isopropoxyaniline where appropriate. (60 mg, 0.141 mmol, 76% yield) as off-white solid. MS (ESI) 406 (M+H).

Step B. Example 125. Preparation of (1S,3S)—N-((4-(5-(1,1-difluoroethyl)-1,2,4-oxadiazol-3-yl)bicyclo[2.2.2]octan-1-yl)methyl)-3-hydroxy-N-(3-isopropoxyphenyl)-3-methylcyclobutane-1-carboxamide The title compound was synthesized according to the method described for the synthesis of Example 1 by substituting Intermediate 125A and corresponding acid where appropriate. (5.2 mg, 9.34 µmol, 19% yield). $^1$H NMR (400 MHz, DMSO-$d_6$) δ 7.29 (t, J=8.1 Hz, 1H), 6.95-6.80 (m, 3H), 4.90 (s, 1H), 4.73-4.60 (m, 1H), 3.63-3.53 (m, 2H), 2.55 (br d, J=3.7 Hz, 1H), 2.21-2.04 (m, 5H), 1.84-1.72 (m, 6H), 1.67-1.57 (m, 2H), 1.50-1.36 (m, 6H), 1.26 (d, J=5.9 Hz, 6H), 1.10-0.85 (m, 3H). FXR EC$_{50}$ (nM)=1525. MS (ESI) 518 (M+H).

The following examples were synthesized according to the method described for the synthesis of Example 1 by substituting Intermediate 125A and corresponding acid where appropriate.

| Ex. No. | Structure & Name | MS (ESI) (M + H) | FXR EC$_{50}$ (nM) |
|---|---|---|---|
| 126 | 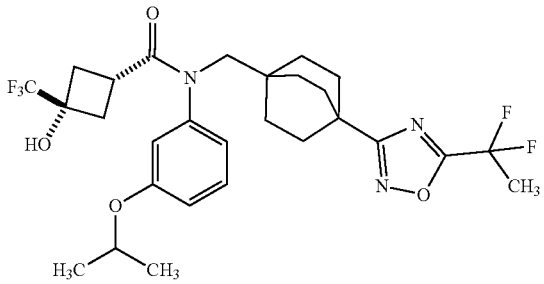 [SMILES: CC(C)Oc1cccc(N(CC23CCC(c4noc(C(C)(F)F)n4)(CC2)CC3)C(=O)[C@H]2C[C@](O)(C(F)(F)F)C2)c1]<br>(1S,3S)-N-((4-(5-(1,1-difluoroethyl)-1,2,4-oxadiazol-3-yl)bicyclo[2..2.2]octan-1-yl)methyl)-3-hydroxy-N-(3-isopropoxyphenyl)-3-(trifluoromethyl)cyclobutane-1-carboxamide | 572 | 610 |
| 127 | 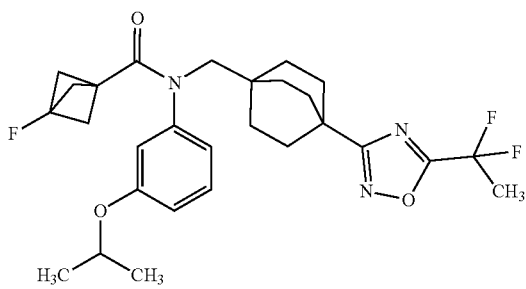 [SMILES: CC(C)Oc1cccc(N(CC23CCC(c4noc(C(C)(F)F)n4)(CC2)CC3)C(=O)C23CC(F)(C2)C3)c1]<br>N-((4-(5-(1,1-difluoroethyl)-1,2,4-oxadiazol-3-yl)bicyclo[2.2.2]octan-1-yl)methyl)-3-fluoro-N-(3-isopropoxyphenyl)bicyclo[1.1.1]pentane-1-carboxamide | 518 | 156 |

| Ex. No. | Structure & Name | MS (ESI) (M + H) | FXR EC$_{50}$ (nM) |
|---|---|---|---|
| 126 | ¹H NMR (400 MHz, DMSO-d$_6$) δ 7.31 (t, J = 7.9 Hz, 1H), 6.99-6.93 (m, 1H), 6.89 (dt, J = 2.0, 7.6 Hz, 2H), 6.52 (s, 1H), 4.68 (quin, J = 6.1 Hz, 1H), 3.64-3.54 (m, 2H), 2.85-2.75 (m, 1H), 2.35-2.26 (m, 2H), 2.20-2.00 (m, 5H), 1.83-1.69 (m, 6H), 1.48-1.37 (m, 6H), 1.25 (d, J = 6.1 Hz, 6H) | | |
| 127 | ¹H NMR (400 MHz, DMSO-d$_6$) δ 7.37-7.28 (m, 1H), 7.00-6.87 (m, 3H), 4.69 (quin, J = 6.0 Hz, 1H), 3.66-3.54 (m, 1H), 3.47 (br s, 1H), 2.14 (t, J = 19.7 Hz, 3H), 1.96-1.82 (m, 6H), 1.82-1.71 (m, 6H), 1.54-1.39 (m, 6H), 1.31-1.23 (m, 6H) | | |

Example 128

N-((4-(3-(tert-butyl)-1,2,4-oxadiazol-5-yl)bicyclo[2.2.2]octan-1-yl)methyl)-3-fluoro-N-(4-fluoro-3-(2-hydroxypropan-2-yl)phenyl)bicyclo[1.1.1]pentane-1-carboxamide

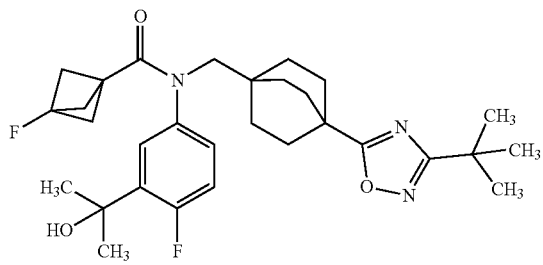

(128)

Example 129

N-((4-(5-(1,1-difluoroethyl)-1,2,4-oxadiazol-3-yl)bicyclo[2.2.2]octan-1-yl)methyl)-3-fluoro-N-(3-methoxyphenyl)bicyclo[1.1.1]pentane-1-carboxamide

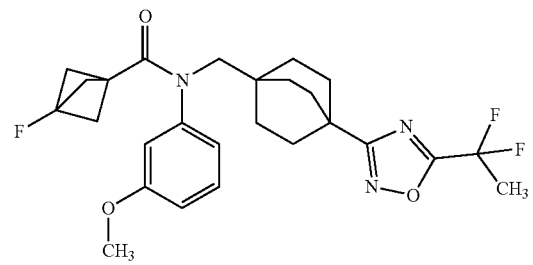

(129)

To a solution of Intermediate 121B (25 mg, 0.047 mmol) in THF (2 mL) at 0° C. was added 3 M methylmagnesium bromide in diethyl ether (0.032 mL, 0.095 mmol). The reaction mixture was slowly allowed to warm up to room temperature and stirred for 1 h. The reaction mixture was quenched with aq. saturated NH$_4$Cl solution (5 mL) and extracted with EtOAc (2×10 mL). The combined organic layers were washed with brine (5 mL), dried over anhydrous sodium sulfate, filtered and concentrated under reduced pressure. The crude material was purified via preparative LC/MS with the following conditions: Column: Waters XBridge C18, 150 mm×19 mm, 5-µm particles; Mobile Phase A: 5:95 acetonitrile: water with 10-mM ammonium acetate; Mobile Phase B: 95:5 acetonitrile: water with 10-mM ammonium acetate; Gradient: a 2-minute hold at 15% B, 15-57% B over 25 minutes, then a 5-minute hold at 100% B; Flow Rate: 15 mL/min; Column Temperature: 25° C. Fraction collection was triggered by signals. Fractions containing the desired product were combined and dried via centrifugal evaporation to afford title compound (10.4 mg, 0.020 mmol, 42% yield). ¹H NMR (400 MHz, DMSO-d$_6$) δ 7.49 (dd, J=2.8, 7.5 Hz, 1H), 7.34-7.27 (m, 1H), 7.20 (dd, J=8.6, 11.2 Hz, 1H), 5.46 (s, 1H), 3.60-3.53 (m, 1H), 3.50-3.43 (m, 1H), 1.91-1.76 (m, 12H), 1.50 (br d, J=10.0 Hz, 6H), 1.46-1.37 (m, 6H), 1.27 (s, 9H). FXR EC$_{50}$ (nM)=4000. MS (ESI) 528 (M+H).

Step A. Intermediate 129A. Preparation of N-((4-(5-(1,1-difluoroethyl)-1,2,4-oxadiazol-3-yl)bicyclo[2.2.2]octan-1-yl)methyl)-3-methoxyaniline

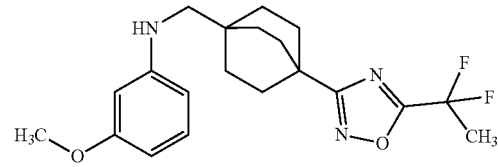 [SMILES: COc1cccc(NCC23CCC(c4noc(C(C)(F)F)n4)(CC2)CC3)c1]

The title compound was synthesized according to the method described for the synthesis of Intermediate 1G by substituting Intermediate 1F and 3-methoxyaniline where appropriate. (25 mg, 0.063 mmol, 57% yield) as off-white solid. MS (ESI) 378 (M+H).

Step B. Example 129. Preparation of N-((4-(5-(1,1-difluoroethyl)-1,2,4-oxadiazol-3-yl) bicyclo[2.2.2]octan-1-yl)methyl)-3-fluoro-N-(3-methoxyphenyl)bicyclo[1.1.1]pentane-1-carboxamide The title compound was synthesized according to the method described for the synthesis of Example 1 by substituting Intermediate 129A and corresponding acid where appropriate. (11 mg, 0.022 mmol, 42% yield). ¹H NMR (400 MHz, DMSO-d$_6$) δ 7.36 (t, J=8.3 Hz, 1H), 7.04-6.88 (m, 3H), 3.80 (s, 3H), 3.68-3.56 (m, 1H), 3.52-3.40 (m, 1H), 2.14 (t, J=19.7 Hz, 3H), 1.97-1.70 (m, 12H), 1.57-1.34 (m, 6H). FXR EC$_{50}$ (nM)=73. MS (ESI) 490 (M+H).

Example 130

N-((4-(5-(1,1-difluoroethyl)-1,2,4-oxadiazol-3-yl)bicyclo[2.2.2]octan-1-yl)methyl)-N-(3-ethoxyphenyl)-3-fluorobicyclo[1.1.1]pentane-1-carboxamide

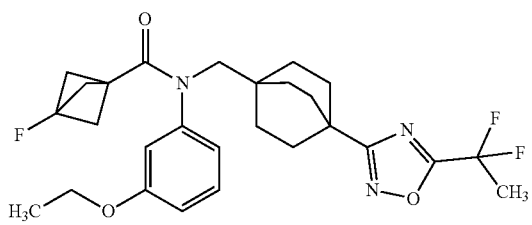

(130)

Step A. Intermediate 130A. Preparation of N-((4-(5-(1,1-difluoroethyl)-1,2,4-oxadiazol-3-yl)bicyclo[2.2.2]octan-1-yl)methyl)-3-ethoxyaniline

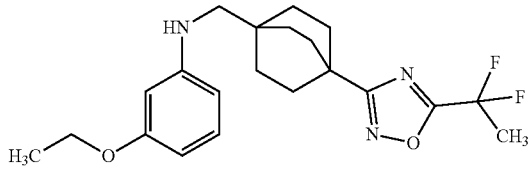 [SMILES: CCOc1cccc(NCC23CCC(c4noc(C(C)(F)F)n4)(CC2)CC3)c1]

The title compound was synthesized according to the method described for the synthesis of Intermediate 1G by substituting Intermediate 1F and 3-ethoxyaniline where appropriate. (30 mg, 0.073 mmol, 66% yield) as off-white solid. MS (ESI) 392 (M+H).

Step B. Example 130. Preparation of N-((4-(5-(1,1-difluoroethyl)-1,2,4-oxadiazol-3-yl)bicyclo[2.2.2]octan-1-yl)methyl)-N-(3-ethoxyphenyl)-3-fluorobicyclo[1.1.1]pentane-1-carboxamide The title compound was synthesized according to the method described for the synthesis of Example 1 by substituting Intermediate 130A and corresponding acid where appropriate. (12 mg, 0.024 mmol, 47% yield). $^1$H NMR (400 MHz, DMSO-d$_6$) δ 7.39-7.29 (m, 1H), 7.00-6.88 (m, 3H), 4.14-4.00 (m, 2H), 3.65-3.56 (m, 1H), 3.51-3.42 (m, 1H), 2.14 (t, J=19.6 Hz, 3H), 1.95-1.82 (m, 6H), 1.82-1.70 (m, 6H), 1.51-1.40 (m, 6H), 1.34 (t, J=6.9 Hz, 3H). FXR EC$_{50}$ (nM)=91. MS (ESI) 504 (M+H).

Example 131

(S)-1-(3-bromophenyl)-1-((4-(5-(1,1-difluoroethyl)-1,2,4-oxadiazol-3-yl) bicyclo[2.2.2]octan-1-yl) methyl)-3-(2-fluoro-3-hydroxy-3-methylbutyl)urea

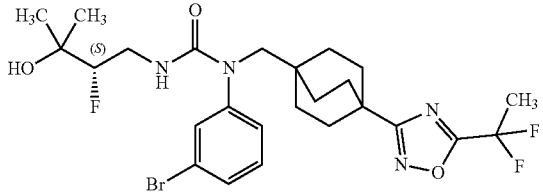

(131)

The title compound was prepared according to method described for the synthesis of Example 30 by substituting Intermediate 30A and (S)-4-amino-3-fluoro-2-methylbutan-2-ol where appropriate: (1.2 mg, 2.093 µmol, 9% yield). $^1$H NMR (400 MHz, DMSO-d$_6$) δ 7.54 (s, 1H), 7.43 (td, J=2.1, 6.5 Hz, 1H), 7.38-7.29 (m, 2H), 7.24-6.92 (m, 1H), 5.91 (t, J=5.5 Hz, 1H), 4.66 (br. s., 1H), 4.26-4.11 (m, 1H), 3.61-3.49 (m, 2H), 3.20-3.08 (m, 1H), 2.13 (t, J=19.7 Hz, 3H), 1.82-1.70 (m, 6H), 1.45-1.33 (m, 6H), 1.08 (s, 6H). FXR EC$_{50}$ (nM)=228. MS (ESI) 573 (M+H).

Example 132

N-(3-bromophenyl)-N-((4-(3-(tert-butyl)-1,2,4-oxadiazol-5-yl)bicyclo[2.2.1]heptan-1-yl) methyl)-3-fluorobicyclo[1.1.1]pentane-1-carboxamide

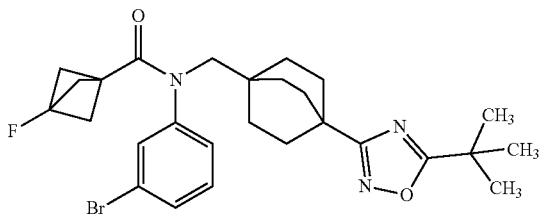

(132)

Step A. Intermediate 132A. Preparation of dimethyl bicyclo[2.2.1]heptane-1,4-dicarboxylate

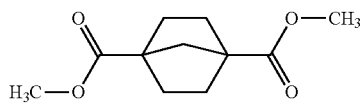

A solution of diisopropylamine (24.52 mL, 172 mmol) in THF (230 mL) was cooled to –20° C. and a 2.5 M solution of n-butyllithium in hexane (45.3 mL, 113 mmol) was added dropwise. The mixture was stirred at –20° C. for 20 min and then cooled to –78° C. To this solution, dry hexamethylphosphoramide (63.0 mL, 362 mmol) was added dropwise. A solution of dimethyl cyclopentane-1,3-dicarboxylate (8.43 g, 45.3 mmol) in THF (40 mL) was added dropwise over a period of 20 min and the reaction mixture was allowed to warm up to 0° C. and stirred for 20 min. The reaction mixture was cooled again to 78° C. and 1-bromo-2-chloroethane (6.78 mL, 81 mmol) was added over a period of 20 min. The cooling bath was removed and the mixture was allowed to warm up to room temperature over a period of 6 h. The reaction mixture was then quenched with aq. saturated NH₄Cl (100 mL), concentrated under reduced pressure to ⅕ volume and diluted with H₂O (120 mL). The aqueous phase was separated and extracted with EtOAc (3×100 mL). The combined organic extracts were washed with water (100 mL), brine (100 mL), dried over MgSO₄, filtered, and concentrated under reduced pressure. The crude compound was purified by flash chromatography (80 g silica gel cartridge; A=Hex, B=EtOAc; 30 min grad.; 0% B to 70% B; flow rate=40 mL/min). The pure fractions were combined, concentrated under reduced pressure and dried in vacuo to afford the title compound (4.2 g, 19.79 mmol, 44% yield) as an off white semi solid. MS (ESI) 213 (M+H).

Step B. Intermediate 132B. Preparation of 4-(methoxycarbonyl)bicyclo[2.2.1]heptane-1-carboxylic Acid

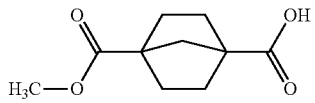

Intermediate 132A (3.5 g, 16.49 mmol) was dissolved in THF (100 mL) and a solution of sodium hydroxide (0.660 g, 16.49 mmol) in MeOH (10 mL) was added dropwise. The reaction mixture was stirred overnight at room temperature. Solvents were evaporated under reduced pressure without heating. The residue was dissolved in water (20 mL) and extracted with CH₂Cl₂ (3×15 mL). The aqueous layer was acidified with 6 N HCl until pH=3. The resulting aqueous solution was extracted with DCM (4×50 mL). The combined organic extracts were dried over anhydrous sodium sulphate, filtered and concentrated under reduced pressure to afford the title compound (2.6 g, 13.12 mmol, 80% yield) as an off-white semi solid. MS (ESI) 197 (M−H).

Step C. Intermediate 132C. Preparation of methyl 4-(3-(tert-butyl)-1,2,4-oxadiazol-5-yl)bicyclo[2.2.1]heptane-1-carboxylate

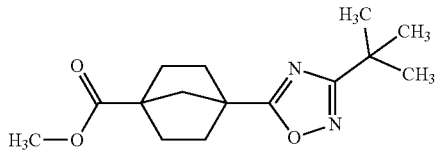

The title compound was prepared according to the method described for the synthesis of Intermediate 1D by substituting Intermediate 132B and N'-hydroxypivalimidamide where appropriate. (900 mg, 3.23 mmol, 51% yield). MS (ESI) 279 (M+H).

Step D. Intermediate 132D. Preparation of (4-(3-(tert-butyl)-1, 2, 4-oxadiazol-5-yl) bicyclo[2.2.1]heptan-1-yl) methanol

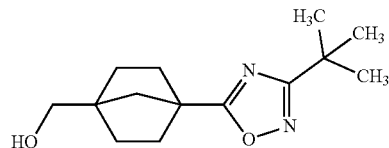 [SMILES: CC(C)(C)c1noc(C23CCC(CO)(CC2)C3)n1]

The title compound was prepared according to the method described for the synthesis of Intermediate 1E by substituting Intermediate 132C where appropriate. (0.9 g, 3.60 mmol, 77% yield) as an off-white solid. ¹H NMR (400 MHz, DMSO-d₆) δ 4.53 (t, J=6.40 Hz, 1H), 3.49 (d, J=5.60 Hz, 2H), 1.98-2.02 (m, 2H), 1.81-1.84 (m, 5H), 1.71-1.79 (m, 2H), 1.24-1.37 (m, 10H).

Step E. Intermediate 132E Preparation of 4-(3-(tert-butyl)-1,2,4-oxadiazol-5-yl) bicyclo[2.2.1]heptane-1-carbaldehyde

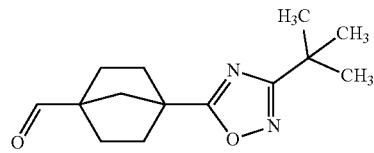 [SMILES: CC(C)(C)c1noc(C23CCC(C=O)(CC2)C3)n1]

The title compound was prepared according to the method described for the synthesis of Intermediate 1F by substituting Intermediate 132D where appropriate. (0.4 g, 1.611 mmol, 58% yield). ¹H NMR (400 MHz, CDCl₃) δ 9.89 (s, 1H), 2.16-2.29 (m, 4H), 1.96-2.01 (m, 4H), 1.67-1.69 (m, 2H), 1.40 (s, 9H).

Step F. Intermediate 132F Preparation of 3-bromo-N-((4-(3-(tert-butyl)-1,2,4-oxadiazol-5-yl)bicyclo[2.2.1]heptan-1-yl)methyl)aniline

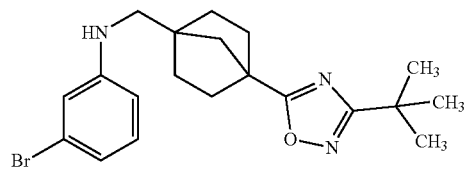 [SMILES: CC(C)(C)c1noc(C23CCC(CNc4cccc(Br)c4)(CC2)C3)n1]

The title compound was prepared according to the method described for the synthesis of Intermediate 1G by substituting Intermediate 132E and 3-bromo aniline where appropriate: (320 mg, 0.791 mmol, 66% yield). MS (ESI) 404 (M+H).

Step G. Example 132. Preparation of N-(3-bromophenyl)-N-((4-(3-(tert-butyl)-1,2,4-oxadiazol-5-yl)bicyclo[2.2.1]heptan-1-yl)methyl)-3-fluorobicyclo[1.1.1]pentane-1-carboxamide The title compound was prepared according to method described for the synthesis of Example 1 by substituting Intermediate 132F and corresponding acid where appropriate: (5.6 mg, 10.84 µmol, 22% yield). $^1$H NMR (400 MHz, DMSO-$d_6$) δ 7.74 (s, 1H), 7.66-7.58 (m, 1H), 7.49-7.33 (m, 2H), 4.05-3.72 (m, 2H), 2.05-1.79 (m, 8H), 1.78-1.69 (m, 2H), 1.67-1.49 (m, 4H), 1.42-1.31 (m, 2H), 1.28 (s, 9H). FXR $EC_{50}$ (nM)=498. MS (ESI) 516 (M+H).

Example 133

(1s, 3s)-N-(3-bromophenyl)-N-((4-(3-(tert-butyl)-1,2,4-oxadiazol-5-yl)bicyclo[2.2.1]heptan-1-yl)methyl)-3-hydroxy-3-(trifluoromethyl) cyclobutane-1-carboxamide (133)

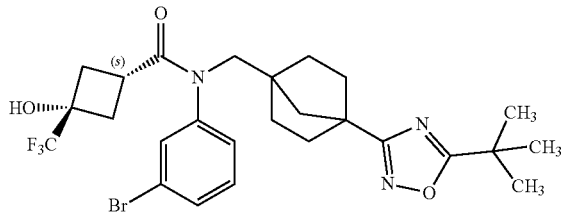

The title compound was prepared according to method described for the synthesis of Example 1 by substituting Intermediate 132F where appropriate: (2 mg, 3.51 µmol, 10% yield). $^1$H NMR (400 MHz, DMSO-$d_6$) δ 7.73 (s, 1H), 7.61-7.52 (m, 1H), 7.48-7.34 (m, 2H), 6.54 (s, 1H), 3.96 (s, 2H), 3.17 (d, J=5.1 Hz, 1H), 2.72 (br t, J=8.9 Hz, 1H), 2.37-2.30 (m, 2H), 2.11-2.03 (m, 2H), 2.00-1.90 (m, 2H), 1.76-1.67 (m, 2H), 1.66-1.56 (m, 2H), 1.53 (s, 2H), 1.40-1.23 (m, 12H). FXR $EC_{50}$ (nM)=4000. MS (ESI) 570 (M+H).

Example 134

N-(3-bromophenyl)-N-((4-(5-(2-fluoropropan-2-yl)-1,2,4-oxadiazol-3-yl)bicyclo[2.2.2]octan-1-yl)methyl)-3-(2-hydroxypropan-2-yl)bicyclo[1.1.1]pentane-1-carboxamide (134)

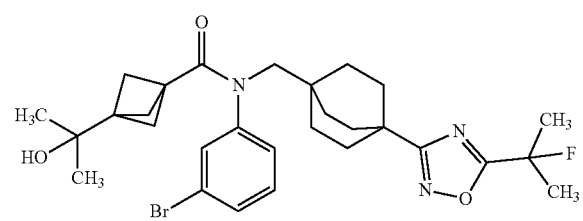

Step A. Intermediate 134A. Preparation of 3-bromo-N-((4-(5-(2-fluoropropan-2-yl)-1,2,4-oxadiazol-3-yl)bicyclo[2.2.2]octan-1-yl)methyl) aniline

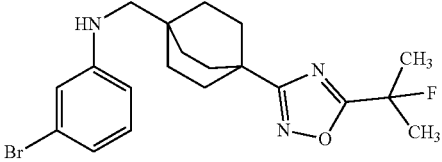 [SMILES: CC(C)(F)c1nc(C23CCC(CNc4cccc(Br)c4)(CC2)CC3)no1]

The title compound was prepared according to the method described for the synthesis of Intermediate 1G by substituting Intermediate 95C and 3-bromo aniline where appropriate: (650 mg, 1.539 mmol, 82% yield). MS (ESI) 422 (M+H).

Step B. Intermediate 134B. Preparation of methyl 3-((3-bromophenyl)((4-(5-(2-fluoropropan-2-yl)-1,2,4-oxadiazol-3-yl)bicyclo[2.2.2]octan-1-yl)methyl)carbamoyl) bicyclo[1.1.1]pentane-1-carboxylate

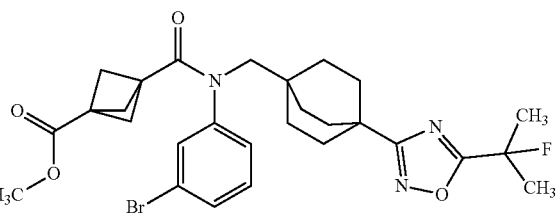

The title compound was prepared according to method described for the synthesis of Example 1 by substituting Intermediate 134A and corresponding acid where appropriate: (290 mg, 0.505 mmol, 71% yield). MS (ESI) 574 (M+H).

Step C. Example 134. Preparation of N-(3-bromophenyl)-N-((4-(5-(2-fluoropropan-2-yl)-1,2,4-oxadiazol-3-yl)bicyclo[2.2.2]octan-1-yl)methyl)-3-(2-hydroxypropan-2-yl) bicyclo[1.1.1]pentane-1-carboxamide To a solution of Intermediate 134B (30 mg, 0.052 mmol) in THF (5 mL) at −78° C., 3 M methylmagnesium chloride in $Et_2O$ (0.174 mL, 0.522 mmol) was added dropwise. The reaction mixture was stirred at −78° C. for 30 min. The reaction mixture was quenched by adding aq. saturated $NH_4Cl$ (10 mL). The resulting aqueous solution was extracted with ethyl acetate (2×10 mL). The combined organic extracts were washed with brine solution (15 mL), dried over anhydrous sodium sulphate, filtered and concentrated under reduced pressure. The crude material was purified via preparative LC/MS with the following conditions: Column: Waters XBridge C18, 150 mm×19 mm, 5-µm particles; Mobile Phase A: 5:95 acetonitrile: water with 10-mM ammonium acetate; Mobile Phase B: 95:5 acetonitrile: water with 10-mM ammonium acetate; Gradient: a 2-minute hold at 15% B, 15-57% B over 25 minutes, then a 5-minute hold at 100% B; Flow Rate: 15 mL/min; Column Temperature: 25° C. Fraction collection was triggered by signals. Fractions containing the desired product were combined and dried via centrifugal evaporation to afford the title compound (4 mg, 6.96 μmol, 13% yield) as an off-white solid. $^1$H NMR (400 MHz, DMSO-$d_6$) δ 7.66-7.63 (m, 1H), 7.57 (dt, J=6.9, 1.7 Hz, 1H), 7.46-7.35 (m, 2H), 4.03 (s, 1H), 3.62-3.43 (m, 2H), 1.82-1.70 (m, 12H), 1.46-1.34 (m, 12H), 0.86 (s, 6H). FXR $EC_{50}$ (nM)=434. MS (ESI) 574 (M+H).

Example 135

N-(3-cyano-5-fluorophenyl)-N-((4-(5-(1,1-difluoro-ethyl)-1,2,4-oxadiazol-3-yl) bicyclo[2.2.2]octan-1-yl)methyl)-3-fluorobicyclo[1.1.1]pentane-1-carboxamide (135)

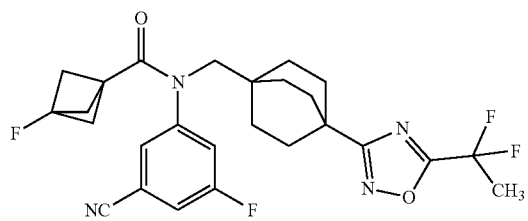

Step A. Intermediate 135A. Preparation of 3-(((4-(5-(1,1-difluoroethyl)-1,2,4-oxadiazol-3-yl)bicyclo[2.2.2]octan-1-yl)methyl)amino)-5-fluorobenzonitrile The title compound was prepared according to method described for the synthesis of Intermediate 1G by substituting Intermediate 1F and commercially available 3-amino-5-fluorobenzonitrile where appropriate: (80 mg, 0.205 mmol, 56% yield). MS (ESI) 391 (M+H).

Step B. Example 135. Preparation of N-(3-cyano-5-fluorophenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide The title compound was prepared according to method described for the synthesis of Example 1 by substituting Intermediate 135A where appropriate: (7.3 mg, 0.015 mmol, 28% yield). $^1$H NMR (400 MHz, DMSO-$d_6$) δ 7.98 (s, 1H), 7.95-7.87 (m, 2H), 3.65-3.47 (m, 2H), 2.14 (t, J=19.7 Hz, 3H), 1.93 (br s, 6H), 1.84-1.66 (m, 6H), 1.47-1.35 (m, 6H). FXR $EC_{50}$ (nM)=18, MS (ESI) 503 (M+H).

The following examples were synthesized according to the method described for the synthesis of Example 1 by substituting Intermediate 135A and corresponding acid where appropriate.

| Ex. | Structure & Name | MS (ESI) (M + H) | FXR $EC_{50}$ (nM) |
| --- | --- | --- | --- |
| 136 | 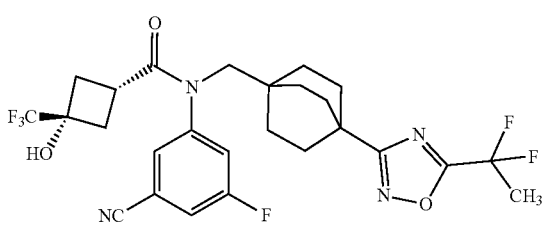 [SMILES: CC(F)(F)c1nc(C23CCC(CN(c4cc(F)cc(C#N)c4)C(=O)[C@H]4C[C@](O)(C(F)(F)F)C4)(CC2)CC3)no1]<br>(1S,3S)-N-(3-cyano-5-fluorophenyl)-N-((4-(5-(1,1-difluoroethyl)-1,2,4-oxadiazol-3-yl)bicyclo[2.2.2]octan-1-yl)methyl)-3-hydroxy-3-(trifluoromethyl)cyclobutane-1 | 557 | 256 |
| 137 | 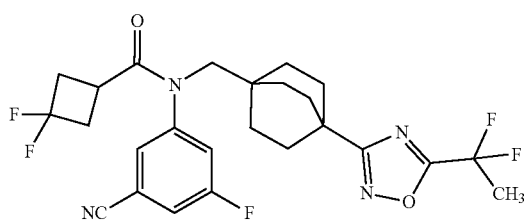 [SMILES: CC(F)(F)c1nc(C23CCC(CN(C(=O)C4CC(F)(F)C4)c4cc(F)cc(C#N)c4)(CC2)CC3)no1]<br>N-(3-cyano-5-fluorophenyl)-N-((4-(5-(1,1-difluoroethyl)-1,2,4-oxadiazol-3-yl)bicyclo[2.2.2]octan-1-yl)methyl)-3,3-difluorocyclobutane-1-carboxamide | 509 | 103 |

-continued

| Ex. | Structure & Name | MS (ESI) (M + H) | FXR EC$_{50}$ (nM) |
|---|---|---|---|
| 138 | 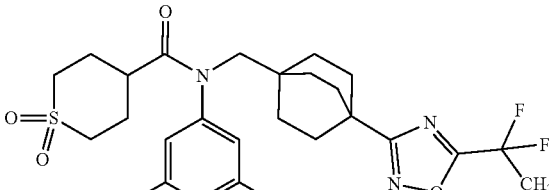 N-(3-cyano-5-fluorophenyl)-N-((4-(5-(1,1-difluoroethyl)-1,2,4-oxadiazol-3-yl)bicyclo[2.2.2]octan-1-yl)methyl)tetrahydro-2H-thiopyran-4-carboxamide 1,1-dioxide | 551 | 4000 |
| 136 | $^1$H NMR (400 MHz, DMSO-d$_6$) δ 7.98-7.75 (m, 3H), 3.62 (s, 2H), 3.08-2.92 (m, 1H), 2.83-2.67 (m, 2H), 2.43-2.28 (m, 2H), 2.13 (t, J = 19.7 Hz, 3H), 1.86-1.67 (m, 6H), 1.48-1.31 (m, 6H) | | |
| 137 | $^1$H NMR (400 MHz, DMSO-d$_6$) δ 7.98-7.75 (m, 3H), 3.62 (s, 2H), 3.08-2.92 (m, 1H), 2.83-2.67 (m, 2H), 2.43-2.28 (m, 2H), 2.13 (t, J = 19.7 Hz, 3H), 1.86-1.67 (m, 6H), 1.48-1.31 (m, 6H) | | |
| 138 | $^1$H NMR (400 MHz, DMSO-d$_6$) δ 8.02-7.81 (m, 3H), 3.58 (br s, 2H), 3.13-2.87 (m, 4H), 2.70-2.60 (m, 1H), 2.21-2.07 (m, 3H), 2.05-1.88 (m, 4H), 1.85-1.66 (m, 6H), 1.50-1.29 (m, 6H) | | |

Example 139

3-(4-(((1S,3S)—N-(3-bromophenyl)-3-hydroxy-3-(trifluoromethyl)cyclobutane-1-carboxamido)methyl)bicyclo[2.2.2]octan-1-yl)-1,2,4-oxadiazole-5-carboxamide (139)

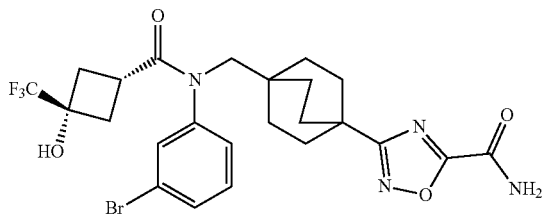

Step A. Intermediate 139A. Preparation of 4-(((3-bromophenyl)amino)methyl) bicyclo[2.2.2]octane-1-carboxylic Acid

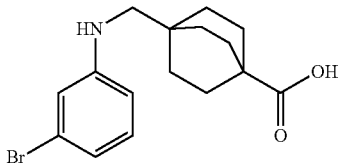 [SMILES: O=C(O)C12CCC(CNc3cccc(Br)c3)(CC1)CC2]

The title compound was synthesized according to the method described for the synthesis of Intermediate 28C by substituting Intermediate 33C where appropriate: (1.9 g, 5.62 mmol, 99% yield) as white solid. MS (ESI) 338 (M+H).

Step B. Intermediate 139B. Preparation of 4-(((3-bromophenyl)amino)methyl) bicyclo[2.2.2]octane-1-carboxamide

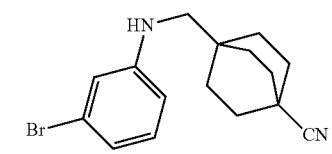 [SMILES: N#CC12CCC(CNc3cccc(Br)c3)(CC1)CC2]

The title compound was synthesized according to the method described for the synthesis of Intermediate 1A by substituting Intermediate 139A where appropriate: (2.0 g, 5.93 mmol, 100% yield). MS (ESI) 338 (M+H).

Step C. Intermediate 139C. Preparation of 4-(((3-bromophenyl)amino)methyl) bicyclo[2.2.2]octane-1-carbonitrile To a stirred solution of Intermediate 139B (2.0 g, 5.93 mmol) in pyridine (50 mL) was added imidazole (1.009 g, 14.83 mmol) and cooled 0° C. To the cooled solution was added POCl$_3$ (0.608 mL, 6.52 mmol) drop wise and the reaction mixture was gradually allowed to warm up to room temperature over 5 h. The reaction mixture was diluted with cold water (100 mL) and extracted with ethyl acetate (2×70 mL). The combined organic layers were washed with aq. 1.5N HCl solution (4×50 mL), water (100 mL) and saturated brine solution (100 mL). The organic layer was dried over anhydrous sodium sulfate, filtered and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (1.0 g, 3.13 mmol, 53% yield) as white solid. MS (ESI) 336 (M+18) (NH$_4$ adduct).

Step D. Intermediate 139D. Preparation of (Z)-4-(((3-bromophenyl)amino)methyl)-N'-hydroxybicyclo[2.2.2]octane-1-carboximidamide

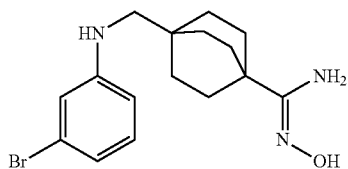 [SMILES: N/C(=N\O)C12CCC(CNc3cccc(Br)c3)(CC1)CC2]

The title compound was synthesized according to the method described for the synthesis of Intermediate 1C by substituting Intermediate 139C where appropriate: (1.0 g, 2.84 mmol, 91% yield) as white solid. MS (ESI) 352 (M+H).

Step E. Intermediate 139E. Preparation of 3-(4-(((3-bromophenyl)amino)methyl)bicyclo [2.2.2]octan-1-yl)-1,2,4-oxadiazole-5-carboxamide

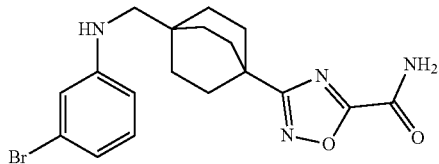 [SMILES: NC(=O)c1nc(C23CCC(CNc4cccc(Br)c4)(CC2)CC3)no1]

The title compound was synthesized according to the method described for the synthesis of Intermediate 1D by substituting Intermediate 139D and 2-amino-2-oxoacetic acid where appropriate: (210 mg, 52% yield) as off white solid. MS (ESI) 405 (M+H).

Step F. Example 139. Preparation of Preparation of 3-(4-(((1S,3S)—N-(3-bromophenyl)-3-hydroxy-3-(trifluoromethyl)cyclobutane-1-carboxamido)methyl)bicyclo[2.2.2]octan-1-yl)-1,2,4-oxadiazole-5-carboxamide The title compound was prepared according to method described for the synthesis of Example 1 by substituting Intermediate 139E and corresponding acid where appropriate: (12.8 mg, 0.02 mmol, 99% yield). $^1$H NMR (400 MHz, DMSO-d$_6$) δ 8.56 (br d, J=2.9 Hz, 1H), 8.40-8.23 (m, 1H), 7.71 (s, 1H), 7.55 (br d, J=7.6 Hz, 1H), 7.48-7.30 (m, 2H), 6.63-6.48 (m, 1H), 3.69-3.53 (m, 2H), 3.18 (s, 1H), 2.79-2.67 (m, 1H), 2.39-2.27 (m, 2H), 2.14-1.97 (m, 2H), 1.86-1.69 (m, 6H), 1.50-1.29 (m, 6H). FXR EC$_{50}$ (nM)=1450, MS (ESI) 573 (M+H).

Example 140

3-(4-((N-(3-bromophenyl)-3-fluorobicyclo[1.1.1]pentane-1-carboxamido)methyl)bicyclo[2.2.2]octan-1-yl)-1,2,4-oxadiazole-5-carboxamide (140)

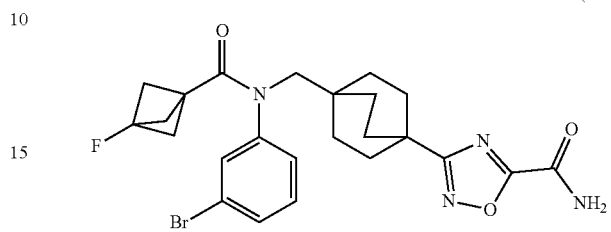

The title compound was prepared according to method described for the synthesis of Example 1 by substituting Intermediate 139E and corresponding acid where appropriate: (28 mg, 0.05 mmol 44% yield). $^1$H NMR (400 MHz, DMSO-d$_6$) δ 8.60-8.49 (m, 1H), 8.32 (br d, J=1.2 Hz, 1H), 7.71 (s, 1H), 7.65-7.56 (m, 1H), 7.49-7.36 (m, 2H), 3.63-3.49 (m, 2H), 1.97-1.67 (m, 10H), 1.52-1.29 (m, 6H). FXR EC$_{50}$ (nM)=721, MS (ESI) 519 (M+H).

Biological Evaluation

The exemplified compounds of the present invention were tested in the transient human FXR/Gal4-luciferase reporter assay, and assay results were reported in Table 1 and Examples 1 to 3 together with other analytical data.

A Gal4-hFXR fusion construct reporter system was used as the primary assay to characterize compound activity. A construct including 5 copies of the Gal4 promoter response element upstream of a firefly luciferase reporter cDNA was stably expressed in HEK293 cells. This reporter cell line was maintained in Dulbecco's Modified Eagle's medium (DMEM; Gibco) supplemented with 1% penicillin-streptomycin (P/S) solution, 500 μg/mL Zeocin and 10% charcoal/dextran-treated fetal bovine serum (cs-FBS) at 37° C. in a humidified 5% CO$_2$ atmosphere. Another plasmid was constructed in which the human cytomegalovirus promoter in the pcDNA3.1 vector directs the expression of the cDNA encoding a fusion protein comprised of the DNA binding domain from the Gal4 transcription factor fused to the ligand binding domain from human FXR.

The day prior to transfection, the reporter cells in culture are detached from the plate with trypsin and plated into a T75 flask at a sufficient density to achieve approximately 90% confluence the next morning. The transfection reagents are prepared by separately diluting 25 μg of the pcDNA3.1-Gal4-FXR plasmid into 1.87 mL of Opti-MEM (Thermo-Fisher), and 40 μL of Lipofectamine 2000 (Thermo-Fisher) into 1.87 mL of Opti-MEM, and then adding the diluted DNA solution into the diluted Lipofectamine 2000 solution and incubating at room temperature for 15-20 minutes. The mixture is further diluted with 10 mL of a solution comprised of DMEM, 10% cs-FBS, and 1% P/S immediately prior to transferring to the cells. The maintenance culture media is aspirated from the cells and the final transfection mixture is added before the cells are incubated overnight at 37° C. in a humidified 5% CO$_2$ atmosphere. This protocol can be scaled up, and the transiently transfected cells can be cryopreserved in an assay-ready format.

For compound testing, 100 nL of the compounds (serial dilutions in DMSO) are dispensed with an Echo acoustic dispenser (Labcyte) into the wells of a Corning/Costar clear bottom 384-well white plate. The transfected cells are harvested, counted, and diluted such that 10-25,000 cells in 25 µL are plated into each well of the 384-well compound assay plate. The compound-treated cells are incubated overnight at 37° C. in a humidified 5% $CO_2$ atmosphere. The next morning 25 µL of Steady-Glo (Promega) are added to each well of the plate, the mixture is incubated for 15 min. with shaking, and luminescence is measured on an Envision (Perkin Elmer) plate reader. Background counts from cells treated with DMSO alone are subtracted from all raw counts, and the corrected values are converted to a percentage of the control response attained with 8 µM GW-4064. These data are fit to a 4-parameter log agonist-response equation to calculate an $EC_{50}$ value.

In Vivo Testing Example: Acute Mouse PK/PD

Male, C57BL6/NTac mice, weighing 25-28 g, are purchased from Taconic Labs (Hudson, NY) and maintained on Teklad Global 18% Protein Rodent Diet (Harlan Laboratories). After 1 week acclimation, mice are sorted into groups based upon body weight. Mice are administered a single oral dose of vehicle or experimental compound. Systemic compound exposure is evaluated in plasma derived from blood collected via the submandibular vein at 1 hour post-dose, and at study termination (6 h). At study termination, the animals are euthanized and rapidly dissected. The medial lobe of the liver is divided, with one half being homogenized and analyzed for compound exposure, and the other half saved in RNAlater (Thermo-Fisher Scientific). The ileum is also dissected and preserved in RNAlater. Tissue samples in RNAlater are homogenized with MP Biomedicals' beads. RNA is extracted using the MagMax-96 Total RNA Isolation kit (Thermo-Fisher Scientific) according to the manufacturer's protocol. RNA Concentration is determined with the Nano-Drop 8000 Spectrophotometer (Thermo Fisher). Reverse transcription is done with Invitrogen's SuperScript® VILO cDNA Synthesis Kit according to the manufacturer's protocol. Real time PCR is done with Applied Biosystems' Taqman PCR master mixture according to the manufacturer's protocol. All primers are purchased from Thermo-Fisher Scientific. Mouse genes analyzed include Nr0b2 (which encodes the small heterodimer partner, SHP), Abcb11 (which encodes the bile salt excretion pump, BSEP), Cyp7a1, & Cyp8b1 in liver, and Fgf15, Fabp6 (which encodes ileal bile acid binding protein, I-BABP), Slc51a (which encodes organic solute transporter alpha subunit, OSTA), and Slc51b (which encodes organic solute transporter beta subunit, OSTB) in the ileum. The statistical significant changes in FGF15 gene expression are expressed as fold increase and CYP7A1 expression as a percent reduction relative to vehicle control.

Other features of the invention should become apparent in the course of the above descriptions of exemplary embodiments that are given for illustration of the invention and are not intended to be limiting thereof. The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

What is claimed is:
1. A compound of Formula (I):

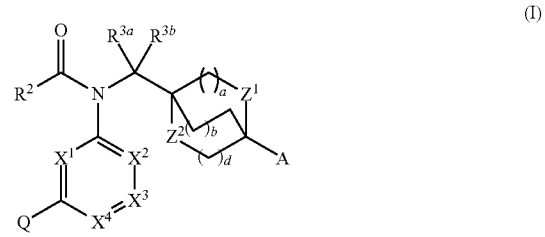

or a stereoisomer, a tautomer, or a salt or solvate thereof, wherein:

$X^1$ is $CR^{5a}$;
$X^2$ is $CR^{5b}$;
$X^3$ is $CR^{5c}$;
$X^4$ is $CR^{5d}$;
$Z^1$ and $Z^2$ are each $CH_2$;
a is zero or 1;
b is zero, 1, or 2;
d is zero, 1, or 2;
Q is:
(i) halo, cyano, hydroxyl, —$NR^xR^x$, —C(O)OH, —$C(O)NH_2$, $C_{1-6}$ alkyl substituted with zero to 6 $R^{1a}$, or —$P(O)R^{1c}R^{1c}$, or
(ii) -L-$R^1$;
L is —O—, —$OCR^{1d}R^{1d}C(O)$—, —C(O)—, —C(O)O—, —$C(O)NR^{1e}$—, —$C(O)NR^{1e}C(O)$—, —$NR^{1e}$—, —$NR^{1e}C(O)$—, —$NR^{1e}C(O)O$—, —$NR^{1e}C(O)NR^{1e}$—, —$NR^{1e}S(O)_2$—, —$S(O)_2$—, or —$S(O)_2NR^{1e}$—;
$R^1$ is $C_{1-6}$ alkyl substituted with zero to 6 $R^{1a}$, or a cyclic group selected from 3- to 8-membered carbocyclyl, 6- to 10-membered aryl, 4- to 10-membered heterocyclyl, and 5- to 10-membered heteroaryl, wherein said cyclic group is substituted with zero to 3 $R^{1b}$;
each $R^{1a}$ is independently halo, hydroxyl, —$NR^wR^w$, oxo, cyano, $C_{1-3}$ alkoxy, $C_{1-3}$ haloalkoxy, —$C(O)OR^x$, —$C(O)NR^wR^w$, or —$NR^xC(O)R^y$;
each $R^{1b}$ is independently halo, oxo, cyano, hydroxyl, —$NH_2$, $C_{1-6}$ alkyl, $C_{1-6}$ alkoxy, —$NH(C_{1-6}$ alkyl), —$N(C_{1-6}$ alkyl$)_2$, —$NR^cC(O)(C_{1-6}$ alkyl), or $C_{3-6}$ cycloalkyl, wherein each of said alkyl, alkoxy, and cycloalkyl is substituted with zero to 6 $R^{1a}$,
each $R^{1c}$ is independently $C_{1-6}$ alkyl;
each $R^{1d}$ is independently hydrogen, halo, $C_{1-3}$ alkyl, or $C_{3-6}$ cycloalkyl;
each $R^{1e}$ is independently hydrogen, $C_{1-3}$ alkyl, or $C_{3-6}$ cycloalkyl;
$R^2$ is:
(i) $C_{1-6}$ alkyl, $C_{2-6}$ alkenyl, $C_{2-6}$ alkynyl, $C_{1-6}$ alkoxy, or —$NR^vR^v$, wherein each of said alkyl, alkenyl, alkynyl, and alkoxy is substituted with zero to 6 $R^{2a}$;
(ii) $C_{3-8}$ carbocyclyl, $C_{6-8}$ spirobicyclyl, 4- to 7-membered heterocyclyl, phenyl, or 5- to 6-membered heteroaryl, wherein each of said carbocyclyl, spirobicyclyl, heterocyclyl, phenyl, and heteroaryl is substituted with zero to 3 $R^{2b}$; or
(iii) —$CH_2(C_{3-6}$ cycloalkyl), —$CH_2$(4- to 6-membered heterocyclyl), —$NR^x(CH_2)_{0-2}(C_{3-6}$ cycloalkyl), —$NR^x(CH_2)_{0-2}(C_{5-8}$ bicycloalkyl), —$NR^x(CH_2)_{0-2}(C_{5-8}$ spirobicycloalkyl), —$NR^x(CH_2)_{0-2}$(4- to 6-membered heterocyclyl), —$NR^x(CH_2)_{0-2}$(5- to 6-membered heteroaryl), —NR$^x$(CH$_2$)$_{0-2}$(phenyl), —O(CH$_2$)$_{0-2}$(C$_{3-6}$ cycloalkyl), —O(CH$_2$)$_{0-2}$(C$_{5-8}$ bicycloalkyl), —O(CH$_2$)$_{0-2}$(C$_{5-8}$ spirobicycloalkyl), —O(CH$_2$)$_{0-2}$(4- to 6-membered heterocyclyl), —O(CH$_2$)$_{0-2}$(5- to 6-membered heteroaryl), or —O(CH$_2$)$_{0-2}$(phenyl), wherein each of said cycloalkyl, heterocyclyl, bicycloalkyl, spirobicycloalkyl, aryl, and heteroaryl is substituted with zero to 3 R$^{2b}$;

each R$^{2a}$ is independently halo, alkyl, cyano, hydroxyl, C$_{1-3}$ haloalkyl, C$_{1-3}$ alkoxy, C$_{1-3}$ haloalkoxy, —NR$^x$R$^x$, —C(O)(C$_{1-6}$ alkyl), —C(O)(C$_{3-6}$ cycloalkyl), —NR$^x$C(O)R$^y$, —C(O)(C$_{1-6}$ alkyl), —C(O)OR$^x$, —C(O)NR$^w$R$^w$, —S(O)$_2$R$^y$, —S(O)$_2$(C$_{1-3}$ fluoroalkyl), —NR$^x$S(O)$_2$(C$_{1-3}$ alkyl), —NR$^x$S(O)$_2$(C$_{3-6}$ cycloalkyl), —S(O)$_2$NR$^z$R$^z$, or —P(O)R$^y$R$^y$;

each R$^{2b}$ is independently halo, cyano, hydroxyl, oxo, C$_{1-6}$ alkyl, C$_{1-6}$ alkoxy, —NR$^x$R$^x$, —NR$^x$C(O)O(C$_{1-3}$ alkyl), —C(O)(C$_{1-3}$ alkyl), or —S(O)$_2$(C$_{1-3}$ alkyl), wherein each of said alkyl and alkoxy is substituted with zero to 6 R$^{2a}$;

R$^{3a}$ and R$^{3b}$ are independently hydrogen, C$_{1-3}$ alkyl, C$_{1-3}$ haloalkyl, or C$_{3-6}$ cycloalkyl, or R$^{3a}$ and R$^{3b}$, taken together with the carbon atom to which they are attached, form a C$_{3-6}$ cycloalkyl;

A is:
(i) cyano;
(ii) phenyl or a 5- to 10-membered heteroaryl containing 1 to 4 heteroatoms independently selected from N, O, and S, wherein each of said phenyl and heteroaryl is substituted with zero to 3 R$^{4a}$; or (iii)

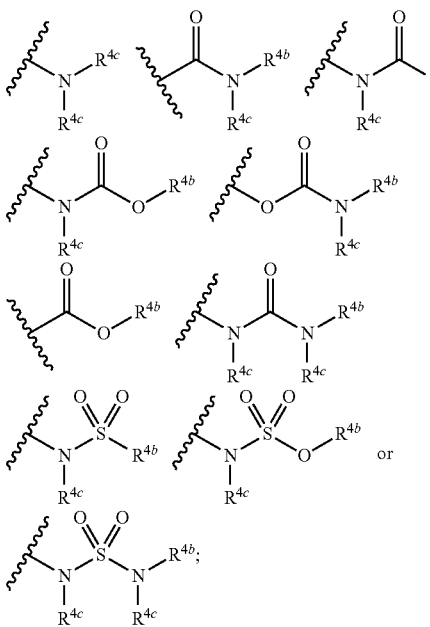

each R$^{4a}$ is independently halo, cyano, hydroxyl, —NH$_2$, C$_{1-6}$ alkyl, C$_{2-6}$ alkenyl, C$_{2-6}$ alkynyl, C$_{1-6}$ alkoxy, —(CH$_2$)$_{0-3}$NH(C$_{1-6}$ alkyl), —(CH$_2$)$_{0-2}$N(C$_{1-6}$ alkyl)$_2$, —(CH$_2$)$_{0-3}$(C$_{3-6}$ carbocyclyl), or —(CH$_2$)$_{0-3}$(4- to 6-membered heterocyclyl), wherein each of said alkyl, alkoxy, alkenyl, and alkynyl is substituted with zero to 6 R$^{4d}$ and each of said carbocyclyl and heterocyclyl is substituted with zero to 3 R$^{4e}$;

R$^{4b}$ is C$_{1-6}$ alkyl, —(CH$_2$)$_{0-3}$(C$_{3-6}$ cycloalkyl), or —(CH$_2$)$_{0-3}$(4- to 6-membered heterocyclyl), wherein each of said alkyl is substituted with zero to 6 R$^{4d}$ and each of said cycloalkyl and heterocyclyl is substituted with zero to 3 R$^{4e}$;

each R$^{4c}$ is independently hydrogen, C$_{1-6}$ alkyl, C$_{3-6}$ cycloalkyl, 4- to 6-membered heterocyclyl, phenyl, or 5- to 6-membered heteroaryl;

each R$^{4d}$ is independently halo, hydroxyl, —NR$^x$R$^x$, oxo, cyano, C$_{1-3}$ alkoxy, or C$_{1-3}$ haloalkoxy;

each R$^{4e}$ is independently halo, oxo, cyano, hydroxyl, —NH$_2$, C$_{1-6}$ alkyl, C$_{1-6}$ alkoxy, —NH(C$_{1-6}$ alkyl), or —N(C$_{1-6}$ alkyl)$_2$, wherein each of said alkyl and alkoxy is substituted with zero to 6 R$^{4d}$;

each of R$^{5a}$, R$^{5b}$, R$^{5c}$, and R$^{5d}$ is independently hydrogen, halo, hydroxy, cyano, C$_{1-6}$ alkyl substituted with zero to 6 R$^{5e}$, C$_{1-6}$ alkoxy substituted with zero to 6 R$^{5e}$, —C(O)OR$^x$, —C(O)NR$^w$R$^w$, —S(O)$_2$R$^y$, —S(O)$_2$NR$^z$R$^z$, or phenyl substituted with zero to 3 R$^{5f}$;

each of R$^{5e}$ is independently halo, hydroxyl, —NR$^x$R$^x$, oxo, cyano, C$_{1-3}$ alkoxy, or C$_{1-3}$ haloalkoxy;

each R$^{5f}$ is independently halo, oxo, cyano, hydroxyl, —NH$_2$, C$_{1-6}$ alkyl, C$_{1-6}$ alkoxy, —NH(C$_{1-6}$ alkyl), or —N(C$_{1-6}$ alkyl)$_2$, wherein each of said alkyl and alkoxy is substituted with zero to 6 R$^{5e}$;

each R$^v$ is independently hydrogen, C$_{1-6}$ alkyl, or alternatively, two R$^v$, taken together with the nitrogen atom to which they are attached, form a 4- to 7-membered bicyclic or spirocyclic ring moiety containing zero to 2 additional heteroatoms independently selected from N, O, and S, wherein each ring can be substituted with zero to 6 R$^{2a}$;

each R$^w$ is independently hydrogen, C$_{1-6}$ alkyl, or C$_{3-6}$ cycloalkyl; or alternatively, two R$^w$, taken together with the nitrogen atom to which they are attached, form a 4- to 7-membered ring moiety containing zero to 2 additional heteroatoms independently selected from N, O, and S;

each R$^x$ is independently hydrogen, C$_{1-6}$ alkyl, or C$_{3-6}$ cycloalkyl;

R$^y$ is C$_{1-6}$ alkyl or C$_{3-6}$ cycloalkyl; and each R$^z$ is independently hydrogen, C$_{1-6}$ alkyl, or C$_{3-6}$ cycloalkyl; or alternatively, two R$^z$, taken together with the nitrogen atom to which they are attached, form a 4- to 7-membered ring moiety containing zero to 2 additional heteroatoms independently selected from N, O, and S.

2. The compound according to claim 1 or a stereoisomer, a tautomer, or a salt or solvate thereof, wherein:
Q is:
(i) F, Cl, Br, cyano, hydroxyl, —NR$^x$R$^x$, —C(O)OH, —C(O)NH$_2$, C$_{1-4}$ alkyl substituted with zero to 6 R$^{1d}$, or —P(O)R$^{1c}$R$^{1c}$; or
(ii) -L-R$^1$;

L is —O—, —OCR$^{1a}$R$^{1a}$C(O)—, —C(O)—, —C(O)O—, —C(O)NR$^{1b}$—, —NR$^{1b}$—, —NR$^{1b}$C(O)—, —NR$^{1b}$C(O)NR$^{1b}$—, —NR$^{1b}$S(O)$_2$—, —S(O)$_2$—, or —S(O)$_2$NR$^{1b}$—;

R$^1$ is C$_{1-6}$ alkyl substituted with zero to 6 R$^{1a}$, or a cyclic group selected from C$_{3-6}$ cycloalkyl, phenyl, 4- to 10-membered heterocyclyl, and 5- to 10-membered heteroaryl, wherein said cyclic group is substituted with zero to 3 R$^{1b}$;

each R$^{1a}$ is independently F, Cl, hydroxyl, —NR$^w$R$^w$, oxo, cyano, C$_{1-3}$ alkoxy, C$_{1-3}$ haloalkoxy, —C(O)OH, or —C(O)O(C$_{1-2}$ alkyl);

each $R^{1b}$ is independently F, Cl, cyano, hydroxyl, oxo, —$NH_2$, $C_{1-4}$ alkyl, $C_{1-4}$ alkoxy, —$NH(C_{1-4}$ alkyl), —$N(C_{1-4}$ alkyl$)_2$, —$NR^xC(O)$ ($C_{1-6}$ alkyl), or $C_{3-4}$ cycloalkyl, wherein each of said alkyl, alkoxy, and cycloalkyl is substituted with zero to 6 $R^{1a}$, each $R^{1c}$ is independently $C_{1-4}$ alkyl;

$R^2$ is:
- (i) $C_{1-4}$ alkyl, $C_{1-4}$ alkoxy, or —$NR^vR^v$, wherein each of said alkyl and alkoxy is substituted with zero to 4 $R^{2a}$;
- (ii) $C_{3-8}$ carbocyclyl, $C_{6-8}$ spirobicyclyl, phenyl, or 4- to 7-membered heterocyclyl, wherein each of said carbocyclyl, spirobicyclyl, and heterocyclyl is substituted with zero to 3 $R^{2b}$; or
- (iii) —$CH_2(C_{3-5}$ cycloalkyl), —$CH_2$(4- to 6-membered heterocyclyl), —$NR^x(CH_2)_{0-2}(C_{3-5}$ cycloalkyl), —$NR^x(CH_2)_{0-2}$(4- to 6-membered heterocyclyl), —$NR^x(CH_2)_{0-2}$(phenyl), or —O(phenyl), wherein each of said cycloalkyl, heterocyclyl, phenyl, and pyridinyl is substituted with zero to 3 $R^{2b}$;

each $R^{2a}$ is independently F, Cl, hydroxyl, —$NR^xR^x$, cyano, $C_{1-3}$ alkoxy, $C_{1-3}$ haloalkoxy, or —C(O)OH;

each $R^{2b}$ is independently F, Cl, cyano, hydroxyl, $C_{1-4}$ alkyl, $C_{1-3}$ alkoxy, —$NR^xR^x$, —$NR^xC(O)O(C_{1-3}$ alkyl), —C(O)($C_{1-2}$ alkyl), or —$S(O)_2(C_{1-2}$ alkyl), wherein each of said alkyl and alkoxy is substituted with zero to 4 $R^{2a}$;

A is:
- (i) cyano;
- (ii) phenyl or a 5- to 6-membered heteroaryl containing zero to 4 heteroatoms independently selected from N, O, and S, wherein each of said phenyl and heteroaryl is substituted with zero to 3 $R^{4a}$; or (iii)

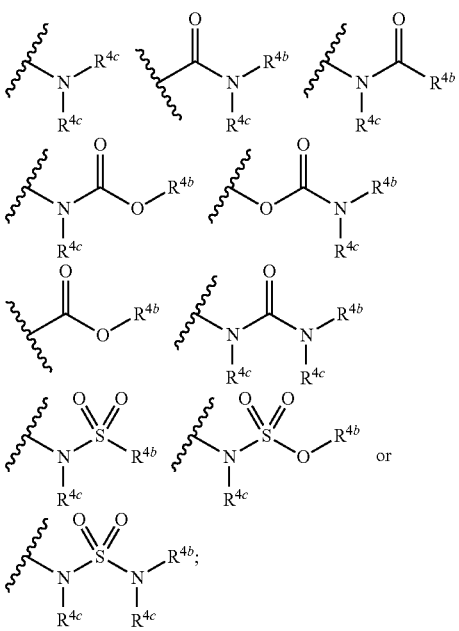

each $R^{4a}$ is independently F, Cl, cyano, hydroxyl, —$NH_2$, $C_{1-4}$ alkyl, $C_{1-4}$ alkoxy, —$(CH_2)_{0-3}NH(C_{1-6}$ alkyl), —$(CH_2)_{0-3}N(C_{1-6}$ alkyl$)_2$, —$(CH_2)_{0-3}(C_{3-6}$ carbocyclyl), or —$(CH_2)_{0-3}$(4- to 6-membered heterocyclyl), wherein each of said alkyl and alkoxy is substituted with zero to 4 $R^{4d}$; and each of said carbocyclyl and heterocyclyl is substituted with zero to 3 $R^{4e}$;

$R^{4b}$ is $C_{1-4}$ alkyl, —$(CH_2)_{0-3}(C_{3-6}$ cycloalkyl), or —$(CH_2)_{0-3}$(4- to 6-membered heterocyclyl), wherein each of said alkyl is substituted with zero to 4 $R^{4d}$ and each of said cycloalkyl and heterocyclyl is substituted with zero to 3 $R^{4e}$;

each $R^{4c}$ is independently hydrogen, $C_{1-3}$ alkyl, or $C_{3-6}$ cycloalkyl;

each $R^{4d}$ is independently F, Cl, hydroxyl, —$NR^xR^x$, oxo, cyano, $C_{1-3}$ alkoxy, or $C_{1-3}$ fluoroalkoxy;

each $R^{4e}$ is independently F, Cl, oxo, cyano, hydroxyl, —$NH_2$, $C_{1-4}$ alkyl, $C_{1-4}$ alkoxy, —$NH(C_{1-6}$ alkyl), or —$N(C_{1-6}$ alkyl$)_2$, wherein each of said alkyl and alkoxy is substituted with zero to 4 $R^{4d}$;

each of $R^{5a}$, $R^{5b}$, $R^{5c}$, and $R^{5d}$ is independently hydrogen, F, Cl, hydroxy, cyano, $C_{1-3}$ alkyl substituted with zero to 4 $R^{5e}$, $C_{1-3}$ alkoxy substituted with zero to 4 $R^{5e}$, —C(O)$OR^x$, —C(O)$NR^wR^w$, —$S(O)_2R^y$, —$S(O)_2NR^zR^z$, or phenyl substituted with zero to 3 $R^{5f}$;

each of $R^{5a}$, $R^{5b}$, $R^{5c}$, and $R^{5d}$ is independently hydrogen, F, Cl, hydroxy, cyano, $C_{1-3}$ alkyl substituted with zero to 4 $R^{5e}$, $C_{1-3}$ alkoxy substituted with zero to 4 $R^{5e}$, —C(O)$OR^x$, —C(O)$NR^wR^w$, —$S(O)_2R^y$, —$S(O)_2NR^zR^z$, or phenyl substituted with zero to 3 $R^{5f}$;

each $R^w$ is independently hydrogen, $C_{1-4}$ alkyl, or $C_{3-6}$ cycloalkyl; or alternatively, two $R^w$, taken together with the nitrogen atom to which they are attached, form a 4- to 7-membered ring moiety containing zero to 2 additional heteroatoms independently selected from N, O, and S;

each $R^x$ is independently H, $C_{1-4}$ alkyl, or $C_{3-6}$ cycloalkyl;

$R^y$ is $C_{1-4}$ alkyl or $C_{3-6}$ cycloalkyl; and each $R^z$ is independently hydrogen, $C_{1-4}$ alkyl, or $C_{3-6}$ cycloalkyl; or alternatively, two $R^z$, taken together with the nitrogen atom to which they are attached, form a 4- to 7-membered ring moiety containing zero to 2 additional heteroatoms independently selected from N, O, and S.

3. The compound according to claim 1 or a stereoisomer, a tautomer, or a salt or solvate thereof, wherein:

$X^1$ is CH;
$X^2$ is CH;
$X^3$ is CH;
$X^4$ is CH;

Q is:
- (i) F, Cl, Br, cyano, hydroxyl, —$CF_3$, —$C(CH_3)_2OH$, —$CH_2CH_2C(O)OCH_3$, —C(O)OH, —C(O)$NH_2$, or —$P(O)(CH_3)_2$; or
- (ii) -L-$R^1$;

L is —O—, —$OCR^{1a}R^{1a}C(O)O$—, —C(O)O—, —C(O)$NR^{1b}$—, —$NR^{1b}$—, —$NR^{1b}C(O)O$—, —$NR^{1b}S(O)_2$—, —$S(O)_2$—, or —$S(O)_2NR^{1b}$—;

$R^1$ is $C_{1-4}$ alkyl substituted with zero to $4R^{1a}$, $C_{3-4}$ cycloalkyl, or a cyclic group selected from phenyl, thiazolyl, pyridinyl, and pyrimidinyl, wherein said cyclic group is substituted with zero to 1 $R^{1b}$;

each $R^{1a}$ is independently F, cyano, hydroxyl, —C(O)OH, or —C(O) $OCH_3$;

each $R^{1b}$ is independently $C_{1-2}$ alkyl, $C_{1-2}$ fluoroalkyl, $C_{1-2}$ alkoxy, —$OC(CH_3)_2CN$, cyclopropyl, or cyano-cyclopropyl;

$R^2$ is —$NHCH_2C(CH_3)_2CH_2OH$, —$NHCH_2CH_2C(CH_3)_2$ OH, —NH(hydroxycyclohexyl), —NH(methyl-hydroxycyclohexyl), or a cyclic group selected from cyclopropyl, cyclobutyl, cyclohexyl, tetrahydropyranyl, bicyclo[1.1.1]pentyl, and dioxotetrahydrothiopyranyl, each cyclic group substituted with zero to 2 substituents independently selected from F, hydroxyl, oxo, —CH$_3$, —CF$_3$, and —C(CH$_3$)$_2$OH;

R$^{3a}$ is hydrogen or —CH$_3$;

R$^{3b}$ is hydrogen;

A is phenyl, pyrazolyl, oxadiazolyl, pyridinyl, or indazolyl, each substituted with zero to 3 heteroatoms independently selected from N, O, and S, substituted with zero to 2 R$^{4a}$;

each R$^{4a}$ is independently Cl, —CH$_3$, —CH$_3$, —C(CH$_3$)$_3$, —CF$_3$, —CF$_2$CH$_3$, —C(CH$_3$)$_2$F, —N(CH$_3$)$_2$, —C(O)NH$_2$, cyclopropyl, or fluorocyclopropyl; and each of R$^{5a}$, R$^{5b}$, R$^{5c}$, and R$^{5d}$ is independently hydrogen, F, Cl, cyano, —CH$_3$, or —CF$_3$.

4. The compound according to claim 1 or a stereoisomer, a tautomer, or a salt or solvate thereof, wherein R$^2$ is C$_{3-5}$ carbocyclic, —NR$^x$(CH$_2$)$_{0-2}$(C$_{3-6}$ cycloalkyl), or 4- to 5-membered heterocyclyl having 1 or 2 heteroatoms independently selected from N, O and S, wherein each of said cycloalkyl, carbocyclic, and heterocyclyl is independently substituted with zero to 3 R$^{2b}$.

5. The compound according to claim 1 or a stereoisomer, a tautomer, or a salt or solvate thereof, wherein A is:
(i) a 5-membered heteroaryl containing zero to 3 heteroatoms independently selected from N, O, and S, wherein said heteroaryl is substituted with zero to 3 R$^{4a}$, or (ii)

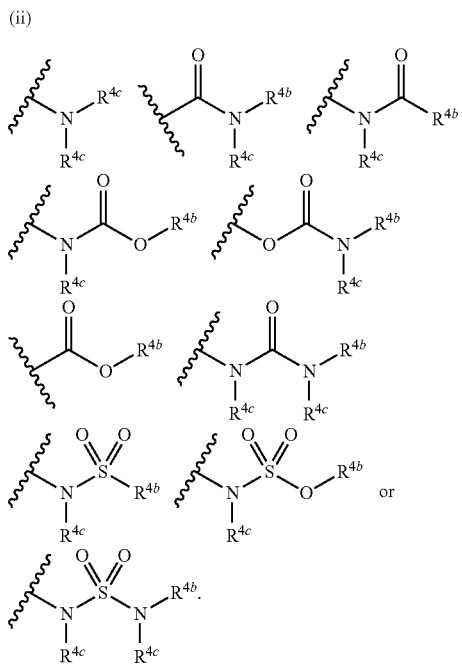

6. The compound according to claim 1 or a stereoisomer, a tautomer, or a salt or solvate thereof, wherein A is a 5-membered heteroaryl containing zero to 3 heteroatoms independently selected from N, O, and S, wherein said heteroaryl is substituted with zero to 3 R$^{4a}$.

7. The compound according to claim 1 or a stereoisomer, a tautomer, or a salt or solvate thereof, wherein: Q is F, Cl, Br, cyano, —CF$_3$, —CH$_2$CH$_2$C(O)OCH$_3$, —C(O)NH$_2$, or —P(O)(CH$_3$)$_2$.

8. The compound according to claim 1 or a stereoisomer, a tautomer, or a salt or solvate thereof, wherein: Q is -L-R$^1$.

9. The compound according to claim 1 or a stereoisomer, a tautomer, or a salt or solvate thereof, wherein:
Q is:
(i) F, Cl, Br, cyano, —CF$_3$, —CH$_2$CH$_2$C(O)OCH$_3$, —C(O)NH$_2$, or —P(O)(CH$_3$)$_2$; or
(ii) —C(O) OCH$_3$, —C(O)NH(CH$_2$CH$_3$), —OCH$_3$, —OCH$_2$CH$_3$, —OCHF$_2$, —OCH$_2$C(O)OCH$_3$, —NHC(O)OC(CH$_3$)$_3$, —NHS(O)$_2$CH$_3$, —S(O)$_2$CH$_3$, —S(O)$_2$NH(cyclopropyl), —S(O)$_2$NH(CH$_3$), —P(O)(CH$_3$)$_2$, —C(O)NH(thiazolyl), —NH(trifluoromethylphenyl), —NH(ethylphenyl), —NH(ethoxyphenyl), or —NH(difluoromethylphenyl); and A is pyrazolyl, oxadiazolyl, phenyl, pyridinyl, or indazolyl, each substituted with zero to 3 R$^{4a}$.

10. The compound of claim 1, or a stereoisomer, a tautomer, or a pharmaceutically acceptable salt or solvate thereof, wherein said compound is:
N-(3-chlorophenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide (1);
N-(3-chlorophenyl)-N-((4-(5-(1,1-difluoroethyl)-1,2,4-oxadiazol-3-yl)bicyclo[2.2.2]octan-1-yl)methyl)-3-hydroxy-3-(trifluoromethyl) cyclobutane-1-carboxamide (2);
N-(3-chlorophenyl)-N-((4-(5-(1,1-difluoroethyl)-1,2,4-oxadiazol-3-yl)bicyclo[2.2.2]octan-1-yl)methyl)-4,4-difluorocyclohexane-1-carboxamide (3);
N-(3-cyanophenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide (4);
N-(3-cyanophenyl)-N-((4-(5-(1,1-difluoroethyl)-1,2,4-oxadiazol-3-yl)bicyclo[2.2.2]octan-1-yl)methyl)-3-hydroxy-3-(trifluoromethyl) cyclobutane-1-carboxamide (5);
N-(3-cyanophenyl)-N-((4-(5-(1,1-difluoroethyl)-1,2,4-oxadiazol-3-yl)bicyclo[2.2.2]octan-1-yl)methyl)-4,4-difluorocyclohexane-1-carboxamide (6);
N-((4-(5-(1,1-difluoroethyl)-1,2,4-oxadiazol-3-yl)bicyclo[2.2.2]octan-1-yl)methyl)-3-fluoro-N-(3-fluorophenyl)bicyclo[1.1.1]pentane-1-carboxamide (7);
N-((4-(5-(1,1-difluoroethyl)-1,2,4-oxadiazol-3-yl)bicyclo[2.2.2]octan-1-yl)methyl)-N-(3-fluorophenyl)-3-hydroxy-3-(trifluoromethyl) cyclobutane-1-carboxamide (8);
N-((4-(5-(1,1-difluoroethyl)-1,2,4-oxadiazol-3-yl)bicyclo[2.2.2]octan-1-yl)methyl)-4,4-difluoro-N-(3-fluorophenyl) cyclohexane-1-carboxamide (9);
N-((4-(5-(1,1-difluoroethyl)-1,2,4-oxadiazol-3-yl)bicyclo[2.2.2]octan-1-yl)methyl)-N-(3,4-difluorophenyl)-3-fluorobicyclo[1.1.1]pentane-1-carboxamide (10);
N-((4-(5-(1,1-difluoroethyl)-1,2,4-oxadiazol-3-yl)bicyclo[2.2.2]octan-1-yl)methyl)-N-(3,4-difluorophenyl)-4,4-difluorocyclohexane-1-carboxamide (11);
N-((4-(5-(1,1-difluoroethyl)-1,2,4-oxadiazol-3-yl)bicyclo[2.2.2]octan-1-yl)methyl)-N-(3-(difluoromethoxy)phenyl)-3-fluorobicyclo[1.1.1]pentane-1-carboxamide (12);
N-((4-(5-(1,1-difluoroethyl)-1,2,4-oxadiazol-3-yl)bicyclo[2.2.2]octan-1-yl)methyl)-N-(3-(difluoromethoxy)phenyl)-3-hydroxy-3-(trifluoromethyl) cyclobutane-1-carboxamide (13);
N-((4-(5-(1,1-difluoroethyl)-1,2,4-oxadiazol-3-yl)bicyclo[2.2.2]octan-1-yl)methyl)-3-fluoro-N-(3-(trifluoromethyl) phenyl)bicyclo[1.1.1]pentane-1-carboxamide (14);

N-((4-(5-(1,1-difluoroethyl)-1,2,4-oxadiazol-3-yl)bicyclo[2.2.2]octan-1-yl)methyl)-3-hydroxy-3-(trifluoromethyl)-N-(3-(trifluoromethyl)phenyl) cyclobutane-1-carboxamide (15);

N-((4-(5-(1,1-difluoroethyl)-1,2,4-oxadiazol-3-yl)bicyclo[2.2.2]octan-1-yl)methyl)-4,4-difluoro-N-(3-(trifluoromethyl) phenyl) cyclohexane-1-carboxamide (16);

N-(3-(N-cyclopropylsulfamoyl) phenyl)-N-((4-(5-(1,1-difluoroethyl)-1,2,4-oxadiazol-3-yl) bicyclo[2.2.2]octan-1-yl)methyl)-3-fluorobicyclo[1.1.1]pentane-1-carboxamide (18);

(1S,3S)—N-(3-(N-cyclopropylsulfamoyl) phenyl)-N-((4-(5-(1,1-difluoroethyl)-1,2,4-oxadiazol-3-yl)bicyclo[2.2.2]octan-1-yl)methyl)-3-hydroxy-3-(trifluoromethyl) cyclobutane-1-carboxamide (19);

N-(3-(N-cyclopropylsulfamoyl) phenyl)-N-((4-(5-(1,1-difluoroethyl)-1,2,4-oxadiazol-3-yl) bicyclo[2.2.2]octan-1-yl)methyl)-4,4-difluorocyclohexane-1-carboxamide (20);

N-((4-(5-(1,1-difluoroethyl)-1,2,4-oxadiazol-3-yl)bicyclo[2.2.2]octan-1-yl)methyl)-3-fluoro-N-(3-(N-methylsulfamoyl) phenyl)bicyclo[1.1.1]pentane-1-carboxamide (21);

(1S,3S)—N-((4-(5-(1,1-difluoroethyl)-1,2,4-oxadiazol-3-yl)bicyclo[2.2.2]octan-1-yl)methyl)-3-hydroxy-N-(3-(N-methylsulfamoyl) phenyl)-3-(trifluoromethyl) cyclobutane-1-carboxamide (22);

N-((4-(5-(1,1-difluoroethyl)-1,2,4-oxadiazol-3-yl)bicyclo[2.2.2]octan-1-yl)methyl)-4,4-difluoro-N-(3-(N-methylsulfamoyl) phenyl) cyclohexane-1-carboxamide (23);

N-((4-(5-(1,1-difluoroethyl)-1,2,4-oxadiazol-3-yl)bicyclo[2.2.2]octan-1-yl)methyl)-N-(3-(dimethylphosphoryl) phenyl)-4,4-difluorocyclohexane-1-carboxamide (24);

N-((4-(5-(1,1-difluoroethyl)-1,2,4-oxadiazol-3-yl)bicyclo[2.2.2]octan-1-yl)methyl)-N-(3-(dimethylphosphoryl) phenyl)-3-fluorobicyclo[1.1.1]pentane-1-carboxamide (25);

(1S,3S)—N-((4-(5-(1,1-difluoroethyl)-1,2,4-oxadiazol-3-yl)bicyclo[2.2.2]octan-1-yl)methyl)-N-(3-(dimethylphosphoryl) phenyl)-3-hydroxy-3-(trifluoromethyl) cyclobutane-1-carboxamide (26);

methyl 3-(N-((4-(5-(1,1-difluoroethyl)-1,2,4-oxadiazol-3-yl)bicyclo[2.2.2]octan-1-yl) methyl)-3-fluorobicyclo[1.1.1]pentane-1-carboxamido) benzoate (27);

N-((4-(5-(1,1-difluoroethyl)-1,2,4-oxadiazol-3-yl)bicyclo[2.2.2]octan-1-yl)methyl)-N-(3-(ethylcarbamoyl) phenyl)-3-fluorobicyclo[1.1.1]pentane-1-carboxamide (28);

N-(3-carbamoylphenyl)-N-((4-(5-(1,1-difluoroethyl)-1,2,4-oxadiazol-3-yl) bicyclo[2.2.2]octan-1-yl)methyl)-3-fluorobicyclo[1.1.1]pentane-1-carboxamide (29);

1-(3-bromophenyl)-1-((4-(5-(1,1-difluoroethyl)-1,2,4-oxadiazol-3-yl)bicyclo[2.2.2]octan-1-yl)methyl)-3-((1R,4R)-4-hydroxy-4-methylcyclohexyl) urea (30);

N-(3-bromophenyl)-N-((4-(5-(1,1-difluoroethyl)-1,2,4-oxadiazol-3-yl)bicyclo[2.2.2]octan-1-yl)methyl)-2,2-difluorocyclopropane-1-carboxamide (31);

tert-butyl (3-(N-((4-(5-(1,1-difluoroethyl)-1,2,4-oxadiazol-3-yl)bicyclo[2.2.2]octan-1-yl) methyl)-3-fluorobicyclo[1.1.1]pentane-1-carboxamido) phenyl) carbamate (32);

N-(3-bromophenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide (33);

N-(3-bromophenyl)-3-fluoro-N-((4-(5-(1-fluorocyclopropyl)-1,2,4-oxadiazol-3-yl) bicyclo[2.2.2]octan-1-yl)methyl)bicyclo[1.1.1]pentane-1-carboxamide (34);

N-(3-bromophenyl)-3-fluoro-N-((4-(5-(trifluoromethyl)-1,2,4-oxadiazol-3-yl) bicyclo[2.2.2]octan-1-yl)methyl) bicyclo[1.1.1]pentane-1-carboxamide (35);

(1S,3S)—N-(3-bromophenyl)-N-((4-(3-(tert-butyl)-1,2,4-oxadiazol-5-yl)bicyclo[2.2.2]octan-1-yl)methyl)-3-hydroxy-3-(trifluoromethyl) cyclobutane-1-carboxamide (36);

N-(3-bromo-4-chlorophenyl)-N-((4-(3-(tert-butyl)-1,2,4-oxadiazol-5-yl)bicyclo[2.2.2]octan-1-yl)methyl)-3-fluorobicyclo[1.1.1]pentane-1-carboxamide (37);

N-((4-(3-(tert-butyl)-1,2,4-oxadiazol-5-yl)bicyclo[2.2.2]octan-1-yl)methyl)-N-(3-cyanophenyl)-3-fluorobicyclo[1.1.1]pentane-1-carboxamide (38);

(1S,3S)—N-((4-(3-(tert-butyl)-1,2,4-oxadiazol-5-yl)bicyclo[2.2.2]octan-1-yl)methyl)-N-(3-cyanophenyl)-3-hydroxy-3-(trifluoromethyl) cyclobutane-1-carboxamide (39);

(1S,3S)—N-((4-(3-(tert-butyl)-1,2,4-oxadiazol-5-yl)bicyclo[2.2.2]octan-1-yl)methyl)-N-(3-cyanophenyl)-3-hydroxy-3-methylcyclobutane-1-carboxamide (40);

N-((4-(3-(tert-butyl)-1,2,4-oxadiazol-5-yl)bicyclo[2.2.2]octan-1-yl)methyl)-N-(3-cyanophenyl)-3,3-difluorocyclobutane-1-carboxamide (41);

N-((4-(3-(tert-butyl)-1,2,4-oxadiazol-5-yl)bicyclo[2.2.2]octan-1-yl)methyl)-N-(3-cyanophenyl)-4,4-difluorocyclohexane-1-carboxamide (42);

N-((4-(3-(tert-butyl)-1,2,4-oxadiazol-5-yl)bicyclo[2.2.2]octan-1-yl)methyl)-N-(3-(dimethylphosphoryl) phenyl)-3-fluorobicyclo[1.1.1]pentane-1-carboxamide (43);

N-((4-(3-(tert-butyl)-1,2,4-oxadiazol-5-yl)bicyclo[2.2.2]octan-1-yl)methyl)-N-(3-(dimethylphosphoryl) phenyl)-3,3-difluorocyclobutane-1-carboxamide (44);

(1S,3S)—N-((4-(3-(tert-butyl)-1,2,4-oxadiazol-5-yl)bicyclo[2.2.2]octan-1-yl)methyl)-N-(3-(dimethylphosphoryl) phenyl)-3-hydroxy-3-(trifluoromethyl) cyclobutane-1-carboxamide (45);

N-((4-(3-(tert-butyl)-1,2,4-oxadiazol-5-yl)bicyclo[2.2.2]octan-1-yl)methyl)-N-(3-(dimethylphosphoryl) phenyl) tetrahydro-2H-pyran-4-carboxamide (46);

N-((4-(3-(tert-butyl)-1,2,4-oxadiazol-5-yl)bicyclo[2.2.2]octan-1-yl)methyl)-N-(3-(dimethylphosphoryl) phenyl) tetrahydro-2H-thiopyran-4-carboxamide 1,1-dioxide (47);

N-(3-bromophenyl)-N-((4-(5-(1,1-difluoroethyl) pyridin-2-yl)bicyclo[2.2.2]octan-1-yl) methyl)-3-fluorobicyclo[1.1.1]pentane-1-carboxamide (48);

N-(3-cyanophenyl)-N-((4-(5-(1,1-difluoroethyl) pyridin-2-yl)bicyclo[2.2.2]octan-1-yl) methyl)-3-fluorobicyclo[1.1.1]pentane-1-carboxamide (49);

(1S,3S)—N-(3-cyanophenyl)-N-((4-(5-(1,1-difluoroethyl) pyridin-2-yl)bicyclo[2.2.2]octan-1-yl)methyl)-3-hydroxy-3-methylcyclobutane-1-carboxamide (50);

(1S,3S)—N-(3-cyanophenyl)-N-((4-(5-(1,1-difluoroethyl) pyridin-2-yl)bicyclo[2.2.2]octan-1-yl)methyl)-3-hydroxy-3-(trifluoromethyl) cyclobutane-1-carboxamide (51);

N-((4-(3-cyclopropyl-1,2,4-oxadiazol-5-yl)bicyclo[2.2.2]octan-1-yl)methyl)-N-(3-ethoxyphenyl)-3-fluorobicyclo[1.1.1]pentane-1-carboxamide (52);

N-((4-(3-cyclopropyl-1,2,4-oxadiazol-5-yl)bicyclo[2.2.2]octan-1-yl)methyl)-N-(3-ethoxyphenyl)-3,3-difluorocyclobutane-1-carboxamide (53);

N-((4-(3-cyclopropyl-1,2,4-oxadiazol-5-yl)bicyclo[2.2.2]octan-1-yl)methyl)-N-(3-ethoxyphenyl)-3-hydroxy-3-(trifluoromethyl) cyclobutane-1-carboxamide (54);

N-((4-(3-cyclopropyl-1,2,4-oxadiazol-5-yl)bicyclo[2.2.2]octan-1-yl)methyl)-N-(3-ethoxyphenyl) tetrahydro-2H-pyran-4-carboxamide (55);

N-((4-(3-cyclopropyl-1,2,4-oxadiazol-5-yl)bicyclo[2.2.2]octan-1-yl)methyl)-N-(3-ethoxyphenyl) tetrahydro-2H-thiopyran-4-carboxamide 1,1-dioxide (56);

(1S,3S)—N-((4-(3-cyclopropyl-1,2,4-oxadiazol-5-yl)bicyclo[2.2.2]octan-1-yl)methyl)-3-hydroxy-N-(3-methoxyphenyl)-3-(trifluoromethyl) cyclobutane-1-carboxamide (57);

N-((4-(3-cyclopropyl-1,2,4-oxadiazol-5-yl)bicyclo[2.2.2]octan-1-yl)methyl)-3-fluoro-N-(3-methoxyphenyl)bicyclo[1.1.1]pentane-1-carboxamide (58);

N-((4-(3-cyclopropyl-1,2,4-oxadiazol-5-yl)bicyclo[2.2.2]octan-1-yl)methyl)-3,3-difluoro-N-(3-methoxyphenyl) cyclobutane-1-carboxamide (59);

N-((4-(3-cyclopropyl-1,2,4-oxadiazol-5-yl)bicyclo[2.2.2]octan-1-yl)methyl)-N-(3-methoxyphenyl) tetrahydro-2H-pyran-4-carboxamide (60);

N-((4-(3-cyclopropyl-1,2,4-oxadiazol-5-yl)bicyclo[2.2.2]octan-1-yl)methyl)-N-(3-methoxyphenyl) tetrahydro-2H-thiopyran-4-carboxamide 1,1-dioxide (61);

N-(3-cyano-5-fluorophenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide (62);

(1S,3S)—N-(3-cyano-5-fluorophenyl)-N-((4-(3-cyclopropyl-1,2,4-oxadiazol-5-yl)bicyclo [2.2.2]octan-1-yl)methyl)-3-hydroxy-3-(trifluoromethyl) cyclobutane-1-carboxamide (63);

N-(3-cyano-5-fluorophenyl)-N-((4-(3-cyclopropyl-1,2,4-oxadiazol-5-yl)bicyclo[2.2.2]octan-1-yl)methyl)-3,3-difluorocyclobutane-1-carboxamide (64);

N-((4-(3-cyclopropyl-1,2,4-oxadiazol-5-yl)bicyclo[2.2.2]octan-1-yl)methyl)-3,3-difluoro-N-(3-(methylsulfonamido) phenyl) cyclobutane-1-carboxamide (65);

N-((4-(3-cyclopropyl-1,2,4-oxadiazol-5-yl)bicyclo[2.2.2]octan-1-yl)methyl)-3-fluoro-N-(3-(methylsulfonamido) phenyl)bicyclo[1.1.1]pentane-1-carboxamide (66);

(1S,3S)—N-((4-(3-cyclopropyl-1,2,4-oxadiazol-5-yl)bicyclo[2.2.2]octan-1-yl)methyl)-3-hydroxy-N-(3-(methylsulfonamido) phenyl)-3-(trifluoromethyl) cyclobutane-1-carboxamide (67);

N-((4-(3-cyclopropyl-1,2,4-oxadiazol-5-yl)bicyclo[2.2.2]octan-1-yl)methyl)-3-fluoro-N-(3-(methylsulfonyl) phenyl)bicyclo[1.1.1]pentane-1-carboxamide (68);

N-((4-(3-cyclopropyl-1,2,4-oxadiazol-5-yl)bicyclo[2.2.2]octan-1-yl)methyl)-4,4-difluoro-N-(3-(methylsulfonyl) phenyl) cyclohexane-1-carboxamide (69);

N-(3-cyanophenyl)-N-(1-(4-(3-cyclopropyl-1,2,4-oxadiazol-5-yl)bicyclo[2.2.2]octan-1-yl) ethyl)-3-fluorobicyclo[1.1.1]pentane-1-carboxamide (70);

N-(3-bromophenyl)-N-((4-(3-cyclopropyl-1,2,4-oxadiazol-5-yl)bicyclo[2.2.2]octan-1-yl) methyl) cyclopropanesulfonamide (71);

N-(3-cyanophenyl)-N-((4-(3-cyclopropyl-1-methyl-1H-pyrazol-5-yl)bicyclo[2.2.2]octan-1-yl)methyl)-3-fluorobicyclo[1.1.1]pentane-1-carboxamide (72);

N-(3-cyanophenyl)-N-((4-(3-cyclopropyl-1-methyl-1H-pyrazol-5-yl)bicyclo[2.2.2]octan-1-yl)methyl)-4,4-difluorocyclohexane-1-carboxamide (73);

(1S,3S)—N-(3-cyanophenyl)-N-((4-(3-cyclopropyl-1-methyl-1H-pyrazol-5-yl) bicyclo[2.2.2]octan-1-yl)methyl)-3-hydroxy-3-methylcyclobutane-1-carboxamide (74);

(1S,3S)—N-(3-cyanophenyl)-N-((4-(3-cyclopropyl-1-methyl-1H-pyrazol-5-yl)bicyclo [2.2.2]octan-1-yl)methyl)-3-hydroxy-3-(trifluoromethyl) cyclobutane-1-carboxamide (75);

(1S,3S)—N-((4-(3-cyclopropyl-1-methyl-1H-pyrazol-5-yl)bicyclo[2.2.2]octan-1-yl)methyl)-3-hydroxy-N-(3-(methylsulfonyl) phenyl)-3-(trifluoromethyl) cyclobutane-1-carboxamide (76);

N-((4-(3-cyclopropyl-1-methyl-1H-pyrazol-5-yl)bicyclo[2.2.2]octan-1-yl)methyl)-4, 4-difluoro-N-(3-(methylsulfonyl) phenyl) cyclohexane-1-carboxamide (77);

N-((4-(3-cyclopropyl-1-methyl-1H-pyrazol-5-yl)bicyclo[2.2.2]octan-1-yl)methyl)-3-fluoro-N-(3-(methylsulfonyl) phenyl)bicyclo[1.1.1]pentane-1-carboxamide (78);

methyl 2-(3-(N-((4-(3-chloro-4-(dimethylamino) phenyl) bicyclo[2.2.2]octan-1-yl)methyl) cyclohexanecarboxamido) phenoxy) acetate (79);

methyl 2-(3-(N-((4-(4-(dimethylamino) phenyl)bicyclo [2.2.2]octan-1-yl)methyl) cyclohexanecarboxamido) phenoxy) acetate (80);

3-(N-((4-(3-methyl-1,2,4-oxadiazol-5-yl)bicyclo[2.2.2]octan-1-yl)methyl cyclohexanecarboxamido)-N-(thiazol-2-yl) benzamide (82);

N-((4-(3-(tert-butyl)-1,2,4-oxadiazol-5-yl)bicyclo[2.2.2]octan-1-yl)methyl)-N-(3-((4-ethoxyphenyl) amino) phenyl)-3-fluorobicyclo[1.1.1]pentane-1-carboxamide (83);

N-((4-(5-(tert-butyl)-1,2,4-oxadiazol-3-yl)bicyclo[2.2.2]octan-1-yl)methyl)-N-(3-((4-(difluoromethoxy) phenyl) amino) phenyl)-3-fluorobicyclo[1.1.1]pentane-1-carboxamide (84);

N-((4-(5-(tert-butyl)-1,2,4-oxadiazol-3-yl)bicyclo[2.2.2]octan-1-yl)methyl)-N-(3-((4-ethoxyphenyl) amino) phenyl)-3-fluorobicyclo[1.1.1]pentane-1-carboxamide (85);

N-((4-(5-(tert-butyl)-1,2,4-oxadiazol-3-yl)bicyclo[2.2.2]octan-1-yl)methyl)-N-(3-((4-ethylphenyl) amino) phenyl)-3-fluorobicyclo[1.1.1]pentane-1-carboxamide (86);

N-((4-(5-(tert-butyl)-1,2,4-oxadiazol-3-yl)bicyclo[2.2.2]octan-1-yl)methyl)-3-fluoro-N-(3-((4-(trifluoromethyl) phenyl) amino) phenyl)bicyclo[1.1.1]pentane-1-carboxamide (87);

N-((4-(5-(tert-butyl)-1,2,4-oxadiazol-3-yl)bicyclo[2.2.2]octan-1-yl)methyl)-3-fluoro-N-(3-((4-fluorophenyl) amino) phenyl)bicyclo[1.1.1]pentane-1-carboxamide (88);

methyl 3-(3-(N-((4-(4-(dimethylamino) phenyl)bicyclo [2.2.2]octan-1-yl)methyl) cyclohexanecarboxamido) phenyl) propanoate (89);

(1S,3S)—N-((4-(3-cyclopropyl-1,2,4-oxadiazol-5-yl)bicyclo[2.2.2]octan-1-yl)methyl)-3-hydroxy-N-(3-(methylsulfonyl) phenyl)-3-(trifluoromethyl) cyclobutane-1-carboxamide (90);

(1S,3S)—N-(3-((4-(1-cyanocyclopropyl) phenyl) amino) phenyl)-N-((4-(5-(1-fluorocyclopropyl)-1,2,4-oxadiazol-3-yl)bicyclo[2.2.2]octan-1-yl)methyl)-3-hydroxy-3-(trifluoromethyl) cyclobutane-1-carboxamide (91);

(1S,3S)—N-(3-((4-((2-cyanopropan-2-yl) oxy) phenyl) amino) phenyl)-N-((4-(5-(1,1-difluoroethyl) pyridin-2-yl)bicyclo[2.2.2]octan-1-yl)methyl)-3-hydroxy-3-(trifluoromethyl) cyclobutane-1-carboxamide (92);

(1S,3S)—N-(3-((4-(1-cyanocyclopropyl) phenyl) amino) phenyl)-N-((4-(5-(1,1-difluoroethyl) pyridin-2-yl)bicyclo[2.2.2]octan-1-yl)methyl)-3-hydroxy-3-(trifluoromethyl) cyclobutane-1-carboxamide (93);

1-(3-cyanophenyl)-1-((4-(5-(2-fluoropropan-2-yl)-1,2,4-oxadiazol-3-yl)bicyclo[2.2.2]octan-1-yl)methyl)-3-((1R,4R)-4-hydroxy-4-methylcyclohexyl) urea (95);

1-(3-cyanophenyl)-1-((4-(5-(2-fluoropropan-2-yl)-1,2,4-oxadiazol-3-yl)bicyclo[2.2.2]octan-1-yl)methyl)-3-((1R,4R)-4-hydroxycyclohexyl) urea (96);

1-(3-cyanophenyl)-1-((4-(5-(2-fluoropropan-2-yl)-1,2,4-oxadiazol-3-yl)bicyclo[2.2.2]octan-1-yl)methyl)-3-(3-hydroxy-2,2-dimethylpropyl) urea (97);

1-(3-cyanophenyl)-1-((4-(5-(1,1-difluoroethyl)-1,2,4-oxadiazol-3-yl)bicyclo[2.2.2]octan-1-yl)methyl)-3-((1R,4R)-4-hydroxycyclohexyl) urea (98);

1-(3-cyanophenyl)-1-((4-(5-(1,1-difluoroethyl)-1,2,4-oxadiazol-3-yl)bicyclo[2.2.2]octan-1-yl)methyl)-3-((1R,4R)-4-hydroxy-4-methylcyclohexyl) urea (99);

1-(3-cyanophenyl)-1-((4-(5-(1,1-difluoroethyl)-1,2,4-oxadiazol-3-yl)bicyclo[2.2.2]octan-1-yl)methyl)-3-(3-hydroxy-2,2-dimethylpropyl) urea (100);

1-(3-bromo-4-fluorophenyl)-1-((4-(5-(2-fluoropropan-2-yl)-1,2,4-oxadiazol-3-yl) bicyclo[2.2.2]octan-1-yl) methyl)-3-((1R,4R)-4-hydroxycyclohexyl) urea (101);

N-((4-(5-(tert-butyl)-1,2,4-oxadiazol-3-yl)bicyclo[2.2.2]octan-1-yl)methyl)-N-(3-((5-(difluoromethoxy) pyrimidin-2-yl) amino) phenyl)-3-fluorobicyclo[1.1.1]pentane-1-carboxamide (102);

N-((4-(5-(tert-butyl)-1,2,4-oxadiazol-3-yl)bicyclo[2.2.2]octan-1-yl)methyl)-N-(3-((2-cyclopropylpyrimidin-5-yl) amino) phenyl)-3-fluorobicyclo[1.1.1]pentane-1-carboxamide (103);

N-((4-(5-(tert-butyl)-1,2,4-oxadiazol-3-yl)bicyclo[2.2.2]octan-1-yl)methyl)-N-(3-((5-(difluoromethoxy) pyridin-2-yl) amino) phenyl)-3-fluorobicyclo[1.1.1]pentane-1-carboxamide (104);

N-(3-((5-cyclopropylpyrimidin-2-yl) amino) phenyl)-3-fluoro-N-((4-(5-(trifluoromethyl) pyridin-2-yl)bicyclo[2.2.2]octan-1-yl)methyl)bicyclo[1.1.1]pentane-1-carboxamide (105);

N-(3-((5-(difluoromethoxy) pyrimidin-2-yl) amino) phenyl)-3-fluoro-N-((4-(5-(trifluoromethyl) pyridin-2-yl) bicyclo[2.2.2]octan-1-yl)methyl)bicyclo[1.1.1]pentane-1-carboxamide (106);

N-(3-((4-(difluoromethoxy) phenyl) amino) phenyl)-3-fluoro-N-((4-(5-(trifluoromethyl) pyridin-2-yl)bicyclo[2.2.2]octan-1-yl)methyl)bicyclo[1.1.1]pentane-1-carboxamide (107);

N-(3-((5-(difluoromethoxy) pyridin-2-yl) amino) phenyl)-3-fluoro-N-((4-(5-(trifluoromethyl) pyridin-2-yl) bicyclo[2.2.2]octan-1-yl)methyl)bicyclo[1.1.1]pentane-1-carboxamide (108);

N-(3-((5-cyclopropylpyridin-2-yl) amino) phenyl)-3-fluoro-N-((4-(5-(trifluoromethyl) pyridin-2-yl)bicyclo[2.2.2]octan-1-yl)methyl)bicyclo[1.1.1]pentane-1-carboxamide (109);

N-((4-(5-(tert-butyl)-1,2,4-oxadiazol-3-yl)bicyclo[2.2.2]octan-1-yl)methyl)-3-fluoro-N-(3-hydroxyphenyl)bicyclo[1.1.1]pentane-1-carboxamide (110);

N-((4-(5-(tert-butyl)-1,2,4-oxadiazol-3-yl)bicyclo[2.2.2]octan-1-yl)methyl)-N-(3-(cyanomethoxy) phenyl)-3-fluorobicyclo[1.1.1]pentane-1-carboxamide (111);

N-((4-(5-(tert-butyl)-1,2,4-oxadiazol-3-yl)bicyclo[2.2.2]octan-1-yl)methyl)-3-fluoro-N-(3-(2-hydroxy-2-methylpropoxy) phenyl)bicyclo[1.1.1]pentane-1-carboxamide (112);

2-(3-(N-((4-(5-(tert-butyl)-1,2,4-oxadiazol-3-yl)bicyclo[2.2.2]octan-1-yl)methyl)-3-fluorobicyclo[1.1.1]pentane-1-carboxamido) phenoxy)-2-methylpropanoic acid (113);

N-(3-cyanophenyl)-3-fluoro-N-((4-(5-(trifluoromethyl)-1,2,4-oxadiazol-3-yl) bicyclo[2.2.2]octan-1-yl)methyl) bicyclo[1.1.1]pentane-1-carboxamide (114);

(1S,3S)—N-(3-cyanophenyl)-3-hydroxy-3-(trifluoromethyl)-N-((4-(5-(trifluoromethyl)-1,2,4-oxadiazol-3-yl) bicyclo[2.2.2]octan-1-yl)methyl) cyclobutane-1-carboxamide (115);

N-(3-cyanophenyl)-N-((4-(5-(trifluoromethyl)-1,2,4-oxadiazol-3-yl)bicyclo[2.2.2]octan-1-yl) methyl) tetrahydro-2H-pyran-4-carboxamide (116);

(1S,3S)—N-(3-cyanophenyl)-3-hydroxy-3-methyl-N-((4-(5-(trifluoromethyl)-1,2,4-oxadiazol-3-yl)bicyclo[2.2.2]octan-1-yl)methyl) cyclobutane-1-carboxamide (117);

N-((4-(5-(tert-butyl)-1,2,4-oxadiazol-3-yl)bicyclo[2.2.2]octan-1-yl)methyl)-N-(3-((5-(difluoromethoxy) pyrimidin-2-yl) oxy) phenyl)-3-fluorobicyclo[1.1.1]pentane-1-carboxamide (118);

N-((4-(5-(tert-butyl)-1,2,4-oxadiazol-3-yl)bicyclo[2.2.2]octan-1-yl)methyl)-N-(3-((5-(difluoromethoxy) pyridin-2-yl) oxy) phenyl)-3-fluorobicyclo[1.1.1]pentane-1-carboxamide (119);

3-(N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamido) benzoic acid (120);

N-((4-(3-(tert-butyl)-1,2,4-oxadiazol-5-yl)bicyclo[2.2.2]octan-1-yl)methyl)-N-(3-carbamoyl-4-fluorophenyl)-3-fluorobicyclo[1.1.1]pentane-1-carboxamide (121);

N-((4-(3-(tert-butyl)-1,2,4-oxadiazol-5-yl)bicyclo[2.2.2]octan-1-yl)methyl)-N-(3-(ethylcarbamoyl)-4-fluorophenyl)-3-fluorobicyclo[1.1.1]pentane-1-carboxamide (122);

(1S,3S)—N-((4-(3-(tert-butyl)-1,2,4-oxadiazol-5-yl)bicyclo[2.2.2]octan-1-yl)methyl)-3-hydroxy-N-(3-isopropoxyphenyl)-3-(trifluoromethyl) cyclobutane-1-carboxamide (123-124);

N-((4-(3-(tert-butyl)-1,2,4-oxadiazol-5-yl)bicyclo[2.2.2]octan-1-yl)methyl)-3-fluoro-N-(3-isopropoxyphenyl) bicyclo[1.1.1]pentane-1-carboxamide (124);

(1S,3S)—N-((4-(5-(1,1-difluoroethyl)-1,2,4-oxadiazol-3-yl)bicyclo[2.2.2]octan-1-yl)methyl)-3-hydroxy-N-(3-isopropoxyphenyl)-3-methylcyclobutane-1-carboxamide (125);

(1S,3S)—N-((4-(5-(1,1-difluoroethyl)-1,2,4-oxadiazol-3-yl)bicyclo[2.2.2]octan-1-yl)methyl)-3-hydroxy-N-(3-isopropoxyphenyl)-3-(trifluoromethyl) cyclobutane-1-carboxamide (126);

N-((4-(5-(1,1-difluoroethyl)-1,2,4-oxadiazol-3-yl)bicyclo[2.2.2]octan-1-yl)methyl)-3-fluoro-N-(3-isopropoxyphenyl)bicyclo[1.1.1]pentane-1-carboxamide (127);

N-((4-(3-(tert-butyl)-1,2,4-oxadiazol-5-yl)bicyclo[2.2.2]octan-1-yl)methyl)-3-fluoro-N-(4-fluoro-3-(2-hydroxypropan-2-yl) phenyl)bicyclo[1.1.1]pentane-1-carboxamide (128);

N-((4-(5-(1,1-difluoroethyl)-1,2,4-oxadiazol-3-yl)bicyclo[2.2.2]octan-1-yl)methyl)-3-fluoro-N-(3-methoxyphenyl)bicyclo[1.1.1]pentane-1-carboxamide (129);

N-((4-(5-(1,1-difluoroethyl)-1,2,4-oxadiazol-3-yl)bicyclo[2.2.2]octan-1-yl)methyl)-N-(3-ethoxyphenyl)-3-fluorobicyclo[1.1.1]pentane-1-carboxamide (130);

(S)-1-(3-bromophenyl)-1-((4-(5-(1,1-difluoroethyl)-1,2,4-oxadiazol-3-yl) bicyclo[2.2.2]octan-1-yl)methyl)-3-(2-fluoro-3-hydroxy-3-methylbutyl) urea (131);

N-(3-bromophenyl)-N-((4-(3-(tert-butyl)-1,2,4-oxadiazol-5-yl)bicyclo[2.2.1]heptan-1-yl) methyl)-3-fluorobicyclo[1.1.1]pentane-1-carboxamide (132);

(1S, 3S)—N-(3-bromophenyl)-N-((4-(3-(tert-butyl)-1, 2, 4-oxadiazol-5-yl)bicyclo[2.2.1]heptan-1-yl)methyl)-3-hydroxy-3-(trifluoromethyl) cyclobutane-1-carboxamide (133);

N-(3-bromophenyl)-N-((4-(5-(2-fluoropropan-2-yl)-1, 2, 4-oxadiazol-3-yl) bicyclo[2.2.2]octan-1-yl)methyl)-3-(2-hydroxypropan-2-yl)bicyclo[1.1.1]pentane-1-carboxamide (134);

N-(3-cyano-5-fluorophenyl)-N-((4-(5-(1,1-difluoroethyl)-1,2,4-oxadiazol-3-yl) bicyclo[2.2.2]octan-1-yl) methyl)-3-fluorobicyclo[1.1.1]pentane-1-carboxamide (135);

(1S,3S)—N-(3-cyano-5-fluorophenyl)-N-((4-(5-(1,1-difluoroethyl)-1,2,4-oxadiazol-3-yl) bicyclo[2.2.2]octan-1-yl)methyl)-3-hydroxy-3-(trifluoromethyl) cyclobutane-1-carboxamide (136);

N-(3-cyano-5-fluorophenyl)-N-((4-(5-(1,1-difluoroethyl)-1,2,4-oxadiazol-3-yl) bicyclo[2.2.2]octan-1-yl) methyl)-3,3-difluorocyclobutane-1-carboxamide (137);

N-(3-cyano-5-fluorophenyl)-N-((4-(5-(1,1-difluoroethyl)-1,2,4-oxadiazol-3-yl) bicyclo[2.2.2]octan-1-yl) methyl) tetrahydro-2H-thiopyran-4-carboxamide 1,1-dioxide (138);

3-(4-(((1S,3S)—N-(3-bromophenyl)-3-hydroxy-3-(trifluoromethyl) cyclobutane-1-carboxamido) methyl)bicyclo[2.2.2]octan-1-yl)-1,2,4-oxadiazole-5-carboxamide (139); or 3-(4-((N-(3-bromophenyl)-3-fluorobicyclo[1.1.1]pentane-1-carboxamido) methyl) bicyclo[2.2.2]octan-1-yl)-1,2,4-oxadiazole-5-carboxamide (140).

11. A pharmaceutical composition comprising a pharmaceutically acceptable carrier and a compound according to claim 1, or a stereoisomer, a tautomer, or a pharmaceutically acceptable salt or solvate thereof.

12. A method of treating a disease or disorder, comprising administering to a mammalian patent a compound according to claim 1 or a pharmaceutically acceptable salt thereof, wherein the disease or disorder is pathological fibrosis, metabolic disorder, or cholestatic disorder and wherein the pathological fibrosis is liver fibrosis, renal fibrosis, biliary fibrosis, or pancreatic fibrosis and the metabolic disorder or cholestatic disorder is nonalcoholic steatohepatitis (NASH), non-alcoholic fatty liver disease (NAFLD), chronic kidney disease, diabetic kidney disease, primary sclerosing cholangitis (PSC), or primary biliary cirrhosis (PBC).

13. A method of treating a disease or disorder, comprising administering to a mammalian patent a compound according to claim 1 or a pharmaceutically acceptable salt thereof, wherein the disease or disorder is idiopathic pulmonary fibrosis (IPF).

* * * * *